US009999619B2

(12) United States Patent
Huang et al.

(10) Patent No.: US 9,999,619 B2
(45) Date of Patent: *Jun. 19, 2018

(54) PIPERIDIN-4-YL AZETIDINE DERIVATIVES AS JAK1 INHIBITORS

(71) Applicants: Incyte Corporation, Wilmington, DE (US); Incyte Holdings Corporation, Wilmington, DE (US)

(72) Inventors: Taisheng Huang, Wilmington, DE (US); Chu-Biao Xue, Hockessin, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/288,641

(22) Filed: Oct. 7, 2016

(65) Prior Publication Data

US 2017/0246157 A1  Aug. 31, 2017

Related U.S. Application Data

(60) Continuation of application No. 14/289,121, filed on May 28, 2014, now Pat. No. 9,464,088, which is a division of application No. 13/043,986, filed on Mar. 9, 2011, now Pat. No. 8,765,734.

(60) Provisional application No. 61/312,588, filed on Mar. 10, 2010, provisional application No. 61/415,602, filed on Nov. 19, 2010.

(51) Int. Cl.
| A61K 31/519 | (2006.01) |
| A61P 37/06 | (2006.01) |
| A61K 31/4545 | (2006.01) |
| A61K 9/00 | (2006.01) |
| C07D 487/04 | (2006.01) |

(52) U.S. Cl.
CPC ........ *A61K 31/4545* (2013.01); *A61K 9/0014* (2013.01); *A61K 9/0019* (2013.01); *A61K 9/0024* (2013.01); *A61K 9/0048* (2013.01); *A61K 31/519* (2013.01)

(58) Field of Classification Search
CPC .............. C07D 487/04; A61K 31/519
See application file for complete search history.

(56) References Cited

U.S. PATENT DOCUMENTS

| 2,985,589 | A | 5/1961 | Broughton et al. |
| 3,832,460 | A | 8/1974 | Kosti |
| 4,140,755 | A | 2/1979 | Sheth |
| 4,402,832 | A | 9/1983 | Gerhold |
| 4,498,991 | A | 2/1985 | Oroskar |
| 4,512,984 | A | 4/1985 | Seufert et al. |
| 4,548,990 | A | 10/1985 | Mueller et al. |
| 4,814,477 | A | 3/1989 | Wijnberg et al. |
| 5,378,700 | A | 1/1995 | Sakuma et al. |
| 5,472,949 | A | 12/1995 | Arasaki |
| 5,510,101 | A | 4/1996 | Stroppolo |
| 5,521,184 | A | 5/1996 | Zimmermann |
| 5,630,943 | A | 5/1997 | Grill |
| 5,795,909 | A | 8/1998 | Shashoua et al. |
| 5,856,326 | A | 1/1999 | Anthony |
| 5,919,779 | A | 7/1999 | Proudfoot et al. |
| 6,025,366 | A | 2/2000 | Walsh et al. |
| 6,060,038 | A | 5/2000 | Burns |
| 6,075,056 | A | 6/2000 | Quigley, Jr. et al. |
| 6,136,198 | A | 10/2000 | Adam et al. |
| 6,217,895 | B1 | 4/2001 | Guo et al. |
| 6,335,342 | B1 | 1/2002 | Longo et al. |
| 6,375,839 | B1 | 4/2002 | Adam et al. |
| 6,413,419 | B1 | 7/2002 | Adam et al. |
| 6,486,322 | B1 | 11/2002 | Longo et al. |
| 6,518,265 | B1 | 2/2003 | Kato et al. |
| 6,548,078 | B2 | 4/2003 | Guo |
| 6,569,443 | B1 | 5/2003 | Dawson |
| 6,579,882 | B2 | 6/2003 | Stewart et al. |
| 6,624,138 | B1 | 9/2003 | Sung et al. |
| 6,635,762 | B1 | 10/2003 | Blumenkopf et al. |
| 6,712,973 | B2 | 3/2004 | Adam et al. |
| 6,713,089 | B1 | 3/2004 | Bertelsen et al. |
| 6,852,727 | B2 | 2/2005 | Goulet et al. |
| 6,953,776 | B2 | 10/2005 | Di Napoli |
| 7,005,436 | B2 | 2/2006 | Lloyd et al. |
| 7,167,750 | B2 | 1/2007 | Knudson et al. |
| 7,265,108 | B2 | 9/2007 | Ozaki |
| 7,335,667 | B2 | 2/2008 | Rodgers et al. |
| 7,358,255 | B2 | 4/2008 | Nakamura |
| 7,517,870 | B2 | 4/2009 | Auricchio |
| 7,598,257 | B2 | 10/2009 | Rodgers et al. |
| 7,683,171 | B2 | 3/2010 | Pitts et al. |
| 7,745,437 | B2 | 6/2010 | Ren et al. |
| 7,750,007 | B2 | 7/2010 | Bearss et al. |
| 7,834,022 | B2 | 11/2010 | Rodgers et al. |
| 8,053,433 | B2 | 11/2011 | Rodgers et al. |
| 8,158,616 | B2 | 4/2012 | Rodgers et al. |
| 8,309,718 | B2 | 11/2012 | Li et al. |
| 8,410,265 | B2 | 4/2013 | Zhou et al. |
| 8,415,362 | B2 | 4/2013 | Rodgers et al. |
| 8,420,629 | B2 | 4/2013 | Rodgers et al. |
| 8,440,679 | B2 | 5/2013 | McAllister |
| 8,445,488 | B2 | 5/2013 | Rodger et al. |
| 8,486,902 | B2 | 7/2013 | Rodgers et al. |
| 8,513,270 | B2 | 8/2013 | Arvanitis et al. |

(Continued)

FOREIGN PATENT DOCUMENTS

| DE | 30 36 390 | 5/1982 |
| EP | 0223420 | 5/1987 |

(Continued)

OTHER PUBLICATIONS

26th Annual JPMorgan Healthcare Conference presentation dated Jan. 8, 2008, 28 pages.

(Continued)

*Primary Examiner* — Susanna Moore

(74) *Attorney, Agent, or Firm* — Fish & Richardson P.C.

(57) ABSTRACT

The present invention provides piperidin-4-yl azetidine derivatives, as well as their compositions and methods of use, that modulate the activity of Janus kinase 1 (JAK1) and are useful in the treatment of diseases related to the activity of JAK1 including, for example, inflammatory disorders, autoimmune disorders, cancer, and other diseases.

2 Claims, 3 Drawing Sheets

(56) References Cited

U.S. PATENT DOCUMENTS

| | | |
|---|---|---|
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,637,529 B2 | 1/2014 | Woller |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,181,271 B2 | 11/2015 | Li et al. |
| 9,206,187 B2 | 12/2015 | Rodgers et al. |
| 9,216,984 B2 | 12/2015 | Li |
| 9,221,845 B2 | 12/2015 | Cao |
| 9,290,506 B2 | 3/2016 | Zhou et al. |
| 9,334,274 B2 | 5/2016 | Rodgers |
| 9,359,358 B2 | 6/2016 | Rodgers |
| 9,376,439 B2 | 6/2016 | Rodgers |
| 9,487,521 B2 | 11/2016 | Zhou et al. |
| 9,498,467 B2 | 11/2016 | Leopold et al. |
| 9,464,088 B2 | 12/2016 | Huang |
| 9,611,269 B2 | 4/2017 | Yao et al. |
| 9,623,029 B2 | 4/2017 | Li et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0099204 A1 | 5/2004 | Nestor |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0225286 A1 | 9/2007 | Ren et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0225057 A1 | 9/2012 | Flynn |
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0004516 A1 | 1/2014 | Sattler et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |

(56) References Cited

U.S. PATENT DOCUMENTS

| | | |
|---|---|---|
| 2014/0303196 A1 | 10/2014 | Rodgers et al. |
| 2014/0343030 A1 | 11/2014 | Li et al. |
| 2014/0378400 A1 | 12/2014 | Rodgers et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons |
| 2015/0164900 A1 | 6/2015 | Rodgers et al. |
| 2015/0183805 A1 | 7/2015 | Liu et al. |
| 2015/0225411 A1 | 8/2015 | Yao et al. |
| 2015/0225412 A1 | 8/2015 | Brameld |
| 2015/0238492 A1 | 8/2015 | Rodgers et al. |
| 2015/0246046 A1 | 9/2015 | Vaddi |
| 2015/0250790 A1 | 9/2015 | Parikh et al. |
| 2015/0315185 A1 | 11/2015 | Rodgers et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0272648 A1 | 9/2016 | Rodgers et al. |
| 2016/0346286 A1 | 12/2016 | Rodgers et al. |
| 2016/0347734 A1 | 12/2016 | Liu et al. |
| 2017/0015674 A1 | 1/2017 | Zhou et al. |
| 2017/0071947 A1 | 3/2017 | Rodgers et al. |
| 2017/0087158 A1 | 3/2017 | Friedman et al. |
| 2017/0253598 A1 | 9/2017 | Yao et al. |

FOREIGN PATENT DOCUMENTS

| | | |
|---|---|---|
| EP | 0727217 | 8/1996 |
| EP | 0795556 | 9/1997 |
| JP | 07-010876 | 1/1995 |
| JP | 2003/155285 | 5/2003 |
| JP | 2006-502183 | 1/2006 |
| JP | 2006/518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| WO | WO 96/030343 | 10/1996 |
| WO | WO 97/002262 | 1/1997 |
| WO | WO 97/002266 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 01/014402 | 3/2001 |
| WO | WO 01/027104 | 4/2001 |
| WO | WO 01/042246 | 6/2001 |
| WO | WO 01/064655 | 9/2001 |
| WO | WO 01/081345 | 11/2001 |
| WO | WO 2001/081346 | 11/2001 |
| WO | WO 01/098344 | 12/2001 |
| WO | WO 02/000196 | 1/2002 |
| WO | WO 02/000661 | 1/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 2003/000688 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 04/003026 | 1/2004 |
| WO | WO 04/005281 | 1/2004 |
| WO | WO 04/005282 | 1/2004 |
| WO | WO 04/026406 | 4/2004 |
| WO | WO 04/041814 | 5/2004 |
| WO | WO 04/046120 | 6/2004 |
| WO | WO 04/047843 | 6/2004 |
| WO | WO 04/056786 | 7/2004 |
| WO | WO 04/072063 | 8/2004 |
| WO | WO 04/080980 | 9/2004 |
| WO | WO 04/092154 | 10/2004 |
| WO | WO 04/099204 | 11/2004 |
| WO | WO 04/099205 | 11/2004 |
| WO | WO 05/005988 | 1/2005 |
| WO | WO 05/013986 | 2/2005 |
| WO | WO 05/020921 | 3/2005 |
| WO | WO 05/026129 | 3/2005 |
| WO | WO 05/028444 | 3/2005 |
| WO | WO 05/049033 | 6/2005 |
| WO | WO 05/051393 | 6/2005 |
| WO | WO 05/060972 | 7/2005 |
| WO | WO 05/061463 | 7/2005 |
| WO | WO 05/062795 | 7/2005 |
| WO | WO 05/089502 | 9/2005 |
| WO | WO 05/095400 | 10/2005 |
| WO | WO 05/105146 | 11/2005 |
| WO | WO 05/105814 | 11/2005 |
| WO | WO 05/105988 | 11/2005 |
| WO | WO 05/110410 | 11/2005 |
| WO | WO 05/117909 | 12/2005 |
| WO | WO 05/121130 | 12/2005 |
| WO | WO 05/123719 | 12/2005 |
| WO | WO 06/004984 | 1/2006 |
| WO | WO 06/013114 | 2/2006 |
| WO | WO 06/022459 | 3/2006 |
| WO | WO 06/039718 | 4/2006 |
| WO | WO 06/046023 | 5/2006 |
| WO | WO 06/046024 | 5/2006 |
| WO | WO 06/052913 | 5/2006 |
| WO | WO 06/056399 | 6/2006 |
| WO | WO 06/067445 | 6/2006 |
| WO | WO 06/069080 | 6/2006 |
| WO | WO 06/077499 | 7/2006 |
| WO | WO 06/096270 | 9/2006 |
| WO | WO 06/101783 | 9/2006 |
| WO | WO 06/108103 | 10/2006 |
| WO | WO 06/122806 | 11/2006 |
| WO | WO 06/127587 | 11/2006 |
| WO | WO 06/129199 | 12/2006 |
| WO | WO 06/136823 | 12/2006 |
| WO | WO 07/002433 | 1/2007 |
| WO | WO 07/025090 | 3/2007 |
| WO | WO 07/041130 | 4/2007 |
| WO | WO 07/043677 | 4/2007 |
| WO | WO 07/044894 | 4/2007 |
| WO | WO 2007/044050 | 4/2007 |
| WO | WO 07/049041 | 5/2007 |
| WO | WO 07/062459 | 6/2007 |
| WO | WO 07/070514 | 6/2007 |
| WO | WO 07/076423 | 7/2007 |
| WO | WO 07/077949 | 7/2007 |
| WO | WO 07/084557 | 7/2007 |
| WO | WO 07/090141 | 8/2007 |
| WO | WO 07/090748 | 8/2007 |
| WO | WO 07/116313 | 10/2007 |
| WO | WO 07/117494 | 10/2007 |
| WO | WO 07/129195 | 11/2007 |
| WO | WO 07/135461 | 11/2007 |
| WO | WO 07/140222 | 12/2007 |
| WO | WO 08/013925 | 1/2008 |
| WO | WO 08/028937 | 3/2008 |

(56) References Cited

FOREIGN PATENT DOCUMENTS

| | | |
|---|---|---|
| WO | WO 08/035376 | 3/2008 |
| WO | WO 08/043031 | 4/2008 |
| WO | WO 08/058126 | 5/2008 |
| WO | WO 08/064157 | 5/2008 |
| WO | WO 08/067119 | 6/2008 |
| WO | WO 08/077712 | 7/2008 |
| WO | WO 08/079291 | 7/2008 |
| WO | WO 08/079292 | 7/2008 |
| WO | WO 08/082198 | 7/2008 |
| WO | WO 08/082839 | 7/2008 |
| WO | WO 08/082840 | 7/2008 |
| WO | WO 08/106692 | 9/2008 |
| WO | WO 08/124323 | 10/2008 |
| WO | WO 08/139161 | 11/2008 |
| WO | WO 08/145681 | 12/2008 |
| WO | WO 08/145688 | 12/2008 |
| WO | WO 08/157207 | 12/2008 |
| WO | WO 08/157208 | 12/2008 |
| WO | WO 09/007839 | 1/2009 |
| WO | WO 09/016460 | 2/2009 |
| WO | WO 09/049028 | 4/2009 |
| WO | WO 09/064486 | 5/2009 |
| WO | WO 09/064835 | 5/2009 |
| WO | WO 09/071577 | 6/2009 |
| WO | WO 09/100130 | 8/2009 |
| WO | WO 09/109576 | 9/2009 |
| WO | WO 09/114512 | 9/2009 |
| WO | WO 09/115572 | 9/2009 |
| WO | WO 09/158687 | 12/2009 |
| WO | WO 10/000978 | 1/2010 |
| WO | WO 10/001169 | 1/2010 |
| WO | WO 10/020905 | 2/2010 |
| WO | WO 10/022076 | 2/2010 |
| WO | WO 10/022081 | 2/2010 |
| WO | WO 10/026121 | 3/2010 |
| WO | WO 10/026122 | 3/2010 |
| WO | WO 10/026124 | 3/2010 |
| WO | WO 10/039939 | 4/2010 |
| WO | WO 10/081692 | 7/2010 |
| WO | WO 10/083283 | 7/2010 |
| WO | WO 10/135621 | 11/2010 |
| WO | WO 10/135650 | 11/2010 |
| WO | WO 11/025685 | 3/2011 |
| WO | WO 11/028685 | 3/2011 |
| WO | WO 11/029802 | 3/2011 |
| WO | WO 11/031554 | 3/2011 |
| WO | WO 11/035900 | 3/2011 |
| WO | WO 11/044481 | 4/2011 |
| WO | WO 11/057784 | 5/2011 |
| WO | WO 11/069141 | 6/2011 |
| WO | WO 2011/066369 | 6/2011 |
| WO | WO 11/112662 | 9/2011 |
| WO | WO 11/130146 | 10/2011 |
| WO | WO 11/144338 | 11/2011 |
| WO | WO 11/146808 | 11/2011 |
| WO | WO 12/003457 | 1/2012 |
| WO | WO 2012/045010 | 4/2012 |
| WO | WO 12/068440 | 5/2012 |
| WO | WO 12/068450 | 5/2012 |
| WO | WO 2012/071612 | 6/2012 |
| WO | WO 12/177606 | 12/2012 |
| WO | WO 13/023119 | 2/2013 |
| WO | WO 13/026025 | 2/2013 |
| WO | WO 13/036611 | 3/2013 |
| WO | WO 13/173720 | 11/2013 |
| WO | WO 14/138168 | 9/2014 |
| WO | WO 2014/186706 | 11/2014 |

OTHER PUBLICATIONS

Abe et al., "Effective Methods for Introducing Some Aryl and Heteroaryl Substituent onto 1-Azaazulene Nuclei", Heterocycles, 2005, 66: 229-240.

Abelson et al., "Alternate reference values for tear film break-up time in normal and dry eye populations, Lacrimal Gland, Tear Film, and Dry Eye Syndromes 3 Part B", Adv Exp Med Biol, 2002, 506: 1121-1125.

Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002, 506: 1079-86.

Abstract of Chilean patent application No. 3496-06 published in Official Gazette of the Republic of Chile (Jun. 1, 2007) and publication (2 pages).

Ahmed et al., "Treatment of Pemphigus Vulgaris with Rituximab and Intravenous Immune Globulin," The New England Journal of Medicine, 2006, 1772-1779.

Aho et al., Expression of human pim family genes is selectively up-regulated by cytokines promoting T helper type 1, but not T helper type 2, cell differentiation, Immunology, 2005, 116: 82-88.

Albach et al., "Diagnosis of keratoconjunctivitis sicca in rheumatoid arthritis. The value of various tests", Ophthalmologe, Apr. 1994.; 91(2):229-34—in German (with English abstract/summaty contained therein).

Anderson et al., "Biochemical characterization of GSK1070916, a potent and selective inhibitor of Aurora B and Aurora C kinases with an extremely long residence time", Biochem. J., 2009, 420(2): 259-265.

Anonymous, "Ruxolitinib for Patients with Low or Intermediate-1 Risk Myelodysplastic Syndrome (MDS)," ClinicalTrials.gov archive, Aug. 2013, XP002739581, Retrieved from the Internet: URL: clinicaltrials.gov/archive/NCT01895842/2013_08_19 [retrieved on Apr. 30, 2015], 5 pages.

Bachmann et al., "The serine/threonine kinase Pim-1," The International Journal of Biochemistry and Cell Biology, 2005, 37: 726-730.

Bain,et al., "Chronic neutrophilic leukaemia," in: Swerdlow, et al., eds. WHO Classification of Tumors of Haematopoietic and Lymphoid Tissues (ed 4th). Lyon: IARC Press, 2008: 38-39.

Banker et al., "Modern Pharmaceuticals" Third Edition, 1996, 596.

Bambino et al., "Tear film and ocular surface tests in animal models of dry eye; uses and limitations," Experimental Eye Research, 2004, 79: 613-621.

Barr et al., "Corneal scarring in the Collaborative Longitudinal Evaluation of Keratoconus (CLEK) Study: baseline prevalence and repeatability of detection", Cornea, 1999, 18(1):34-46.

Baudouin et al., "Flow cytometry in impression cytology specimens. A new method for evaluation of conjunctival Inflammation," Invest Ophthalmol Vis Sci, 1997, 38: 1458-1464.

Baxter et al., "Acquired mutation of the tyrosine kinase JAK2 in human myeloproliferative disorders," Lancet., 2005, 365:1054-1061.

Baxter et al., "Reductive Aminations of Carbonyl Compounds with Borohydride and Borane Reducing Agents," Organic Reactions, 2002, 1-57.

Baytel et al., "The human Pim-2 proto-oncogene and its testicular expression," Biochimica et Biophysica Acta., 1998, 1442: 274-285.

Beck et al., "Brief Report: Alleviation of Systemic Manifestations of Castleman's Disease by Monoclonal Anti-Interleukin-6 Antibody," N. Engl. J. Med., 1994, 330(9):602-605.

Begley et al., "Use of the dry eye questionnaire to measure symptoms of ocular irritation in patients with aqueous tear deficient dry eye", Cornea, 2002, 21: 664-70.

Bell and Zalay, "Synthesis of Substituted 3-Amino [6, 5-b] triazinoindoles." Journal of Heterocyclic Chemistry, Oct. 1975, 12(5):1001-1004.

Bennett et al., "Proposals for the classification of the myelodysplastic syndromes," British Journal of Haematology, 1982, 51: 189-199.

Berge et al., "Pharmaceutical salts", J. Pharma. Science, 1977, 66(1): 1-19.

Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).

(56) References Cited

OTHER PUBLICATIONS

Bhattacharya et al., "Polymorphism in Pharmaceutical Solids," Second Edition, 2009, 192:327-345.
Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-18.
Blom, "Two-Pump at-Column-Dilution Configuration for Preparative Liquid Chromatography—Mass Spectrometry," J. Comb. Chem., 2002, 4: 295-301.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blume-Jensen et al, "Oncogenic kinase signaling", Nature, 2001, 411(6835):355-365.
Bock et al. "Managing drug resistance in cancer: lessons from HIV therapy." Nature, Jul. 2012, 12: 494-501.
Bolen, "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 2009, 15:91-102.
Borie et al., "Combined Use of the Jak3 Inhibitor CP-690, 550 with Mycophenolate Mofetil to Prevent Kidney Allograft Rejection in Nonhuman Primates", Transplantation, Dec. 2005, 80(12):1756-64.
Bosworth, "JAK1/JAK2 Inhibitor Ruxolitinib is a Rising Start" Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest Ophthalmol Vis Sci, 2000, 41:120-126.
Bowman et al. "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests", Cornea, 2003, 22(7):640-50.
Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.
Brunton et al., "Chemotherapy of Neoplastic Diseases," Goodman & Gillman's: The Pharmacological Basis of Therapeutics, 11th edition, 2008, 853-908.
Brunning et al., "Myelodysplastic syndromes/neoplasms, overview," WHO Classification of Tumours of Haematopoietic and Lymphoid Tissues, 4th edition, 2008, 88-103.
Burger et al., "Gp130 and ras mediated signaling in human plasma cell line IN/a-6: a cytokine-regulated tumor model for plasmacytoma", Hematol J., 2001, 2:42-53.
Burger et al., "Janus kinase inhibitor INCB20 has antiproliferative and apoptotic effects on human myeloma cells in vitro and in vivo", Mol. Cancer Ther., Jan. 2009, 8(1): 26-35.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.
Candotti et al., "Structural and functional basis for JAK3-deficient severe combined immunodeficiency.", Blood, 1997, 90(10): 3996-4003.
Candotti et al., "Molecular aspects of primary immuno-deficiencies: lessons from cytokine and other signaling pathways.", J Clin Invest, May 2002, 109(10): 1261-9.
Carey and Sundberg, Advanced Organic Chemistry, Part B: Reactions and Synthesis, 4th ed., Kluwer Academic/Plenum Publishers:New York, 2001, 111-119.
Carey and Sundberg, Advanced Organic Chemistry, Part B: Reactions and Synthesis, Oxidations, 4th ed., Kluwer Academic/Plenum Publishers:New York, 2001, 747-757.
Cermak et al, "Is complete androgen insensitivity syndrome associated with alterations in the meibomian gland and ocular surface," Cornea, 2003, 22:516-521.
Cetkovic-Cvrlje et al., "Targeting JAK3 with JANEX-1 for prevention of autoimmune type 1 diabetes in NOD mice.", Clin Immunol, 2003, 106(3): 213-25.
Chalandon, "Targeting mutated protein tyrosine kinases and their signaling pathways in hematologic malignancies," Haematologica, 2005, 90(7):949-68.
Changelian et al., "Prevention of Organ Allograft Rejection by a Specific Janus Kinase 3 Inhibitor", Science, 2003, 302: 875-878.
Chari et al., "Complete Remission Achieved with Single Agent CNTO 328, an Anti-IL-6 Monoclonal Antibody, in Relapsed and Refractory Myeloma," Clinical Lymphoma, Myeloma & Leukemia, 2013, 13(3):333-337.
Chauhan et al, "Autoimmunity in Dry Eye due to resistance of Th17 to Treg Suppression", J. Immunology, 2009, 182(3):1247-52.
Chauhan et al., "A concise review on sustained drug delivery system and its opportunities," International Journal on Pharmtech Research, Mar. 2012, 2: 227-238.
Chemical encyclopedia publication "Soviet Encyclopedia," Moscow, 1988, 1:242-243.
Chen et al., "Blockade of interleukin-6 signaling augments regulatory T-cell reconstitution and attenuates the severity of graft-versus-host disease," Blood, Jul. 2009, 114(4): 891-900.
Chen et al., "Stat3 Activation in Human Endometrial and Cervical Cancer", British Journal of Cancer, 2007, 96: 591-599.
Chen et al., "Induction of myelodysplasia by myeloid-derived suppressor cells," J Clin Invest, Nov. 2013, 123(11): 4595-611.
Cheson et al., "Report of an international working group to standardize response criteria for myelodysplastic syndromes," Blood, Dec. 2000, 96(12): 3671-4.
Chew et al., "An instrument for quantifying meibomian lipid on the lid margin: the Meibometer", Curr Eye Res, 1993, 12:247-254.
Chew et al., "The casual level of meibomian lipids in humans", Current Eye Research, 1993, 12:255-259.
Chinese Office Action in Chinese Application No. 201480024761.9, dated Oct. 8, 2016, 21 pages (English Translation).
Chinese Notice of Reexamination in Chinese Application No. 201080033675.6, dated May 10, 2016, 18 pages (English Translation).
Cho et al, "Review of the tear break-up time and a closer look at the tear break-up time of Hong Kong Chinese", Optom Vis Sci, 1993, 70(1):30-8.
Choi Ha-Soon et al., "Design and synthesis of 7H-pyrrolo [2,3-d]pyrimidines as focal adhesion kinase inhibitors. Part 1", Bioorg. & Med. Chem. Lett., 2006, 16(8):2173-2176.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.

(56) References Cited

OTHER PUBLICATIONS

Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995, 60(17):5721-5725.
Cilloni et al., "Emerging drugs for chronic myeloid leukemia", Expert Opinion on Emerging Drugs, Jun. 2010, 15(2): 175-184.
Claessens et al., "In vitro proliferation and differentitation of eiythyroid progenitors from patients with myelodysplastic syndromes: evidence for Fas-dependent apoptosis," Blood, Mar. 2002, 1594-1601.
Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.
Clark et al., "Discovery and Development of Janus Kinase (JAK) inhibitors for Inflammatory Diseases," J Med Chem., 2014, A-P.
Clinical Trial NCT01787487 ('487 Trial), dated Feb. 7, 2013, 6 pages.
ClinicalTrials.gov, <http:clinicaltrials.gov/ct2/show/NCT00227591>, downloaded Dec. 6, 2016.
Columbian Office Action in Columbian Application No. 12-213.010, dated Jun. 17, 2014, 20 pages.
Communication dated Jan. 22, 2009 for European Appln. No. 06839328.9 (5 pgs.).
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.
Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ohthalmic Physiol Opt, 1995, 15(6):569-74.
Daniels et al., "Imatinib mesylate inhibits the profibrogenic activity of TGF-? and prevents bleomycinmediated lung fibrosis," J. Clin. Invest, Nov. 2004, 114(9):1308-1316.
Danjo et al., "Observation of precorneal tear film in patients with Sjogren's syndrome", Acta Ophthalmol Scand, 1995, 73:501-505.
De Paiva et al, "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Deng Jun et al, "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Divkovic et al., "Hapten-protein binding: from theory to practical application in the in vitro prediction of skin sensitization," Contact Dermatitis, 2005, 189-200.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro [1.2.4]triazino [1,6-c]quinazolin-5-ium-1-olates," Tetrahedron, 1974, 30:3997-4012.
Dorwald, "Side Reactions in Organic Synthesis: A Guide to Successful Synthesis Design," Wiley-VCH, 2005, Chapter 1, 32 pages.
Dudley et al. "A VEGF/JAK2/STAT5 axis may partially mediate endothelial cell tolerance to hypoxia", Biochem. J., 2005, 390(Pt 2):427-36.

Eghtedar et al., "Phase 2 study of the JAK kinase inhibitor ruxolitinib in patients with refractory leukemias, including postmyeloproliferative neoplasm acute myeloid leukemia," Blood, May 2012, 119(20): 4614-4618.
Eghtedar, "Phase II Study of the JAK2 Inhibitor, INCB018424, in Patients with Refmctoiy Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Elliott et al., "WHO-defined chronic neutrophilic leukemia: a long-term analysis of 12 cases and a critical review of the literature," Leukemia, 2005, 19:313-317.
Expert Scientific Group on Phase One Clinical Trials Final Report, Nov. 30, 2006, pp. C1, C35-C38.
Saettone and Salminen, "Ocular inserts for topical delivery", Advanced Drug Delivery Reviews, 1995, 16:95-106.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Fleischman et al., "The CSF3R T618I mutation causes a lethal neutrophilic neoplasia in mice that is responsive to therapeutic JAK inhibition," Blood, Nov. 2013, 122: 3628-3632.
Flex et al., "Somatically acquired JAK1 mutations in adult acute lymphoblastic leukemia", J. Exp Med., 2008, 205:751-8.
Fonseca et al., "Interleukin-6 as a key player in systemic inflammation and joint destruction", Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Foucar (Am J Olin Pathol 2009;132:281-289).
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Preclinical evaluation of local JAK1 and JAK2 inhibition in cutaneous inflammation", Journal of Investigative Dermatology, Sep. 2011, 131(9): 1838-1844.
Fridman et al., "Efficacy and Tolerability of Novel JAK Inhibitors in Animal Models of Rheumatoid Arthritis" poster presented at the

(56) References Cited

OTHER PUBLICATIONS

ACR/ARHP (American College of Rheumatology/Association of Rheumatology Health Professionals) Scientific Meeting 2007, Boston, MA. Nov. 10, 2007. Abstract 1771, poster 285 (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Froberg et al., "Demonstration of clonality in neutrophils using FISH in a case of chronic neutrophilic leukemia," Leukemia, 1998, 12:623-626.
Fujihara et al., "Evaluation of human conjunctival epithelium by a combination of brush cytology and flow cytometry: an approach to the quantitative technique", Diagn Cytopathol, 1997, 17:456-60.
Fujii et al., "Aberrant expression of serine/threonine kinase Pim-3 in hepatocellular carcinoma development and its role in the proliferation of human hepatoma cell lines" International Journal of Cancer, 2005, 114: 209-218.
Fukagawa et al., "Histological evaluation of brush cytology of rabbit conjunctiva", Nippon Ganka Gakkai Zasshi, 1993, 97:1173-8 (contains English abstract within the article).
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.
Gilchrist et al., "5H-2-Pyrindines from 2-Bromocyclopentene-1-carboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, "Improvements in the Preparation of DL-Threonic and DL-Erythronic Acids", J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns", Cornea, Jan. 1994, 13(1):58-66.
Gomtsyan et al, "Design, synthesis, and structure-activity relationship of 6-alkynylpyrimidines as potent adenosine kinase inhibitors," J. Med. Chem., 2002, 45(17):3639-3648.
Goodman et al., "IL-6 Signaling in Psoriasis Prevents Immune Suppression by Regulatory T Cells," J. Immunol., Sep. 2009, 183: 3170-3176.
Gooseman et al., "The intramolecular b-fluorine . . . ammonium interaction in 4- and 8-membered rings", Chem. Commun, 2006, 30:3190-3192.
Gorre et al., "Clinical Resistance to STI-571 Cancer Therapy Caused by BCR-ABL Gene Mutation or Amplification." Science, 2001, 293:876-880.
Gotlieb, Alice, Presentation at the 2008 American Academy of Dermatology, 66th Annual Meeting, San Antonio, TX. Feb. 1, 2008, symposium-303 (12 pp.).
Goto et al., "Color mapping of tear lipid layer thickness distribution from the image analysis in DR-1 tear lipid layer interference images," ARVO abstract, 2004, 2 pages.
Goto et al., "Computer-synthesis of an interference color chart of human tear lipid layer by a colorimetric approach," Invest Ophthalmol Vis Sci, 2003, 44:4693-7.
Goto et al., "Differentiation of lipid tear deficiency dry eye by kinetic analysis of tear interference images,",Arch Ophthalmol, 2003, 121:173-80.
Goto et al., "Evaluation of the tear film stability after laser in situ keratomileusis using the tear film stability analysis system," Am J Ophthalmol, Jan. 2004, 137(1):116-20.
Goto et al., "Tear Film Stability Analysis System: Introducing a new application for videokeratography", Cornea, Nov. 2004, 23(8):S65-S70.
Goto et al., "Kinetic analysis of tear interference images in aqueous tear deficiency dry eye before and after punctal occlusion," Invest Ophthalmol Vis Sci, 2003, 44:1897-905.
Gottlieb, "Psoriasis: Emerging Therapeutic Strategies," Nat Rev Drug Disc., Jan. 2005, 4:19-34.
Grabbe et al., "Immunoregulatory mechanisms involved in elicitation of allergic-contact hypersensitivity," Immunol Today, Jan. 1998, 19(1):37-44 (only 1 page provide and marked "best available copy").
Greenberg, "The Role of Hemopoietic Growth Factors in the Treatment of Myelodysplastic Syndromes," International Journal of Pediatric Hematology/Oncology, 1997, 4(3): 231-238.
Greenberg, "The myelodysplastic syndromes" in Hoffman, et al, eds. Hematology: Basic Principles and Practice (3rd ed.), Churchill Livingston; 2000:1106-1129.
Greene et al., Greene's Protective Groups in Organic Synthesis, 2007, 4th Edition, 54-55.
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Guillon, "Tear film photography and contact lens wear", J Br Contact Lens Assoc, 1982;5:84-7.
Gura, "Systems for Identifying New Drugs are Often Faulty," Science, Nov. 1997, 278(5340):1041-1042.
Guschin et al, "A major role for the protein tyrosine kinase JAK1 in the JAK/STAT signal transduction pathway in response to interleukin-6", Embo J 14:1421-1429 (1995).
Hamze' et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "World Health Organization classification of neoplastic diseases of the hematopoietic and lymphoid tissues: report of the Clinical Advisory Committee meeting—Airlie House, Virginia, Nov. 1997," J Clin Oncol, 1999, 17:3835-3849.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.
Heine et al., "The JAK-inhibitor ruxolitinib impairs dendritic cell function in vitro and in vivo," Blood, 2013, 122(7): 1192-1202.
Helal et al., "Stereoselective Synthesis of cis-1,3-Disubstituted Cyclobutyl Kinase Inhibitors," Organic Letters, (2004), 6(11), pp. 1853-1856.
Hernandez et al., "Clinical, hematological and cytogenetic characteristics of atypical chronic myeloid leukemia," Ann. Oncol., Apr. 2000, 11(4): 441-444.
Hickenbottom "Reactions of organic compounds," State Scientific-Technical Publishing Association, Chemical Literature Section, Moscow, 1939, pp. 360-362.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).

(56) References Cited

OTHER PUBLICATIONS

Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
Hyung-Bae et al., "CP-690550, a Janus Kinase Inhibitor, Suppresses CD4+ T-Cell-Mediated Acute Graft-Versus-Host Disease by Inhibiting the Interferon-Y Pathway," *Transplantation*, 2010, 90(8):825-835.
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 dated Dec. 17, 2009 (7 pages).
International Preliminary Report on Patentability for PCT/US2009/036635 dated Sep. 14, 2010 (6 pages).
International Preliminary Report on Patentability for PCT/US2009/059203 dated Apr. 5, 2011 (6 pages).
International Preliminary Report on Patentability for PCT/US2010/021003 dated Jul. 19, 2011(11 pages).
International Preliminary Report on Patentability for PCT/US2010/052011 dated Apr. 11, 2012 (4 pages).
International Preliminary Report on Patentability for PCT/US2011/025433 dated Aug. 21, 2012 (7 pages).
International Preliminary Report on Patentability for PCT/US2011/027665 dated Sep. 11, 2012 (7 pages).
International Preliminary Report on Patentability for PCT/US2011/037291 dated Nov. 27, 2012 (7 pages).
International Preliminary Report on Patentability for PCT/US2011/061351 dated May 30, 2013 (7 pages).
International Preliminary Report on Patentability for PCT/US2011/061374 dated May 30, 2013 (5 pages).
International Preliminary Report on Patentability for PCT/US2012/043099 dated Dec. 23, 2013, 6 pages.
International Preliminary Report on Patentability for PCT/US2012/050210 dated Feb. 11, 2014, 8 pages.
International Preliminary Report on Patentability for PCT/US2012/051439 dated Feb. 27, 2014, 7 pages.
International Preliminary Report on Patentability for PCT/US2012/053921 dated Mar. 20, 2014, 8 pages.
International Preliminary Report on Patentability for PCT/US2013/041601, dated Nov. 18, 2014, 7 pages.
International Preliminary Report on Patentability in International Application No. PCT/US2014/051678, dated Mar. 3, 2016, 15 pages.
International Preliminary Report on Patentability in International Application No. PCT/US2015/028224, dated Nov. 10, 2016, 7 pages.
International Preliminary Report on Patentability in International Application No. PCT/US2014/049940, dated Feb. 18, 2016, 9 pages.
International Search Report and the Written Opinion, PCT/US2012/051439, dated Nov. 30, 2012 (15 pages).
International Search Report and the Written Opinion, PCT/US2012/053921, dated Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pgs.).
International Search Report and Written Opinion for International Appln. No. PCT/US2009/036635 dated Jun. 3, 2009 14 pages.
International Search Report and Written Opinion for PCT/US2006/047369, 16 pages (dated Apr. 24, 2007).
International Search Report and Written Opinion for PCT/US2008/083319, 29 pages dated Mar. 13, 2009.
International Search Report and Written Opinion for PCT/US2011/025433, 12 pages (dated Jul. 20, 2011).
International Search Report and Written Opinion for PCT/US2011/027665 dated Jun. 27, 2011 (14 pages).
International Search Report and Written Opinion for PCT/US2011/037291, 11 pages (dated Apr. 19, 2012).
International Search Report and Written Opinion for PCT/US2011/061351 dated Feb. 17, 2012 (12 pages).
International Search Report and Written Opinion for PCT/US2011/061374 dated Mar. 27, 2012 (10 pages).
International Search Report and Written Opinion for PCT/US2012/025581, 16 pages (dated Apr. 26, 2012).
International Search Report and Written Opinion for PCT/US2012/043099, 11 pages (dated Sep. 13, 2012).
International Search Report and Written Opinion for PCT/US2012/050252 dated Jan. 2, 2013, 17 pages.
International Search Report and Written Opinion in International Application No. PCT/US2013/067794, dated Dec. 17, 2013, 14 pages.
International Search Report and Written Opinion in International Application No. PCT/US2014/020554, dated Jul. 16, 2014, 17 pages.
International Search Report and Written Opinion in International Application No. PCT/US2014/049940, dated Nov. 4, 2014, 13 pages.
International Search Report and Written Opinion in International Application No. PCT/US2014/051678, dated Feb. 11, 2015, 22 pages.
International Search Report and Written Opinion in International Application No. PCT/US2015/017963, dated Jun. 5, 2015, 13 pages.
International Search Report and Written Opinion in International Application No. PCT/US2015/033254, dated Oct. 7, 2015, 12 pages.
International Search Report for PCT/US2008/66658 dated Dec. 23, 2008 (4 pages).
International Search Report for PCT/US2010/021003 dated Aug. 16, 2010 (8 pages).
International Search Report for PCT/US2010/035728 dated Jul. 8, 2010 (3 pages).
International Search Report for PCT/US2010/035783 dated Aug. 23, 2010 (4 pages).
International Search Report for PCT/US2010/047252 dated Nov. 17, 2010 (4 pages).
International Search Report for PCT/US2010/052011 dated Nov. 30, 2010 (3 pages).
International Search Report in International Application No. PCT/US2013/041601, dated Sep. 3, 2013, 3 pages.
International Search Report and Written Opinion in International Application No. PCT/US2015/028224, dated Jul. 15, 2015, 9 pages.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Ishizaki et al., "Pharmacological Properties of Y-27632, a Specific Inhibitor of Rho-Associated Kinases", Molecular Pharmacology, 2000, 57, 976-983.
Itagaki et al, "Expedient Synthesis of Potent Cannabinoid Receptor Agonist (−)-CP55,940", Organic Letters, 2005, 7(19): 4181-4183.
Jädersten et al., "Long-term outcome of treatment of anemia in MDS with erythropoietin and G-CSF," Blood, Aug. 2005, 106(3): 803-11.

(56) References Cited

OTHER PUBLICATIONS

James et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Japanese Office Action in Japanese Application No. 2015-219637, dated Oct. 4, 2016, 6 pages.
Japanese Office Action in Japanese Application No. 2013-540049, dated Aug. 11, 2015, 3 pages (English Translation).
Japanese Office Action in Japanese Application No. 2015-042933, dated Feb. 2, 2016, 6 pages (English Translation).
Japanese Office Action in Japanese Application No. 2015-241393, dated Sep. 27, 2016, 4 pages (English Translation).
Japanese Office Action in Japanese Application No. 2017-000685, dated Jan. 31, 2017, 7 pages (with English translation).
Jee et al., "Overview: animal models of osteopenia and osteoporosis", J Musculoskel. Neuron, Interact., 1(3):193-207 (2001).
Jester et al., "In vivo biomicroscopy and photography of meibomian glands in a rabbit model of meibomian gland dysfunction", Invest Ophthalmol Vis Sci, 1982;22:660-7.
Johnson et al., "The effect of instilled fluorescein solution volume on the values and repeatability of TBUT measurements", Cornea, 2005;24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syddromes", Graefe's Arch Clin Exp Ophthalmol, 2004;495-500.
Kamb, "What's wrong with our cancer models?," Nature Reviews, Feb. 2005, 161-165.
Kantarjian et al., "Decitabine improves patient outcomes in myelodysplastic syndromes: results of phase III randomized study," Cancer, Apr. 2006, 106(8): 1794-803.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Killedar et al., "Early pathogenic events associated with Sjogren's syndrome (SjS)-like disease of the NOD mouse using microarray analysis," Lab Invest, Dec. 2006, 86(12): 1243-1260.
Kim et al., "Zinc-Modified Cyanoborohydride as a Selective Reducing Agent," J. Org. Chem., 1985, 50: 1927-1932.
Kuster, "Kinase Inhibitors," Methods and Protocols, 2012, 46 pages.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.
Kojima et al., "A new noninvasive tear stability analysis system for the assessment of dry eyes", Invest Ophthalmol Vis Sci, 2004, 45(5):1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer", Adv Exp Med Biol, 2002, 506:517-520.
Korb et al., "The effect of two novel lubricant eye drops on tear film lipid layer thickness in subjects with dry eye symptoms", Optom Vis Sci, 2005, 82: 594-601.

Korb et al., "Increase in tear film lipid layer thickness following treatment of meibomian gland dysfunction", Adv Exp Med Biol, 1994, 350:293-8.
Korolev et al., "Pd-EDTA as an efficient catalyst for Suzuki-Miyaura reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.
Kontzias et al., "Jakinibs: a new class of kinase inhibitors in cancer and autoimmune disease," Curr. Opin. Pharm., 2012, 12: 464-470.
Kruh et al., "The complete coding sequence of arg defines the Abelson subfamily of cytoplasmic tyrosine kinases.", Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia", European Journal of Pharmacology, 2008, 582: 154-161.
Kumar, "Kinase drug discovery approaches in chronic myeloproliferative disorders", Oncogene, Jun. 2009, 28(24): 2305-23.
Kuo et al., "Pd-EDTA as an efficient catalyst for Suzuki-Miyaura reactions in water", Chem Commun, 2007, 301-3.
Kuppens et al., "Basal tear turnover and topical timolol in glaucoma patients and healthy controls by Fluorophotometry", Invest Ophthalmol Vis Sci, 1992, 33:3442-3448.
Kurzrock et al., "Serum Interleukin 6 Levels are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al, "Tear Cytokine Profiles in Dysfunctional Tear Syndrome", Am J Ophthalmol., 2009, 147(2) : 198-205.
Larock, "Comprehensive Organic Transformations", Wiley-VCH, 2nd Ed. (1999) pp. 1949-1950, 1958-1959, 1976, and 1983-1985.
Larson, "Myelodysplasia: when to treat and how," Best Pract Res Clin Haematol, 2006, 19(2): 293-300.
Lasho et al., "Chronic neutrophilic leukemia with concurrent CSF3R and SETBP1 mutations: single colony clonality studies, in vitro sensitivity to JAK inhibitors and lack of treatment response to ruxolitnib," Leukemia, 2014, 3 pages.
Lawrence "Skin inflammatory disorders," In In Vivo Models of Inflammation, 2006, 85-120.
Leaf, Clifton, Health Administrator vol. XVII, 2005, 1:172-183.
Lemp "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (dated Jul. 5, 2010) (4 pages).
Levine et al., "Activating mutation in the tyrosine kinase JAK2 in polycythemia vera, essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.

(56) References Cited

OTHER PUBLICATIONS

Li et al., "The synthesis and the antitumor activity of 5,7-disubstituted pyrazolo [1,5-a] pyrimidines," Chinese J Med Chem., Feb. 28, 2007, 17(1):18-22.
Li et al., "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lima and Barreiro, "Bioisosterism: a useful strategy for molecular modification and drug design," Curr Med Chem., 2005, 12(1):23-49.
Lin, "Constitutive Activation of JAK3/STAT3 in Colon Carcinoma Tumors and Cell Lines," Am J Pathol., 2005, 167(4):969-80.
Lin et al., "Enantioselective synthesis of Janus kinase inhibitor INCB018424 via an organocatalytic aza-Michael reaction," Organic Letters, 2009, 11(9): 1999-2002.
Ling et al., "Knockdown of STAT3 Expression by RNA Interference Inhibits the Induction of Breast Tumors in Immunocompetent Mice," Cancer Res, Apr. 2005 65:2532.
List et al., "Efficacy of lenalidomide in myelodysplastic syndromes," N Engl J Med, Feb. 2005, 352(6): 549-57.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lübbert et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi et al., "Mutations of Jak-3 gene in patients with autosomal severe combined immune deficiency (SCID)", Nature, 1995, 377:65-8.
Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdCl2 in Aqueous Acetonitrile", Organic Letters, 2005, 7(23): 5237-39.
Main et al, "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Malaysian Examination Report in Malaysian Application No. PI2013002970, dated May 31, 2016, 4 pages.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.

Manjula et al., "Rapid Method of Converting Primary Amides to Nitriles and Nitriles to Primary Amides by ZnCl2 using Microwaves under Different Reaction Conditions", Syn. Commun, 2007, 37:1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons:New York, pp. 845-855 (1985).
Marelli et al., "Tumor targeting via integrin ligands," Frontiers in Oncology, 2013, 1-12.
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.
Maruyama et al., "Effect of environmental conditions on tear dynamics in soft contact lens wearers," Invest Ophthalmol Vis Sci, 2004, 45(8):2563-8.
Mascarenhas et al., "Ruxolitinib: The First FDA Approvided Therapy for the Treatment of Myelofibrosis," Clinical Cancer Research, Jun. 2012, 18(11): 3008-3014.
Matano et al., "Deletion of the long arm of chormosome 20 in a patient with chronic neutrophilic leukemia: cytogenetic findings in chronic neutrophilic leukemia," Am. J. Hematol., Jan. 1997, 54(1): 72-5.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996, 103:664-669.
Mathers et al., "Video imaging of the meibomian gland", Arch Ophthalmol, 1994, 112:448-9.
Mathers, "Evaporation from the ocular surface", Exp Eye Res, 2004, 78:389-394.
Maxson et al., "Oncogenic CSF3R Mutations in Chronic Neutrophilic Leukemia and Atypical CML," N. Engl. J. Med., 2013, 368(19):1781-1790.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/D500104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/my-asthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McMillan, "The systemic inflammation-based Glasgow Prognostic Score: a decade of experience in patients with cancer," Cancer Treat Rev, Aug. 2013, 39(5): 534-40.
McNamara et al., "Fluorometry in contact lens research: The next step," Optom Vis Sci, 1998, 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986, 64(4):441-4.

(56) References Cited

OTHER PUBLICATIONS

Mesa et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.
Mesa et al., "Emerging drugs for the therapy of primary and post essential thrombocythemia, post polycythemia vera myelofibrosis", Expert Opinion on Emerging Drugs England, 2009, 14(3): 471-479.
Meydan et al., "Inhibition of acute lymphoblastic leukaemia by a Jak-2 inhibitor", Nature, Feb. 1996, 379(6566):645-8.
Meyer et al., "Anti-inflammatory activity and neutrophil reductions mediated by the JAK1/JAK3 inhibitor, CP-690,550, in rat adjuvant-induced arthritis," Journal of Inflammation, 2010, 1-12.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi et al., "Human Tyrosine Kinase 2 Deficiency Reveals Its Requisite Roles in Multiple Cytokine Signals Involved in Innate and Acquired Immunity", Immunity, 2006, 25:745-55.
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol., Sep. 2010, 85(3):192-9 Epub Jun. 2, 2010.
Mishima et al., "Determination of tear volume and tear flow", Invest Ophthalmol, 1966, 5:264-276.
Mishima, "Some physiological aspects of the precorneal tear film", Arch Ophthalmol, 1965, 73:233-241.
Mitsunobu, "The Use of Diethyl Azodicarboxylate and Triphenylphosphine in Synthesis and Transformation of Natural Products." Synthesis, 1981, (1): 1-28.
Miyata, et al., "Stereospecific nucleophilic addition reactions to olefins.", J. Org. Chem., 1991, 56:6556-6564.
Miyaura et al., "Palladium-Catalyzed Cross-Coupling Reactions of Organoboron Compounds," Chem. Rev., 1995, 95: 2457-2483.
Miyoshi et al., "Interleukin-8 concentrations in conjunctival epithelium brush cytology samples correlate with neutrophil, eosinophil infiltration, and corneal damage", Cornea, 2001, 20:743-7.
Molldrem et al., "Antithymocyte globulin for patients with myelodysplastic syndrome," Br J Haematol, Dec. 1997, 99(3): 699-705.
Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al, "JAK mutations in high-risk childhood acute lymphoblastic leukemia", Proc Natl Acad Sci USA, 2009, 106:9414-8.
Mundle et al., "Evidence for Involvement of Tumor Necrosis Factor-α in Apoptotic Death of Bone Marrow Cells in Myelodysplastic Syndromes," Am J Hematol, 1999, 60:36-47.

Naka, "The paradigm of IL-6: from basic science to medicine", Arthritis Res., 2002, 4 Suppl 3:S233-42.
Nakagawara, "Trk receptor tyrosine kinases: A bridge between cancer and neural development." Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Naqvi et al., "A potential role of ruxolitinib in leukemia", Expert Opinion on Investigational Drugs, Aug. 2011, 20(8): 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus et al., "6-(Het)aryl-7-Deazapurine Ribonucleosides as Novel Potent Cytostatic Agents", J. Med. Chem., 2010, 53(1):460-470.
Neidle Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Neuner et al., "Increased IL-6 Production by Monocytes and Keratinocytes in Patients with Psoriasis," J. Invest. Dermatol., 1991, 97: 27-33.
Nicholoff et al., "Recent Insights into the immunopathogenesis of psoriasis provide new therapeutic opportunities", J. Clin. Invest., 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishimoto. al., "Improvement in Castleman's disease by humanized anti-interleukin-6 receptor antibody theraphy," *Blood*, 2000, 95(1):56-61.
Nishio et al., "Tyrosine kinase-dependent modulation by interferon-α of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Norman, "Selective JAK1 inhibitor and selective Tyk2 inhibitor patents," *Expert Opinion*, Informa Healthcare. 2012, available at: <http://informahealthcare.com/doi/pdfplus/10.1517/13543776.2012.723693>.
Norn, "Quantitative tear ferning. Clinical investigations", Acta. Ophthalmol (Copenh), 1994, 72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.).
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).
Office Action in U.S. Appl. No. 14/186,338, dated May 5, 2014, 18 pages.
Office Action received for European Application No. 06 839 328.9 (dated Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).

(56) References Cited

OTHER PUBLICATIONS

Office Action received for Singapore Application No. 2008-04386-1 (dated Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 dated Oct. 21, 2010.
Office Action, European Patent Office, dated Nov. 6, 2009 Application 06839328.9.
Office Action, Mexico, Patent Appl. No. MX/a/2008/007635 as received from foreign associate dated Jun. 15, 2010 (1 page).
Office Action, Mexico, Patent Appl. No. MX/a/2008/007635 as received from foreign associate dated Nov. 13, 2009 (4 pages).
Office Action/Examination Report received for Pakistan Application No. 211/2009 dated Jan. 18, 2010 (1 page).
Oguz et al., "The height and radius of the tear meniscus and methods for examining these parameters", Cornea, 2000, 19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Ortmann et al., "Janus kinases and signal transducers and activators of transcription: their roles in cytokine signaling, development and immunoregulation," Arthritis Res, 2000, 2(1): 16-32.
Ostojic et al., "Ruxolitinib: a new JAK1/2 inhibitor that offers promising options for treatment of myelofibrosis," Future Oncology, 2011, 7(9): 1035-1043.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVP (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Panteli et al., "Serum interleukin (IL)-1, IL-2, sIL-2Ra, IL-6 and thrombopoietin levels in patients with chronic myeloproliferative diseases," British Journal of Haematology, 2005, 130: 709-715.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Pardanani et al., "CSF3R T618I is a highly prevalent and specific mutation in chronic neutrophilic leukemia," Leukemia, 2013, 27: 1870-1873.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design", Chem. Rev., 1996, 96: 3147-3176.
Patrick, "An Introduction to medicinal chemistry" *Oxford University Press Inc.*, New York, 1995 (31 pages) (cited in Opposition from India dated Nov. 12, 2012.
Pearce et al., "Spatial location studies on the chemical composition of human tear ferns", Ophthalmic Physiol Opt, 2000, 20(4):306-13.
Pearce et al., "An improved fluorophotometric method for tear turnover assessment", Optom Vis Sci, 2001, 78(1):30-36.
Pedranzini et al., "Pyridone 6, A Pan-Janus-Activated Kinase Inhibitor, Induces Growth Inhibition of Multiple Myeloma Cells," Cancer Res., 2006, 66(19):9714-9721.
Pensyl et al., "The repeatability of tear mucus ferning grading", Optom Vis Sci, 1998, 75(8):600-4.
Perris et al., "JAK-STAT signaling in asthma." J Clin Invest, 2002, 109(10): 1279-83.
Peters et al., "Functional Significance of Tie2 Signaling in the Adult Vasculature", 2004, © The Endocrine Society (21 pages).
Pflugfelder et al., "Evaluation of subjective assessments and objective diagnostic tests for diagnosing tear-film disorders known to cause ocular irritation," Cornea, 1998, 17(1):38-56.
Pillonel "Evaluation of phenylaminopyrimidines as antifungal protein kinase inhibitors," Pest Management Science, Wiley & Sons, Jun. 2005, 61: 1069-1076.
Pirard et al., "Classification of Kinase Inhibitors Using BCUT Descriptors", J. Chem. Inf. Comput. Sci., 2000, 40: 1431-1440.
Pisella et al., "Flow cytometric analysis of conjunctival epithelium in ocular rosacea and keratoconjunctivitis sicca," Ophthalmology, 2000, 107:1841-1849.
Pisella et al., "Conjunctival proinflammatoiy and proapoptotic effects of latanoprost, preserved timolol and unpreserved timolol: an ex vivo and in vitro study." Invest Ophthalmol Vis Sci, 2004, 45:1360-1368.
Phillipines Examination Report in Phillipines Application No. 1-2013-501001, dated Mar. 23, 2017, 3 pages.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.
Quesada et al, "One-pot conversion of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, "Prefomulation", Remington's Pharmaceutical Sciences, 17th ed., Mack Publishing Company, Easton, Pa., 1985, Chapter 76, 1409-1423.

(56) References Cited

OTHER PUBLICATIONS

Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Raza et al., "Novel insights into the biology of myelodyplastic syndromes: excessive apoptosis and the role of cytokines," Int J Hematol, 1996, 63:265-278.
Raza et al., "The Myelodysplastic Syndromes in 1996: Complex Stem Cell Disorders Confounded by Dual Actions of Cytokines," Leuk Res, 1996, 20:881-890.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action dated Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].
Riese et al., "Inhibition of JAK kinases in patients with rheumatoid arthritis: scientific rationale and clinical outcomes," Best Practice & Research Clinical Rheumatology, 2010, 513-526.
Roberts et al., "Trends in the Risks and Benefits to Patients With Cancer Participating in Phase 1 Clinical Trials," JAMA, 2004, 292(17):2130-2140.
Robin et al., "In vivo transillumination biomicroscopy and photography of meibomian gland dysfunction," Ophthalmology, 1985, 92:1423-6.
Rodig et al., "Disruption of the Jak1 gene demonstrates obligatory and nonredundant roles of the Jaks in cytokine-induced biologic responses." Cell, 1998, 93(3): 373-83.
Rolando et al., "Tear mucus crystallization in children with cystic fibrosis", Ophthalmologica, 1988, 197(4):202-6.
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbock (Texas, USA), Dry Eye Institute, 1986, 203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Thy Eye Disease," Survey of Ophthalmology, Mar. 2001, 45(Supplement 2): S203-S210.
Rolando, "Tear mucus ferning test in normal and keratoconjunctivitis sicca eyes," Chibret Int J Ophthalmol, 1984, 2(4):32-41.
Rollison et al., "Epidemiology of myelodysplastic syndromes and chronic myeloproliferative disorders in the United States, 2001-2004, using data from the NAACCR and SEER programs," Blood, Jul. 2008, 112(1): 45-52.
Roudebush et al., "Pharmacologic manipulation of a four day marine delayed type hyper sensitivity model", Agents Actions, 1993, 38(1-2):116-21.
Rousvoal et al. "Janus kinase 3 inhibition with CP-690,550 prevents allograft vasculopathy", Transpl Int., 2006, 19(12):1014-21.

Saemann et al., "Prevention of CD40-triggered dendritic cell maturation and induction of T-cell hyporeactivity by targeting of Janus kinase 3," Am J Transplant 2003, 3(11): 1341-9.
Saemann et al., "Suppression of early T-cell-receptor-triggered cellular activation by the Janus kinase 3 inhibitor MHI-P-154," Transplantation, 2003, 75(11): 1864-1872.
Saettone et al., "Ocular inserts for topical delivery," Advanced Drug Delivery Reviews, 1995, 16: 95-106.
Samanta et al., "Janus kinase 2: a critical target in chronic myelogenous leukemia," Cancer Res., Jul. 2006, 66(13):6468-72.
Santini et al., "Hepcidin Levels and Their Determinants in Different Types of Myelodysplastic Syndromes," PLoS One, 2011, 6(8): e23109, pp. 1-8.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, 288(3):1317-1326, p. 1321, compound 26.
Schiffer, "Clinical issues in the management of patients with myelodysplasia," Hematology Am Soc Hematol Educ Program, 2006, 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling," Adv Pharmacol., 2000, 47:113-74.
Schmidt et al., "Rituximab in autoimmune bullous diseases: mixed responses and adverse effects," British Journal of Dermatology, 2007, 352-356.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Search Report in TW Application No. 100117866, dated Dec. 2014, 1 page.
Seefeld et al, "Discovery of 5-pyrrolopyridiny1-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2', 3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol., 2004, 24(4):931-4.
Seto et al., "Enhanced Th2 cell-mediated allergic inflammation in Tyk2-deficient mice." J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al, "Basic pathogenic mechanisms operating in experimental model acute anterior uveitis," Immunology and Cell Biology, 1998, 76: 497-512.
Smolen et al, "Effect of interleukin-6 receptor inhibition with tocilizumab in patients with rheumatoid arthritis (OPTION study): a double-blind, placebo-controlled, randomized trial", Lancet, 2008, 371:987.

(56) References Cited

OTHER PUBLICATIONS

Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, 2014, 123(24): 3832-3842.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodegeneration", J. Biol. Chem., 2004, 279(19):19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
State Intellectual Property Office, PR China, Office Action, dated Sep. 3, 2010 Pat. Appl. No. 200680052750.7 (8 pages).
Steensma et al., "The JAK2 V617F activating tyrosine kinase mutation is an infrequent event in both "atypical" myeloproliferative disorders and mylodysplastic syndromes," Blood, Aug. 2005, 106(4): 1207-9.
Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Symington et al., "The relationship of serum IL-6 levels to acute graft-versus-host disease and hepatorenal disease after human bone marrow transplantation," Transplantation, 1992, 54(3): 457-462 (Abstract only).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sci USA, 1997, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tan et al, "Racemization processes at a quaternary carbon center in the context of the asymmetric Michael reaction", Tetrahedron Lett., 2001, 42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, "Primary myelofibrosis: 2012 update on diagnosis, risk stratification, and management" American Journal of Hematology, Dec. 2011, 86(12): 1017-1026.
Tefferi et al., "Serious adverse events during ruxolitinib treatment discontinuation in patients with myelofibrosis", Mayo Clinic Proceedings, Dec. 2011, 86(12): 1188-1191.
Textbook of Clinical Trials 264 (D. Machin et al., eds., 2nd ed., 2006).
Thompson et al., "Photochemical Preparation of a Pyridone Containing Tetracycle: A Jak Protein Kinase Inhibitor", Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer", Cancer Lett., 2003, 201(1):107-16.
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta. Cytol, 1990, 34(2):233-5.
Tsubota et al., "Detection by brush cytology of mast cells and eosinophils in allergic and vernal conjunctivitis," Cornea, 1991, 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem., 1985, 50:760-763.
Vaillant et al., "Turbidity of pulpy fruit juice: A key factor for predicting cross-flow microfiltration performance," J Membrane Sci., 2008, 325:404-412.
Van Best et al., "Measurement of basal tear turnover using a standardized protocol", Graefe's Arch Clin Exp Ophthalmol, 1995, 233:1-7.
Van Bijsterveld, "Diagnostic tests in the sicca syndrome", Arch Ophthalmol, 1969, 82:10-14.
Van Rhee et al., "Anti-Interleukin-6 Monoclonal man's Disease," J. Clin. Oncol., 2010, 28(23):3701-3708.
Vanhoutte, "Selective JAK1 Inhibition in the Treatment of Rheumatoid Arthritis: Proof of Concept with GLPG0634," Arthritis Rheum, 2012, 64.10: S1051-1.
Vannucchi et al., "The mTOR Inhibitor, RAD001, Inhibits the Growth of Cells From Patients with Myeloproliferative Neoplasms", Blood: ASH Annual Meeting Abstracts, 51$^{st}$ Annual Meeting of the American Society of Hematology, 2009, 114(22), 2 pages.
Vannucchi et al., "Inhibitors of PI3K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vardiman et al., "Atypical chronic myeloid leukaemia, BCR-ABL1 negative," in: Swerdlow, et al., WHO Classification of Tumors of Haematopoietic and Lymphoid Tissues (ed 4th). Lyon: IARC Press; 2008:80-81.
Vardiman et al., "The World Health Organization (WHO) classification of the myeloid neoplasms," Blood, 2002, 100:2292-2302.

(56) References Cited

OTHER PUBLICATIONS

Vardiman et al., "The 2008 revision of the World Health Organization (WHO) Classification of myeloid neoplasms and acute leukemia: rationale and important changes," Blood, 2009, 114:937-951.
Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.
Venugopal et al., "Special clinical concerns/problems in the management of MDS and secondary acute myeloid leukemias," Cancer Treat Res, 2001, 108: 257-65.
Verma et al., "Jak family of kinases in cancer", Cancer and Metastasis Reviews, 2003, 22(4): 423-434, DOI: 10.1023/A:1023805715476.
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAK5 V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424, "50th ASH Annual Meeting and Exposition, Abstract No. 2802 (2008).
Vitali et al. "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.
Wagh et al., "Polymers used in ocular dosage form and drug delivery systems", Asian J. Pharm., Jan. 2008, 12-17.
Wang and Deisboeck, "Mathematical modeling in cancer drug discovery," Drug Discovery Today, 2014, 145-150.
WebMD. "Diabetes Health Center." Available at: < http://diabetes.webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.
Welch et al., "An approach to a more standardized method of evaluating tear film break-up time", Invest Ophthalmol Vis Sci, 2003, 2485/B324 (abstract only—2 pages).

White et al., "Human basic tear fluid osmolality. I. Importance of sample collection strategy", Acta Ophthalmol (Copenh), Aug. 1993, 71(4):524-9.
Wilks, "The JAK kinases: Not just another kinase drug discovery target," Seminars in Cell & Developmental Biology, 2008, 319-328.
Williams and Ibrahim, "Carbodiimide Chemistry: Recent Advances", Chem. Rev., 1981, 81:589-636.
Williams et al., "Dissecting Specificity in the Janus Kinases: The Structures of JAK-Specific Inhibitors Complexed to the JAK1 and JAK2 Protein Tyrosine Kinase Domains," Journal of Molecular Biology, 2009, 219-232.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf et al., "Burger's Medicinal Chemistry and Drug Discovery", 5th Ed. Part I, 1995, 975-977.
Wu et al., One-Pot Two-Step Microwave-Assisted Reaction in Construction 4,5-Disubstituted Pyrazolopyrimidines Organic Letters, 2003, 5(20): 3587-3590.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, Nov. 2011, 7(4): 306-312.
Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.
Yao et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.
Yokoi et al., "A newly developed video-meibography system featuring a newly designed probe", Jpn J Ophthalmol, 2007, 51: 53-6.
Yokoi et al., "Assessment of meibomian gland function in dry eye using meibometry", Arch Ophthalmol, 1999, 117:723-9.
Yokoi et al., "Correlation of tear lipid layer interference patterns with the diagnosis and severity of dry eye", Am J Ophthalmol, 1996, 122:818-24.
Yokoi et al., "Non-invasive methods of assessing the tear film", Exp Eye Res, 2004, 78:399-407.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," J. Clin. Oncol., 2012, 30(33):4161-4167.
Yu et al., "Role of Janus Kinase/Signal Transducers and Activators of Transcription in the Pathogenesis of Pancreatitis and Pancreatic Cancer," Gut and Liver, Oct. 2012, 6(4): 417-422.
Yu et al., "Constitutive activation of the Janus kinase-STAT pathway in T lymphoma overexpressing the Lck protein tyrosine kinase," J Immunol., 1997, 159(11):5206-10.
Zaidi et al., "Dermatology in Clinical Practice," Springer, 2010, 157 pages.
Zheng et al., "Discovery of INCB108201PF-4178903, a potent, selective, and orally bioavailable dual CCR2 and CCR5 antagonist", Bioorganic & Medicinal Chemistry Letters, 2011, 21: 1442-45.
Zoppellaro et al., "A Multifunctional High-Spin Biradical Pyrazolylbipyridine-bisnitronylnitroxide", Org. Lett., 2004, 6(26):4929-4932.
Zou et al "Signaling Pathways Activated by Oncogenic Forms of Ab1 Tyrosine Kinase." Journal of Biological Chemistry, 1999, 274(26):18141-18144.

(56) References Cited

OTHER PUBLICATIONS

Australian Office Action in Australian Application No. 2016204689, dated Mar. 22, 2017, 4 pages.
Eurasian Office Action in Eurasian Application No. 201291310, dated Mar. 9, 2017, 4 pages (English Translation).
Eurasian Search Report in Eurasian Application No. 201200132, dated Sep. 1, 2016, 6 pages (English Translation).
European Office Action in European Application No. 15195698.4, dated Mar. 15, 2017, 4 pages.
European Search Report in European Application No. 16197502.4, dated Mar. 20, 2017, 15 pages.
Korean Office Action in Korean Application No. 10-2012-7033308, dated Mar. 21, 2017, 6 pages (English Translation Only).
Arber et al., "The 2016 revision to the World Health Organization classification of myeloid neoplasms and acute leukemia," Blood, May 2016, 2391-2405.
Japanese Office Action in Japanese Application No. 2016-143513, dated May 23, 2017, 3 pages (English Summary).

PIPERIDIN-4-YL AZETIDINE DERIVATIVES AS JAK1 INHIBITORS

TECHNICAL FIELD

The present invention provides piperidin-4-yl azetidine derivatives, as well as their compositions and methods of use, that modulate the activity of Janus kinase 1 (JAK1) and are useful in the treatment of diseases related to the activity of JAK1 including, for example, inflammatory disorders, autoimmune disorders, cancer, and other diseases.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm*. 49:349-355, 2002). Activation of STAT signaling, as well as other pathways downstream of JAKs (e.g., Akt), has been correlated with poor prognosis in many cancer types (Bowman, T., et al. Oncogene 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol*. 2000; 47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY

The present invention provides, inter alia, compounds of Formula (I):

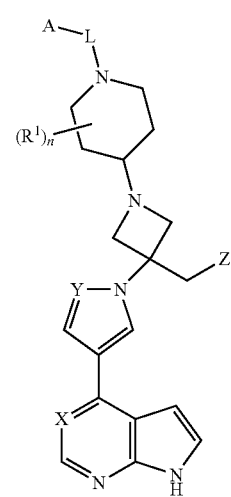

or pharmaceutically acceptable salts thereof; wherein the variables are defined infra.

The present invention further provides compositions comprising a compound of Formula I, or a pharmaceutically acceptable salt thereof, and a pharmaceutically acceptable carrier.

The present invention further provides methods of modulating an activity of JAK1 comprising contacting JAK1 with a compound of Formula I, or a pharmaceutically acceptable salt thereof.

The present invention further provides methods of treating a disease or a disorder associated with abnormal kinase expression or activity in a patient by administering to a patient a therapeutically effective amount of a compound of Formula I, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I, or a pharmaceutically acceptable salt thereof.

The present invention also provides compounds of Formula I, or pharmaceutically acceptable salts thereof, as described herein for use in treatment of autoimmune diseases, cancer, myeloproliferative disorders, inflammatory diseases, a bone resorption disease, or organ transplant rejection.

The present invention further provides compounds of Formula I as described herein, or pharmaceutically acceptable salts thereof, for use in modulating JAK1.

The present invention also provides uses of compounds of Formula I as described herein, or pharmaceutically acceptable salts thereof, for the preparation of medicaments for use in methods of modulating JAK1.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
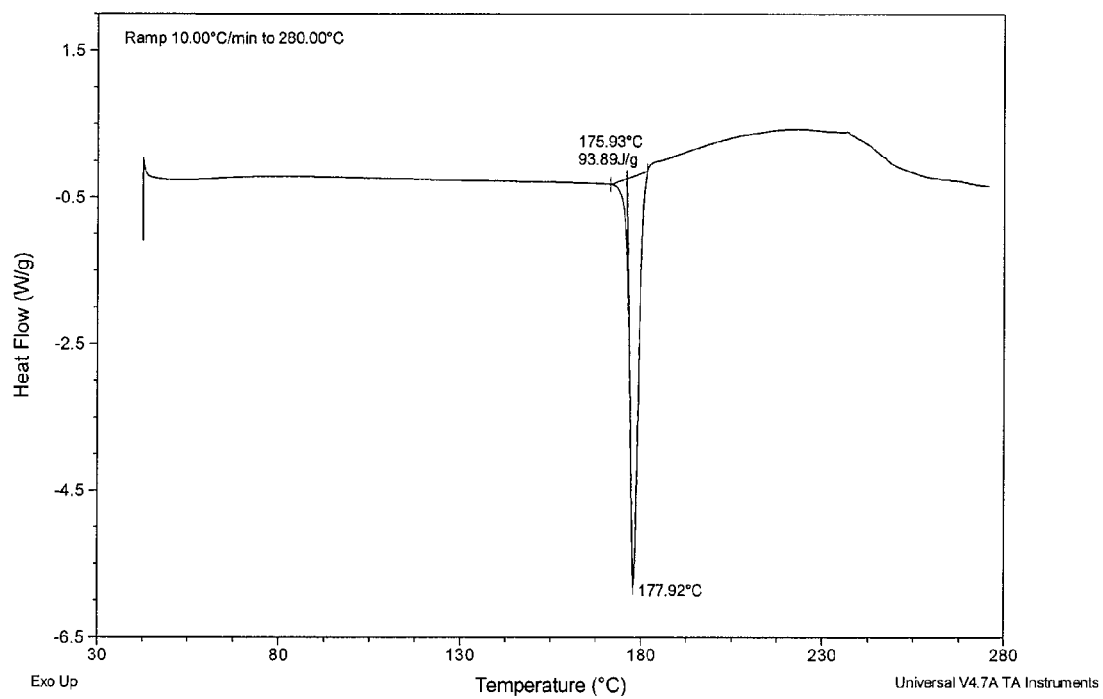
FIG. 1 depicts the DSC thermogram for the product of Example 358.

The present invention provides, inter alia, a compound of Formula (I):

I or a pharmaceutically acceptable salt thereof; wherein:

X is N or $CR^2$;

Y is N or $CR^3$;

Z is H, cyano, halo, $C_{1-3}$ alkyl, or $C_{1-3}$ haloalkyl;

L is $C(R^4)_2$, $C(=O)$, $C(=O)N(R^{4a})$, $C(=O)C(R^{4b})_2$, $S(=O)_2$, $C(=O)O$, $C(=O)OC(R^{4b})_2$ or $C(=O)N(R^{4a})C(R^{4b})_2$;

A is $C_{1-6}$ alkyl, $C_{3-14}$ cycloalkyl, $C_{2-13}$ heterocycloalkyl, $C_{6-14}$ aryl, or $C_{1-14}$ heteroaryl; wherein said $C_{1-6}$ alkyl, $C_{3-14}$ cycloalkyl, $C_{2-13}$ heterocycloalkyl, $C_{6-14}$ aryl, and $C_{1-14}$ heteroaryl are each optionally substituted with 1, 2, 3, 4, 5, or 6 independently selected $R^5$ groups;

each $R^1$ is, independently, $C_{1-4}$ alkyl, hydroxyl, $C_{1-4}$ alkoxy, fluoro, hydroxyl-$C_{1-4}$ alkyl, or $C_{1-4}$ alkoxy-$C_{1-4}$ alkyl; or two $R^1$ groups together form a 2- or 3-carbon bridge or a bridge of formula —$CH_2$—O—$CH_2$—;

$R^2$ is H, halo, hydroxyl, cyano, $C_{1-4}$ alkyl, $C_{1-4}$ haloalkyl, or $C_{1-4}$ alkoxy;

$R^3$ is H, cyano, nitro, halo, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, or $C_{1-6}$ alkoxycarbonyl;

each $R^4$ is, independently, H or $C_{1-4}$ alkyl; or two $R^4$ groups, together with the carbon atom to which they are attached, form a 3-, 4-, 5-, or 6-membered cycloalkyl ring;

$R^{4a}$ is H or $C_{1-4}$ alkyl;

each $R^{4b}$ is, independently, H or $C_{1-4}$ alkyl; or two $R^{4b}$ groups, together with the carbon atom to which they are attached, form a 3-, 4-, 5-, or 6-membered cycloalkyl ring;

each $R^5$ is, independently, halo, cyano, nitro, $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, $C_{1-10}$ heteroaryl-$C_{1-3}$ alkyl, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, or $S(O)_2NR^cR^d$; wherein $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl are each optionally substituted with 1, 2, 3, 4, or 5 independently selected $R^6$ groups;

each $R^6$ is, independently, halo, cyano, nitro, $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, $C_{1-10}$ heteroaryl-$C_{1-3}$ alkyl, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$ $NR^{c1}C(O)R^{b1}$, $NR^{c1}C(O)OR^{a1}$, $NR^{c1}C(O)NR^{c1}R^{d1}$, $NR^{c1}S(O)R^{b1}$ $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl are each optionally substituted by 1, 2, 3, 4, or 5 independently selected $R^h$ groups;

each $R^a$, $R^b$, $R^c$, and $R^d$ is, independently, H, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, or $C_{1-10}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl is optionally substituted with 1, 2, 3, 4, or 5 independently selected $R^g$ groups;

or any $R^c$ and $R^d$ together with the N atom to which they are attached form a 3-, 4-, 5-, 6-, or 7-membered heterocycloalkyl group or a heteroaryl group, each optionally substituted with 1, 2, 3 or 4 substituents independently selected from halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, and $C_{1-6}$ alkoxycarbonyl;

each $R^e$ is, independently, H, $C_{1-6}$ alkyl, CN, hydroxyl, $C_{1-6}$ alkoxy, $C_{1-6}$ alkylsulfonyl, carboxy, $C_{1-6}$ alkylcarbonyl, aminosulfonyl, $C_{1-6}$ alkylaminosulfonyl, di-$C_{1-6}$ alkylaminosulfonyl, carbamyl, $C_{1-6}$ alkylcarbamyl, or di-$C_{1-6}$ alkylcarbamyl;

each $R^{a1}$, $R^{b1}$, $R^{c1}$, and $R^{d1}$ is, independently, H, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, or $C_{1-10}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl is optionally substituted with 1, 2, 3, 4, or 5 independently selected $R^{g'}$ groups;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, 3 or 4 substituents independently selected from halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, $C_{1-6}$ alkoxycarbonyl, and $C_{1-6}$ alkylcarbonylamino;

each $R^{e1}$ is, independently, H, $C_{1-6}$ alkyl, CN, hydroxyl, $C_{1-6}$ alkoxy, $C_{1-6}$ alkylsulfonyl, carboxy, $C_{1-6}$ alkylcarbonyl, aminosulfonyl, $C_{1-6}$ alkylaminosulfonyl, di-$C_{1-6}$ alkylaminosulfonyl, carbamyl, $C_{1-6}$ alkylcarbamyl, or di-$C_{1-6}$ alkylcarbamyl;

each $R^g$, $R^{g'}$, and $R^h$ is, independently, halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, $C_{1-6}$ alkoxycarbonyl, or $C_{1-6}$ alkylcarbonylamino; and n is 0, 1, 2, 3, or 4.

In some embodiments:

X is N or $CR^2$;

Y is N or $CR^3$;

Z is H, cyano, halo, $C_{1-3}$ alkyl, or $C_{1-3}$ haloalkyl;

L is $C(R^4)_2$, $C(=O)$, $C(=O)N(R^{4a})$, $C(=O)C(R^{4b})_2$, or $S(=O)_2$;

A is $C_{1-6}$ alkyl, $C_{3-14}$ cycloalkyl, $C_{2-13}$ heterocycloalkyl, $C_{6-14}$ aryl, or $C_{1-14}$ heteroaryl; wherein said $C_{1-6}$ alkyl, $C_{3-14}$ cycloalkyl, $C_{2-13}$ heterocycloalkyl, $C_{6-14}$ aryl, and $C_{1-14}$ heteroaryl are each optionally substituted with 1, 2, 3, 4, 5, or 6 independently selected $R^5$ groups;

each $R^1$ is, independently, $C_{1-4}$ alkyl; or two $R^1$ groups together form a 2- or 3-carbon bridge;

$R^2$ is H, halo, hydroxyl, cyano, $C_{1-4}$ alkyl, $C_{1-4}$ haloalkyl, or $C_{1-4}$ alkoxy;

$R^3$ is H, cyano, nitro, halo, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, or $C_{1-6}$ alkoxycarbonyl;

each $R^4$ is, independently, H or $C_{1-4}$ alkyl; or two $R^4$ groups, together with the carbon atom to which they are attached, form a 3-, 4-, 5-, or 6-membered cycloalkyl ring;

$R^{4a}$ is H or $C_{1-4}$ alkyl;

each $R^{4b}$ is, independently, H or $C_{1-4}$ alkyl; or two $R^{4b}$ groups, together with the carbon atom to which they are attached, form a 3-, 4-, 5-, or 6-membered cycloalkyl ring;

each $R^5$ is, independently, halo, cyano, nitro, $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, $C_{1-10}$ heteroaryl-$C_{1-3}$ alkyl, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, or $S(O)_2NR^cR^d$; wherein $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl are each optionally substituted with 1, 2, 3, 4, or 5 independently selected $R^6$ groups;

each $R^6$ is, independently, halo, cyano, nitro, $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, $C_{1-10}$ heteroaryl-$C_{1-3}$ alkyl, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, or $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl are each optionally substituted by 1, 2, 3, 4, or 5 independently selected $R^h$ groups;

each $R^a$, $R^b$, $R^c$, and $R^d$ is, independently, H, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, or $C_{1-10}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl is optionally substituted with 1, 2, 3, 4, or 5 independently selected $R^g$ groups;

or any $R^c$ and $R^d$ together with the N atom to which they are attached form a 3-, 4-, 5-, 6-, or 7-membered heterocycloalkyl group or a heteroaryl group, each optionally substituted with 1, 2, 3 or 4 substituents independently selected from halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, and $C_{1-6}$ alkoxycarbonyl;

each $R^e$ is, independently, H, $C_{1-6}$ alkyl, CN, hydroxyl, $C_{1-6}$ alkoxy, $C_{1-6}$ alkylsulfonyl, carboxy, $C_{1-6}$ alkylcarbonyl, aminosulfonyl, $C_{1-6}$ alkylaminosulfonyl, di-$C_{1-6}$ alkylaminosulfonyl, carbamyl, $C_{1-6}$ alkylcarbamyl, or di-$C_{1-6}$ alkylcarbamyl;

each $R^{a1}$, $R^{b1}$, $R^{c1}$, and $R^{d1}$ is, independently, H, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, or $C_{1-10}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl is optionally substituted with 1, 2, 3, 4, or 5 independently selected $R^{g'}$ groups;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, 3 or 4 substituents independently selected from halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, $C_{1-6}$ alkoxycarbonyl, and $C_{1-6}$ alkylcarbonylamino;

each $R^{e1}$ is, independently, H, $C_{1-6}$ alkyl, CN, hydroxyl, $C_{1-6}$ alkoxy, $C_{1-6}$ alkylsulfonyl, carboxy, $C_{1-6}$ alkylcarbonyl, aminosulfonyl, $C_{1-6}$ alkylaminosulfonyl, di-$C_{1-6}$ alkylaminosulfonyl, carbamyl, $C_{1-6}$ alkylcarbamyl, or di-$C_{1-6}$ alkylcarbamyl;

each $R^g$, $R^{g'}$, and $R^h$ is, independently, halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, $C_{1-6}$ alkoxycarbonyl, or $C_{1-6}$ alkylcarbonylamino; and n is 0, 1, 2, 3, or 4.

In some embodiments, X is N.
In some embodiments, X is $CR^2$.
In some embodiments, X is C(H), C(F), or C(CN).
In some embodiments, X is CH.
In some embodiments, Y is N.
In some embodiments, Y is $CR^3$.
In some embodiments, Y is CH.
In some embodiments, Z is cyano.
In some embodiments, L is C(=O)NH, C(=O), S(=O)$_2$, CH$_2$, C(=O)CH$_2$, or

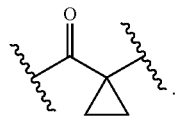 [SMILES: *C(=O)C1(*)CC1]

In some embodiments, L is C(=O)NH, C(=O), S(=O)$_2$, CH$_2$, C(=O)CH$_2$,

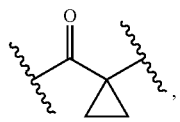

C(=O)O, or C(=O)OCH$_2$.

In some embodiments, L is C(=O).
In some embodiments, L is C(=O)O.
In some embodiments, L is C(=O)OCH$_2$.
In some embodiments, L is C(=O)NH.
In some embodiments, L is S(=O)$_2$.
In some embodiments, L is C(R$^4$)$_2$.
In some embodiments, L is CH$_2$.
In some embodiments, L is C(=O)CH$_2$ or

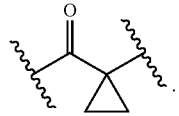

In some embodiments, L is C(=O)CH$_2$.
In some embodiments, L is

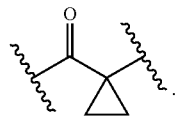 [SMILES: *C(=O)C1(*)CC1]

In some embodiments, n is 0, 1, or 2.
In some embodiments, n is 0.
In some embodiments, n is 1.
In some embodiments, n is 2.
In some embodiments, $R^1$ is $C_{1-4}$ alkyl.
In some embodiments, $R^1$ is methyl.
In some embodiments, two $R^1$ groups form a 2-carbon bridge.

In some embodiments, A is $C_{6-14}$ aryl, which is optionally substituted with 1, 2, 3, 4, 5, or 6 independently selected $R^5$ groups.

In some embodiments, A is phenyl, which is optionally substituted with 1, 2, 3, 4, or 5 independently selected $R^5$ groups.

In some embodiments, A is monocyclic $C_{3-9}$ cycloalkyl or bicyclic $C_{3-9}$ cycloalkyl, each of which is optionally substituted with 1, 2, 3, 4, 5, or 6 independently selected $R^5$ groups.

In some embodiments, A is monocyclic $C_{2-10}$ heterocycloalkyl or bicyclic $C_{2-10}$ heterocycloalkyl, each of which is optionally substituted with 1, 2, 3, 4, 5, or 6 independently selected $R^5$ groups.

In some embodiments, A is monocyclic $C_{1-10}$ heteroaryl or bicyclic $C_{1-10}$ heteroaryl, each of which is optionally substituted with 1, 2, 3, 4, 5, or 6 independently selected $R^5$ groups.

In some embodiments, A is $C_{1-6}$ alkyl, which is optionally substituted with 1, 2, 3, 4, 5, or 6 independently selected $R^5$ groups.

In some embodiments, A is $C_{1-6}$ alkyl.

In some embodiments, A is $C_{1-6}$ alkyl, phenyl, a naphthyl ring, monocyclic or bicyclic $C_{3-10}$ cycloalkyl, monocyclic or bicyclic $C_{2-10}$ heterocycloalkyl, or monocyclic or bicyclic $C_{1-10}$ heteroaryl; each of which is optionally substituted with 1, 2, 3, 4, or 5 independently selected $R^5$ groups.

In some embodiments, A is phenyl, a naphthyl ring, monocyclic $C_{3-10}$ cycloalkyl, bicyclic $C_{3-10}$ cycloalkyl, monocyclic $C_{2-10}$ heterocycloalkyl, bicyclic $C_{2-10}$ heterocycloalkyl, monocyclic $C_{1-10}$ heteroaryl, or bicyclic $C_{1-10}$ heteroaryl; each of which is optionally substituted with 1, 2, 3, 4, or 5 independently selected $R^5$ groups.

In some embodiments, A is methyl, ethyl, isopropyl, phenyl, a naphthalene ring, a pyridine ring, a pyrimidine ring, a thiophene ring, a pyrazine ring, an oxazole ring, an isoxazole ring, an imidazole ring, a thiazole ring, a furan ring, a pyrazole ring, a quinoline ring, a benzothiophene ring, a benzothiazole ring, a benzoimidazole ring, a benzofuran ring, cyclopropyl, cyclopentyl, cyclohexyl, cycloheptyl, an indene ring, a tetrahydronaphthalene ring, dihydro-1,4-benzodioxoxine ring, or a piperidine ring; each of which is optionally substituted with 1, 2, 3, 4, or 5 independently selected $R^5$ groups, as permitted by valency.

In some embodiments, A is phenyl, a naphthalene ring, a pyridine ring, a pyrimidine ring, a thiophene ring, a pyrazine ring, an oxazole ring, an isoxazole ring, an imidazole ring, a thiazole ring, a furan ring, a pyrazole ring, a quinoline ring, a benzothiophene ring, a benzothiazole ring, a benzoimidazole ring, a benzofuran ring, cyclopropyl, cyclopentyl, cyclohexyl, cycloheptyl, an indene ring, a tetrahydronaphthalene ring, dihydro-1,4-benzodioxoxine ring, or a piperidine ring; each of which is optionally substituted with 1, 2, 3, 4, or 5 independently selected $R^5$ groups, as permitted by valency.

In some embodiments, A is phenyl or a pyridine ring; each of which are optionally substituted with 1, 2, 3, or 4 independently selected $R^5$ groups.

In some embodiments, A is pyridin-4-yl; which is optionally substituted with 1, 2, 3, or 4 independently selected $R^5$ groups.

In some embodiments, A is a pyridine ring; which is optionally substituted with 1, 2, 3, or 4 independently selected $R^5$ groups.

In some embodiments, each $R^5$ is, independently, halo, cyano, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, $C_{1-10}$ heteroaryl-$C_{1-3}$ alkyl, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, or $S(O)_2NR^cR^d$; wherein $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl are each optionally substituted with 1, 2, 3, 4, or 5 independently selected $R^6$ groups.

In some embodiments, each $R^5$ is, independently, halo, cyano, $C_{1-6}$ alkyl, $C_{1-6}$ haloalkyl, $C_{3-10}$ cycloalkyl, $C_{2-10}$ heterocycloalkyl, $C_{6-10}$ aryl, $C_{6-10}$ aryl-$C_{1-3}$ alkyl, $C_{1-10}$ heteroaryl, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)_2R^b$, or $S(O)_2NR^cR^d$; wherein $C_{1-6}$ alkyl, $C_{2-6}$ alkenyl, $C_{2-6}$ alkynyl, $C_{1-6}$ haloalkyl, halosulfanyl, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-10}$ heteroaryl, and $C_{1-10}$ heteroaryl-$C_{1-3}$ alkyl are each optionally substituted with 1, 2, 3, 4, or 5 independently selected $R^6$ groups.

In some embodiments, each $R^5$ is, independently, halo, cyano, $C_{1-6}$ alkyl, $C_{1-6}$ haloalkyl, $C_{6-10}$ aryl, $C_{1-10}$ heteroaryl, $OR^a$, $SR^a$, $C(O)OR^a$, $NR^cR^d$, or $NR^cC(O)R^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups.

In some embodiments, each $R^5$ is, independently, halo, cyano, $C_{1-6}$ alkyl, $C_{1-6}$ haloalkyl, $C_{6-10}$ aryl, $C_{1-10}$ heteroaryl, $OR^a$, $SR^a$, $C(O)OR^a$, $NR^cR^d$, or $NR^cC(O)R^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups; and each $R^a$, $R^b$, $R^c$, and $R^d$ is, independently, H, $C_{1-6}$ alkyl, $C_{1-6}$ haloalkyl, or $C_{6-10}$ aryl; wherein said $C_{1-6}$ alkyl and $C_{6-10}$ aryl is optionally substituted with 1, 2, 3, 4, or 5 independently selected $R^g$ groups.

In some embodiments, each $R^5$ is, independently, halo, cyano, $C_{1-6}$ alkyl, $C_{1-6}$ haloalkyl, hydroxyl, $C_{1-6}$ alkoxy, $C_{1-6}$ haloalkoxy, $C_{6-12}$ aryloxy, amino, $C_{1-6}$ alkylamino, di-$C_{1-6}$ alkylamino, $C_{1-6}$ alkylcarbonylamino, $C_{1-6}$ alkoxycarbonyl, $C_{1-6}$ alkylthio, $C_{6-12}$ aryl, or $C_{1-9}$ heteroaryl; wherein said $C_{6-12}$ aryl or $C_{1-9}$ heteroaryl are each optionally substituted with 1, 2, 3, 4, or 5 independently selected $R^6$ groups.

In some embodiments, each $R^5$ is, independently, chloro, fluoro, bromo, cyano, methyl, ethyl, trifluoromethyl, hydroxyl, methoxy, trifluoromethoxy, difluoromethoxy, phenoxy, dimethylamino, t-butylcarbonylamino, methoxycarbonyl, methylthio, phenyl, a pyridine ring, a thiazole ring, a quinoline ring, an isoquinoline ring, an imidazo[1,2-a]pyrimidine ring, a benzoxazole ring, or an oxadiazole ring; wherein said phenyl, pyridine ring, thiazole ring, quinoline ring, isoquinoline ring, imidazo[1,2-a]pyrimidine ring, benzoxazole ring, and oxadiazole ring are each optionally substituted with 1, 2, 3, 4, or 5 independently selected $R^6$ groups.

In some embodiments, each $R^5$ is, independently, halo or $C_{1-6}$ haloalkyl.

In some embodiments, each $R^5$ is, independently, fluoro or trifluoromethyl.

In some embodiments, each $R^6$ is, independently, halo, cyano, nitro, hydroxyl, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di-$C_{1-6}$ alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di-$C_{1-6}$ alkylcarbamyl, carboxy, $C_{1-6}$ alkylcarbonyl, $C_{1-6}$ alkoxycarbonyl, or $C_{1-6}$ alkylcarbonylamino.

In some embodiments, each $R^6$ is, independently, halo, cyano, $C_{1-6}$ alkyl, $C_{1-6}$ haloalkyl, $OR^{a1}$, $NR^{c1}R^{d1}$, or $OC(O)R^{b1}$; and each $R^{a1}$, $R^{b1}$, $R^{c1}$, and $R^{d1}$ is, independently, H or $C_{1-6}$ alkyl; wherein said $C_{1-6}$ alkyl is optionally substituted with a substituent independently selected from $C_{1-4}$ alkoxy and hydroxyl;

or any $R^{c1}$ and $R^{d1}$ together with the N atom to which they are attached form a 4-, 5-, 6-, or 7-membered heterocycloalkyl group, optionally substituted with 1, 2, 3 or 4 substituents independently selected from halo.

In some embodiments, each $R^5$ is, independently, halo, cyano, $C_{1-6}$ alkyl, $C_{1-6}$ haloalkyl, $C_{6-10}$ aryl, $C_{1-10}$ heteroaryl, $OR^a$, $SR^a$, $C(O)OR^a$, $NR^cR^d$, or $NR^cC(O)R^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups;

each $R^a$, $R^b$, $R^c$, and $R^d$ is, independently, H, $C_{1-6}$ alkyl, $C_{1-6}$ haloalkyl, or $C_{6-10}$ aryl; wherein said $C_{1-6}$ alkyl and $C_{6-10}$ aryl is optionally substituted with 1, 2, 3, 4, or 5 independently selected $R^g$ groups;

each $R^6$ is, independently, halo, cyano, $C_{1-6}$ alkyl, $C_{1-6}$ haloalkyl, $OR^{a1}$, $NR^{c1}R^{d1}$, or $OC(O)R^{b1}$; and each $R^{a1}$, $R^{b1}$, $R^{c1}$, and $R^{d1}$ is, independently, H or $C_{1-6}$ alkyl; wherein said $C_{1-6}$ alkyl is optionally substituted with a substituent independently selected from $C_{1-4}$ alkoxy and hydroxyl;

or any $R^{c1}$ and $R^{d1}$ together with the N atom to which they are attached form a 4-, 5-, 6-, or 7-membered heterocycloalkyl group, optionally substituted with 1, 2, 3 or 4 substituents independently selected from halo.

In some embodiments, each $R^6$ is, independently, halo, cyano, or $C_{1-6}$ alkyl.

In some embodiments, each $R^6$ is, independently, chloro, fluoro, cyano, or methyl.

In some embodiments, wherein $R^2$ is H, halo, or cyano.

In some embodiments, $R^2$ is H, F, or cyano.

In some embodiments, $R^3$ is H.

In some embodiments, the compound is a compound of Formula (II):

II or a pharmaceutically acceptable salt thereof.

In some embodiments, the compound is a compound of Formula (IIa):

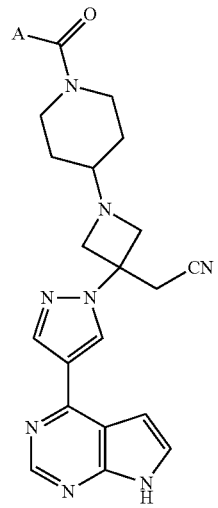

IIa or a pharmaceutically acceptable salt thereof.

In some embodiments, the compound is a compound of Formula (III):

III or a pharmaceutically acceptable salt thereof.

In some embodiments, the compound is a compound of Formula (IIIa):

IIIa

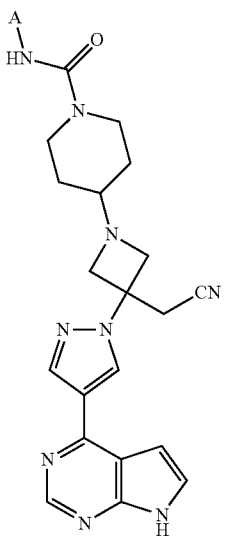

or a pharmaceutically acceptable salt thereof.

In some embodiments:
X is N or CR$^2$;
Y is N or CR$^3$;
each R$^1$ is, independently, C$_{1-4}$ alkyl; or
two R$^1$ groups form a 2-carbon bridge.
R$^2$ is H, halo, or cyano;
R$^3$ is H;
Z is cyano;
L is C(=O)NH, C(=O), S(=O)$_2$, CH$_2$, C(=O)CH$_2$, or

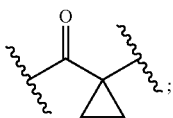 [SMILES: *C(=O)C1(*)CC1]

A is C$_{1-6}$ alkyl, phenyl, a naphthyl ring, monocyclic C$_{3-10}$ cycloalkyl, bicyclic C$_{3-10}$ cycloalkyl, monocyclic C$_{2-10}$ heterocycloalkyl, bicyclic C$_{2-10}$ heterocycloalkyl, monocyclic C$_{1-10}$ heteroaryl, or bicyclic C$_{1-10}$ heteroaryl; each of which is optionally substituted with 1, 2, 3, 4, or 5 independently selected R$^5$ groups;

each R$^5$ is, independently, halo, cyano, C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-10}$ heterocycloalkyl, C$_{2-10}$ heterocycloalkyl-C$_{1-3}$ alkyl, C$_{6-10}$ aryl, C$_{6-10}$ aryl-C$_{1-3}$ alkyl, C$_{1-10}$ heteroaryl, C$_{1-10}$ heteroaryl-C$_{1-3}$ alkyl, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)$_2$R$^b$, NR$^c$S(O)$_2$NR$^c$R$^d$, S(O)R$^b$, S(O)NR$^c$R$^d$, S(O)$_2$R$^b$, or S(O)$_2$NR$^c$R$^d$; wherein C$_{1-6}$ alkyl, C$_{2-6}$ alkenyl, C$_{2-6}$ alkynyl, C$_{1-6}$ haloalkyl, halosulfanyl, C$_{3-10}$ cycloalkyl, C$_{3-10}$ cycloalkyl-C$_{1-3}$ alkyl, C$_{2-10}$ heterocycloalkyl, C$_{2-10}$ heterocycloalkyl-C$_{1-3}$ alkyl, C$_{6-10}$ aryl, C$_{6-10}$ aryl-C$_{1-3}$ alkyl, C$_{1-10}$ heteroaryl, and C$_{1-10}$ heteroaryl-C$_{1-3}$ alkyl are each optionally substituted with 1, 2, 3, 4, or 5 independently selected R$^6$ groups; and n is 0, 1, or 2.

In some embodiments:
X is N or CR$^2$;
Y is N or CR$^3$;
each R$^1$ is, independently, C$_{1-4}$ alkyl; or
two R$^1$ groups form a 2-carbon bridge.
R$^2$ is H, halo, or cyano;
R$^3$ is H;
Z is cyano;
L is C(=O)NH, C(=O), S(=O)$_2$, CH$_2$, C(=O)CH$_2$, or

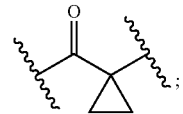 [SMILES: *C(=O)C1(*)CC1]

A is C$_{1-6}$ alkyl, phenyl, a naphthyl ring, monocyclic C$_{3-10}$ cycloalkyl, bicyclic C$_{3-10}$ cycloalkyl, monocyclic C$_{2-10}$ heterocycloalkyl, bicyclic C$_{2-10}$ heterocycloalkyl, monocyclic C$_{1-10}$ heteroaryl, or bicyclic C$_{1-10}$ heteroaryl; each of which is optionally substituted with 1, 2, 3, 4, or 5 independently selected R$^5$ groups;

each R$^5$ is, independently, halo, cyano, C$_{1-6}$ alkyl, C$_{1-6}$ haloalkyl, C$_{3-10}$ cycloalkyl, C$_{2-10}$ heterocycloalkyl, C$_{6-10}$ aryl, C$_{6-10}$ aryl-C$_{1-3}$ alkyl, C$_{1-10}$ heteroaryl, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)$_2$R$^b$, NR$^c$S(O)$_2$NR$^c$R$^d$, S(O)$_2$R$^b$, or S(O)$_2$NR$^c$R$^d$; wherein C$_{1-6}$ alkyl, C$_{2-6}$ alkenyl, C$_{2-6}$ alkynyl, C$_{1-6}$ haloalkyl, halosulfanyl, C$_{3-10}$ cycloalkyl, C$_{3-10}$ cycloalkyl-C$_{1-3}$ alkyl, C$_{2-10}$ heterocycloalkyl, C$_{2-10}$ heterocycloalkyl-C$_{1-3}$ alkyl, C$_{6-10}$ aryl, C$_{6-10}$ aryl-C$_{1-3}$ alkyl, C$_{1-10}$ heteroaryl, and C$_{1-10}$ heteroaryl-C$_{1-3}$ alkyl are each optionally substituted with 1, 2, 3, 4, or 5 independently selected R$^6$ groups; and n is 0, 1, or 2.

In some embodiments:
X is N or CR$^2$;
Y is N or CR$^3$;
each R$^1$ is, independently, C$_{1-4}$ alkyl; or
two R$^1$ groups form a 2-carbon bridge.
R$^2$ is H, halo, or cyano;
R$^3$ is H;
Z is cyano;
L is C(=O)NH, C(=O), S(=O)$_2$, CH$_2$, C(=O)CH$_2$, or;

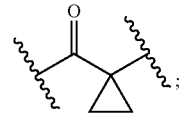 [SMILES: *C(=O)C1(*)CC1]

A is phenyl, a naphthyl ring, monocyclic C$_{3-10}$ cycloalkyl, bicyclic C$_{3-10}$ cycloalkyl, monocyclic C$_{2-10}$ heterocycloalkyl, bicyclic C$_{2-10}$ heterocycloalkyl, monocyclic C$_{1-10}$ heteroaryl, or bicyclic C$_{1-10}$ heteroaryl; each of which is optionally substituted with 1, 2, 3, 4, or 5 independently selected R$^5$ groups;

each R$^5$ is, independently, halo, cyano, C$_{1-6}$ alkyl, C$_{1-6}$ haloalkyl, C$_{3-10}$ cycloalkyl, C$_{2-10}$ heterocycloalkyl, C$_{6-10}$ aryl, C$_{6-10}$ aryl-C$_{1-3}$ alkyl, C$_{1-10}$ heteroaryl, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)$_2$R$^b$, NR$^c$S(O)$_2$NR$^c$R$^d$, S(O)$_2$R$^b$, or S(O)$_2$NR$^c$R$^d$; wherein C$_{1-6}$ alkyl, C$_{2-6}$ alkenyl, C$_{2-6}$ alkynyl, C$_{1-6}$ haloalkyl, halosulfanyl, C$_{3-10}$ cycloalkyl, C$_{3-10}$ cycloalkyl-C$_{1-3}$ alkyl, C$_{2-10}$ heterocycloalkyl, C$_{2-10}$ heterocycloalkyl-C$_{1-3}$ alkyl, C$_{6-10}$ aryl, C$_{6-10}$ aryl-C$_{1-3}$ alkyl, C$_{1-10}$ heteroaryl, and $C_{1-10}$ heteroaryl-$C_{1-3}$ alkyl are each optionally substituted with 1, 2, 3, 4, or 5 independently selected $R^6$ groups; and n is 0, 1, or 2.

In some embodiments:

X is N or $CR^2$;
Y is N or $CR^3$;
each $R^1$ is, independently, $C_{1-4}$ alkyl; or
two $R^1$ groups form a 2-carbon bridge.
$R^2$ is H, halo, or cyano;
$R^3$ is H;
Z is cyano;
L is C(=O)NH, C(=O), S(=O)$_2$, CH$_2$, C(=O)CH$_2$, or

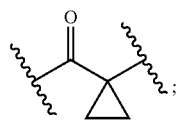 [SMILES: *C(=O)C1(*)CC1]

A is $C_{1-6}$ alkyl, phenyl, a naphthyl ring, monocyclic $C_{3-10}$ cycloalkyl, bicyclic $C_{3-10}$ cycloalkyl, monocyclic $C_{2-10}$ heterocycloalkyl, bicyclic $C_{2-10}$ heterocycloalkyl, monocyclic $C_{1-10}$ heteroaryl, or bicyclic $C_{1-10}$ heteroaryl; each of which is optionally substituted with 1, 2, 3, 4, or 5 independently selected $R^5$ groups;

each $R^5$ is, independently, halo, cyano, $C_{1-6}$ alkyl, $C_{1-6}$ haloalkyl, $C_{6-10}$ aryl, $C_{1-10}$ heteroaryl, OR$^a$, SR$^a$, C(O)OR$^a$, NR$^c$R$^d$, NR$^c$C(O)R$^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups; and n is 0, 1, or 2.

In some embodiments:

X is N or $CR^2$;
Y is N or $CR^3$;
each $R^1$ is, independently, $C_{1-4}$ alkyl; or
two $R^1$ groups form a 2-carbon bridge.
$R^2$ is H, halo, or cyano;
$R^3$ is H;
Z is cyano;
L is C(=O)NH, C(=O), S(=O)$_2$, CH$_2$, C(=O)CH$_2$, or

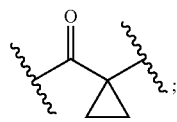 [SMILES: *C(=O)C1(*)CC1]

A is phenyl, a naphthyl ring, monocyclic $C_{3-10}$ cycloalkyl, bicyclic $C_{3-10}$ cycloalkyl, monocyclic $C_{2-10}$ heterocycloalkyl, bicyclic $C_{2-10}$ heterocycloalkyl, monocyclic $C_{1-10}$ heteroaryl, or bicyclic $C_{1-10}$ heteroaryl; each of which is optionally substituted with 1, 2, 3, 4, or 5 independently selected $R^5$ groups;

each $R^5$ is, independently, halo, cyano, $C_{1-6}$ alkyl, $C_{1-6}$ haloalkyl, $C_{6-10}$ aryl, $C_{1-10}$ heteroaryl, OR$^a$, SR$^a$, C(O)OR$^a$, NR$^c$R$^d$, NR$^c$C(O)R$^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups; and n is 0, 1, or 2.

In some embodiments:

X is N or $CR^2$;
Y is N or $CR^3$;
each $R^1$ is, independently, methyl; or
two $R^1$ groups form a 2-carbon bridge.
$R^2$ is H, halo, or cyano;
$R^3$ is H;
Z is cyano;
L is C(=O)NH, C(=O), S(=O)$_2$, CH$_2$, C(=O)CH$_2$, or

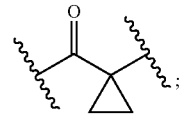 [SMILES: *C(=O)C1(*)CC1]

A is methyl, ethyl, isopropyl, phenyl, a naphthalene ring, a pyridine ring, a pyrimidine ring, a thiophene ring, a pyrazine ring, an oxazole ring, an isoxazole ring, an imidazole ring, a thiazole ring, a furan ring, a pyrazole ring, a quinoline ring, a benzothiophene ring, a benzothiazole ring, a benzoimidazole ring, a benzofuran ring, cyclopropyl, cyclopentyl, cyclohexyl, cycloheptyl, an indene ring, a tetrahydronaphthalene ring, dihydro-1,4-benzodioxoxine ring, or a piperidine ring; each of which are optionally substituted with 1, 2, 3, 4, 5, or 6 independently selected $R^5$ groups, as permitted by valency;

each $R^5$ is, independently, chloro, fluoro, bromo, cyano, methyl, ethyl, trifluoromethyl, hydroxyl, methoxy, trifluoromethoxy, difluoromethoxy, phenoxy, dimethylamino, t-butylcarbonylamino, methoxycarbonyl, methylthio, phenyl, a pyridine ring, a thiazole ring, a quinoline ring, an isoquinoline ring, an imidazo[1,2-a]pyrimidine ring, a benzoxazole ring, or an oxadiazole ring; wherein said phenyl, pyridine ring, thiazole ring, quinoline ring, isoquinoline ring, imidazo[1,2-a]pyrimidine ring, benzoxazole ring, and oxadiazole ring are each optionally substituted with 1, 2, 3, 4, or 5 independently selected $R^6$ groups; and n is 0, 1, or 2.

In some embodiments:

X is N or $CR^2$;
Y is N or $CR^3$;
each $R^1$ is, independently, methyl; or
two $R^1$ groups form a 2-carbon bridge.
$R^2$ is H, halo, or cyano;
$R^3$ is H;
Z is cyano;
L is C(=O)NH, C(=O), S(=O)$_2$, CH$_2$, C(=O)CH$_2$, or

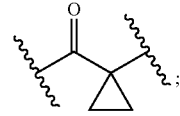 [SMILES: *C(=O)C1(*)CC1]

A is phenyl, a naphthalene ring, a pyridine ring, a pyrimidine ring, a thiophene ring, a pyrazine ring, an oxazole ring, an isoxazole ring, an imidazole ring, a thiazole ring, a furan ring, a pyrazole ring, a quinoline ring, a benzothiophene ring, a benzothiazole ring, a benzoimidazole ring, a benzofuran ring, cyclopropyl, cyclopentyl, cyclohexyl, cycloheptyl, an indene ring, a tetrahydronaphthalene ring, dihydro-1,4-benzodioxoxine ring, or a piperidine ring; each of which are optionally substituted with 1, 2, 3, 4, 5, or 6 independently selected $R^5$ groups;

each $R^5$ is, independently, chloro, fluoro, bromo, cyano, methyl, ethyl, trifluoromethyl, hydroxyl, methoxy, trifluoromethoxy, difluoromethoxy, phenoxy, dimethylamino, t-butylcarbonylamino, methoxycarbonyl, methylthio, phenyl, a pyridine ring, a thiazole ring, a quinoline ring, an isoquinoline ring, an imidazo[1,2-a]pyrimidine ring, a benzoxazole ring, or an oxadiazole ring; wherein said phenyl, pyridine ring, thiazole ring, quinoline ring, isoquinoline ring, imidazo[1,2-a]pyrimidine ring, benzoxazole ring, and oxadiazole ring are each optionally substituted with 1, 2, 3, 4, or 5 independently selected $R^6$ groups; and
n is 0, 1, or 2.

In some embodiments:
X is N or $CR^2$;
Y is N or $CR^3$;
each $R^1$ is, independently, $C_{1-4}$ alkyl; or
two $R^1$ groups form a 2-carbon bridge.
$R^2$ is H, halo, or cyano;
$R^3$ is H;
Z is cyano;
L is $S(=O)_2$;
A is $C_{1-6}$ alkyl; and
n is 0, 1, or 2.

In some embodiments:
X is N or CH;
Y is N;
Z is cyano;
L is $C(=O)$ or $C(=O)NH$;
A is phenyl or a pyridine ring, each of which is optionally substituted with 1, 2, 3, or 4 independently selected $R^5$ groups;
each $R^5$ is, independently, halo or $C_{1-6}$ haloalkyl; and
n is 0.

In some embodiments:
X is N or CH;
Y is N;
Z is cyano;
L is $C(=O)$ or $C(=O)NH$;
A is phenyl or pyridin-4-yl, each of which is optionally substituted with 1 or 2 independently selected $R^5$ groups;
each $R^5$ is, independently, fluoro or trifluoromethyl; and
n is 0.

In some embodiments:
X is N or $CR^2$;
Y is N or $CR^3$;
each $R^1$ is, independently, $C_{1-4}$ alkyl, hydroxyl, $C_{1-4}$ alkoxy, or fluoro;
two $R^1$ groups together form a 2- or 3-carbon bridge or a bridge of formula $-CH_2-O-CH_2-$;
$R^2$ is H, halo, or cyano;
$R^3$ is H;
Z is cyano;
L is $C(=O)NH$, $C(=O)$, $S(=O)_2$, $CH_2$, $C(=O)CH_2$,

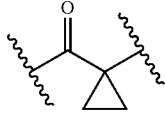 [SMILES: *C(=O)C1(*)CC1]

$C(=O)O$, or $C(=O)OCH_2$;
A is $C_{1-6}$ alkyl, phenyl, a naphthyl ring, monocyclic $C_{3-10}$ cycloalkyl, bicyclic $C_{3-10}$ cycloalkyl, monocyclic $C_{2-10}$ heterocycloalkyl, bicyclic $C_{2-10}$ heterocycloalkyl, monocyclic $C_{1-10}$ heteroaryl, or bicyclic $C_{1-10}$ heteroaryl; each of which is optionally substituted with 1, 2, 3, 4, or 5 independently selected $R^5$ groups;
each $R^5$ is, independently, halo, cyano, $C_{1-6}$ alkyl, $C_{1-6}$ haloalkyl, $C_{6-10}$ aryl, $C_{1-10}$ heteroaryl, $OR^a$, $SR^a$, $C(O)OR^a$, $NR^cR^d$, $NR^cC(O)R^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups;
n is 0, 1, or 2;
each $R^5$ is, independently, halo, cyano, $C_{1-6}$ alkyl, $C_{1-6}$ haloalkyl, $C_{6-10}$ aryl, $C_{1-10}$ heteroaryl, $OR^a$, $SR^a$, $C(O)OR^a$, $NR^cR^d$, or $NR^cC(O)R^b$; wherein said $C_{1-6}$ alkyl, $C_{1-6}$ haloalkyl, $C_{6-10}$ aryl, and $C_{1-10}$ heteroaryl are each optionally substituted with 1, 2, 3, 4, or 5 independently selected $R^6$ groups;
each $R^a$, $R^b$, $R^c$, and $R^d$ is, independently, H, $C_{1-6}$ alkyl, $C_{1-6}$ haloalkyl, or $C_{6-10}$ aryl; wherein said $C_{1-6}$ alkyl and $C_{6-10}$ aryl is optionally substituted with 1, 2, 3, 4, or 5 independently selected $R^g$ groups;
each $R^6$ is, independently, halo, cyano, $C_{1-6}$ alkyl, $C_{1-6}$ haloalkyl, $OR^{a1}$, $NR^{c1}R^{d1}$, or $OC(O)R^{b1}$; and
each $R^{a1}$, $R^{b1}$, $R^{c1}$, and $R^{d1}$ is, independently, H or $C_{1-6}$ alkyl; wherein said $C_{1-6}$ alkyl is optionally substituted with a substituent independently selected from $C_{1-4}$ alkoxy and hydroxyl;
or any $R^{c1}$ and $R^{d1}$ together with the N atom to which they are attached form a 4-, 5-, 6-, or 7-membered heterocycloalkyl group, optionally substituted with 1, 2, 3 or 4 substituents independently selected from halo.

In some embodiments, the compound is selected from:
{1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;
{1-[1-(3-fluoro-4-quinolin-6-ylbenzoyl)piperidin-4-yl]-3-[4-(7H-pyrrolo[2,3-d]pyrimidin-4-yl)-1H-pyrazol-1-yl] azetidin-3-yl}acetonitrile;
{1-[1-(3,5-difluorobenzoyl)piperidin-4-yl]-3-[4-(7H-pyrrolo[2,3-d]pyrimidin-4-yl)-1H-pyrazol-1-yl]azetidin-3-yl}acetonitrile;
{3-[4-(7H-pyrrolo[2, 3-d]pyrimidin-4-yl)-1H-pyrazol-1-yl]-1-[1-(3,4,5-trifluorobenzoyl)piperidin-4-yl]azetidin-3-yl}acetonitrile;
{1-[1-(3-fluoro-4-methoxybenzoyl)piperidin-4-yl]-3-[4-(7H-pyrrolo[2,3-d]pyrimidin-4-yl)-1H-pyrazol-1-yl]azetidin-3-yl}acetonitrile;
{1-[1-(3-fluoro-4-hydroxybenzoyl)piperidin-4-yl]-3-[4-(7H-pyrrolo[2,3-d]pyrimidin-4-yl)-1H-pyrazol-1-yl]azetidin-3-yl}acetonitrile;
{1-{1-[2-fluoro-3-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile;
{1-[1-(cyclohexylcarbonyl)piperidin-4-yl]-3-[4-(7H-pyrrolo[2,3-d]pyrimidin-4-yl)-1H-pyrazol-1-yl]azetidin-3-yl}acetonitrile;
{1-(1-benzoylpiperidin-4-yl)-3-[4-(7H-pyrrolo[2,3-d]pyrimidin-4-yl)-1H-pyrazol-1-yl]azetidin-3-yl}acetonitrile;
2-[(4-{3-(cyanomethyl)-3-[4-(7H-pyrrolo[2, 3-d]pyrimidin-4-yl)-1H-pyrazol-1-yl]azetidin-1-yl}piperidin-1-yl)carbonyl]benzonitrile;
3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]benzonitrile;
4-[(4-{3-(cyanomethyl)-3-[4-(7H-pyrrolo[2, 3-d]pyrimidin-4-yl)-1H-pyrazol-1-yl]azetidin-1-yl}piperidin-1-yl)carbonyl]benzonitrile;
{1-{1-[(6-chloropyridin-2-yl)carbonyl]piperidin-4-yl}-3-[4-(7H-pyrrolo[2,3-d]pyrimidin-4-yl)-1H-pyrazol-1-yl] azetidin-3-yl}acetonitrile;
{1-[1-(pyrazin-2-1carbonyl)piperidin-4-yl]-3-[4-(7H-pyrrolo[2,3-d]pyrimidin-4-yl)-1H-pyrazol-1-yl]azetidin-3-1}acetonitrile;

{3-[4-(7H-pyrrolo[2,3-d]pyrimidin-4-yl)-1H-pyrazol-1-yl]-1-[1-(3-thienylcarbonyl)piperidin-4-yl]azetidin-3-yl}acetonitrile;

{1-[1-(1,3-oxazol-2-ylcarbonyl)piperidin-4-yl]-3-[4-(7H-pyrrolo[2,3-d]pyrimidin-4-yl)-1H-pyrazol-1-yl]azetidin-3-yl}acetonitrile;

{1-(1-{[2-methyl-5-(trifluoromethyl)-1,3-oxazol-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-5-fluorobenzonitrile;

{1-[1-(3-chlorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-bromobenzoyl)piperidin-4-yl]-3-[4-(7H-pyrrolo[2,3-d]pyrimidin-4-yl)-1H-pyrazol-1-yl]azetidin-3-yl}acetonitrile;

(3-[4-(7H-pyrrolo[2,3-d]pyrimidin-4-yl)-1H-pyrazol-1-yl]-1-{1-[3-(trifluoromethoxy)benzoyl]piperidin-4-yl}azetidin-3-yl)acetonitrile;

(3-[4-(7H-pyrrolo[2,3-d]pyrimidin-4-yl)-1H-pyrazol-1-yl]-1-{1-[3-(trifluoromethyl)benzoyl]piperidin-4-yl}azetidin-3-yl)acetonitrile;

{1-{1-[3-fluoro-5-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile;

{1-[1-(3,5-dichlorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(4-fluoro-3-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2-fluoro-5-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-chloro-5-fluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-bromo-5-fluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-{1-[(2,5-dichloro-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-[1-(3-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{3-[4-(7H-pyrrolo[2,3-d]pyrimidin-4-yl)-1H-pyrazol-1-yl]-1-[1-(2,4,5-trifluoro-3-methoxybenzoyl)piperidin-4-yl]azetidin-3-yl}acetonitrile;

{1-[1-(3,5-dimethoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-chloro-4-fluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3,4-difluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-5-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2-chloro-6-methoxyisonicotinoyl)piperidin-4-yl]-3-[4-(7H-pyrrolo[2,3-d]pyrimidin-4-yl)-1H-pyrazol-1-yl]azetidin-3-yl}acetonitrile;

{1-[1-(5-fluoro-2-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2-fluoro-6-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(4-fluoro-2-methoxybenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,3-difluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,4-difluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,5-difluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,6-difluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-{1-[2-fluoro-6-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile;

{3-[4-(7H-pyrrolo[2,3-d]pyrimidin-4-yl)-1H-pyrazol-1-yl]-1-[1-(2,3,4-trifluorobenzoyl)piperidin-4-yl]azetidin-3-yl}acetonitrile;

{3-[4-(7H-pyrrolo[2,3-d]pyrimidin-4-yl)-1H-pyrazol-1-yl]-1-[1-(2,3,6-trifluorobenzoyl)piperidin-4-yl]azetidin-3-yl}acetonitrile;

{3-[4-(7H-pyrrolo[2,3-d]pyrimidin-4-yl)-1H-pyrazol-1-yl]-1-[1-(2,4,5-trifluorobenzoyl)piperidin-4-yl]azetidin-3-yl}acetonitrile;

{3-[4-(7H-pyrrolo[2,3-d]pyrimidin-4-yl)-1H-pyrazol-1-yl]-1-[1-(2,4,6-trifluorobenzoyl)piperidin-4-yl]azetidin-3-yl}acetonitrile;

{1-[1-(3,5-dibromo-4-methoxybenzoyl)piperidin-4-yl]-3-[4-(7H-pyrrolo[2,3-d]pyrimidin-4-yl)-1H-pyrazol-1-yl]azetidin-3-yl}acetonitrile;

3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-6-(dimethylamino)-2-fluorobenzonitrile;

{1-{1-[3-fluoro-4-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile;

{1-(1-{[4-chloro-6-(trifluoromethyl)pyridin-2-yl]carbonyl}piperidin-4-yl)-3-[4-(7H-pyrrolo[2,3-d]pyrimidin-4-yl)-1H-pyrazol-1-yl]azetidin-3-yl}acetonitrile;

{3-[4-(7H-pyrrolo[2,3-d]pyrimidin-4-yl)-1H-pyrazol-1-yl]-1-[1-(2,3,4,5-tetrafluorobenzoyl)piperidin-4-yl]azetidin-3-yl}acetonitrile;

5-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2-methoxybenzonitrile;

{3-[4-(7H-pyrrolo[2,3-d]pyrimidin-4-yl)-1H-pyrazol-1-yl]-1-[1-(2,3,5,6-tetrafluorobenzoyl)piperidin-4-yl]azetidin-3-yl}acetonitrile;

(3-[4-(7H-pyrrolo[2,3-d]pyrimidin-4-yl)-1H-pyrazol-1-yl]-1-{1-[2-(trifluoromethyl)isonicotinoyl]piperidin-4-yl}azetidin-3-yl)acetonitrile;

{1-[1-(4-fluoro-3-hydroxybenzoyl)piperidin-4-yl]-3-[4-(7H-pyrrolo[2,3-d]pyrimidin-4-yl)-1H-pyrazol-1-yl]azetidin-3-yl}acetonitrile;

5-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2-(dimethylamino)benzonitrile;

{1-{1-[4-(dimethylamino)-2,3,5,6-tetrafluorobenzoyl]piperidin-4-yl}-3-[4-(7H-pyrrolo[2,3-d]pyrimidin-4-yl)-1H-pyrazol-1-yl]azetidin-3-yl}acetonitrile;

{1-[1-(3,5-difluoroisonicotinoyl)piperidin-4-yl]-3-[4-(7H-pyrrolo[2,3-d]pyrimidin-4-yl)-1H-pyrazol-1-yl]azetidin-3-yl}acetonitrile;

{1-{1-[3-fluoro-4-(methylthio)benzoyl]piperidin-4-yl}-3-[4-(7H-pyrrolo[2,3-d]pyrimidin-4-yl)-1H-pyrazol-1-yl]azetidin-3-yl}acetonitrile;

{1-[1-(4-chloro-3-fluorobenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-methylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,5-dimethyl-3-furoyl)piperidin-4-yl]-3-[4-(7H-pyrrolo[2,3-d]pyrimidin-4-yl)-1H-pyrazol-1-yl]azetidin-3-yl}acetonitrile;

4-[(4-{3-(cyanomethyl)-3-[4-(7H-pyrrolo[2, 3-d]pyrimidin-4-yl)-1H-pyrazol-1-yl]azetidin-1-yl}piperidin-1-yl)carbonyl]-2-fluorobenzonitrile;

{1-[1-(2-fluorobenzoyl)piperidin-4-yl]-3-[4-(7H-pyrrolo[2, 3-d]pyrimidin-4-yl)-1H-pyrazol-1-yl]azetidin-3-yl}acetonitrile;

{1-[1-(4-fluorobenzoyl)piperidin-4-yl]-3-[4-(7H-pyrrolo[2, 3-d]pyrimidin-4-yl)-1H-pyrazol-1-yl]azetidin-3-yl}acetonitrile;

{1-[1-(2-thienylcarbonyl)piperidin-4-yl]-3-[4-(7H-pyrrolo[2,3-d]pyrimidin-4-yl)-1H-pyrazol-1-yl]azetidin-3-yl}acetonitrile;

{1-{1-[3-methoxy-5-(trifluoromethyl)-2-thienylcarbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[3-hydroxy-5-(trifluoromethyl)-2-thienylcarbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(4-methoxy-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(5-methyl-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(5-chloro-4-methoxy-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(2-bromo-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(3-chloro-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(5-chloro-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(3-methyl-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(4-methyl-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(5-methyl-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(3-methoxy-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[2-fluoro-4-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile;

4-[(4-{3-(cyanomethyl)-3-[4-(7H-pyrrolo[2, 3-d]pyrimidin-4-yl)-1H-pyrazol-1-yl]azetidin-1-yl}piperidin-1-yl)carbonyl]-3,5-difluorobenzonitrile;

{1-[1-(3-chloro-4-hydroxybenzoyl)piperidin-4-yl]-3-[4-(7H-pyrrolo[2,3-d]pyrimidin-4-yl)-1H-pyrazol-1-yl]azetidin-3-yl}acetonitrile;

[3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile;

[3-[4-(7H-pyrrolo[2,3-d]pyrimidin-4-yl)-1H-pyrazol-1-yl]-1-(1-{[6-(trifluoromethyl)pyrazin-2-yl]carbonyl}piperidin-4-yl)azetidin-3-yl]acetonitrile;

{1-[1-(1-naphthoyl)piperidin-4-yl]-3-[4-(7H-pyrrolo[2,3-d]pyrimidin-4-yl)-1H-pyrazol-1-yl]azetidin-3-yl}acetonitrile;

{3-[4-(7H-pyrrolo[2,3-d]pyrimidin-4-yl)-1H-pyrazol-1-yl]-1-[1-(quinolin-3-ylcarbonyl)piperidin-4-yl]azetidin-3-yl}acetonitrile;

{3-[4-(7H-pyrrolo[2,3-d]pyrimidin-4-yl)-1H-pyrazol-1-yl]-1-[1-(quinolin-6-ylcarbonyl)piperidin-4-yl]azetidin-3-yl}acetonitrile;

{1-[1-(1-benzothien-2-ylcarbonyl)piperidin-4-yl]-3-[4-(7H-pyrrolo[2,3-d]pyrimidin-4-yl)-1H-pyrazol-1-yl]azetidin-3-yl}acetonitrile;

{1-{1-[(3-chloro-6-fluoro-1-benzothien-2-yl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(3-chloro-4-fluoro-1-benzothien-2-yl)carbonyl]piperidin-4-yl}-3-[4-(7H-pyrrolo[2,3-d]pyrimidin-4-yl)-1H-pyrazol-1-yl]azetidin-3-yl}acetonitrile;

[3-[4-(7H-pyrrolo[2,3-d]pyrimidin-4-yl)-1H-pyrazol-1-yl]-1-(1-{[4-(trifluoromethyl)-1-benzothien-2-yl]carbonyl}piperidin-4-yl)azetidin-3-yl]acetonitrile;

[3-[4-(7H-pyrrolo[2,3-d]pyrimidin-4-yl)-1H-pyrazol-1-yl]-1-(1-{[6-(trifluoromethyl)-1-benzothien-2-yl]carbonyl}piperidin-4-yl)azetidin-3-yl]acetonitrile;

[3-[4-(7H-pyrrolo[2,3-d]pyrimidin-4-yl)-1H-pyrazol-1-yl]-1-(1-{[7-(trifluoromethyl)-1-benzothien-2-yl]carbonyl}piperidin-4-yl)azetidin-3-yl]acetonitrile;

{1-[1-(1-benzothien-3-ylcarbonyl)piperidin-4-yl]-3-[4-(7H-pyrrolo[2,3-d]pyrimidin-4-yl)-1H-pyrazol-1-yl]azetidin-3-yl}acetonitrile;

{3-[4-(7H-pyrrolo[2, 3-d]pyrimidin-4-yl)-1H-pyrazol-1-yl]-1-[1-(1,2,3,4-tetrahydronaphthalen-2-ylcarbonyl)piperidin-4-yl]azetidin-3-yl}acetonitrile;

[3-[4-(7H-pyrrolo[2,3-d]pyrimidin-4-yl)-1H-pyrazol-1-yl]-1-(1-{[4-(trifluoromethyl)cyclohexyl]carbonyl}piperidin-4-yl)azetidin-3-yl]acetonitrile;

{1-[1-(2,3-dihydro-1H-inden-2-ylcarbonyl)piperidin-4-yl]-3-[4-(7H-pyrrolo[2,3-d]pyrimidin-4-yl)-1H-pyrazol-1-yl]azetidin-3-yl}acetonitrile;

{1-{1-[(4,4-difluorocyclohexyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-[1-(cyclopentylcarbonyl)piperidin-4-yl]-3-[4-(7H-pyrrolo[2,3-d]pyrimidin-4-yl)-1H-pyrazol-1-yl]azetidin-3-yl}acetonitrile;

{1-[1-(cycloheptylcarbonyl)piperidin-4-yl]-3-[4-(7H-pyrrolo[2,3-d]pyrimidin-4-yl)-1H-pyrazol-1-yl]azetidin-3-yl}acetonitrile;

{1-{1-[(3-methoxycyclohexyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(4-phenylcyclohexyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-(1-{[4-(4-chlorophenyl)cyclohexyl]carbonyl}piperidin-4-yl)-3-[4-(7H-pyrrolo[2,3-d]pyrimidin-4-yl)-1H-pyrazol-1-yl]azetidin-3-yl}acetonitrile;

6-{4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]piperidin-1-yl}nicotinonitrile;

{1-(1-{[1-(5-chloro-3-fluoropyridin-2-yl)piperidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

2-{4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]piperidin-1-yl}-6-methylnicotinonitrile;

{1-[1-(phenylacetyl)piperidin-4-yl]-3-[4-(7H-pyrrolo[2,3-d]pyrimidin-4-yl)-1H-pyrazol-1-yl]azetidin-3-yl}acetonitrile;

{1-{1-[(1-phenylcyclopropyl)carbonyl]piperidin-4-yl}-3-[4-(7H-pyrrolo[2,3-d]pyrimidin-4-yl)-1H-pyrazol-1-yl]azetidin-3-yl}acetonitrile;

{1-(1-{[1-(4-chlorophenyl)cyclopropyl]carbonyl}piperidin-4-yl)-3-[4-(7H-pyrrolo[2,3-d]pyrimidin-4-yl)-1H-pyrazol-1-yl]azetidin-3-yl}acetonitrile;

{1-{1-[(2,6-dichlorophenyl)acetyl]piperidin-4-yl}-3-[4-(7H-pyrrolo[2,3-d]pyrimidin-4-yl)-1H-pyrazol-1-yl]azetidin-3-yl}acetonitrile;

{1-[1-(mesitylacetyl)piperidin-4-yl]-3-[4-(7H-pyrrolo[2,3-d]pyrimidin-4-yl)-1H-pyrazol-1-yl]azetidin-3-yl}acetonitrile;

{1-[1-(biphenyl-4-ylcarbonyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-isoquinolin-6-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,6-difluoro-4-pyridin-3-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-pyridin-4-ylbenzoyl)piperidin-4-yl]-3-[4-(7H-pyrrolo[2,3-d]pyrimidin-4-yl)-1H-pyrazol-1-yl]azetidin-3-yl}acetonitrile;

4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2'-fluorobiphenyl-4-carbonitrile;

4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2',3-difluorobiphenyl-4-carbonitrile;

{1-[1-(2-fluoro-4-pyridin-3-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-{1-[4-fluoro-3-(1,3-thiazol-2-yl)benzoyl]piperidin-4-yl}-3-[4-(7H-pyrrolo[2,3-d]pyrimidin-4-yl)-1H-pyrazol-1-yl]azetidin-3-yl}acetonitrile;

{1-{1-[3-fluoro-4-(1,3-thiazol-2-yl)benzoyl]piperidin-4-yl}-3-[4-(7H-pyrrolo[2,3-d]pyrimidin-4-yl)-1H-pyrazol-1-yl]azetidin-3-yl}acetonitrile;

{1-[1-(3-fluoro-4-pyridin-3-ylbenzoyl)piperidin-4-yl]-3-[4-(7H-pyrrolo[2,3-d]pyrimidin-4-yl)-1H-pyrazol-1-yl]azetidin-3-yl}acetonitrile;

4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2'-fluorobiphenyl-2-carbonitrile;

4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2'-fluorobiphenyl-3-carbonitrile;

4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]biphenyl-4-carbonitrile;

(3-[4-(7H-pyrrolo[2,3-d]pyrimidin-4-yl)-1H-pyrazol-1-yl]-1-{1-[(2,3',4'-trifluorobiphenyl-4-yl)carbonyl]piperidin-4-yl}azetidin-3-yl)acetonitrile;

4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2',5-difluorobiphenyl-3-carbonitrile;

{1-[1-(3-fluoro-4-quinolin-5-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-isoquinolin-5-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-isoquinolin-8-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-quinolin-8-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-isoquinolin-7-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-quinolin-7-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-fluoro-4-imidazo[1,2-a]pyridin-6-ylbenzoyl)piperidin-4-yl]-3-[4-(7H-pyrrolo[2,3-d]pyrimidin-4-yl)-1H-pyrazol-1-yl]azetidin-3-yl}acetonitrile;

{1-{1-[4-(1,3-benzoxazol-2-yl)benzoyl]piperidin-4-yl}-3-[4-(7H-pyrrolo[2,3-d]pyrimidin-4-yl)-1H-pyrazol-1-yl]azetidin-3-yl}acetonitrile;

{1-{1-[4-(1,3-benzoxazol-2-yl)-3-fluorobenzoyl]piperidin-4-yl}-3-[4-(7H-pyrrolo[2,3-d]pyrimidin-4-yl)-1H-pyrazol-1-yl]azetidin-3-yl}acetonitrile;

3-[(3-{3-(cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)carbonyl]-5-fluorobenzonitrile;

{1-[8-(3,4-difluorobenzoyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile;

4-[(3-{3-(cyanomethyl)-3-[4-(7H-pyrrolo[2, 3-d]pyrimidin-4-yl)-1H-pyrazol-1-yl]azetidin-1-yl}-8-azabicyclo[3.2.1]oct-8-yl)carbonyl]-2-fluorobenzonitrile;

{1-[8-(4-chloro-3-fluorobenzoyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile;

{1-{8-[3-fluoro-2-(trifluoromethyl)isonicotinoyl]-8-azabicyclo[3.2.1]oct-3-yl}-3-[4-(7H-pyrrolo[2,3-d]pyrimidin-4-yl)-1H-pyrazol-1-yl]azetidin-3-yl}acetonitrile;

[3-[4-(7H-pyrrolo[2, 3-d]pyrimidin-4-yl)-1H-pyrazol-1-yl]-1-(8-{[6-(trifluoromethyl)pyridin-3-yl]carbonyl}-8-azabicyclo[3.2.1]oct-3-yl)azetidin-3-yl]acetonitrile;

(3-[4-(7H-pyrrolo[2, 3-d]pyrimidin-4-yl)-1H-pyrazol-1-yl]-1-{8-[2-(trifluoromethyl)isonicotinoyl]-8-azabicyclo[3.2.1]oct-3-yl}azetidin-3-yl)acetonitrile;

{1-[8-(cyclopentylcarbonyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile;

{3-[4-(7H-pyrrolo[2,3-d]pyrimidin-4-yl)-1H-pyrazol-1-yl]-1-[8-(tetrahydro-2H-pyran-4-ylcarbonyl)-8-azabicyclo[3.2.1]oct-3-yl]azetidin-3-yl}acetonitrile;

{1-[8-(cyclohexylcarbonyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile;

{1-{8-[(4,4-difluorocyclohexyl)carbonyl]-8-azabicyclo[3.2.1]oct-3-yl}-3-[4-(7H-pyrrolo[2,3-d]pyrimidin-4-yl)-1H-pyrazol-1-yl]azetidin-3-yl}acetonitrile;

{1-[1-(3-fluorobenzoyl)-2-methylpiperidin-4-yl]-3-[4-(7H-pyrrolo[2,3-d]pyrimidin-4-yl)-1H-pyrazol-1-yl]azetidin-3-yl}acetonitrile;

{1-[1-(3-fluorobenzoyl)-2-methylpiperidin-4-yl]-3-[4-(7H-pyrrolo[2,3-d]pyrimidin-4-yl)-1H-pyrazol-1-yl]azetidin-3-yl}acetonitrile;

{1-{1-[(4,4-difluorocyclohexyl)carbonyl]-2-methylpiperidin-4-yl}-3-[4-(7H-pyrrolo[2,3-d]pyrimidin-4-yl)-1H-pyrazol-1-yl]azetidin-3-yl}acetonitrile;

{1-[1-(3-fluorobenzoyl)-4-methylpiperidin-4-yl]-3-[4-(7H-pyrrolo[2,3-d]pyrimidin-4-yl)-1H-pyrazol-1-yl]azetidin-3-yl}acetonitrile;

{1-[1-(cyclohexylcarbonyl)-4-methylpiperidin-4-yl]-3-[4-(7H-pyrrolo[2,3-d]pyrimidin-4-yl)-1H-pyrazol-1-yl]azetidin-3-yl}acetonitrile;

4-{3-(cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,6-difluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[2-(trifluoromethyl)phenyl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[2-(trifluoromethoxy)phenyl]piperidine-1-carboxamide;

N-(4-bromo-3-thienyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,6-dichlorophenyl)piperidine-1-carboxamide;

N-(2-chloro-6-methylphenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

N-(2-chloro-4-fluorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

N-(2-chlorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[2-(difluoromethoxy)phenyl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[4-(trifluoromethyl)pyridin-3-yl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[3-(trifluoromethyl)phenyl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[4-(trifluoromethyl)phenyl]piperidine-1-carboxamide;

N-(5-chloro-2-methylphenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2-fluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[2-fluoro-3-(trifluoromethyl)phenyl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,4-difluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,3,4-trifluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,3,5-trifluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,5-difluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(3,5-difluorophenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(3,4-difluorophenyl)piperidine-1-carboxamide;

N-(3-chloro-2-fluorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

N-(4-chloro-2-fluorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-3-thienylpiperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2-methoxyphenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(3-methoxyphenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[4-(trifluoromethoxy)phenyl]piperidine-1-carboxamide;

N-(3-chlorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

N-(4-chlorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2-methylphenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,5-dimethoxyphenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(4-fluoro-2-methylphenyl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[6-(trifluoromethyl)pyridin-2-yl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2,6-dimethylpyridin-3-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-1,3-thiazol-2-ylpiperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(4-methyl-1,3-thiazol-2-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(4,5-dimethyl-1,3-thiazol-2-yl)piperidine-1-carboxamide;

N-1,3-benzothiazol-2-yl-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(1-methyl-1H-benzimidazol-2-yl)piperidine-1-carboxamide;

N-[4-(4-chlorophenyl)-1,3-thiazol-2-yl]-4-{3-(cyanomethyl)-3-[4-(7H-pyrrolo[2,3-d]pyrimidin-4-yl)-1H-pyrazol-1-yl]azetidin-1-yl}piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(1-ethyl-1H-pyrazol-5-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(1,3-dimethyl-1H-pyrazol-5-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2-methylpyridin-3-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(6-fluoro-2-methylpyridin-3-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2-fluoro-6-methylpyridin-3-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[3-(trifluoromethyl)pyridin-2-yl]piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(3-fluoropyridin-2-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(3,5-difluoropyridin-2-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-(2-methoxypyridin-3-yl)piperidine-1-carboxamide;

4-{3-(cyanomethyl)-3-[4-(7H-pyrrolo[2,3-d]pyrimidin-4-yl)-1H-pyrazol-1-yl]azetidin-1-yl}-N-[2-methyl-6-(trifluoromethyl)pyridin-3-yl]piperidine-1-carboxamide;

methyl 2-{[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]amino}benzoate;

methyl 2-{[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]amino}-5-fluorobenzoate;

methyl 4-{[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]amino}-3-fluorobenzoate;

3-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]-6-(dimethylamino)-2-fluorobenzonitrile;

{1-[1-(3,5-dichlorobenzyl)piperidin-4-yl]-3-[4-(7H-pyrrolo[2,3-d]pyrimidin-4-yl)-1H-pyrazol-1-yl]azetidin-3-yl}acetonitrile;

{1-{1-[2-chloro-5-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile;

{1-{1-[2-fluoro-3-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile;

{1-{1-[2-fluoro-6-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile;

{1-{1-[(2-chloroquinolin-3-yl)methyl]piperidin-4-yl}-3-[4-(7H-pyrrolo[2,3-d]pyrimidin-4-yl)-1H-pyrazol-1-yl]azetidin-3-yl}acetonitrile;

{1-[1-(3,5-difluorobenzyl)piperidin-4-yl]-3-[4-(7H-pyrrolo[2,3-d]pyrimidin-4-yl)-1H-pyrazol-1-yl]azetidin-3-yl}acetonitrile;

{1-{1-[2-fluoro-4-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile;

{1-[1-(2,4-difluorobenzyl)piperidin-4-yl]-3-[4-(7H-pyrrolo[2,3-d]pyrimidin-4-yl)-1H-pyrazol-1-yl]azetidin-3-yl}acetonitrile;

{1-[1-(2-fluoro-6-methoxybenzyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,3-dichlorobenzyl)piperidin-4-yl]-3-[4-(7H-pyrrolo[2,3-d]pyrimidin-4-yl)-1H-pyrazol-1-yl]azetidin-3-yl}acetonitrile;

5-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]-2-fluorobenzonitrile;

{1-{1-[4-(1,2,3-oxadiazol-4-yl)benzyl]piperidin-4-yl}-3-[4-(7H-pyrrolo[2,3-d]pyrimidin-4-yl)-1H-pyrazol-1-yl]azetidin-3-yl}acetonitrile;

2-[(4-{3-(cyanomethyl)-3-[4-(7H-pyrrolo[2, 3-d]pyrimidin-4-yl)-1H-pyrazol-1-yl]azetidin-1-yl}piperidin-1-yl)methyl]benzonitrile;

3-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]benzonitrile;

6-[(4-{3-(cyanomethyl)-3-[4-(7H-pyrrolo[2, 3-d]pyrimidin-4-yl)-1H-pyrazol-1-yl]azetidin-1-yl}piperidin-1-yl)methyl]-2-methoxynicotinonitrile;

{1-{1-[(2,6-dibromopyridine-4-yl)methyl]piperidin-4-yl}-3-[4-(7H-pyrrolo[2,3-d]pyrimidin-4-yl)-1H-pyrazol-1-yl]azetidin-3-yl}acetonitrile;

{1-{1-[(2-bromopyridin-4-yl)methyl]piperidin-4-yl}-3-[4-(7H-pyrrolo[2,3-d]pyrimidin-4-yl)-1H-pyrazol-1-yl]azetidin-3-yl}acetonitrile;

{1-[1-(2-chloro-6-fluorobenzyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-chloro-2,6-difluorobenzyl)piperidin-4-yl]-3-[4-(7H-pyrrolo[2,3-d]pyrimidin-4-yl)-1H-pyrazol-1-yl]azetidin-3-yl}acetonitrile;

4-[(4-{3-(cyanomethyl)-3-[4-(7H-pyrrolo[2, 3-d]pyrimidin-4-yl)-1H-pyrazol-1-yl]azetidin-1-yl}piperidin-1-yl)methyl]-2-fluorobenzonitrile;

{1-{1-[(5-methyl-3-phenylisoxazol-4-yl)methyl]piperidin-4-yl}-3-[4-(7H-pyrrolo[2,3-d]pyrimidin-4-yl)-1H-pyrazol-1-yl]azetidin-3-yl}acetonitrile;

{1-(1-{[3-fluoro-2-(trifluoromethyl)pyridin-4-yl]methyl}piperidin-4-yl)-3-[4-(7H-pyrrolo[2,3-d]pyrimidin-4-yl)-1H-pyrazol-1-yl]azetidin-3-yl}acetonitrile;

{1-[1-(1-benzofuran-2-ylmethyl)piperidin-4-yl]-3-[4-(7H-pyrrolo[2,3-d]pyrimidin-4-yl)-1H-pyrazol-1-yl]azetidin-3-yl}acetonitrile;

{1-[1-(3-phenoxybenzyl)piperidin-4-yl]-3-[4-(7H-pyrrolo[2,3-d]pyrimidin-4-yl)-1H-pyrazol-1-yl]azetidin-3-yl}acetonitrile;

{1-[1-(2,3-dihydro-1,4-benzodioxin-6-ylmethyl)piperidin-4-yl]-3-[4-(7H-pyrrolo[2,3-d]pyrimidin-4-yl)-1H-pyrazol-1-yl]azetidin-3-yl}acetonitrile;

N-{4-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]pyridin-2-yl}-2,2-dimethylpropanamide;

{1-{1-[3-chloro-2-fluoro-6-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile;

{1-{1-[(3,5-dichloropyridin-4-yl)methyl]piperidin-4-yl}-3-[4-(7H-pyrrolo[2,3-d]pyrimidin-4-yl)-1H-pyrazol-1-yl]azetidin-3-yl}acetonitrile;

{1-{1-[(2-chloro-6-methoxyquinolin-3-yl)methyl]piperidin-4-yl}-3-[4-(7H-pyrrolo[2,3-d]pyrimidin-4-yl)-1H-pyrazol-1-yl]azetidin-3-yl}acetonitrile;

{1-[1-(2-chloro-3,4-dimethoxybenzyl)piperidin-4-yl]-3-[4-(7H-pyrrolo[2,3-d]pyrimidin-4-yl)-1H-pyrazol-1-yl]azetidin-3-yl}acetonitrile;

3-[(3-{3-(cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)methyl]-6-(dimethylamino)-2-fluorobenzonitrile;

{1-[8-(2-chloro-3,6-difluorobenzyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile;

3-[(4-{3-(cyanomethyl)-3-[4-(7H-pyrrolo[2,3-d]pyrimidin-4-yl)-1H-pyrazol-1-yl]azetidin-1-yl}-2-methylpiperidin-1-yl)methyl]-6-(dimethylamino)-2-fluorobenzonitrile;

3-[(4-{3-(cyanomethyl)-3-[4-(7H-pyrrolo[2,3-d]pyrimidin-4-yl)-1H-pyrazol-1-yl]azetidin-1-yl}-2-methylpiperidin-1-yl)methyl]-6-(dimethylamino)-2-fluorobenzonitrile;

{1-[1-(2-chloro-6-fluorobenzyl)-2-methylpiperidin-4-yl]-3-[4-(7H-pyrrolo[2,3-d]pyrimidin-4-yl)-1H-pyrazol-1-yl]azetidin-3-yl}acetonitrile;

{1-[1-(2-chloro-6-fluorobenzyl)-2-methylpiperidin-4-yl]-3-[4-(7H-pyrrolo[2,3-d]pyrimidin-4-yl)-1H-pyrazol-1-yl]azetidin-3-yl}acetonitrile;

{1-{1-[(1-methyl-1H-pyrazol-5-yl)sulfonyl]piperidin-4-yl}-3-[4-(7H-pyrrolo[2,3-d]pyrimidin-4-yl)-1H-pyrazol-1-yl]azetidin-3-yl}acetonitrile;

2-[(4-{3-(cyanomethyl)-3-[4-(7H-pyrrolo[2, 3-d]pyrimidin-4-yl)-1H-pyrazol-1-yl]azetidin-1-yl}piperidin-1-yl) sulfonyl]benzonitrile;

3-[(4-{3-(cyanomethyl)-3-[4-(7H-pyrrolo[2,3-d]pyrimidin-4-yl)-1H-pyrazol-1-yl]azetidin-1-yl}piperidin-1-yl) sulfonyl]benzonitrile;

4-[(4-{3-(cyanomethyl)-3-[4-(7H-pyrrolo[2, 3-d]pyrimidin-4-yl)-1H-pyrazol-1-yl]azetidin-1-yl}piperidin-1-yl)sulfonyl]benzonitrile;

5-[(4-{3-(cyanomethyl)-3-[4-(7H-pyrrolo[2,3-d]pyrimidin-4-yl)-1H-pyrazol-1-yl]azetidin-1-yl}piperidin-1-yl) sulfonyl]-2-(dimethylamino)benzonitrile;

{1-{1-[(1-methyl-1H-pyrazol-3-yl)sulfonyl]piperidin-4-yl}-3-[4-(7H-pyrrolo[2,3-d]pyrimidin-4-yl)-1H-pyrazol-1-yl]azetidin-3-yl}acetonitrile;

{1-[1-(cyclohexylsulfonyl)piperidin-4-yl]-3-[4-(7H-pyrrolo[2,3-d]pyrimidin-4-yl)-1H-pyrazol-1-yl]azetidin-3-yl}acetonitrile;

{1-[1-(cyclopentylsulfonyl)piperidin-4-yl]-3-[4-(7H-pyrrolo[2,3-d]pyrimidin-4-yl)-1H-pyrazol-1-yl]azetidin-3-yl}acetonitrile;

{1-[1-(methylsulfonyl)piperidin-4-yl]-3-[4-(7H-pyrrolo[2, 3-d]pyrimidin-4-yl)-1H-pyrazol-1-yl]azetidin-3-yl}acetonitrile;

{1-[1-(ethylsulfonyl)piperidin-4-yl]-3-[4-(7H-pyrrolo[2,3-d]pyrimidin-4-yl)-1H-pyrazol-1-yl]azetidin-3-yl}acetonitrile;

{1-[1-(cyclopropylsulfonyl)piperidin-4-yl]-3-[4-(7H-pyrrolo[2,3-d]pyrimidin-4-yl)-1H-pyrazol-1-yl]azetidin-3-yl}acetonitrile;

{1-[1-(isopropylsulfonyl)piperidin-4-yl]-3-[4-(7H-pyrrolo[2,3-d]pyrimidin-4-yl)-1H-pyrazol-1-yl]azetidin-3-yl}acetonitrile;

{1-{1-[(1-methyl-1H-imidazol-4-yl)sulfonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(1,2-dimethyl-1H-imidazol-4-yl)sulfonyl]piperidin-4-yl}-3-[4-(7H-pyrrolo[2,3-d]pyrimidin-4-yl)-1H-pyrazol-1-yl]azetidin-3-yl}acetonitrile;

{1-{1-[(3,5-dimethylisoxazol-4-yl)sulfonyl]piperidin-4-yl}-3-[4-(7H-pyrrolo[2,3-d]pyrimidin-4-yl)-1H-pyrazol-1-yl]azetidin-3-yl}acetonitrile;

{1-{1-[3-fluoro-2-(trifluoromethyl)isonicotinoyl]piperidin-4-yl}-3-[3-(7H-pyrrolo[2,3-d]pyrimidin-4-yl)-1H-pyrrol-1-yl]azetidin-3-yl}acetonitrile;

3-[(4-{3-(cyanomethyl)-3-[3-(7H-pyrrolo[2,3-d]pyrimidin-4-yl)-1H-pyrrol-1-yl]azetidin-1-yl}piperidin-1-yl)carbonyl]benzonitrile;

3-[(4-{3-(cyanomethyl)-3-[3-(7H-pyrrolo[2,3-d]pyrimidin-4-yl)-1H-pyrrol-1-yl]azetidin-1-yl}piperidin-1-yl)carbonyl]-5-fluorobenzonitrile;

4-[(4-{3-(cyanomethyl)-3-[3-(7H-pyrrolo[2, 3-d]pyrimidin-4-yl)-1H-pyrrol-1-yl]azetidin-1-yl}piperidin-1-yl)carbonyl]-3-fluorobenzonitrile;

4-[(4-{3-(cyanomethyl)-3-[3-(7H-pyrrolo[2, 3-d]pyrimidin-4-yl)-1H-pyrrol-1-yl]azetidin-1-yl}piperidin-1-yl)carbonyl]-3,5-difluorobenzonitrile;

{1-{1-[5-fluoro-2-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

{1-{1-[3-fluoro-4-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

(3-[3-(7H-pyrrolo[2, 3-d]pyrimidin-4-yl)-1H-pyrrol-1-yl]-1-{1-[3-(trifluoromethyl)benzoyl]piperidin-4-yl}azetidin-3-yl)acetonitrile;

{1-{1-[2-fluoro-5-(trifluoromethoxy)benzoyl]piperidin-4-yl}-3-[3-(7H-pyrrolo[2,3-d]pyrimidin-4-yl)-1H-pyrrol-1-yl]azetidin-3-yl}acetonitrile;

{3-[3-(7H-pyrrolo[2,3-d]pyrimidin-4-yl)-1H-pyrrol-1-yl]-1-[1-(2,3,6-trifluorobenzoyl)piperidin-4-yl]azetidin-3-yl}acetonitrile;

{3-[3-(7H-pyrrolo[2,3-d]pyrimidin-4-yl)-1H-pyrrol-1-yl]-1-[1-(2-thienylcarbonyl)piperidin-4-yl]azetidin-3-yl}acetonitrile;

{1-{1-[2-fluoro-4-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

{1-{1-[2-fluoro-5-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

{1-{1-[3-fluoro-5-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

{1-{1-[4-fluoro-3-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

{1-[1-(2,3-difluorobenzoyl)piperidin-4-yl]-3-[3-(7H-pyrrolo[2,3-d]pyrimidin-4-yl)-1H-pyrrol-1-yl]azetidin-3-yl}acetonitrile;

{1-[1-(3,4-difluorobenzoyl)piperidin-4-yl]-3-[3-(7H-pyrrolo[2,3-d]pyrimidin-4-yl)-1H-pyrrol-1-yl]azetidin-3-yl}acetonitrile;

{1-[1-(2,5-difluorobenzoyl)piperidin-4-yl]-3-[3-(7H-pyrrolo[2,3-d]pyrimidin-4-yl)-1H-pyrrol-1-yl]azetidin-3-yl}acetonitrile;

{1-[1-(2,6-difluorobenzoyl)piperidin-4-yl]-3-[3-(7H-pyr-rolo[2,3-d]pyrimidin-4-yl)-1H-pyrrol-1-yl]azetidin-3-yl}acetonitrile;

{3-[3-(7H-pyrrolo[2, 3-d]pyrimidin-4-yl)-1H-pyrrol-1-yl]-1-[1-(2,3,4-trifluorobenzoyl)piperidin-4-yl]azetidin-3-yl}acetonitrile;

{1-{1-[2-fluoro-3-(trifluoromethoxy)benzoyl]piperidin-4-yl}-3-[3-(7H-pyrrolo[2,3-d]pyrimidin-4-yl)-1H-pyrrol-1-yl]azetidin-3-yl}acetonitrile;

{1-{1-[4-hydroxy-3-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile;

4-{3-(cyanomethyl)-3-[3-(7H-pyrrolo[2,3-d]pyrimidin-4-yl)-1H-pyrrol-1-yl]azetidin-1-yl}-N-[4-fluoro-2-(trifluoromethyl)phenyl]piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-(2-methoxypyridin-3-yl)piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-[2-methyl-6-(trifluoromethyl)pyridin-3-yl]piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-(2,4-difluorophenyl)piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-(2-cyanophenyl)piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-(2-methoxyphenyl)piperidine-1-carboxamide;

N-(2-chloro-4-fluorophenyl)-4-{3-(cyanomethyl)-3-[3-(7H-pyrrolo[2,3-d]pyrimidin-4-yl)-1H-pyrrol-1-yl]azetidin-1-yl}piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-[3-(trifluoromethyl)pyridin-2-yl]piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-[4-(trifluoromethyl)pyridin-3-yl]piperidine-1-carboxamide;

4-{3-(cyanomethyl)-3-[3-(7H-pyrrolo[2,3-d]pyrimidin-4-yl)-1H-pyrrol-1-yl]azetidin-1-yl}-N-(3-fluoropyridin-2-yl)piperidine-1-carboxamide;

N-(4-chloro-2-cyanophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide;

{1-{1-[3-fluoro-2-(trifluoromethyl)isonicotinoyl]piperidin-4-yl}-3-[4-(1H-pyrrolo[2,3-b]pyridin-4-yl)-1H-pyrazol-1-yl]azetidin-3-yl}acetonitrile;

4-[(4-{3-(cyanomethyl)-3-[4-(1H-pyrrolo[2, 3-b]pyridin-4-yl)-1H-pyrazol-1-yl]azetidin-1-yl}piperidin-1-yl)carbonyl]-3-fluorobenzonitrile;

{1-[1-(3-fluoro-4-hydroxybenzoyl)piperidin-4-yl]-3-[4-(1H-pyrrolo[2,3-b]pyridin-4-yl)-1H-pyrazol-1-yl]azetidin-3-yl}acetonitrile;

{1-[1-(2-fluoro-4-hydroxybenzoyl)piperidin-4-yl]-3-[4-(1H-pyrrolo[2,3-b]pyridin-4-yl)-1H-pyrazol-1-yl]azetidin-3-yl}acetonitrile;

{1-{1-[5-chloro-2-(trifluoromethyl)isonicotinoyl]piperidin-4-yl}-3-[4-(1H-pyrrolo[2,3-b]pyridin-4-yl)-1H-pyrazol-1-yl]azetidin-3-yl}acetonitrile;

[3-[4-(1H-pyrrolo[2,3-b]pyridin-4-yl)-1H-pyrazol-1-yl]-1-(1-{[2-(trifluoromethyl)pyrimidin-4-yl]carbonyl}piperidin-4-yl)azetidin-3-yl]acetonitrile;

[3-[4-(1H-pyrrolo[2,3-b]pyridin-4-yl)-1H-pyrazol-1-yl]-1-(1-{[6-(trifluoromethyl)pyrazin-2-yl]carbonyl}piperidin-4-yl)azetidin-3-yl]acetonitrile;

[3-[4-(1H-pyrrolo[2,3-b]pyridin-4-yl)-1H-pyrazol-1-yl]-1-(1-{[5-(trifluoromethyl)pyrazin-2-yl]carbonyl}piperidin-4-yl)azetidin-3-yl]acetonitrile;

{1-{1-[(4,4-difluorocyclohexyl)carbonyl]piperidin-4-yl}-3-[4-(1H-pyrrolo[2,3-b]pyridin-4-yl)-1H-pyrazol-1-yl]azetidin-3-yl}acetonitrile;

4-{3-(cyanomethyl)-3-[4-(1H-pyrrolo[2,3-b]pyridin-4-yl)-1H-pyrazol-1-yl]azetidin-1-yl}-N-[4-fluoro-2-(trifluoromethyl)phenyl]piperidine-1-carboxamide;

4-{3-(cyanomethyl)-3-[4-(1H-pyrrolo[2,3-b]pyridin-4-yl)-1H-pyrazol-1-yl]azetidin-1-yl}-N-(2,4-difluorophenyl)piperidine-1-carboxamide;

N-(2-chloro-4-fluorophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide;

4-{3-(cyanomethyl)-3-[4-(1H-pyrrolo[2,3-b]pyridin-4-yl)-1H-pyrazol-1-yl]azetidin-1-yl}-N-(2-methoxypyridin-3-yl)piperidine-1-carboxamide;

4-{3-(cyanomethyl)-3-[4-(1H-pyrrolo[2,3-b]pyridin-4-yl)-1H-pyrazol-1-yl]azetidin-1-yl}-N-[3-(trifluoromethyl)pyridin-4-yl]piperidine-1-carboxamide;

4-{3-(cyanomethyl)-3-[4-(1H-pyrrolo[2,3-b]pyridin-4-yl)-1H-pyrazol-1-yl]azetidin-1-yl}-N-[4-(trifluoromethyl)pyridin-3-yl]piperidine-1-carboxamide;

4-{3-(cyanomethyl)-3-[4-(1H-pyrrolo[2,3-b]pyridin-4-yl)-1H-pyrazol-1-yl]azetidin-1-yl}-N-(2-fluorophenyl)piperidine-1-carboxamide;

N-(2-chlorophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide;

4-3-(cyanomethyl)-3-[4-(1H-pyrrolo[2,3-b]pyridin-4-yl)-1H-pyrazol-1-yl]azetidin-1-yl)-N-[4-cyano-2-(trifluoromethyl)phenyl]piperidine-1-carboxamide;

N-(4-cyano-2-fluorophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide;

N-(2-chloro-4-cyanophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide;

(3-[4-(5-fluoro-1H-pyrrolo[2,3-b]pyridin-4-yl)-1H-pyrazol-1-yl]-1-{1-[3-fluoro-2-(trifluoromethyl)isonicotinoyl]piperidin-4-yl}azetidin-3-yl)acetonitrile;

5-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]isophthalonitrile;

3-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-5-fluorobenzonitrile;

4-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-3-fluorobenzonitrile;

5-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-2-fluorobenzonitrile;

{1-{1-[(5-fluoropyridin-2-yl)carbonyl]piperidin-4-yl}-3-[4-(5-fluoro-1H-pyrrolo[2,3-b]pyridin-4-yl)-1H-pyrazol-1-yl]azetidin-3-yl}acetonitrile;

{1-[1-(3-fluoroisonicotinoyl)piperidin-4-yl]-3-[4-(5-fluoro-1H-pyrrolo[2,3-b]pyridin-4-yl)-1H-pyrazol-1-yl]azetidin-3-yl}acetonitrile;

{1-[1-(3,5-difluoroisonicotinoyl)piperidin-4-yl]-3-[4-(5-fluoro-1H-pyrrolo[2,3-b]pyridin-4-yl)-1H-pyrazol-1-yl]azetidin-3-yl}acetonitrile;

{1-[1-(3-fluoro-4-hydroxybenzoyl)piperidin-4-yl]-3-[4-(5-fluoro-1H-pyrrolo[2,3-b]pyridin-4-yl)-1H-pyrazol-1-yl]azetidin-3-yl}acetonitrile;

{1-[1-(2-fluoro-4-hydroxybenzoyl)piperidin-4-yl]-3-[4-(5-fluoro-1H-pyrrolo[2,3-b]pyridin-4-yl)-1H-pyrazol-1-yl]azetidin-3-yl}acetonitrile;
2-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]terephthalonitrile;
4-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-2-fluorobenzonitrile;
{1-{1-[5-chloro-2-(trifluoromethyl)isonicotinoyl]piperidin-4-yl}-3-[4-(5-fluoro-1H-pyrrolo[2,3-b]pyridin-4-yl)-1H-pyrazol-1-yl]azetidin-3-yl}acetonitrile;
{1-{1-[(4,4-difluorocyclohexyl)carbonyl]piperidin-4-yl}-3-[4-(5-fluoro-1H-pyrrolo[2,3-b]pyridine-4-yl)-1H-pyrazol-1-yl]azetidin-3-yl}acetonitrile;
4-3-(cyanomethyl)-3-[4-(5-fluoro-1H-pyrrolo[2,3-b]pyridin-4-yl)-1H-pyrazol-1-yl]azetidin-1-yl)-N-[4-fluoro-2-(trifluoromethyl)phenyl]piperidine-1-carboxamide;
4-{3-(cyanomethyl)-3-[4-(5-fluoro-1H-pyrrolo[2,3-b]pyridin-4-yl)-1H-pyrazol-1-yl]azetidin-1-yl}-N-[3-(trifluoromethyl)pyridin-2-yl]piperidine-1-carboxamide;
4-{3-(cyanomethyl)-3-[4-(5-fluoro-1H-pyrrolo[2,3-b]pyridin-4-yl)-1H-pyrazol-1-yl]azetidin-1-yl}-N-[4-(trifluoromethyl)pyridin-3-yl]piperidine-1-carboxamide;
4-{3-(cyanomethyl)-3-[4-(5-fluoro-1H-pyrrolo[2,3-b]pyridin-4-yl)-1H-pyrazol-1-yl]azetidin-1-yl}-N-[3-(trifluoromethyl)pyridin-4-yl]piperidine-1-carboxamide;
4-[1-(3-(cyanomethyl)-1-{1-[3-fluoro-2-(trifluoromethyl)isonicotinoyl]piperidin-4-yl}azetidin-3-yl)-1H-pyrazol-4-yl]-1H-pyrrolo[2,3-b]pyridine-5-carbonitrile;
4-{1-[1-[1-(3-cyano-5-fluorobenzoyl)piperidin-4-yl]-3-(cyanomethyl)azetidin-3-yl]-1H-pyrazol-4-yl}-1H-pyrrolo[2,3-b]pyridine-5-carbonitrile;
4-{1-[1-[1-(4-cyano-3-fluorobenzoyl)piperidin-4-yl]-3-(cyanomethyl)azetidin-3-yl]-1H-pyrazol-4-yl}-1H-pyrrolo[2,3-b]pyridine-5-carbonitrile;
4-(1-{3-(cyanomethyl)-1-[1-(2,5-dibromobenzoyl)piperidin-4-yl]azetidin-3-yl}-1H-pyrazol-4-yl)-1H-pyrrolo[2,3-b]pyridine-5-carbonitrile;
4-(1-{3-(cyanomethyl)-1-[1-(3,5-dibromobenzoyl)piperidin-4-yl]azetidin-3-yl}-1H-pyrazol-4-yl)-1H-pyrrolo[2,3-b]pyridine-5-carbonitrile;
2-[(4-{3-(cyanomethyl)-3-[4-(5-cyano-1H-pyrrolo[2,3-b]pyridin-4-yl)-1H-pyrazol-1-yl]azetidin-1-yl}piperidin-1-yl)carbonyl]terephthalonitrile;
5-[(4-{3-(cyanomethyl)-3-[4-(5-cyano-1H-pyrrolo[2,3-b]pyridin-4-yl)-1H-pyrazol-1-yl]azetidin-1-yl}piperidin-1-yl)carbonyl]isophthalonitrile;
4-{1-[1-[1-(4-cyano-2-fluorobenzoyl)piperidin-4-yl]-3-(cyanomethyl)azetidin-3-yl]-1H-pyrazol-4-yl}-1H-pyrrolo[2,3-b]pyridine-5-carbonitrile;
4-{1-[1-[1-(4-cyano-2, 6-difluorobenzoyl)piperidin-4-yl]-3-(cyanomethyl)azetidin-3-yl]-1H-pyrazol-4-yl}-1H-pyrrolo[2,3-b]pyridine-5-carbonitrile;
4-{1-[1-{1-[5-chloro-2-(trifluoromethyl)isonicotinoyl]piperidin-4-yl}-3-(cyanomethyl)azetidin-3-yl]-1H-pyrazol-4-yl)}-1H-pyrrolo[2,3-b]pyridine-5-carbonitrile;
{1-{1-[5-Chloro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;
{1-{1-[5-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;
[3-[4-(7H-Pyrrolo[2,3-d]pyrimidin-4-yl)-1H-pyrazol-1-yl]-1-(1-{[4-(trifluoromethyl)-1,3-thiazol-2-yl]carbonyl}piperidin-4-yl)azetidin-3-yl]acetonitrile;
[3-[3-(7H-Pyrrolo[2,3-d]pyrimidin-4-yl)-1H-pyrrol-1-yl]-1-(1-{[2-(trifluoromethyl)pyrimidin-4-yl]carbonyl}piperidin-4-yl)azetidin-3-yl]acetonitrile;
[3-[3-(7H-Pyrrolo[2,3-d]pyrimidin-4-yl)-1H-pyrrol-1-yl]-1-(1-{[4-(trifluoromethyl)-1,3-thiazol-2-yl]carbonyl}piperidin-4-yl)azetidin-3-yl]acetonitrile;
[3-[3-(7H-Pyrrolo[2,3-d]pyrimidin-4-yl)-1H-pyrrol-1-yl]-1-(1-{[5-(trifluoromethyl)pyrazin-2-yl]carbonyl}piperidin-4-yl)azetidin-3-yl]acetonitrile;
{1-[1-(Methylsulfonyl)piperidin-4-yl]-3-[3-(7H-pyrrolo[2,3-d]pyrimidin-4-yl)-1H-pyrrol-1-yl]azetidin-3-yl}acetonitrile;
[3-[4-(1H-Pyrrolo[2,3-b]pyridin-4-yl)-1H-pyrazol-1-yl]-1-(1-{[5-(trifluoromethyl)pyrazin-2-yl]carbonyl}piperidin-4-yl)azetidin-3-yl]acetonitrile;
[3-[4-(1H-Pyrrolo[2,3-b]pyridin-4-yl)-1H-pyrazol-1-yl]-1-(1-{[4-(trifluoromethyl)-1,3-thiazol-2-yl]carbonyl}piperidin-4-yl)azetidin-3-yl]acetonitrile;
{1-[1-(Methylsulfonyl)piperidin-4-yl]-3-[4-(1H-pyrrolo[2,3-b]pyridin-4-yl)-1H-pyrazol-1-yl]azetidin-3-yl}acetonitrile;
[3-[4-(5-Fluoro-1H-pyrrolo[2,3-b]pyridin-4-yl)-1H-pyrazol-1-yl]-1-(1-{[6-(trifluoromethyl)pyrazin-2-yl]carbonyl}piperidin-4-yl)azetidin-3-yl]acetonitrile;
[3-[4-(5-Fluoro-1H-pyrrolo[2,3-b]pyridin-4-yl)-1H-pyrazol-1-yl]-1-(1-{[2-(trifluoromethyl)pyrimidin-4-yl]carbonyl}piperidin-4-yl)azetidin-3-yl]acetonitrile;
[3-[4-(5-Fluoro-1H-pyrrolo[2, 3-b]pyridin-4-yl)-1H-pyrazol-1-yl]-1-(1-{[5-(trifluoromethyl)pyrazin-2-yl]carbonyl}piperidin-4-yl)azetidin-3-yl]acetonitrile;
{3-[4-(5-Fluoro-1H-pyrrolo[2, 3-b]pyridin-4-yl)-1H-pyrazol-1-yl]-1-[1-(methylsulfonyl)piperidin-4-yl]azetidin-3-yl}acetonitrile;
4-[1-(3-(Cyanomethyl)-1-{1-[5-fluoro-2-(trifluoromethyl)isonicotinoyl]piperidin-4-yl}azetidin-3-yl)-1H-pyrazol-4-yl]-1H-pyrrolo[2,3-b]pyridine-5-carbonitrile; and
4-(1-{3-(Cyanomethyl)-1-[1-(methylsulfonyl)piperidin-4-yl]azetidin-3-yl}-1H-pyrazol-4-yl)-1H-pyrrolo[2,3-b]pyridine-5-carbonitrile;
or a pharmaceutically acceptable salt of any of the aforementioned.

In some embodiments, the compound is selected from:
cis-{1-{3-Methoxy-1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;
{1-(cis-3-Methoxy-1-{[2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;
{1-{cis-3-Fluoro-1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;
{1-(cis-3-Fluoro-1-{[2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;
{1-{1-[3-Fluoro-2-(trifluoromethyl)isonicotinoyl]-4-deuteropiperidin-4-yl}-3-[4-(7H-pyrrolo[2,3-d]pyrimidin-4-yl)-1H-pyrazol-1-yl]azetidin-3-yl}acetonitrile;
{1-{1-[3-Fluoro-2-(trifluoromethyl)isonicotinoyl]3,3,4,5,5-pentadeuteropiperidin-4-yl)}-3-[4-(7H-pyrrolo[2,3-d]pyrimidin-4-yl)-1H-pyrazol-1-yl]azetidin-3-yl}acetonitrile;
{1-{7-[3-Fluoro-2-(trifluoromethyl)isonicotinoyl]-3-oxa-7-azabicyclo[3.3.1]non-9-yl)}-3-[4-(7H-pyrrolo[2,3-d]pyrimidin-4-yl)-1H-pyrazol-1-yl]azetidin-3-yl}acetonitrile;
{1-(1-{[4-[(dimethylamino)methyl]-6-(trifluoromethyl)pyridin-2-yl]carbonyl}piperidin-4-yl)-3-[4-(7H-pyrrolo[2,3-d]pyrimidin-4-yl)-1H-pyrazol-1-yl]azetidin-3-yl}acetonitrile;

4-{3-(cyanomethyl)-3-[4-(7H-pyrrolo[2,3-d]pyrimidin-4-yl)-1H-pyrazol-1-yl]azetidin-1-yl}-N-isopropylpiperidine-1-carboxamide;

{1-{1-[6-[(dimethylamino)methyl]-3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile;

3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-5-[(dimethylamino)methyl]benzonitrile;

{1-(1-{[6-[(dimethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-[(methylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-(azetidin-1-ylmethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-[(diethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-{[ethyl(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{3-(difluoromethyl)-5-[(dimethylamino)methyl]benzoyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-(pyrrolidin-1-ylmethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-{[(3 S)-3-fluoropyrrolidin-1-yl]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-{[(3R)-3-fluoropyrrolidin-1-yl]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-[(3,3-difluoropyrrolidin-1-yl)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-[(tert-butylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-(hydroxymethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-[(isopropylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-[(ethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-{[(2-methoxyethyl)(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

{1-(1-{[6-{[(3-hydroxypropyl)(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile;

propyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

cyclobutylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

ethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

benzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

isobutyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

cyclopropylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

(1-methylcyclopropyl)methyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

2,4-difluorobenzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

3,4-difluorobenzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

3,5-difluorobenzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

cyclopentylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate; and cyclohexylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate;

or a pharmaceutically acceptable salt of any of the aforementioned.

In some embodiments, the salt is a 1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt. In some embodiments, the salt is a 1:1 1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile:adipic acid salt. In some embodiments, the salt is that described in Example 358.

In some embodiments, the salt is characterized by a melting point of about 178° C. In some embodiments, the salt has a differential scanning calorimetry thermogram which is characterized by an endothermic peak with an onset temperature of about 176° C. In some embodiments, the salt has a differential scanning calorimetry thermogram substantially as shown in FIG. 1.

Figure 2:
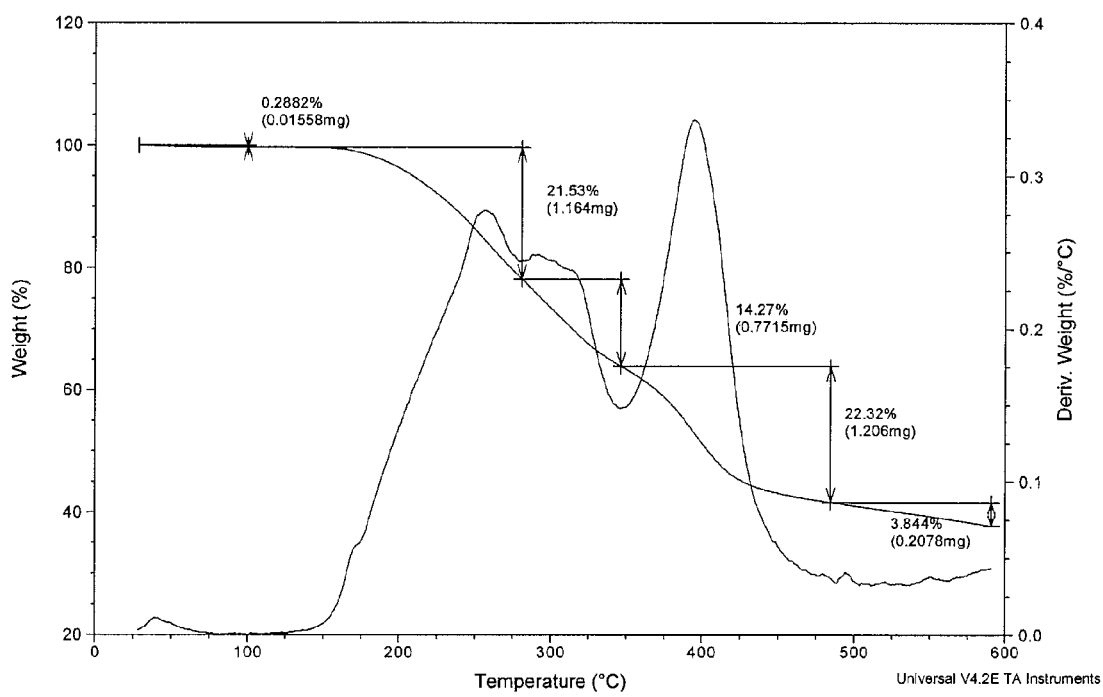
FIG. 2 depicts the TGA thermogram for the product of Example 358.
Figure 3:
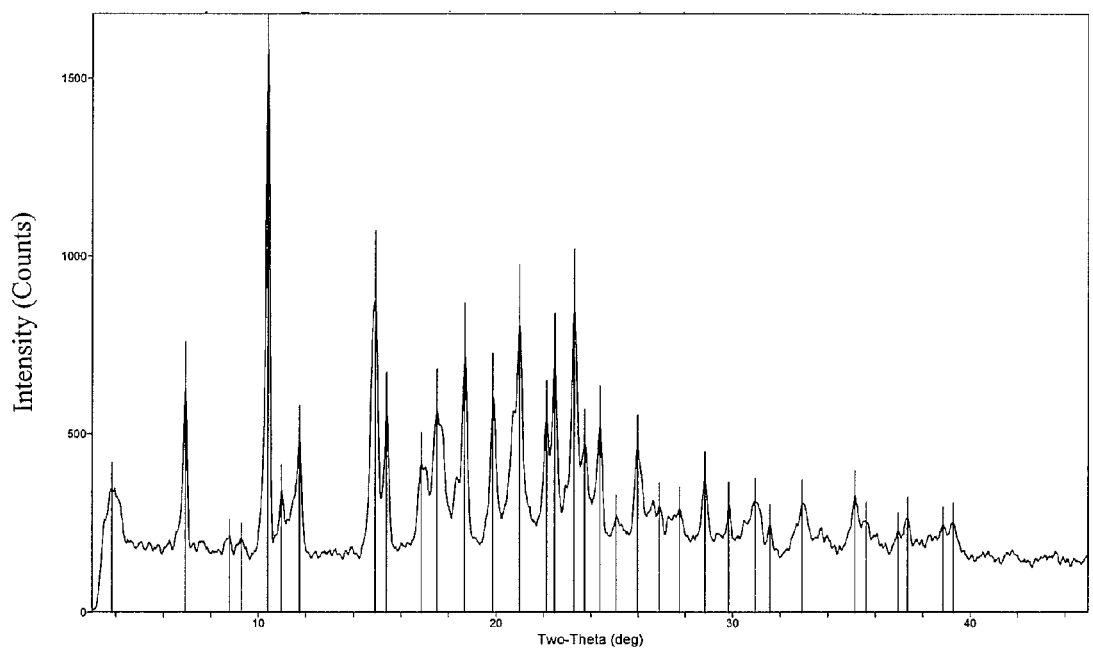
FIG. 3 depicts the XRPD pattern for the product of Example 358.

In some embodiments, the salt has a thermal gravimetric analysis thermogram substantially as shown in FIG. 2. In some embodiments, the salt has an X-ray powder diffraction pattern comprising a characteristic peak expressed in degrees 2θ at about 10.4. In some embodiments, the salt has an X-ray powder diffraction pattern comprising a characteristic peak expressed in degrees 2θ at about 6.9. In some embodiments, the salt has an X-ray powder diffraction pattern comprising a characteristic peak expressed in degrees 2θ at about 21.0. In some embodiments, the salt has an X-ray powder diffraction pattern comprising a characteristic peak expressed in degrees 2θ at about 23.3. In some embodiments, the salt has an X-ray powder diffraction pattern comprising a characteristic peak expressed in degrees 2θ at about 6.9, 10.4, 21.0, and 23.3. In some embodiments, the salt has an X-ray powder diffraction pattern substantially as shown in FIG. 3.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about +3° C. depending on the instrument, particular settings, sample preparation, etc. Accordingly, a crystalline form reported herein having a DSC thermogram "substantially" as shown in any of the Figures is understood to accommodate such variation.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is to be understood that the "alkyl" or "aryl" represents a linking alkylene group or arylene group, respectively.

At various places in the present specification, rings are described (e.g., "a piperidine ring"). Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

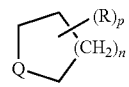

then it is to be understood that substituent R can occur p number of times on the ring, and R can be a different moiety at each occurrence. It is to be understood that each R group may replace any hydrogen atom attached to a ring atom, including one or both of the (CH$_2$)$_n$ hydrogen atoms. Further, in the above example, should the variable Q be defined to include hydrogens, such as when Q is said to be CH$_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, n-octyl, and the like.

As used herein, "$C_{n-m}$ alkenyl", employed alone or in combination with other terms, refers to an alkyl group having one or more carbon-carbon double bonds and n to m carbon atoms. In some embodiments, the alkenyl moiety contains 2 to 6, or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more carbon-carbon triple bonds and n to m carbon atoms. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo.

As used herein, "hydroxyl" or "hydroxy" refer to a group of formula —OH.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms.

Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, the term "$C_{n-m}$ fluoroalkyl", employed alone or in combination with other terms, refers to a $C_{n-m}$ haloalkyl wherein the halogen atoms are selected from fluorine. In some embodiments, $C_{n-m}$ fluroalkyl is fluoromethyl, difluoromethyl, or trifluoromethyl.

As used herein, the term "$C_{n-m}$ alkoxy", employed alone or in combination with other terms, refers to an group of formula —O-alkyl, wherein the alkyl group has n to m carbon atoms. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "$C_{n-m}$ haloalkoxy", employed alone or in combination with other terms, refers to a group of formula —O-(haloalkyl), wherein the haloalkyl group has n to m carbon atoms. In some embodiments, the alkyl group has 1 to 6 or 1 to 4 carbon atoms. An example haloalkoxy group is —$OCF_3$. In some embodiments, the haloalkoxy group is a fluoroalkoxy group.

As used herein, the term "$C_{n-m}$ fluoroalkoxy", employed alone or in combination with other terms, refers to a $C_{n-m}$ alkoxy group, wherein the halogen atoms are selected from fluorine.

As used herein, "amino", employed alone or in combination with other terms, refers to —$NH_2$.

As used herein, the term "$C_{n-m}$ alkylamino", employed alone or in combination with other terms, refers to a group of formula —NH(alkyl), wherein the alkyl group has n to m carbon atoms. In some embodiments, alkyl group has 1 to 6 or 1 to 4 carbon atoms. Example $C_{n-m}$ alkylamino groups include methylamino, ethylamino, propylamino (e.g., n-propylamino and isopropylamino), and the like.

As used herein, the term "di-$C_{n-m}$-alkylamino", employed alone or in combination with other terms, refers to a group of formula —N(alkyl)$_2$, wherein each alkyl group has independently n to m carbon atoms. Example di-$C_{n-m}$-alkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "carboxy", employed alone or in combination with other terms, refers to a group of formula —C(O)OH.

As used herein, the term "$C_{n-m}$ alkoxycarbonyl", employed alone or in combination with other terms, refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl", employed alone or in combination with other terms, refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino", employed alone or in combination with other terms, refers to a group of formula —NHC(O)-alkyl, wherein the alkyl group has n to m carbon atoms. In some embodiments, the alkyl group has 1 to 6 or 1 to 4 carbon atoms.

As used herein, the term "carbamyl", employed alone or in combination with other terms, refers to a group of formula —C(O)—$NH_2$.

As used herein, the term "$C_{n-m}$ alkylcarbamyl", employed alone or in combination with other terms, refers to a group of formula —C(O)—NH(alkyl), wherein the alkyl group has n to m carbon atoms. In some embodiments, the alkyl group has 1 to 6 or 1 to 4 carbon atoms.

As used herein, the term "di-$C_{n-m}$ alkylcarbamyl", employed alone or in combination with other terms, refers to a group of formula —C(O)—N(alkyl)$_2$, wherein the each alkyl group independently has n to m carbon atoms. In some embodiments, the alkyl group independently has 1 to 6 or 1 to 4 carbon atoms.

As used herein, the term "thio" refers to a group of formula —SH.

As used herein, the term "$C_{n-m}$ alkylthio", employed alone or in combination with other terms, refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl", employed alone or in combination with other terms, refers to a group of formula —S(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl", employed alone or in combination with other terms, refers to a group of formula —S(O)$_2$-alkyl, wherein the alkyl group has n to m carbon atoms. In some embodiments, the alkyl group has 1 to 6 or 1 to 4 carbon atoms.

As used herein, "halosulfanyl" refers to a sulfur group having one or more halogen substituents. Example halosulfanyl groups include pentahalosulfanyl groups such as $SF_5$.

As used herein, the term "2- or 3-carbon bridge" means that two different R groups on different ring member atoms form a bridge (—$CH_2$—$CH_2$— or —$CH_2$—$CH_2$—$CH_2$—) between the two ring member atoms, wherein the two or three carbons does not include the ring member atoms. For a non-limiting examples, see Example 138, where two $R^1$ groups form a 2-carbon bridge.

As used herein, the term "bridge of formula —$CH_2$—O—$CH_2$—" means that two different R groups on different ring member atoms form a bridge between the two ring member atoms of formula —$CH_2$—O—$CH_2$—, where the ring member atoms are not part of formula —$CH_2$—O—$CH_2$—.

As used herein, the term "hydroxyl-$C_{1-4}$ alkyl" refers to a group of formula —$C_{1-4}$ alkylene-OH.

As used herein, the term "$C_{1-4}$ alkoxy-$C_{1-4}$ alkyl" refers to a group of formula —$C_{1-4}$ alkylene-O—($C_{1-4}$ alkyl).

As used herein, the term "$C_{n-m}$ cycloalkyl", employed alone or in combination with other terms, refers to a non-aromatic cyclic hydrocarbon including cyclized alkyl, alkenyl, and alkynyl groups, and which has n to m ring member carbon atoms. Cycloalkyl groups can include mono- or polycyclic (e.g., having 2,3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclopentene, cyclohexane, and the like. Ring-forming carbon atoms of a cycloalkyl group can be optionally substituted by oxo. Cycloalkyl groups also include cycloalkylidenes. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 7 ring members. In some embodiments, the cycloalkyl group is monocyclic, bicyclic or tricyclic. In some embodiments, the cycloalkyl group is monocyclic. In some embodiments, the cycloalkyl group is a $C_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, tetrahydronaphthalenyl, octahydronaphthalenyl, indanyl, and the like.

As used herein, the term "$C_{n-m}$ cycloalkyl-$C_{o-p}$ alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "$C_{n-m}$ heterocycloalkyl", "$C_{n-m}$ heterocycloalkyl ring", or "$C_{n-m}$ heterocycloalkyl group", employed alone or in combination with other terms, refers to non-aromatic ring or ring system, which may optionally contain one or more alkenylene or alkynylene groups as part of the ring structure, which has at least one heteroatom ring member independently selected from nitrogen, sulfur oxygen and phosphorus, and which has n to m ring member carbon atoms. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic ring, for example, 1,2,3,4-tetrahydro-quinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 14 ring-forming atoms, 3 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or hetereoatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. Examples of heterocycloalkyl groups include 1,2,3,4-tetrahydro-quinoline, azetidine, azepane, pyrrolidine, piperidine, piperazine, morpholine, thiomorpholine, and pyran.

As used herein, the term "$C_{n-m}$ heterocycloalkyl-$C_{o-p}$ alkyl", employed alone or in combination with other terms, refers to a group of formula -alkylene-heterocycloalkyl, wherein the heterocycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "$C_{n-m}$ aryl", employed alone or in combination with other terms, refers to a monocyclic or polycyclic (e.g., having 2, 3 or 4 fused rings) aromatic hydrocarbon moiety having n to m ring member carbon atoms, such as, but not limited to, phenyl, 1-naphthyl, 2-naphthyl, anthracenyl, phenanthrenyl, and the like. In some embodiments, aryl groups have from 6 to 20 carbon atoms, from 6 to 14 carbon atoms, from 6 to 10 carbon atoms, or 6 carbon atoms. In some embodiments, the aryl group is a monocyclic or bicyclic group.

As used herein, the term "$C_{n-m}$ aryl-$C_{o-p}$-alkyl", employed alone or in combination with other terms, refers to a group of formula -alkylene-aryl, wherein the aryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "$C_{n-m}$ heteroaryl", "$C_{n-m}$ heteroaryl ring", or "$C_{n-m}$ heteroaryl group", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen and having n to m ring member carbon atoms. In some embodiments, the heteroaryl group is a monocyclic or bicyclic group having 1, 2, 3, or 4 hetereoatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, pyrrolyl, azolyl, oxazolyl, quinolinyl, isoquinolinyl, indolyl, benzothienyl, benzofuranyl, benzisoxazolyl, imidazo[1,2-b]thiazolyl or the like. The carbon atoms or hetereoatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 1 to 20 carbon atoms, from 3 to 20 carbon atoms, from 3 to 15 carbon atoms, from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "$C_{n-m}$ heteroaryl-$C_{o-p}$-alkyl", employed alone or in combination with other terms, refers to a group of formula -alkylene-heteroaryl, wherein the heteroaryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 hetereoatoms independently selected from nitrogen, sulfur and oxygen. In some embodiments, the heteroaryl portion has 5 to 10 carbon atoms.

As used herein, the term "$C_{n-m}$ aryloxy" refers to a moiety of formula —O-aryl, wherein the aryl ring has n to m carbon atoms.

As used herein, the appearance of the term "bicyclic" before the name of a moiety indicates that the moiety has two fused rings.

As used herein, the appearance of the term "monocyclic" before the name of a moiety indicates that the moiety has a single ring.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ groups in the azetidine ring of Formula I are replaced by a CHD or $CD_2$ group. In some embodiments, 1, 2, or 3 $CH_2$ or CH groups in the piperidine ring of Formula I are replaced by a CHD, $CD_2$ or CD group, respectively. In some embodiments, 1, 2, 3, 4, or 5 $CH_2$ or CH groups in the piperidine ring of Formula I are replaced by a CHD, $CD_2$ or CD group, respectively.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. In some embodiments, the compounds described herein include the N-oxide forms.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

Compounds of Formula I can be prepared using methods outlined in Schemes 1-4. Intermediates of formula 1-5 can be synthesized according to the methods described in Scheme 1. The commercially available starting material pyrrolo[2,3-d]pyrimidine-4-halide or 5-substituted pyrrolo[2,3-b]pyridine-4-halide (1-1) can be converted to a SEM (2-(trimethylsilyl)ethoxymethyl) protected intermediate of formula 1-2 by treating with sodium hydride followed by 2-(trimethylsilyl)ethoxymethyl chloride. Suzuki coupling of 1-2 with a boronic acid of pyrazole, such as 1-(1-ethoxyethyl)-4-(4,4,5,5-tetramethyl-1,3,2-dioxaborolan-2-yl)-1H-pyrazole (1-3), using a palladium reagent, such as tetrakis(triphenylphosphine)palladium(0), gives rise to the intermediate 1-4, which in situ can be converted to the desired product 1-5 after prolongation of the reaction.

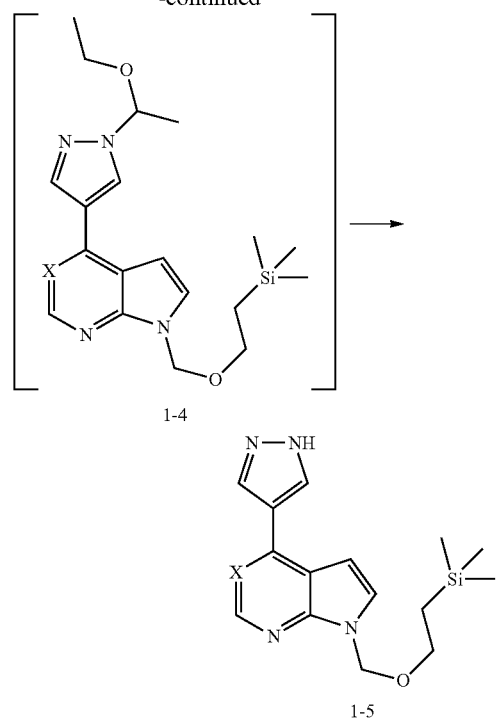

W = Cl, Br, or I
X = N or CR²

Intermediates of formula 2-3 can be synthesized according the sequence depicted in Scheme 2. The SEM-protected intermediate 1-2 is subjected to a Suzuki coupling with a boronic acid of a protected pyrrole, such as 1-(triisopropylsilyl)pyrrole-3-boronic acid (2-1), using a palladium reagent, such as tetrakis(triphenylphosphine)palladium(0), in the presence of a base. The coupling product of formula 2-2 can be converted to the desired product of formula 2-3 in situ by carrying out the reaction overnight in the same media.

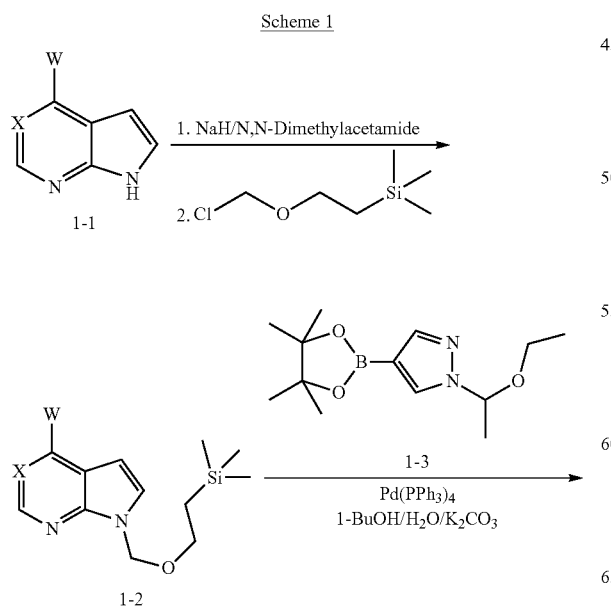

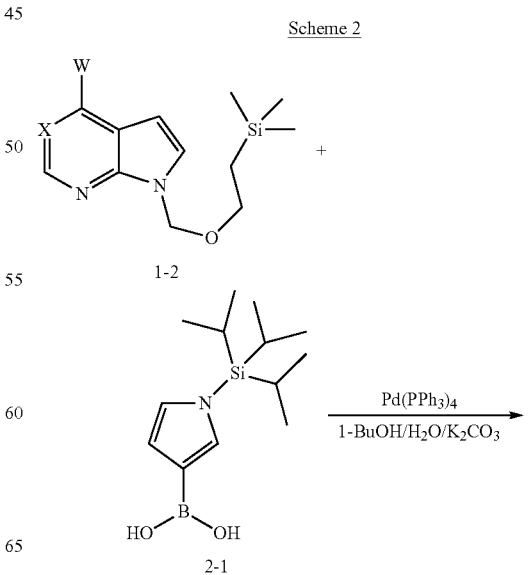

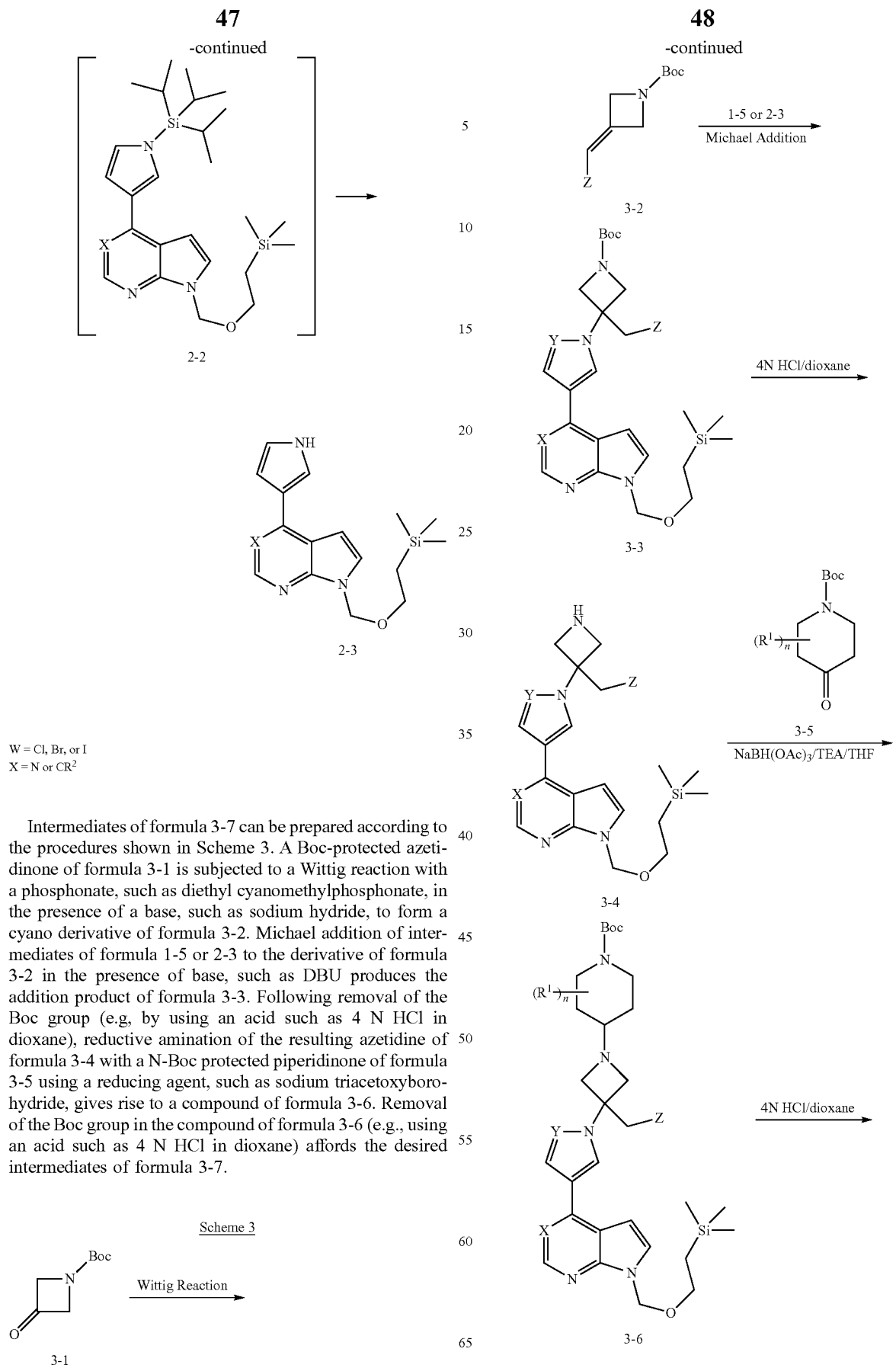

W = Cl, Br, or I
X = N or CR²

Intermediates of formula 3-7 can be prepared according to the procedures shown in Scheme 3. A Boc-protected azetidinone of formula 3-1 is subjected to a Wittig reaction with a phosphonate, such as diethyl cyanomethylphosphonate, in the presence of a base, such as sodium hydride, to form a cyano derivative of formula 3-2. Michael addition of intermediates of formula 1-5 or 2-3 to the derivative of formula 3-2 in the presence of base, such as DBU produces the addition product of formula 3-3. Following removal of the Boc group (e.g, by using an acid such as 4 N HCl in dioxane), reductive amination of the resulting azetidine of formula 3-4 with a N-Boc protected piperidinone of formula 3-5 using a reducing agent, such as sodium triacetoxyborohydride, gives rise to a compound of formula 3-6. Removal of the Boc group in the compound of formula 3-6 (e.g., using an acid such as 4 N HCl in dioxane) affords the desired intermediates of formula 3-7.

Scheme 3

-continued

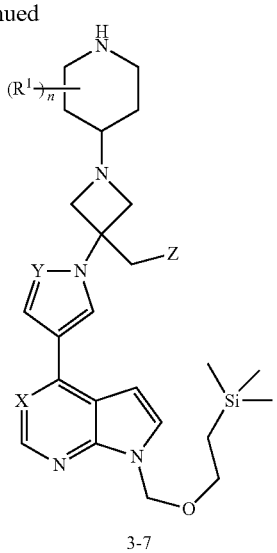

X = N or CR²
Y = N or CR³

Intermediates of formula 3-7 can be derivatized at the piperidine nitrogen to produce a series of compounds of Formula I as depicted in Scheme 4. Reaction of the compound of formula 3-7 with a sulfonyl chloride followed by treating first with TFA and and then with ethylenediamine to remove the SEM group yields sulfonamide derivatives of formula 4-1. Coupling of the compound of formula 3-7 with a carboxylic acid using a coupling agent such as BOP or with an acyl chloride, followed by removal of the SEM group provides amide compounds of formula 4-2. Reductive amination of the compound of formula 3-7 with an aldehyde using a reducing agent, such as sodium triacetoxyborohydride, followed by removal of the SEM group gives rise to the N-alkyl derivatives of formula 4-3. Reaction of the compound of formula 3-7 with an isocyanate, followed by removing the SEM group affords the urea compounds of formula 4-4.

Scheme 4

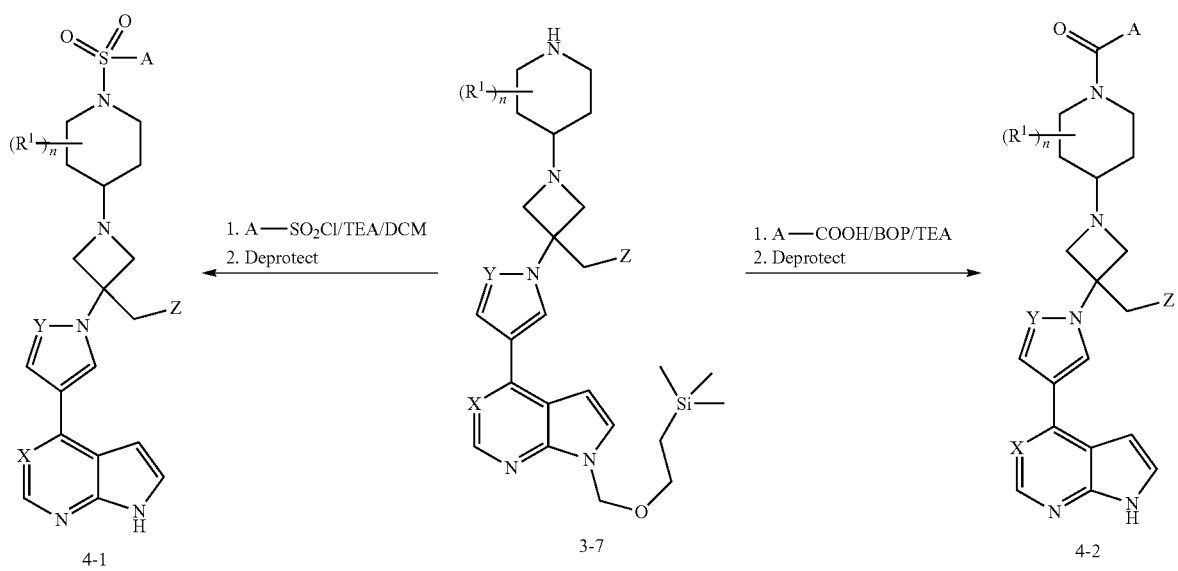

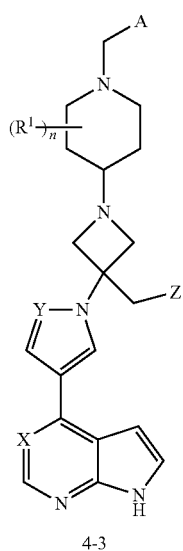

4-3

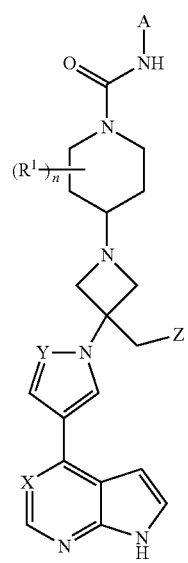

4-4

Methods

Compounds of the invention are JAK inhibitors, and the majority of the compounds of the invention, are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 $IC_{50}$ ratio >1). In some embodiments, the compounds are about 10-fold more selective for JAK1 over JAK2. In some embodiments, the compounds are about 3-fold, about 5-fold, about 10-fold, about 15-fold, or about 20-fold more selective for JAK1 over JAK2 as calculated by measuring $IC_{50}$ at 1 mM ATP (e.g., see Example A).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106: 9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET). In some embodiments, the myeloproliferative disorder is post polycythemia vera myelofibrosis (Post-PV MF).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anticancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279(19): 19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 Apr. 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted subepithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating JAK1. In some embodiments, the present invention also provides use of a compound of Formula I as described herein, or a pharmaceutically acceptable salt thereof, for the preparation of a medicament for use in a method of modulating JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxyline). In some embodiments, the additional therapeutic agent binds to FKBP 12.

In some embodiments, the additional therapeutic agent is an alkylating agent or DNA cross-linking agent; an anti-metabolite/demethylating agent (e.g., 5-flurouracil, capecitabine or azacitidine); an anti-hormone therapy (e.g., hormone receptor antagonists, SERMs, or aromatase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmicin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paromomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxypropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the choroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety.

In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly (lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art.

Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein.

EXAMPLES

The example compounds below containing one or more chiral centers were obtained in enantiomerically pure form or as scalemic mixtures, unless otherwise specified.

Unless otherwise indicated, the example compounds were purified by preparative HPLC using acidic conditions (method A) and were obtained as a TFA salt or using basic conditions (method B) and were obtained as a free base.

Method A:
Column: Waters Sun Fire C18, 5 μm particle size, 30×100 mm;
Mobile phase: water (0.1% TFA)/acetonitrile
Flow rate: 60 mL/min
Gradient: 5 min or 12 min from 5% acetonitrile/95% water to 100% acetonitrile
Method B:
Column: Waters X Bridge C18, 5 m particle size, 30×100 mm;
Mobile phase: water (0.15% NH₄OH)/acetonitrile
Method C:
Column: C18 column, 5 μm OBD
Mobile phase: water+0.05% NH₄₀H (A), CH₃CN+0.05% NH₄OH (B)
Gradient: 5% B to 100% B in 15 min
Flow rate: 60 mL/min Example 1

{1-{1-[3-Fluoro-2-(trifluoromethyl)isonicotinoyl] piperidin-4-yl}-3-[4-(7H-pyrrolo[2,3-d]pyrimidin-4-yl)-1H-pyrazol-1-yl]azetidin-3-yl}acetonitrile

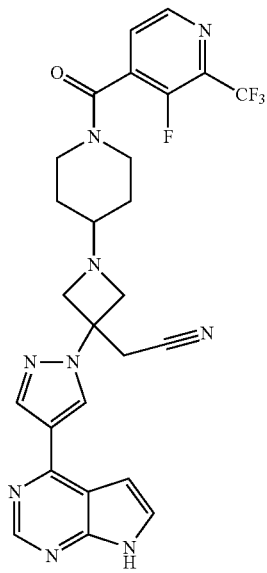 [SMILES: N#CCC1(n2cc(-c3ncnc4[nH]ccc34)cn2)CN(C2CCN(C(=O)c3ccnc(C(F)(F)F)c3F)CC2)C1]

Step A: tert-Butyl 3-Oxoazetidine-1-carboxylate

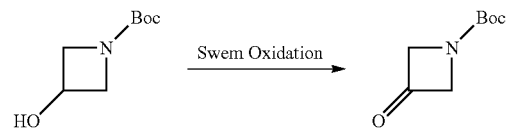 [SMILES: CC(C)(C)OC(=O)N1CC(O)C1 ; CC(C)(C)OC(=O)N1CC(=O)C1]

To a mixture of tert-butyl 3-hydroxyazetidine-1-carboxylate (10.0 g, 57.7 mmol), dimethyl sulfoxide (24.0 mL, 338 mmol), triethylamine (40 mL, 300 mmol) and methylene chloride (2.0 mL) was added sulfur trioxide-pyridine complex (40 g, 200 mmol) portionwise at 0° C. The mixture was stirred for 3 hours, quenched with brine, and extracted with methylene chloride. The combined extracts were dried over anhydrous Na₂SO₄, filtered, and concentrated under reduced pressure. The residue was purified by silica gel column (0-6% ethyl acetate (EtOAc) in hexanes) to give tert-butyl 3-oxoazetidine-1-carboxylate (5.1 g, 52% yield).

Step B: tert-Butyl 3-(Cyanomethylene)azetidine-1-carboxylate

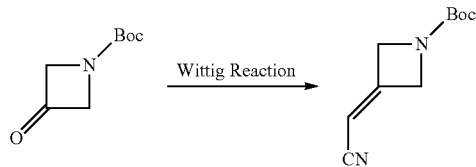 [SMILES: CC(C)(C)OC(=O)N1CC(=O)C1 ; CC(C)(C)OC(=O)N1CC(=CC#N)C1]

An oven-dried 1 L 4-neck round bottom flask fitted with stir bar, septa, nitrogen inlet, 250 ml addition funnel and thermocouple was charged with sodium hydride (5.6 g, 0.14 mol) and tetrahydrofuran (THF) (140 mL) under a nitrogen atmosphere. The mixture was chilled to 3° C., and then charged with diethyl cyanomethylphosphonate (22.4 mL, 0.138 mol) dropwise via a syringe over 20 minutes. The solution became a light yellow slurry. The reaction was then stirred for 75 minutes while warming to 18.2° C. A solution of tert-butyl 3-oxoazetidine-1-carboxylate (20 g, 0.1 mol) in tetrahydrofuran (280 mL) was prepared in an oven-dried round bottom, charged to the addition funnel via canula, then added to the reaction mixture dropwise over 25 minutes. The reaction solution became red in color. The reaction was allowed to stir overnight. The reaction was checked after 24 hours by TLC (70% hexane/EtOAc) and found to be complete. The reaction was diluted with 200 mL of 20% brine and 250 mL of EtOAc. The solution was partitioned and the aqueous phase was extracted with 250 mL of EtOAc. The combined organic phase was dried over MgSO₄ and filtered, evaporated under reduced pressure, and purified by flash chromatography (0% to 20% EtOAc/hexanes, 150 g flash column) to give the desired product, tert-butyl 3-(cyanomethylene)azetidine-1-carboxylate (15 g, 66.1% yield).

Step C: 4-Chloro-7-{[2-(trimethylsilyl)ethoxy]methyl}-7H-pyrrolo[2,3-d]pyrimidine

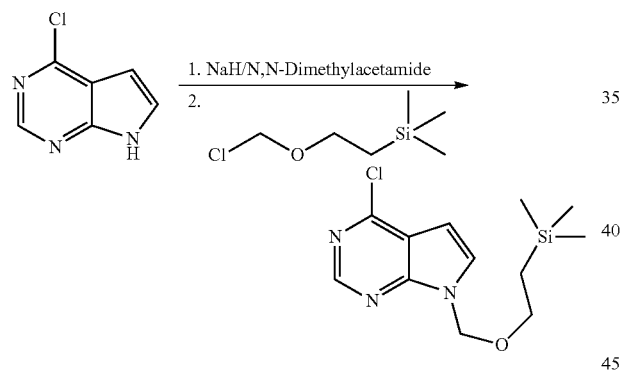

To a suspension of sodium hydride (36.141 g, 903.62 mmol) in N,N-dimethylacetamide (118 mL) at −5° C. (ice/salt bath) was added a dark solution of 4-chloropyrrolo[2,3-d]pyrimidine (119.37 g, 777.30 mmol) in N,N-dimethylacetamide (237 mL) slowly. The flask and addition funnel were rinsed with N,N-dimethylacetamide (30 mL). A large amount of gas was evolved immediately. The mixture became a slightly cloudy orange mixture. The mixture was stirred at 0° C. for 60 min to give a light brown turbid mixture. To the mixture was slowly added [2-(trimethylsilyl)ethoxy]methyl chloride (152.40 g, 914.11 mmol) and the reaction was stirred at 0° C. for 1 h. The reaction was quenched by addition of 12 mL of H₂O slowly. More water (120 mL) was added followed by methyl tert-butyl ether (MTBE) (120 mL). The mixture was stirred for 10 min. The organic layer was separated. The aqueous layer was extracted with another portion of MTBE (120 mL). The organic extracts were combined, washed with brine (120 mL×2) and concentrated under reduced pressure to give the crude product 4-chloro-7-{[2-(trimethylsilyl)ethoxy]methyl}-7H-pyrrolo[2,3-d]pyrimidine as a dark oil. Yield: 85.07 g (97%); LC-MS: 284.1 (M+H)⁺. It was carried to the next reaction without purification.

Step D: 4-(1H-Pyrazol-4-yl)-7-{[2-(trimethylsilyl)ethoxy]methyl}-7H-pyrrolo[2,3-d]pyrimidine

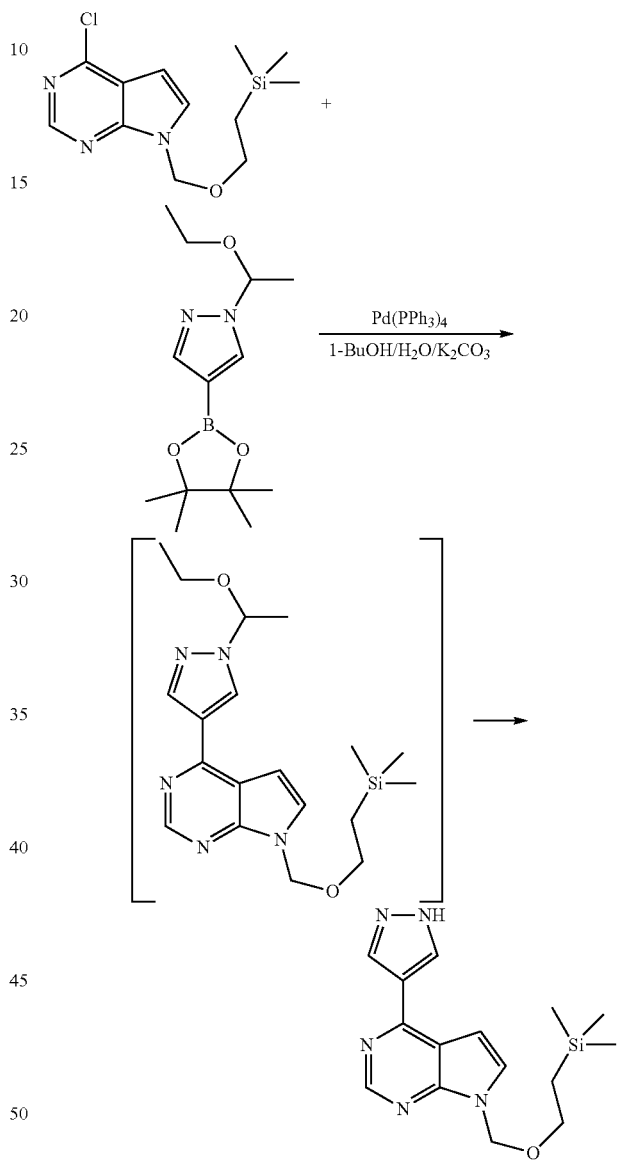

A 1000 mL round bottom flask was charged with 4-chloro-7-{[2-(trimethylsilyl)ethoxy]methyl}-7H-pyrrolo[2,3-d]pyrimidine (10.00 g, 35.23 mmol), 1-butanol (25.0 mL), 1-(1-ethoxyethyl)-4-(4,4,5,5-tetramethyl-1,3,2-dioxaborolan-2-yl)-1H-pyrazole (15.66 g, 52.85 mmol), water (25.0 mL) and potassium carbonate (12.17 g, 88.08 mmol). This solution was degased 4 times, filling with nitrogen each time. To the solution was added tetrakis(triphenylphosphine)palladium(0) (4.071 g, 3.523 mmol). The solution was degased 4 times, filling with nitrogen each time. The mixture was stirred overnight at 100° C. After being cooled to room temperature, the mixture was filtered through a bed of celite and the celite was rinsed with ethyl acetate (42 mL). The filtrate was combined, and the organic layer was separated.

The aqueous layer was extracted with ethyl acetate. The organic extracts were combined and concentrated under vacuum with a bath temperature of 30-70° C. to give the final compound 4-(1H-pyrazol-4-yl)-7-{[2-(trimethylsilyl)ethoxy]methyl}-7H-pyrrolo[2,3-d]pyrimidine. Yield: 78%. LC-MS: 316.2 (M+H)+.

Step E: tert-Butyl 3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidine-1-carboxylate

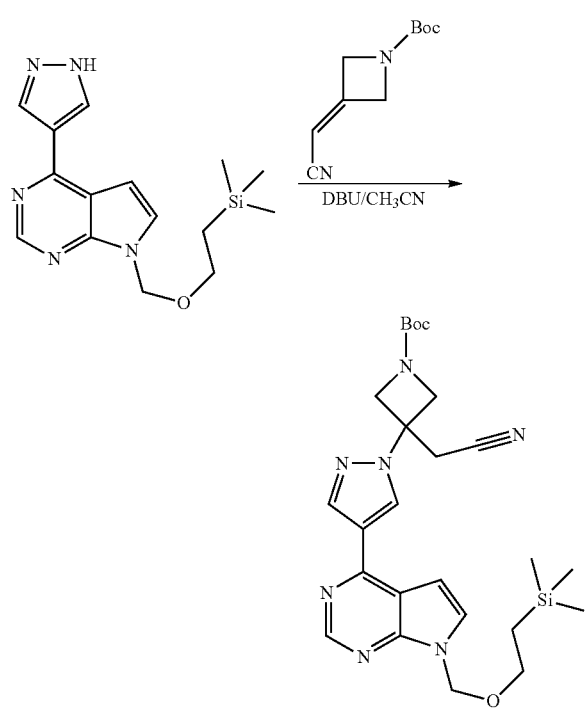

A 2 L round bottom flask fitted with overhead stirring, septa and nitrogen inlet was charged with tert-butyl 3-(cyanomethylene)azetidine-1-carboxylate (9.17 g, 0.0472 mol), 4-(1H-pyrazol-4-yl)-7-{[2-(trimethylsilyl)ethoxy]methyl}-7H-pyrrolo[2,3-d]pyrimidine (14.9 g, 0.0472 mol) and acetonitrile (300 mL). The resulting solution was heterogeneous. To the solution was added 1,8-diazabicyclo[5.4.0]undec-7-ene (8.48 mL, 0.0567 mol) portionwise via syringe over 3 min at room temperature. The solution slowly became homogeneous and yellow in color. The reaction was allowed to stir at room temperature for 3 h. The reaction was complete by HPLC and LC/MS and was concentrated by rotary evaporation to remove acetonitrile (~150 mL). EtOAc (100 mL) was added followed by 100 ml of 20% brine. The two phases were partitioned. The aqueous phase was extracted with 150 mL of EtOAC. The combine organic phases were dried over MgSO4, filtered and concentrated to yield an orange oil. Purification by flash chromatography (150 grams silica, 60% EtOAc/hexanes, loaded with CH2Cl2) yielded the title compound tert-butyl 3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidine-1-carboxylate as a yellow oil (21.1 g, 88% yield). LC-MS: [M+H]+=510.3.

Step F: {3-[4-(7-{[2-(Trimethylsilyl)ethoxy]methyl}-7H-pyrrolo[2,3-d]pyrimidin-4-yl)-1H-pyrazol-1-yl]azetidin-3-yl}acetonitrile dihydrochloride

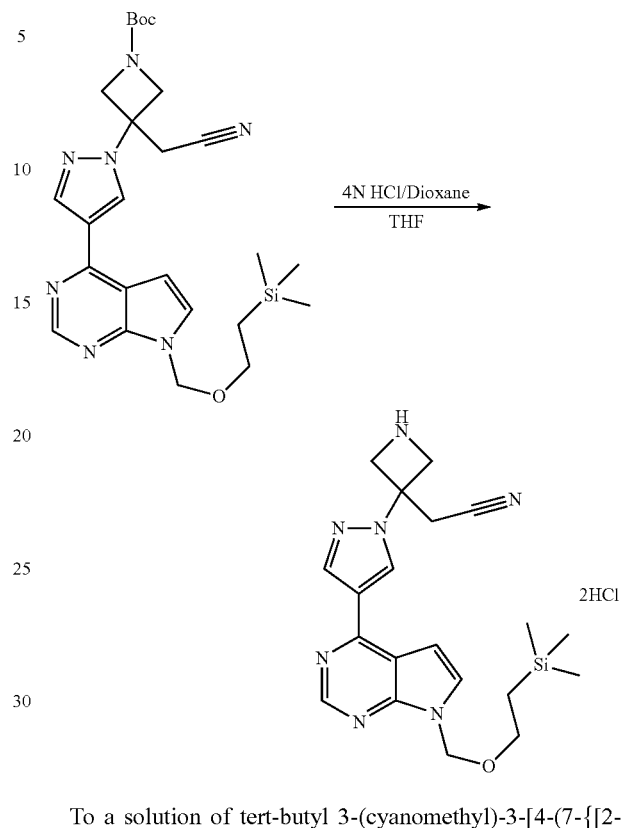

To a solution of tert-butyl 3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidine-1-carboxylate (2 g, 3.9 mmol) in 10 mL of THF was added 10 mL of 4 N HCl in dioxane. The solution was stirred at room temperature for 1 hour and concentrated in vacuo to provide 1.9 g (99%) of the title compound as a white powder solid, which was used for the next reaction without purification. LC-MS: [M+H]+=410.3.

Step G: tert-Butyl 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidine-1-carboxylate

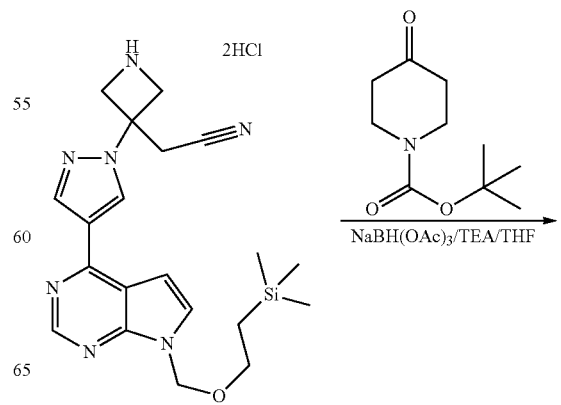

-continued

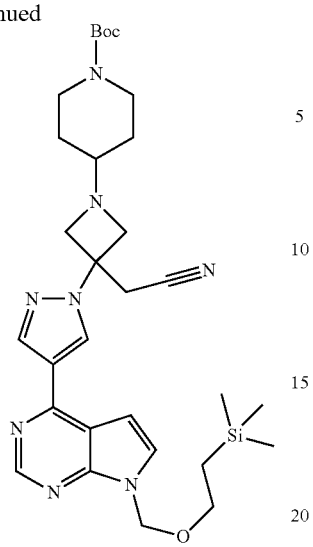

Into the solution of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (2.6 g, 6.3 mmol), tert-butyl 4-oxo-1-piperidinecarboxylate (1.3 g, 6.3 mmol) in THF (30 mL) were added N,N-diisopropylethylamine (4.4 mL, 25 mmol) and sodium triacetoxyborohydride (2.2 g, 10 mmol). The mixture was stirred at room temperature overnight. After adding 20 mL of brine, the solution was extracted with EtOAc. The extract was dried over anhydrous $Na_2SO_4$ and concentrated. The residue was purified by combiflash column eluting with 30-80% EtOAc in hexanes to give the desired product, tert-butyl 4-{3-(cyanomethyl)-3-[4-(7-{[2-(trimethylsilyl) ethoxy]methyl}-7H-pyrrolo[2,3-d]pyrimidin-4-yl)-1H-pyrazol-1-yl]azetidin-1-yl}piperidine-1-carboxylate. Yield: 3.2 g (86%); LC-MS: [M+H]$^+$=593.3.

Step H: {1-Piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride

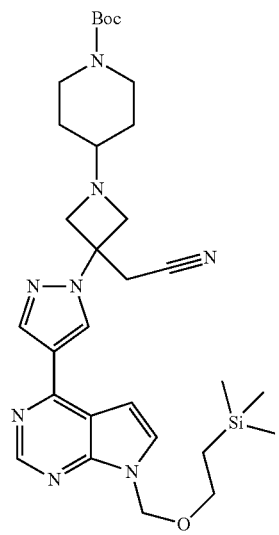

4N HCl/Dioxane
THF
→

-continued

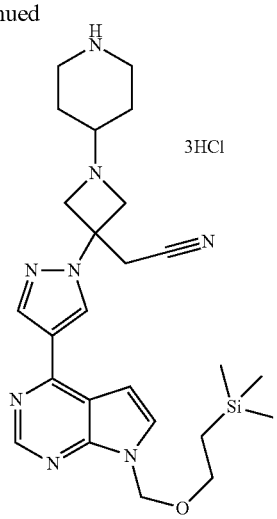

To a solution of tert-butyl 4-{3-(cyanomethyl)-3-[4-(7-{[2-(trimethylsilyl) ethoxy]methyl}-7H-pyrrolo[2,3-d]pyrimidin-4-yl)-1H-pyrazol-1-yl]azetidin-1-yl}piperidine-1-carboxylate (3.2 g, 5.4 mmol) in 10 mL of THF was added 10 mL of 4 N HCl in dioxane. The reaction mixture was stirred at room temperature for 2 hours. Removing solvents under reduced pressure yielded 3.25 g (100%) of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride as a white powder solid, which was used directly in the next reaction. LC-MS: [M+H]$^+$=493.3. $^1$H NMR (400 MHz, DMSO-$d_6$): δ 9.42 (s 1H), 9.21 (s, 1H), 8.89 (s, 1H), 8.69 (s, 1H), 7.97 (s, 1H), 7.39 (d, 1H), 5.68 (s, 2H), 4.96 (d, 2H), 4.56 (m, 2H), 4.02-3.63 (m, 2H), 3.55 (s, 2H), 3.53 (t, 2H), 3.49-3.31 (3, 3H), 2.81 (m, 2H), 2.12 (d, 2H), 1.79 (m, 2H), 0.83 (t, 2H), –0.10 (s, 9H).

Step I: {1-{1-[3-Fluoro-2-(trifluoromethyl)isonicotinoyl]piperidin-4-yl}-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

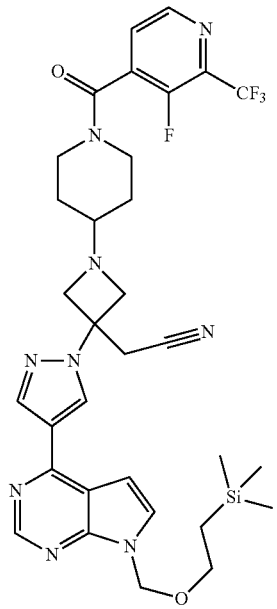 [SMILES: C[Si](C)(C)CCOCn1ccc2c(-c3cnn(C4(CC#N)CN(C5CCN(C(=O)c6ccnc(C(F)(F)F)c6F)CC5)C4)c3)ncnc21]

A mixture of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride (1.22 g, 2.03 mmol), 3-fluoro-2-(trifluoromethyl)isonicotinic acid (460 mg, 2.2 mmol), benzotriazol-1-yloxytris(dimethylamino)phosphonium hexafluorophosphate (1.07 g, 2.42 mmol), and triethylamine (2.0 mL, 14 mmol) in dimethylformamide (DMF) (20.0 mL) was stirred at room temperature overnight. LS-MS showed the reaction was complete. EtOAc (60 mL) and saturated NaHCO$_3$ aqueous solution (60 mL) were added to the reaction mixture. After stirring at room temperature for 10 minutes, the organic phase was separated and the aqueous layer was extracted with EtOAc three times. The combined organic phase was washed with brine, dried over anhydrous Na$_2$SO$_4$, filtered and evaporated under reduced pressure. Purification by flash chromatography provided the desired product {1-{1-[3-fluoro-2-(trifluoromethyl)isonicotinoyl]piperidin-4-yl}-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. LC-MS: 684.3 (M+H)$^+$.

Step J: {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile

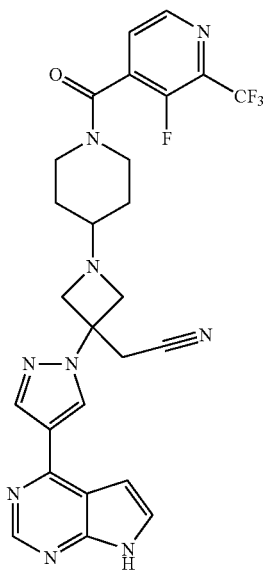 [SMILES: N#CCC1(n2cc(-c3ncnc4[nH]ccc34)cn2)CN(C2CCN(C(=O)c3ccnc(C(F)(F)F)c3F)CC2)C1]

Into a solution of {1-{1-[3-fluoro-2-(trifluoromethyl)isonicotinoyl]piperidin-4-yl}-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (56 mg, 0.1 mmol) in methylene chloride (1.5 mL) was added trifluoroacetic acid (1.5 mL). The mixture was stirred at room temperature for 2 hours. After removing the solvents in vacuum, the residue was dissolved in a methanol solution containing 20% ethylenediamine. After being stirred at room temperature for 1 hour, the solution was purified by HPLC (method B) to give the title compound. LC-MS: 554.3 (M+H)$^+$; $^1$H NMR (400 MHz, CDCl$_3$): 9.71 (s, 1H), 8.82 (s, 1H), 8.55 (d, J=4.6 Hz, 1H), 8.39 (s, 1H), 8.30 (s, 1H), 7.52 (t, J=4.6 Hz, 1H), 7.39 (dd, J$_1$=3.4 Hz, J$_2$=1.5 Hz, 1H), 6.77 (dd, J$_1$=3.6 Hz, J$_2$=0.7 Hz, 1H), 4.18 (m, 1H), 3.75 (m, 2H), 3.63 (dd, J$_1$=7.8 Hz, J$_2$=3.7 Hz, 2H), 3.45 (m, 2H), 3.38 (s, 2H), 3.11 (m, 1H), 2.57 (m, 1H), 1.72 (m, 1H), 1.60 (m, 1H), 1.48 (m, 1H), 1.40 (m, 1H).

Example 2

{1-[1-(3-Fluoro-4-quinolin-6-ylbenzoyl)piperidin-4-yl]-3-[4-(7H-pyrrolo[2,3-d]pyrimidin-4-yl)-1H-pyrazol-1-yl]azetidin-3-yl}acetonitrile

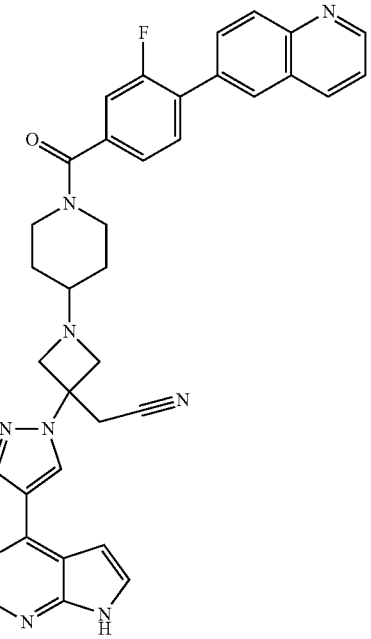

Step A: {4-[(4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)carbonyl]-2-fluorophenyl}boronic acid

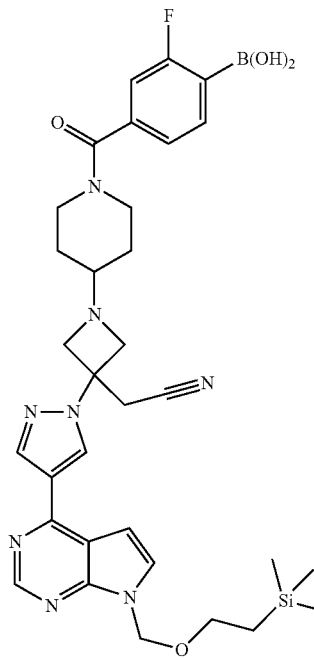

To a solution of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride (1.0 g, 2.0 mmol) in methylene chloride (DCM) (10 mL) were added benzotriazol-1-yloxytris(dimethylamino)phosphonium hexafluorophosphate (1.2 g, 2.6 mmol), N,N-diisopropylethylamine (1.1 mL, 6.1 mmol), and 4-(dihydroxyboryl)-3-fluorobenzoic acid (0.37 g, 2.0 mmol). The mixture was stirred at room temperature overnight. Solvents were removed under reduced pressure and the residue was purified using HPLC to give 0.54 g (41%) of the corresponding product {4-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)carbonyl]-2-fluorophenyl}boronic acid. LC-MS: 659.3 (M+H)$^+$.

Step B: {1-[1-(3-Fluoro-4-quinolin-6-ylbenzoyl)piperidin-4-yl]-3-[4-(7H-pyrrolo[2,3-d]pyrimidin-4-yl)-1H-pyrazol-1-yl]azetidin-3-yl}acetonitrile To a solution of {4-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-yl piperidin-1-yl)carbonyl]-2-fluorophenyl}boronic acid (50 mg, 0.08 mmol) in DMF (2 mL) were added 6-bromoquinoline (15 mg, 0.076 mmol), triethylamine (0.021 mL, 0.15 mmol) and 3 drops of 2 N K$_2$CO$_3$ aqueous solution. The mixture was degased and bis(triphenylphosphine)palladium(II) chloride (5.4 mg, 0.0076 mmol) was added. The reaction mixture was stirred at 140° C. in a microwave oven for 25 minutes, then cooled to room temperature and filtered. The filtrate was purified by HPLC to afford a white powder. The white powder was dissolved in a 5 mL of DCM/TFA (1:2). After being stirred at room temperature for 1 hour, the solution was concentrated. The residue was dissolved in 5 mL of 10% ethylenediamine in THF. After being stirred at room temperature for 2 hours, the solution was concentrated. The residue was purified by HPLC (method B) to afford the title compound {1-[1-(3-fluoro-4-quinolin-6-ylbenzoyl)piperidin-4-yl]-3-[4-(7H-pyrrolo[2,3-d]pyrimidin-4-yl)-1H-pyrazol-1-yl]azetidin-3-yl}acetonitrile. LC-MS: 612.2 (M+H)$^+$.

The following compounds were prepared by a method analogous to that for Example 1 or Example 2.

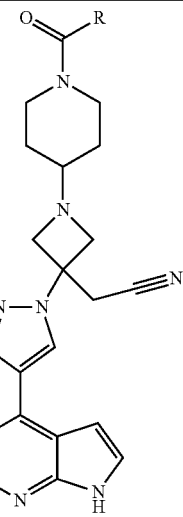

| Example # | R | Compound | LC-MS (M + H)$^+$ |
|---|---|---|---|
| 3 | 3,5-difluorophenyl | {1-[1-(3,5-difluorobenzoyl)piperidin-4-yl]-3-[4-(7H-pyrrolo[2,3-d]pyrimidin-4-yl)-1H-pyrazol-1-yl]azetidin-3-yl}acetonitrile | 503.2 |
| 4 | 3,4,5-trifluorophenyl | {3-[4-(7H-pyrrolo[2,3-d]pyrimidin-4-yl)-1H-pyrazol-1-yl]-1-[1-(3,4,5-trifluorobenzoyl)piperidin-4-yl]azetidin-3-yl}acetonitrile | 521.2 |
| 5 | 3-fluoro-4-methoxyphenyl | {1-[1-(3-fluoro-4-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |

-continued

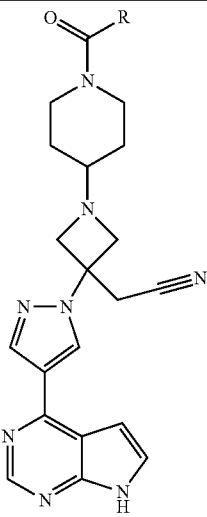

| Example # | R | Compound | LC-MS (M + H)+ |
|---|---|---|---|
| 6 | 3-fluoro-4-hydroxyphenyl | {1-[1-(3-fluoro-4-hydroxybenzoyl)piperidin-4-yl]-3-[4-(7H-pyrrolo[2,3-d]pyrimidin-4-yl)-1H-pyrazol-1-yl]azetidin-3-yl}acetonitrile | 501.2 |
| 7 | 2-fluoro-3-(trifluoromethyl)phenyl | {1-{1-[2-fluoro-3-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile | 553.2 |
| 8 | cyclohexyl | {1-[1-(cyclohexylcarbonyl)piperidin-4-yl]-3-[4-(7H-pyrrolo[2,3-d]pyrimidin-4-yl)-1H-pyrazol-1-yl]azetidin-3-yl}acetonitrile | 473.2 |
| 9 | phenyl | {1-(1-benzoylpiperidin-4-yl)-3-[4-(7H-pyrrolo[2,3-d]pyrimidin-4-yl)-1H-pyrazol-1-yl]azetidin-3-yl}acetonitrile | 467.2 |
| 10 | 2-cyanophenyl | 2-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]benzonitrile | 492.2 |
| 11 | 3-cyanophenyl | 3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]benzonitrile | 492.2 |
| 12 | 4-cyanophenyl | 4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]benzonitrile | 492.2 |
| 13 | 6-chloropyridin-2-yl | {1-{1-[(6-chloropyridin-2-yl)carbonyl]piperidin-4-yl}-3-[4-(7H-pyrrolo[2,3-d]pyrimidin-4-yl)-1H-pyrazol-1-yl]azetidin-3-yl}acetonitrile | 502.2 |

-continued

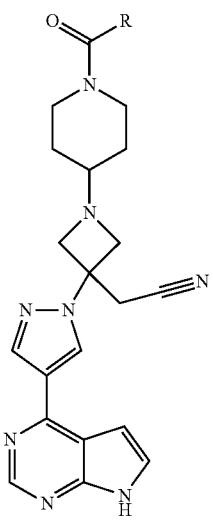

| Example # | R | Compound | LC-MS (M + H)⁺ |
|---|---|---|---|
| 14 | pyrazin-2-yl | {1-[1-(pyrazin-2-lcarbonyl)piperidin-4-yl]-3-[4-(7H-pyrrolo[2,3-d]pyrimidin-4-yl)-1H-pyrazol-1-yl]azetidin-3-l}acetonitrile | 469.2 |
| 15 | thien-3-yl | {3-[4-(7H-pyrrolo[2,3-d]pyrimidin-4-yl)-1H-pyrazol-1-yl]-1-[1-(3-thienylcarbonyl)piperidin-4-yl]azetidin-3-yl}acetonitrile | 473.2 |
| 16 | 1,3-oxazol-2-yl | {1-[1-(1,3-oxazol-2-ylcarbonyl)piperidin-4-yl]-3-[4-(7H-pyrrolo[2,3-d]pyrimidin-4-yl)-1H-pyrazol-1-yl]azetidin-3-yl}acetonitrile | 458.2 |
| 17 | 2-methyl-5-(trifluoromethyl)-1,3-oxazol-4-yl | {1-(1-{[2-methyl-5-(trifluoromethyl)-1,3-oxazol-4-yl]carbonyl}piperidin-4-yl)-3-[4-(7H-pyrrolo[2,3-d]pyrimidin-4-yl)-1H-pyrazol-1-yl]azetidin-3-yl}acetonitrile | 540.2 |
| 18 | 3-fluoro-5-cyanophenyl | 3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-5-fluorobenzonitrile | 510.2 |
| 19 | 3-chlorophenyl | {1-[1-(3-chlorobenzoyl)piperidin-4-yl]-3-[4-(7H-pyrrolo[2,3-d]pyrimidin-4-yl)-1H-pyrazol-1-yl]azetidin-3-yl}acetonitrile | 501.1 |
| 20 | 3-bromophenyl | {1-[1-(3-bromobenzoyl)piperidin-4-yl]-3-[4-(7H-pyrrolo[2,3-d]pyrimidin-4-yl)-1H-pyrazol-1-yl]azetidin-3-yl}acetonitrile | 545.1 547.1 |

-continued

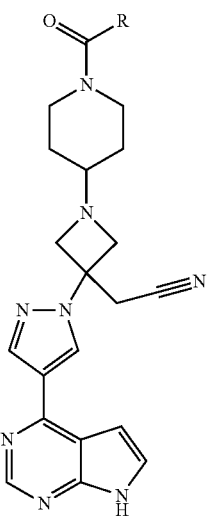

| Example # | R | Compound | LC-MS (M + H)+ |
|---|---|---|---|
| 21 | 3-OCF₃-phenyl | (3-[4-(7H-pyrrolo[2,3-d]pyrimidin-4-yl)-1H-pyrazol-1-yl]-1-{1-[3-(trifluoromethoxy)benzoyl]piperidin-4-yl}azetidin-3-yl)acetonitrile | 551.2 |
| 22 | 3-CF₃-phenyl | (3-[4-(7H-pyrrolo[2,3-d]pyrimidin-4-yl)-1H-pyrazol-1-yl]-1-{1-[3-(trifluoromethyl)benzoyl]piperidin-4-yl}azetidin-3-yl)acetonitrile | 535.2 |
| 23 | 3-CF₃-5-F-phenyl | {1-{1-[3-fluoro-5-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile | 553.2 |
| 24 | 3,5-diCl-phenyl | {1-[1-(3,5-dichlorobenzoyl)piperidin-4-yl]-3-[4-(7H-pyrrolo[2,3-d]pyrimidin-4-yl)-1H-pyrazol-1-yl]azetidin-3-yl}acetonitrile | 535.1 |
| 25 | 3-F-phenyl | {1-[1-(3-fluorobenzoyl)piperidin-4-yl]-3-[4-(7H-pyrrolo[2,3-d]pyrimidin-4-yl)-1H-pyrazol-1-yl]azetidin-3-yl}acetonitrile | 485.1 |
| 26 | 3-OMe-4-F-phenyl | {1-[1-(4-fluoro-3-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |

-continued

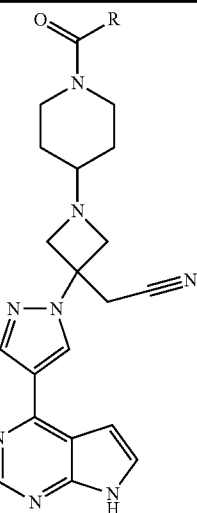

| Example # | R | Compound | LC-MS (M + H)+ |
|---|---|---|---|
| 27 | 2-F, 5-OMe phenyl | {1-[1-(2-fluoro-5-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |
| 28 | 3-Cl, 5-F phenyl | {1-[1-(3-chloro-5-fluorobenzoyl)piperidin-4-yl]-3-[4-(7H-pyrrolo[2,3-d]pyrimidin-4-yl)-1H-pyrazol-1-yl]azetidin-3-yl}acetonitrile | 519.1 |
| 29 | 3-Br, 5-F phenyl | {1-[1-(3-bromo-5-fluorobenzoyl)piperidin-4-yl]-3-[4-(7H-pyrrolo[2,3-d]pyrimidin-4-yl)-1H-pyrazol-1-yl]azetidin-3-yl}acetonitrile | 563.1 565.1 |
| 30 | 2,5-dichloro-3-thienyl | {1-{1-[(2,5-dichloro-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 541.1 |
| 31 | 3-OMe phenyl | {1-[1-(3-methoxybenzoyl)piperidin-4-yl]-3-[4-(7H-pyrrolo[2,3-d]pyrimidin-4-yl)-1H-pyrazol-1-yl]azetidin-3-yl}acetonitrile | 497.2 |
| 32 | 2,4,5-trifluoro-3-methoxyphenyl | {3-[4-(7H-pyrrolo[2,3-d]pyrimidin-4-yl)-1H-pyrazol-1-yl]-1-[1-(2,4,5-trifluoro-3-methoxybenzoyl)piperidin-4-yl]azetidin-3-yl}acetonitrile | 551.2 |

-continued

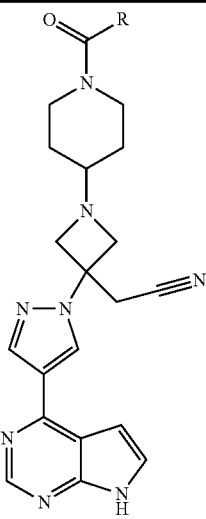

| Example # | R | Compound | LC-MS (M + H)+ |
|---|---|---|---|
| 33 | 3,5-dimethoxyphenyl (OMe, OMe) | {1-[1-(3,5-dimethoxybenzoyl)piperidin-4-yl]-3-[4-(7H-pyrrolo[2,3-d]pyrimidin-4-yl)-1H-pyrazol-1-yl]azetidin-3-yl}acetonitrile | 527.2 |
| 34 | 3-chloro-4-fluorophenyl | {1-[1-(3-chloro-4-fluorobenzoyl)piperidin-4-yl]-3-[4-(7H-pyrrolo[2,3-d]pyrimidin-4-yl)-1H-pyrazol-1-yl]azetidin-3-yl}acetonitrile | 519.1 |
| 35 | 3,4-difluorophenyl | {1-[1-(3,4-difluorobenzoyl)piperidin-4-yl]-3-[4-(7H-pyrrolo[2,3-d]pyrimidin-4-yl)-1H-pyrazol-1-yl]azetidin-3-yl}acetonitrile | 503.1 |
| 36 | 3-fluoro-5-methoxyphenyl | {1-[1-(3-fluoro-5-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |
| 37 | 2-chloro-6-methoxypyridin-4-yl | {1-[1-(2-chloro-6-methoxyisonicotinoyl)piperidin-4-yl]-3-[4-(7H-pyrrolo[2,3-d]pyrimidin-4-yl)-1H-pyrazol-1-yl]azetidin-3-yl}acetonitrile | 532.1 |
| 38 | 5-fluoro-2-methoxyphenyl | {1-[1-(5-fluoro-2-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |

-continued

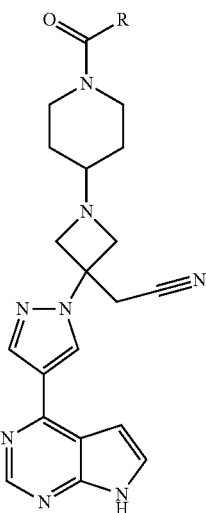

| Example # | R | Compound | LC-MS (M + H)+ |
|---|---|---|---|
| 39 | 2-fluoro-6-methoxyphenyl | {1-[1-(2-fluoro-6-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |
| 40 | 4-fluoro-2-methoxyphenyl | {1-[1-(4-fluoro-2-methoxybenzoyl)piperidin-4-yl]-3-[4-(7H-pyrrolo[2,3-d]pyrimidin-4-yl)-1H-pyrazol-1-yl]azetidin-3-yl}acetonitrile | 515.2 |
| 41 | 2,3-difluorophenyl | {1-[1-(2,3-difluorobenzoyl)piperidin-4-yl]-3-[4-(7H-pyrrolo[2,3-d]pyrimidin-4-yl)-1H-pyrazol-1-yl]azetidin-3-yl}acetonitrile | 503.2 |
| 42 | 2,4-difluorophenyl | {1-[1-(2,4-difluorobenzoyl)piperidin-4-yl]-3-[4-(7H-pyrrolo[2,3-d]pyrimidin-4-yl)-1H-pyrazol-1-yl]azetidin-3-yl}acetonitrile | 503.2 |
| 43 | 2,5-difluorophenyl | {1-[1-(2,5-difluorobenzoyl)piperidin-4-yl]-3-[4-(7H-pyrrolo[2,3-d]pyrimidin-4-yl)-1H-pyrazol-1-yl]azetidin-3-yl}acetonitrile | 503.2 |
| 44 | 2,6-difluorophenyl | {1-[1-(2,6-difluorobenzoyl)piperidin-4-yl]-3-[4-(7H-pyrrolo[2,3-d]pyrimidin-4-yl)-1H-pyrazol-1-yl]azetidin-3-yl}acetonitrile | 503.2 |

-continued

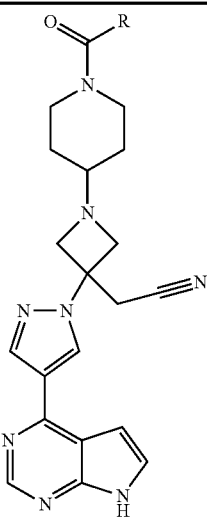

| Example # | R | Compound | LC-MS (M + H)+ |
|---|---|---|---|
| 45 | F₃C, F (2-fluoro-6-(trifluoromethyl)phenyl) | {1-{1-[2-fluoro-6-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile | 553.2 |
| 46 | 2,3,4-trifluorophenyl | {3-[4-(7H-pyrrolo[2,3-d]pyrimidin-4-yl)-1H-pyrazol-1-yl]-1-[1-(2,3,4-trifluorobenzoyl)piperidin-4-yl]azetidin-3-yl}acetonitrile | 521.1 |
| 47 | 2,3,6-trifluorophenyl | {3-[4-(7H-pyrrolo[2,3-d]pyrimidin-4-yl)-1H-pyrazol-1-yl]-1-[1-(2,3,6-trifluorobenzoyl)piperidin-4-yl]azetidin-3-yl}acetonitrile | 521.1 |
| 48 | 2,4,5-trifluorophenyl | {3-[4-(7H-pyrrolo[2,3-d]pyrimidin-4-yl)-1H-pyrazol-1-yl]-1-[1-(2,4,5-trifluorobenzoyl)piperidin-4-yl]azetidin-3-yl}acetonitrile | 521.1 |
| 49 | 2,4,6-trifluorophenyl | {3-[4-(7H-pyrrolo[2,3-d]pyrimidin-4-yl)-1H-pyrazol-1-yl]-1-[1-(2,4,6-trifluorobenzoyl)piperidin-4-yl]azetidin-3-yl}acetonitrile | 521.1 |
| 50 | 3,5-dibromo-4-methoxyphenyl | {1-[1-(3,5-dibromo-4-methoxybenzoyl)piperidin-4-yl]-3-[4-(7H-pyrrolo[2,3-d]pyrimidin-4-yl)-1H-pyrazol-1-yl]azetidin-3-yl}acetonitrile | 653.0 655.0 657.0 |

-continued

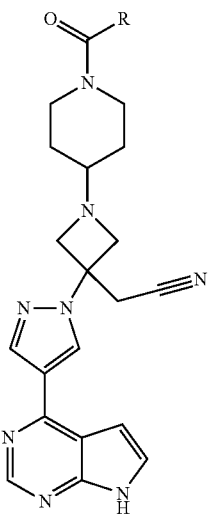

| Example # | R | Compound | LC-MS (M + H)+ |
|---|---|---|---|
| 51 | 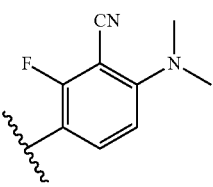 [SMILES: *c1ccc(N(C)C)c(C#N)c1F] | 3-[(4-{3-(cyanomethyl)-3-[4-(7H-pyrrolo[2,3-d]pyrimidin-4-yl)-1H-pyrazol-1-yl]azetidin-1-yl}piperidin-1yl)carbonyl]-6-(dimethylamino)-2-fluorobenzonitrile | 553.2 |
| 52 | 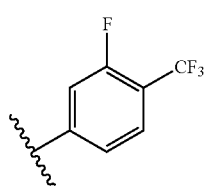 [SMILES: *c1ccc(C(F)(F)F)c(F)c1] | {1-{1-[3-fluoro-4-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile | 553.2 |
| 53 | 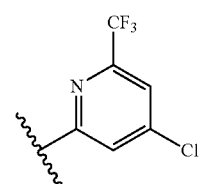 [SMILES: *c1cc(Cl)cc(C(F)(F)F)n1] | {1-(1-{[4-chloro-6-(trifluoromethyl)pyridin-2-yl]carbonyl}piperidin-4-yl)-3-[4-(7H-pyrrolo[2,3-d]pyrimidin-4-yl)-1H-pyrazol-1-yl]azetidin-3-yl}acetonitrile | 570.1 |
| 54 | 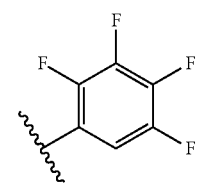 [SMILES: *c1cc(F)c(F)c(F)c1F] | {3-[4-(7H-pyrrolo[2,3-d]pyrimidin-4-yl)-1H-pyrazol-1-yl]-1-[1-(2,3,4,5-tetrafluorobenzoyl)piperidin-4-yl]azetidin-3-yl}acetonitrile | 539.1 |
| 55 | 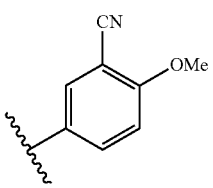 [SMILES: *c1ccc(OC)c(C#N)c1] | 5-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2-methoxybenzonitrile | 522.2 |

-continued

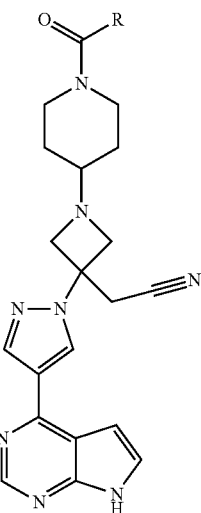

| Example # | R | Compound | LC-MS (M + H)+ |
|---|---|---|---|
| 56 | 2,3,5,6-tetrafluorophenyl | {3-[4-(7H-pyrrolo[2,3-d]pyrimidin-4-yl)-1H-pyrazol-1-yl]-1-[1-(2,3,5,6-tetrafluorobenzoyl)piperidin-4-yl]azetidin-3-yl}acetonitrile | 539.1 |
| 57 | 2-(trifluoromethyl)pyridin-4-yl | (3-[4-(7H-pyrrolo[2,3-d]pyrimidin-4-yl)-1H-pyrazol-1-yl]-1-{1-[2-(trifluoromethyl)isonicotinoyl]piperidin-4-yl}azetidin-3-yl)acetonitrile | 536.2 |
| 58 | 4-fluoro-3-hydroxyphenyl | {1-[1-(4-fluoro-3-hydroxybenzoyl)piperidin-4-yl]-3-[4-(7H-pyrrolo[2,3-d]pyrimidin-4-yl)-1H-pyrazol-1-yl]azetidin-3-yl}acetonitrile | 501.2 |
| 59 | 3-cyano-4-(dimethylamino)phenyl | 5-[(4-{3-(cyanomethyl)-3-[4-(7H-pyrrolo[2,3-d]pyrimidin-4-yl)-1H-pyrazol-1-yl]azetidin-1-yl}piperidin-1yl)carbonyl]-2-(dimethylamino)benzonitrile | 535.2 |
| 60 | 4-(dimethylamino)-2,3,5,6-tetrafluorophenyl | {1-{1-[4-(dimethylamino)-2,3,5,6-tetrafluorobenzoyl]piperidin-4-yl}-3-[4-(7H-pyrrolo[2,3-d]pyrimidin-4-yl)-1H-pyrazol-1-yl]azetidin-3-yl}acetonitrile | 582.2 |
| 61 | 3,5-difluoropyridin-4-yl | {1-[1-(3,5-difluoroisonicotinoyl)piperidin-4-yl]-3-[4-(7H-pyrrolo[2,3-d]pyrimidin-4-yl)-1H-pyrazol-1-yl]azetidin-3-yl}acetonitrile | 504.1 |

-continued

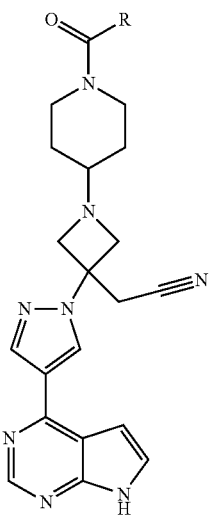

| Example # | R | Compound | LC-MS (M + H)+ |
|---|---|---|---|
| 62 | 3-fluoro-4-(methylthio)phenyl | {1-{1-[3-fluoro-4-(methylthio)benzoyl]piperidin-4-yl}-3-[4-(7H-pyrrolo[2,3-d]pyrimidin-4-yl)-1H-pyrazol-1-yl]azetidin-3-yl}acetonitrile | 531.1 |
| 63 | 4-chloro-3-fluorophenyl | {1-[1-(4-chloro-3-fluorobenzoyl)piperidin-4-yl]-3-[4-(7H-pyrrolo[2,3-d]pyrimidin-4-yl)-1H-pyrazol-1-yl]azetidin-3-yl}acetonitrile | 519.1 |
| 64 | 3-fluoro-4-methylphenyl | {1-[1-(3-fluoro-4-methylbenzoyl)piperidin-4-yl]-3-[4-(7H-pyrrolo[2,3-d]pyrimidin-4-yl)-1H-pyrazol-1-yl]azetidin-3-yl}acetonitrile | 499.2 |
| 65 | 2,5-dimethyl-3-furyl | {1-[1-(2,5-dimethyl-3-furoyl)piperidin-4-yl]-3-[4-(7H-pyrrolo[2,3-d]pyrimidin-4-yl)-1H-pyrazol-1-yl]azetidin-3-yl}acetonitrile | 485.2 |
| 66 | 2-fluoro-4-cyanophenyl | 4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2-fluorobenzonitrile | 510.2 |
| 67 | 2-fluorophenyl | {1-[1-(2-fluorobenzoyl)piperidin-4-yl]-3-[4-(7H-pyrrolo[2,3-d]pyrimidin-4-yl)-1H-pyrazol-1-yl]azetidin-3-yl}acetonitrile | 485.1 |
| 68 | 4-fluorophenyl | {1-[1-(4-fluorobenzoyl)piperidin-4-yl]-3-[4-(7H-pyrrolo[2,3-d]pyrimidin-4-yl)-1H-pyrazol-1-yl]azetidin-3-yl}acetonitrile | 485.1 |

-continued

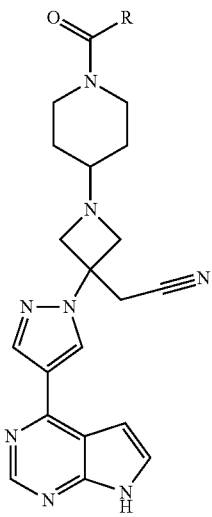

| Example # | R | Compound | LC-MS (M + H)+ |
|---|---|---|---|
| 69 | 2-thienyl | {1-[1-(2-thienylcarbonyl)piperidin-4-yl]-3-[4-(7H-pyrrolo[2,3-d]pyrimidin-4-yl)-1H-pyrazol-1-yl]azetidin-3-yl}acetonitrile | 473.1 |
| 70 | 3-methoxy-5-(trifluoromethyl)-2-thienyl | {1-{1-[3-methoxy-5-(trifluoromethyl)-2-thienylcarbonyl]piperidin-4-yl}-3-[4-(7H-pyrrolo[2,3-d]pyrimidin-4-yl)-1H-pyrazol-1-yl]azetidin-3-yl}acetonitrile | 571.1 |
| 71 | 3-hydroxy-5-(trifluoromethyl)-2-thienyl | {1-{1-[3-hydroxy-5-(trifluoromethyl)-2-thienylcarbonyl]piperidin-4-yl}-3-[4-(7H-pyrrolo[2,3-d]pyrimidin-4-yl)-1H-pyrazol-1-yl]azetidin-3-yl}acetonitrile | 557.1 |
| 72 | 4-methoxy-3-thienyl | {1-{1-[(4-methoxy-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 503.1 |
| 73 | 5-methyl-3-thienyl | {1-{1-[(5-methyl-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 487.1 |
| 74 | 5-chloro-4-methoxy-3-thienyl | {1-{1-[(5-chloro-4-methoxy-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 537.1 |
| 75 | 2-bromo-3-thienyl | {1-{1-[(2-bromo-3-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 551.0 553.0 |

-continued

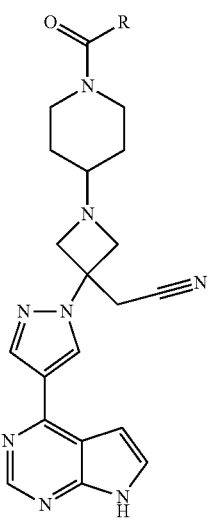

| Example # | R | Compound | LC-MS (M + H)+ |
|---|---|---|---|
| 76 | 3-chloro-2-thienyl | {1-{1-[(3-chloro-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 507.1 |
| 77 | 5-chloro-2-thienyl | {1-{1-[(5-chloro-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 507.1 |
| 78 | 3-methyl-2-thienyl | {1-{1-[(3-methyl-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 487.1 |
| 79 | 4-methyl-2-thienyl | {1-{1-[(4-meth1-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 487.1 |
| 80 | 5-methyl-2-thienyl | {1-{1-[(5-methyl-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 487.1 |
| 81 | 3-methoxy-2-thienyl | {1-{1-[(3-methoxy-2-thienyl)carbonyl]piperidin-4-yl}-3-[4-(7H-pyrrolo[2,3-d]pyrimidin-4-yl)-1H-pyrazol-1-yl]azetidin-3-yl}acetonitrile | 503.1 |
| 82 | 2-fluoro-4-(trifluoromethyl)phenyl | {1-{1-[2-fluoro-4-(trifluoromethyl)benzoyl]piperidin-4-yl}-3-[4-(7H-pyrrolo[2,3-d]pyrimidin-4-yl)-1H-pyrazol-1-yl]azetidin-3-yl}acetonitrile | 553.2 |

-continued

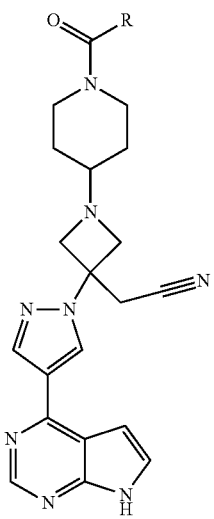

| Example # | R | Compound | LC-MS (M + H)+ |
|---|---|---|---|
| 83 | 3,5-difluoro-4-cyanophenyl | 4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-3,5-difluorobenzonitrile | 528.2 |
| 84 | 3-chloro-4-hydroxyphenyl | {1-[1-(3-chloro-4-hydroxybenzoyl)piperidin-4-yl]-3-[4-(7H-pyrrolo[2,3-d]pyrimidin-4-yl)-1H-pyrazol-1-yl]azetidin-3-yl}acetonitrile | 517.1 |
| 85 | 2-(trifluoromethyl)pyrimidin-4-yl | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 537.2 |
| 86 | 6-(trifluoromethyl)pyrazin-2-yl | [3-[4-(7H-pyrrolo[2,3-d]pyrimidin-4-yl)-1H-pyrazol-1-yl]-1-(1-{[6-(trifluoromethyl)pyrazin-2-yl]carbonyl}piperidin-4-yl)azetidin-3-yl]acetonitrile | 537.2 |
| 87 | 1-naphthyl | {1-[1-(1-naphthoyl)piperidin-4-yl]-3-[4-(7H-pyrrolo[2,3-d]pyrimidin-4-yl)-1H-pyrazol-1-yl]azetidin-3-yl}acetonitrile | 517.2 |
| 88 | quinolin-3-yl | {3-[4-(7H-pyrrolo[2,3-d]pyrimidin-4-yl)-1H-pyrazol-1-yl]-1-[1-(quinolin-3-ylcarbonyl)piperidin-4-yl]azetidin-3-yl}acetonitrile | 518.2 |

-continued

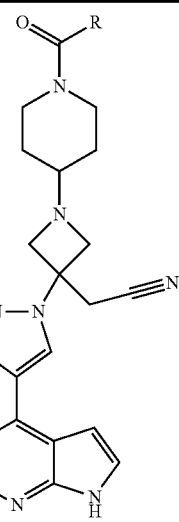

| Example # | R | Compound | LC-MS (M + H)+ |
|---|---|---|---|
| 89 | quinolin-6-yl | {3-[4-(7H-pyrrolo[2,3-d]pyrimidin-4-yl)-1H-pyrazol-1-yl]-1-[1-(quinolin-6-ylcarbonyl)piperidin-4-yl]azetidin-3-yl}acetonitrile | 518.2 |
| 90 | 1-benzothien-2-yl | {1-[1-(1-benzothien-2-ylcarbonyl)piperidin-4-yl]-3-[4-(7H-pyrrolo[2,3-d]pyrimidin-4-yl)-1H-pyrazol-1-yl]azetidin-3-yl}acetonitrile | 523.2 |
| 91 | 3-chloro-6-fluoro-1-benzothien-2-yl | {1-{1-[(3-chloro-6-fluoro-1-benzothien-2-yl)carbonyl]piperidin-4-yl}-3-[4-(7H-pyrrolo[2,3-d]pyrimidin-4-yl)-1H-pyrazol-1-yl]azetidin-3-yl}acetonitrile | 575.1 |
| 92 | 3-chloro-4-fluoro-1-benzothien-2-yl | {1-{1-[(3-chloro-4-fluoro-1-benzothien-2-yl)carbonyl]piperidin-4-yl}-3-[4-(7H-pyrrolo[2,3-d]pyrimidin-4-yl)-1H-pyrazol-1-yl]azetidin-3-yl}acetonitrile | 575.1 |
| 93 | 4-(trifluoromethyl)-1-benzothien-2-yl | [3-[4-(7H-pyrrolo[2,3-d]pyrimidin-4-yl)-1H-pyrazol-1-yl]-1-(1-{[4-(trifluoromethyl)-1-benzothien-2-yl]carbonyl}piperidin-4-yl)azetidin-3-yl]acetonitrile | 591.1 |
| 94 | 6-(trifluoromethyl)-1-benzothien-2-yl | [3-[4-(7H-pyrrolo[2,3-d]pyrimidin-4-yl)-1H-pyrazol-1-yl]-1-(1-{[6-(trifluoromethyl)-1-benzothien-2-yl]carbonyl}piperidin-4-yl)azetidin-3-yl]acetonitrile | 591.1 |
| 95 | 7-(trifluoromethyl)-1-benzothien-2-yl | [3-[4-(7H-pyrrolo[2,3-d]pyrimidin-4-yl)-1H-pyrazol-1-yl]-1-(1-{[7-(trifluoromethyl)-1-benzothien-2-yl]carbonyl}piperidin-4-yl)azetidin-3-yl]acetonitrile | 591.1 |

-continued

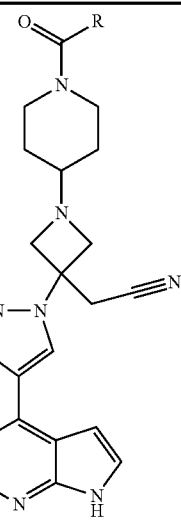

| Example # | R | Compound | LC-MS (M + H)+ |
|---|---|---|---|
| 96 | 1-benzothien-3-yl | {1-[1-(1-benzothien-3-ylcarbonyl)piperidin-4-yl]-3-[4-(7H-pyrrolo[2,3-d]pyrimidin-4-yl)-1H-pyrazol-1-yl]azetidin-3-yl}acetonitrile | 523.2 |
| 97 | 1,2,3,4-tetrahydronaphthalen-2-yl | {3-[4-(7H-pyrrolo[2,3-d]pyrimidin-4-yl)-1H-pyrazol-1-yl]-1-[1-(1,2,3,4-tetrahydronaphthalen-2-ylcarbonyl)piperidin-4-yl]azetidin-3-yl}acetonitrile | 521.2 |
| 98 | 4-(trifluoromethyl)cyclohexyl | {3-[4-(7H-pyrrolo[2,3-d]pyrimidin-4-yl)-1H-pyrazol-1-yl]-1-(1-{[4-(trifluoromethyl)cyclohexyl]carbonyl}piperidin-4-yl)azetidin-3-yl]acetonitrile | 541.2 |
| 99 | 2,3-dihydro-1H-inden-2-yl | {1-[1-(2,3-dihydro-1H-inden-2-ylcarbonyl)piperidin-4-yl]-3-[4-(7H-pyrrolo[2,3-d]pyrimidin-4-yl)-1H-pyrazol-1-yl]azetidin-3-yl}acetonitrile | 507.2 |
| 100 | 4,4-difluorocyclohexyl | {1-{1-[(4,4-difluorocyclohexyl)carbonyl]piperidin-4-yl}-3-[4-(7H-pyrrolo[2,3-d]pyrimidin-4-yl)-1H-pyrazol-1-yl]azetidin-3-yl}acetonitrile | 509.2 |
| 101 | cyclopentyl | {1-[1-(cyclopentylcarbonyl)piperidin-4-yl]-3-[4-(7H-pyrrolo[2,3-d]pyrimidin-4-yl)-1H-pyrazol-1-yl]azetidin-3-yl}acetonitrile | 459.2 |
| 102 | cycloheptyl | {1-[1-(cycloheptylcarbonyl)piperidin-4-yl]-3-[4-(7H-pyrrolo[2,3-d]pyrimidin-4-yl)-1H-pyrazol-1-yl]azetidin-3-yl}acetonitrile | 487.2 |
| 103 | 3-methoxycyclohexyl | {1-{1-[(3-methoxycyclohexyl)carbonyl]piperidin-4-yl}-3-[4-(7H-pyrrolo[2,3-d]pyrimidin-4-yl)-1H-pyrazol-1-yl]azetidin-3-yl}acetonitrile | 503.2 |

-continued

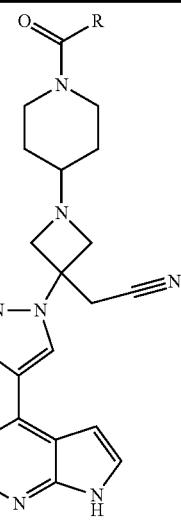

| Example # | R | Compound | LC-MS (M + H)+ |
|---|---|---|---|
| 104 | 4-phenylcyclohexyl | {1-{1-[(4-phenylcyclohexyl)carbonyl]piperidin-4-yl}-3-[4-(7H-pyrrolo[2,3-d]pyrimidin-4-yl)-1H-pyrazol-1-yl]azetidin-3-yl}acetonitrile | 549.2 |
| 105 | 4-(4-chlorophenyl)cyclohexyl | {1-(1-{[4-(4-chlorophenyl)cyclohexyl]carbonyl}piperidin-4-yl)-3-[4-(7H-pyrrolo[2,3-d]pyrimidin-4-yl)-1H-pyrazol-1-yl]azetidin-3-yl}acetonitrile | 583.2 |
| 106 | 1-(5-cyanopyridin-2-yl)piperidin-4-yl | 6-{4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]piperidin-1-yl}nicotinonitrile | 576.2 |
| 107 | 1-(5-chloro-3-fluoropyridin-2-yl)piperidin-4-yl | {1-(1-{[1-(5-chloro-3-fluoropyridin-2-yl)piperidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile | 603.2 |
| 108 | 1-(3-cyano-6-methylpyridin-2-yl)piperidin-4-yl | 2-{4-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]piperidin-1-yl}-6-methylnicotinonitrile | 590.2 |
| 109 | benzyl | {1-[1-(phenylacetyl)piperidin-4-yl]-3-[4-(7H-pyrrolo[2,3-d]pyrimidin-4-yl)-1H-pyrazol-1-yl]azetidin-3-yl}acetonitrile | 481.2 |
| 110 | 1-phenylcyclopropyl | {1-{1-[(1-phenylcyclopropyl)carbonyl]piperidin-4-yl}-3-[4-(7H-pyrrolo[2,3-d]pyrimidin-4-yl)-1H-pyrazol-1-yl]azetidin-3-yl}acetonitrile | 507.2 |

-continued

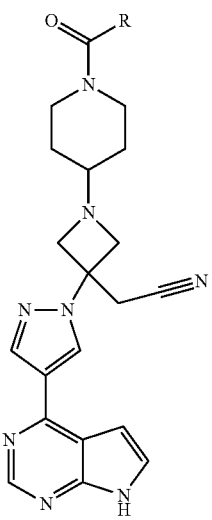

| Example # | R | Compound | LC-MS (M + H)+ |
|---|---|---|---|
| 111 | 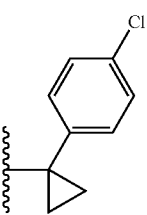 [SMILES: *C1(c2ccc(Cl)cc2)CC1] | {1-(1-{[1-(4-chlorophenyl)cyclopropyl]carbonyl}piperidin-4-yl)-3-[4-(7H-pyrrolo[2,3-d]pyrimidin-4-yl)-1H-pyrazol-1-yl]azetidin-3-yl}acetonitrile | 541.2 |
| 112 | 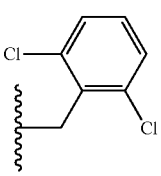 | {1-{1-[(2,6-dichlorophenyl)acetyl]piperidin-4-yl}-3-[4-(7H-pyrrolo[2,3-d]pyrimidin-4-yl)-1H-pyrazol-1-yl]azetidin-3-yl}acetonitrile | 549.1 |
| 113 | 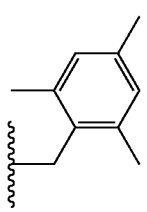 [SMILES: *Cc1c(C)cc(C)cc1C] | {1-[1-(mesitylacetyl)piperidin-4-yl]-3-[4-(7H-pyrrolo[2,3-d]pyrimidin-4-yl)-1H-pyrazol-1-yl]azetidin-3-yl}acetonitrile | 523.2 |
| 114 | 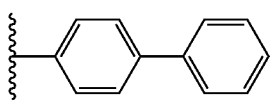 | {1-[1-(biphenyl-4-ylcarbonyl)piperidin-4-yl]-3-[4-(7H-pyrrolo[2,3-d]pyrimidin-4-yl)-1H-pyrazol-1-yl]azetidin-3-yl}acetonitrile | 543.2 |
| 115 | 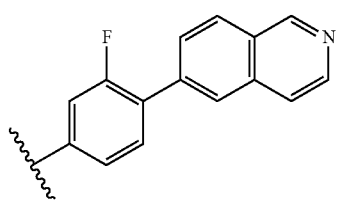 [SMILES: *c1ccc(-c2ccc3cnccc3c2)c(F)c1] | {1-[1-(3-fluoro-4-isoquinolin-6-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |

-continued

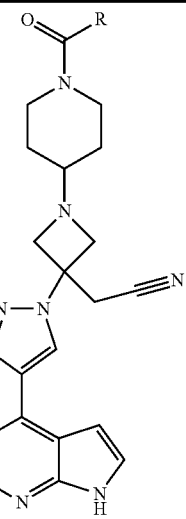

| Example # | R | Compound | LC-MS (M + H)+ |
|---|---|---|---|
| 116 | (3,5-difluoro-4-yl)-phenyl-pyridin-3-yl | {1-[1-(2,6-difluoro-4-pyridin-3-ylbenzoyl)piperidin-4-yl]-3-[4-(7H-pyrrolo[2,3-d]pyrimidin-4-yl)-1H-pyrazol-1-yl]azetidin-3-yl}acetonitrile | 580.2 |
| 117 | (2-fluoro-4-yl)-phenyl-pyridin-4-yl | {1-[1-(3-fluoro-4-pyridin-4-ylbenzoyl)piperidin-4-yl]-3-[4-(7H-pyrrolo[2,3-d]pyrimidin-4-yl)-1H-pyrazol-1-yl]azetidin-3-yl}acetonitrile | 562.2 |
| 118 | 2-fluoro-4-(4-cyanophenyl)phenyl | 4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2'-fluorobiphenyl-4-carbonitrile | 586.2 |
| 119 | 2,3'-difluoro-4-(4-cyanophenyl)phenyl | 4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2',3-difluorobiphenyl-4-carbonitrile | 604.2 |
| 120 | 3-fluoro-4-pyridin-3-yl-phenyl | {1-[1-(2-fluoro-4-pyridin-3-ylbenzoyl)piperidin-4-yl]-3-[4-(7H-pyrrolo[2,3-d]pyrimidin-4-yl)-1H-pyrazol-1-yl]azetidin-3-yl}acetonitrile | 562.2 |

-continued

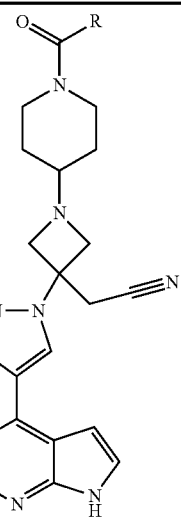

| Example # | R | Compound | LC-MS (M + H)+ |
|---|---|---|---|
| 121 | (5-(1,3-thiazol-2-yl)-2-fluorophenyl) | {1-{1-[4-fluoro-3-(1,3-thiazol-2-yl)benzoyl]piperidin-4-yl}-3-[4-(7H-pyrrolo[2,3-d]pyrimidin-4-yl)-1H-pyrazol-1-yl]azetidin-3-yl}acetonitrile | 568.1 |
| 122 | (2-fluoro-4-(1,3-thiazol-2-yl)phenyl) | {1-{1-[3-fluoro-4-(1,3-thiazol-2-yl)benzoyl]piperidin-4-yl}-3-[4-(7H-pyrrolo[2,3-d]pyrimidin-4-yl)-1H-pyrazol-1-yl]azetidin-3-yl}acetonitrile | 568.1 |
| 123 | (2-fluoro-4-pyridin-3-ylphenyl) | {1-[1-(3-fluoro-4-pyridin-3-ylbenzoyl)piperidin-4-yl]-3-[4-(7H-pyrrolo[2,3-d]pyrimidin-4-yl)-1H-pyrazol-1-yl]azetidin-3-yl}acetonitrile | 562.2 |
| 124 | (2'-cyano-2-fluorobiphenyl-4-yl) | 4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2'-fluorobiphenyl-2-carbonitrile | 586.2 |
| 125 | (3'-cyano-2-fluorobiphenyl-4-yl) | 4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2'-fluorobiphenyl-3-carbonitrile | 586.2 |

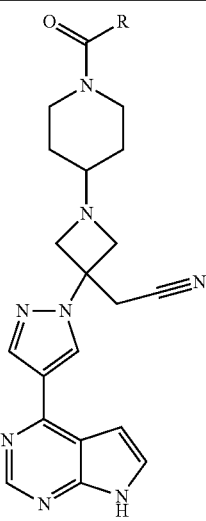

| Example # | R | Compound | LC-MS (M + H)+ |
|---|---|---|---|
| 126 | 4-cyanobiphenyl-4'-yl | 4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]biphenyl-4-carbonitrile | 568.2 |
| 127 | 2,3',4'-trifluorobiphenyl-4-yl | (3-[4-(7H-pyrrolo[2,3-d]pyrimidin-4-yl)-1H-pyrazol-1-yl]-1-{1-[(2,3',4'-trifluorobiphenyl-4-yl)carbonyl]piperidin-4-yl}azetidin-3-yl)acetonitrile | 597.2 |
| 128 | 2',5-difluoro-3-cyanobiphenyl-3'-yl | 4'-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-2',5-difluorobiphenyl-3-carbonitrile | 604.2 |
| 129 | 3-fluoro-4-quinolin-5-ylphenyl | {1-[1-(3-fluoro-4-quinolin-5-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |
| 130 | 3-fluoro-4-isoquinolin-5-ylphenyl | {1-[1-(3-fluoro-4-isoquinolin-5-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |

-continued

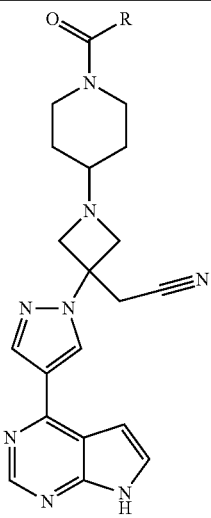

| Example # | R | Compound | LC-MS (M + H)+ |
|---|---|---|---|
| 131 | 2-fluoro-4-(isoquinolin-8-yl)phenyl | {1-[1-(3-fluoro-4-isoquinolin-8-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |
| 132 | 2-fluoro-4-(quinolin-8-yl)phenyl | {1-[1-(3-fluoro-4-quinolin-8-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |
| 133 | 2-fluoro-4-(isoquinolin-7-yl)phenyl | {1-[1-(3-fluoro-4-isoquinolin-7-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |
| 134 | 2-fluoro-4-(quinolin-7-yl)phenyl | {1-[1-(3-fluoro-4-quinolin-7-ylbenzoyl)piperidin-4-yl]-3-[4-(7H-pyrrolo[2,3-d]pyrimidin-4-yl)-1H-pyrazol-1-yl]azetidin-3-yl}acetonitrile | 612.2 |
| 135 | 2-fluoro-4-(imidazo[1,2-a]pyridin-6-yl)phenyl | {1-[1-(3-fluoro-4-imidazo[1,2-a]pyridin-6-ylbenzoyl)piperidin-4-yl]-3-[4-(7H-pyrrolo[2,3-d]pyrimidin-4-yl)-1H-pyrazol-1-yl]azetidin-3-yl}acetonitrile | 601.2 |

-continued

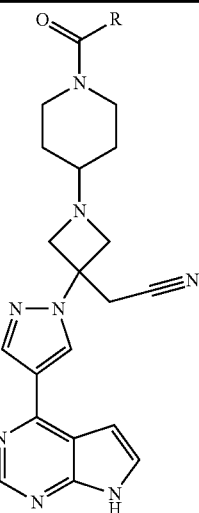

| Example # | R | Compound | LC-MS (M + H)+ |
|---|---|---|---|
| 136 | (4-(1,3-benzoxazol-2-yl)phenyl) | {1-{1-[4-(1,3-benzoxazol-2-yl)benzoyl]piperidin-4-yl}-3-[4-(7H-pyrrolo[2,3-d]pyrimidin-4-yl)-1H-pyrazol-1-yl]azetidin-3-yl}acetonitrile | 584.2 |
| 137 | (4-(1,3-benzoxazol-2-yl)-3-fluorophenyl) | {1-{1-[4-(1,3-benzoxazol-2-yl)-3-fluorobenzoyl]piperidin-4-yl}-3-[4-(7H-pyrrolo[2,3-d]pyrimidin-4-yl)-1H-pyrazol-1-yl]azetidin-3-y4}acetonitrile | 602.2 |

$^1$H NMR (300 MHz, DMSO-d$_6$) of Example 3: δ 12.26 (brs, 1H), 8.94 (s, 1H), 8.82 (s, 1H), 8.53 (s, 1H), 7.72 (dd, 1H), 7.43 (dd, 1H), 7.26 (d, 2H), 7.17 (dd, 1H), 4.13 (m, 1H), 3.85 (d, 2H), 3.62 (d, 2H), 3.58 (m, 2H), 3.44 (s, 2H), 3.21 (m, 2H), 1.80 (m, 2H), 1.34 (m, 2H).

$^1$H NMR (300 MHz, DMSO-d$_6$) of Example 9: δ 12.13 (brs, 1H), 8.82 (s, 1H), 8.71 (s, 1H), 8.42 (s, 1H), 7.62 (s, 1H), 7.53-7.30 (m, 5H), 7.07 (s, 1H), 4.13 (m, 1H), 3.75 (d, 2H), 3.55 (d, 2H), 3.45 (m, 2H), 3.33 (s, 2H), 3.10 (m, 2H), 1.71 (m, 2H), 1.25 (m, 2H).

$^1$H NMR (300 MHz, DMSO-d$_6$) of Example 15: δ 12.26 (brs, 1H), 8.92 (s, 1H), 8.81 (s, 1H), 8.53 (s, 1H), 7.85 (d, 1H), 7.72 (dd, 1H), 7.69 (dd, 1H), 7.28 (dd, 1H), 7.18 (d, 1H), 4.15 (m, 1H), 3.87 (d, 2H), 3.69 (d, 2H), 3.61 (m, 1H), 3.43 (s, 2H), 3.22 (m, 2H), 2.61 (m, 1H), 1.82 (m, 2H), 1.33 (m, 2H).

$^1$H NMR (300 MHz, DMSO-d$_6$) of Example 18: δ 12.03 (brs, 1H), 9.32 (s, 1H), 9.22 (s, 1H), 8.63 (s, 1H), 7.85 (s, 1H), 7.55 (d, 1H), 7.12 (d, 1H), 6.99 (d, 2H), 4.10 (m, 1H), 3.65 (d, 2H), 3.60 (d, 2H), 3.35 (s, 2H), 3.34 (m, 2H), 3.20 (m, 1H), 2.59 (m, 1H), 1.86-1.63 (m, 2H), 1.32 (m, 2H).

$^1$H NMR (300 MHz, DMSO-d$_6$) of Example 25: δ 12.09 (brs, 1H), 8.75 (s, 1H), 8.63 (s, 1H), 8.37 (s, 1H), 7.55 (dd, 1H), 7.42 (dd, 1H), 7.26 (dd, 1H), 7.21 (dd, 1H), 7.15 (dd, 1H), 7.01 (dd, 1H), 4.02 (m, 1H), 3.70 (d, 2H), 3.51 (d, 2H), 3.44 (m, 2H), 3.29 (s, 2H), 3.04 (m, 2H), 1.62 (m, 2H), 1.19 (m, 2H).

$^1$H NMR (400 MHz, DMSO-d$_6$) of Example 30: δ 12.08 (brs, 1H), 8.76 (s, 1H), 8.63 (s, 1H), 8.36 (s, 1H), 7.54 (d, J=3.60 Hz, 1H), 7.15 (s, 1H), 7.00 (d, J=3.60 Hz, 1H), 3.98 (m, 1H), 3.69 (m, 2H), 3.52 (m, 2H), 3.48 (s, 2H), 3.41 (m, 1H), 3.06 (m, 2H), 2.47 (m, 1H), 1.65 (m, 2H), 1.17 (m, 2H).

$^1$H NMR (400 MHz, DMSO-d$_6$) of Example 36 (TFA salt): δ 12.28 (s, 1H), 9.03 (s, 1H), 8.74 (s, 1H), 8.54 (s, 1H), 7.67 (m, 1H), 7.11 (m, 1H), 6.92 (m, 1H), 6.75 (m, 2H), 4.01-4.85 (m, 6H), 3.78 (s, 3H), 3.73 (s, 2H), 3.61 (m, 1H), 3.03 (m, 2H), 2.81 (m, 1H), 2.21 (m, 1H), 1.32 (m, 2H).

$^1$H NMR (400 MHz, DMSO-d$_6$) of Example 37 (TFA salt): δ 12.12 (s, 1H), 9.03 (s, 1H), 8.87 (s, 1H), 8.59 (s, 1H), 8.39 (s, 1H), 7.52 (m, 1H), 6.94 (m, 2H), 6.67 (m, 1H), 4.34-4.82 (m, 6H), 3.72 (s, 3H), 3.57 (s, 2H), 3.39 (m, 1H), 2.91 (t, 1H), 2.65 (t, 1H), 1.90 (m, 1H), 1.74 (m, 1H), 1.17 (m, 2H).

$^1$H NMR (400 MHz, DMSO-d$_6$) of Example 38 (TFA salt): δ 12.24 (s, 1H), 9.03 (s, 1H), 8.73 (s, 1H), 8.53 (s, 1H), 7.99 (s, 1H), 7.52 (m, 1H), 7.03-7.09 (m, 3H), 4.34-4.82 (m, 2H), 3.76 (s, 7H), 3.38 (s, 1H), 3.03 (m, 4H), 2.73 (m, 1H), 2.05 (m, 1H), 1.89 (m, 1H), 1.38 (m, 1H).

$^1$H NMR (400 MHz, DMSO-d$_6$) of Example 39 (TFA salt): δ 12.24 (s, 1H), 9.02 (s, 1H), 8.72 (s, 1H), 8.53 (s, 1H), 7.66 (t, 1H), 7.41 (m, 1H), 7.09 (m, 1H), 6.94 (dd, 1H), 6.87 (t, 1H), 4.36-5.07 (m, 4H), 3.78 (s, 3H), 3.70 (s, 2H), 3.41 (d, 2H), 3.00 (m, 2H), 2.77 (m, 1H), 2.06 (m, 1H), 1.91 (m, 1H), 1.27 (m, 2H), $^1$H NMR (400 MHz, DMSO-d$_6$) of Example 40 (TFA salt): δ 12.24 (s, 1H), 9.02 (s, 1H), 8.73 (s, 1H), 8.54 (s, 1H), 7.67 (t, 1H), 7.19 (t, 1H), 7.09 (s, 1H), 7.01 (d, 1H), 6.83 (t, 1H), 3.98-4.90 (m, 4H), 3.79 (s, 3H), 3.71 (s, 2H), 3.38 (d, 2H), 2.95 (m, 1H), 2.75 (m, 1H), 2.06 (m, 1H), 2.05 (m, 1H), 1.90 (m, 1H), 1.29 (m, 2H).

$^1$H NMR (400 MHz, DMSO-d$_6$) of Example 59 (TFA salt): δ 12.25 (s, 1H), 9.00 (s, 1H), 8.73 (s, 1H), 8.54 (s, 1H), 7.67 (t, 1H), 7.58 (t, 1H), 7.49 (dd, 1H), 7.10 (d, 1H), 7.02 (dd, 1H), 3.72 (s, 3H), 3.07 (s, 6H), 2.95 (m, 3H), 2.51 (m, 3H), 1.98 (m, 3H), 1.31 (m, 3H).

$^1$H NMR (400 MHz, DMSO-d$_6$) of Example 60 (TFA salt): δ 12.20 (s, 1H), 8.71 (s, 1H), 8.50 (s, 1H), 7.91 (m, 1H), 7.64 (s, 1H), 7.08 (m, 1H), 4.9 (m, 2H), 3.68 (s, 3H), 3.46 (s, 6H), 2.92 (s, 6H), 2.00 (m, 2H), 1.22 (m, 2H).

$^1$H NMR (300 MHz, DMSO-d$_6$) of Example 68: δ 12.11 (brs, 1H), 8.73 (s, 1H), 8.43 (s, 1H), 8.23 (s, 1H), 7.39 (dd, 1H), 7.15 (dd, 2H), 6.98 (dd, 2H), 6.80 (dd, 1H), 3.98 (m, 1H), 3.60 (d, 2H), 3.41 (d, 2H), 3.35 (m, 1H), 3.18 (s 2H), 3.13 (m, 1H), 3.00 (m, 1H), 2.57 (m, 1H), 1.73-1.55 (m, 2H), 1.22 (m, 2H).

$^1$H NMR (300 MHz, DMSO-d$_6$) of Example 69 (TFA salt): δ 12.04 (brs, 1H), 8.76 (s, 1H), 8.63 (s, 1H), 8.36 (s, 1H), 7.67 (dd, 1H), 7.54 (d, 1H), 7.31 (dd, 1H), 7.05 (d, 1H), 7.00 (s, 1H), 3.92 (d, 2H), 3.69 (d, 2H), 3.52 (d, 2H), 3.27 (s, 2H), 3.18 (m, 2H), 2.53 (m, 1H), 1.67 (m, 2H), 1.18 (m, 2H).

$^1$H NMR (300 MHz, DMSO-d$_6$) of Example 70 (TFA salt): δ 12.35 (brs, 1H), 9.06 (s, 1H), 8.76 (s, 1H), 8.56 (s, 1H), 7.76 (d, 1H), 7.70 (s, 1H), 7.12 (s, 1H), 4.95 (m, 2H), 4.72 (m, 1H), 3.92 (s, 3H), 3.89 (d, 2H), 3.74 (d, 2H), 3.62 (s, 2H), 2.91 (m, 2H), 2.05 (m, 2H), 1.36 (m, 2H).

$^1$H NMR (300 MHz, DMSO-d6) of Example 72: δ 12.08 (brs, 1H), 8.76 (s, 1H), 8.63 (s, 1H), 8.36 (s, 1H), 7.54 (t, 1H, J=3.0 Hz), 7.47 (d, 1H, J=3.0 Hz), 7.00 (m, 1H), 6.60 (d, 1H, J=3.30 Hz), 4.00 (m, 1H), 3.69 (m, 5H), 3.49 (m, 4H), 2.95 (m, 3H), 2.45 (m, 1H), 1.64 (m, 2H), 1.11 (m, 2H).

$^1$H NMR (300 MHz, DMSO-d6) of Example 73: δ 12.15 (brs, 1H), 8.76 (s, 1H), 8.61 (s, 1H), 8.36 (s, 1H), 7.54 (d, 1H, J=3.60 Hz), 7.39 (d, 1H, J=1.80 Hz), 7.00 (d, 1H, J=3.90 Hz), 6.80 (t, 1H, J=1.2 Hz), 3.99 (m, 1H), 3.69 (m, 2H), 3.51 (m, 2H), 3.48 (s, 2H), 3.05 (m, 3H), 2.45 (m, 1H), 2.37 (s, 3H), 1.62 (m, 2H), 1.14 (m, 2H).

$^1$H NMR (300 MHz, DMSO-d6) of Example 74: δ 8.76 (s, 1H), 8.63 (s, 1H), 8.36 (s, 1H), 7.54 (d, 1H, J=3.60 Hz), 7.45 (s, 1H), 7.00 (d, 1H, J=3.90 Hz), 3.99 (m, 1H), 3.71 (s, 3H), 3.69 (m, 2H), 3.52 (m, 4H), 3.49 (s, 2H), 3.06 (m, 1H), 2.55 (m, 1H), 1.65 (m, 2H), 1.16 (m, 2H).

$^1$H NMR (300 MHz, DMSO-d6) of Example 75: δ 8.75 (s, 1H), 8.63 (s, 1H), 8.36 (s, 1H), 7.60 (d, 1H, J=5.40 Hz), 7.54 (d, 1H, J=3.60 Hz), 7.00 (d, 1H, J=3.90 Hz), 6.95 (d, 1H, J=5.70 Hz), 4.03 (m, 1H), 3.68 (d, 2H, J=8.1 Hz), 3.51 (m, 2H), 3.48 (s, 2H), 3.06 (m, 3H), 2.46 (m, 1H), 1.62 (m, 2H), 1.16 (m, 2H).

$^1$H NMR (400 MHz, DMSO-d$_6$) of Example 76: δ 12.07 (s, 1H), 8.75 (d, 1H), 8.63 (s, 1H), 8.35 (d, 1H), 7.73 (m, 1H), 7.54 (t, 1H), 7.05 (d, 1H), 6.99 (dd, 1H), 3.68 (m, 2H), 3.49 (m, 4H), 3.43 (s, 2H), 3.11 (m, 2H), 2.46 (m, 1H) 1.65 (m, 2H), 1.17 (m, 2H).

$^1$H NMR (400 MHz, DMSO-d$_6$) of Example 77: δ 12.08 (s, 1H), 8.77 (d, 1H), 8.63 (s, 1H), 8.36 (d, 1H), 7.54 (dd, 1H), 7.22 (t, 1H), 7.07 (m, 1H), 6.99 (m, 1H), 3.91 (m, 2H), 3.69 (m, 2H), 3.49 (m, 4H), 3.19 (m, 2H), 2.49 (m, 1H), 1.67 (m, 2H), 1.19 (m, 2H).

$^1$H NMR (400 MHz, DMSO-d$_6$) of Example 78: δ 12.07 (s, 1H), 8.75 (s, 1H), 8.63 (d, 1H), 8.35 (d, 1H), 7.54 (d, 1H), 7.49 (d, 1H), 7.01 (m, 1H), 6.87 (m, 1H), 3.69 (m, 3H), 3.51 (m, 4H), 3.27 (s, 2H), 3.07 (m, 2H), 2.10 (s, 3H), 1.62 (m, 2H), 1.12 (m, 2H).

$^1$H NMR (400 MHz, DMSO-d$_6$) of Example 79: δ 12.07 (s, 1H), 8.75 (s, 1H), 8.63 (d, 1H), 8.35 (d, 1H), 7.54 (d, 1H), 7.49 (d, 1H), 7.01 (m, 1H), 6.87 (m, 1H), 3.92 (m, 2H), 3.69 (m, 2H), 3.45 (m, 3H), 3.27 (s, 2H), 3.10 (m, 2H), 2.15 (d, 3H), 1.65 (m, 2H), 1.16 (m, 2H).

$^1$H NMR (400 MHz, DMSO-d$_6$) of Example 80: δ 12.08 (s, 1H), 8.76 (s, 1H), 8.63 (d, 1H), 8.36 (s, 1H), 7.54 (d, 1H), 7.11 (d, 1H), 7.01 (m, 1H), 6.73 (m, 1H), 3.92 (m, 2H), 3.69 (m, 2H), 3.51 (m, 3H), 3.27 (s, 2H), 3.10 (m, 2H), 2.19 (s, 3H), 1.65 (m, 2H), 1.16 (m, 2H).

$^1$H NMR (300 MHz, DMSO-d$_6$) of Example 81: δ 12.07 (brs, 1H), 8.76 (s, 1H), 8.63 (s, 1H), 8.36 (s, 1H), 7.58 (d, 1H), 7.55 (d, 1H), 7.00 (d, 1H), 6.95 (d, 1H), 3.79 (s, 3H), 3.72 (m, 1H), 3.68 (d, 2H), 3.51 (d, 2H), 3.50 (m, 2H), 3.27 (s, 2H), 3.04 (m, 2H), 1.65 (m, 2H), 1.14 (m, 2H).

$^1$H NMR (300 MHz, DMSO-d$_6$) of Example 82: δ 11.89 (brs, 1H), 8.81 (s, 1H), 8.69 (s, 1H), 8.41 (s, 1H), 7.81 (d, 1H), 7.65 (s, 2H), 7.61 (d, 1H), 7.06 (d, 1H), 4.10 (m, 1H), 3.75 (d, 2H), 3.58 (d, 2H), 3.37 (m, 1H), 3.33 (s, 2H), 3.22 (m, 1H), 3.03 (m, 1H), 2.55 (m, 1H), 1.70 (m, 2H), 1.22 (m, 2H).

$^1$H NMR (300 MHz, DMSO-d$_6$) of Example 83: δ 12.01 (brs, 1H), 8.74 (s, 1H), 8.62 (s, 1H), 8.33 (s, 1H), 7.89 (dd, 2H), 7.53 (d, 1H), 6.99 (d, 1H), 4.03 (m, 1H), 3.70 (dd, 2H), 3.51 (dd, 2H), 3.50 (m, 1H), 3.35 (m, 1H), 3.25 (s, 2H), 3.22 (m, 1H), 3.02 (m, 1H), 1.62 (m, 2H), 1.15 (m, 2H).

$^1$H NMR (300 MHz, DMSO-d$_6$) of Example 85: δ 12.09 (brs, 1H), 9.10 (d, 1H), 8.81 (s, 1H), 8.68 (s, 1H), 8.40 (s, 1H), 7.99 (d, 1H), 7.61 (d, 1H), 7.03 (d, 1H), 4.02 (m, 1H), 3.75 (d, 2H), 3.54 (d, 2H), 3.45 (m, 1H), 3.31 (s 2H), 3.25 (m, 1H), 3.10 (m, 1H), 2.53 (m, 1H), 1.80-1.61 (m, 2H), 1.23 (m, 2H).

$^1$H NMR (300 MHz, DMSO-d$_6$) of Example 86: δ 12.01 (brs, 1H), 9.23 (s, 1H), 9.12 (s, 1H), 8.76 (s, 1H), 8.63 (s, 1H), 8.36 (d, 1H), 7.55 (d, 1H), 7.00 (d, 1H), 4.03 (m, 1H), 3.70 (d, 2H), 3.51 (d, 2H), 3.45 (m, 1H), 3.28 (s 2H), 3.23 (m, 1H), 3.11 (m, 1H), 2.56 (m, 1H), 1.80-1.55 (m, 2H), 1.22 (m, 2H).

$^1$H NMR (400 MHz, DMSO-d$_6$) of Example 90 (TFA salt): δ 12.33 (brs, 1H), 9.06 (s, 1H), 8.76 (s, 1H), 8.56 (s, 1H), 8.02 (dd, 1H), 7.92 (dd, 1H), 7.73 (s, 1H), 7.69 (dd, 1H), 7.47 (dd, 1H), 7.45 (dd, 1H), 7.12 (d, 1H), 4.95 (m, 1H), 4.82 (m, 1H), 4.41 (m, 1H), 3.75 (s, 4H), 3.65 (m, 1H), 3.31 (s 2H), 3.05 (m, 1H), 2.08 (m, 2H), 1.39 (m, 2H).

$^1$H NMR (400 MHz, DMSO-d$_6$) of Example 91: δ 12.13 (brs, 1H), 8.81 (s, 1H), 8.68 (s, 1H), 8.41 (s, 1H), 8.08 (dd, 1H), 7.85 (dd, 1H), 7.60 (d, 1H), 7.46 (m, 1H), 7.06 (dd, 1H), 4.07 (m, 1H), 3.74 (d, 2H), 3.57 (d, 2H), 3.50 (m, 1H), 3.33 (s, 2H), 3.22 (m, 2H), 2.55 (m, 1H), 1.74 (m, 2H), 1.27 (m, 2H).

$^1$H NMR (400 MHz, DMSO-d$_6$) of Example 92: δ 12.12 (brs, 1H), 8.81 (s, 1H), 8.68 (s, 1H), 8.41 (s, 1H), 7.94 (d, 1H), 7.60 (d, 1H), 7.55 (m, 1H), 7.34 (dd, 1H), 7.06 (d, 1H), 4.08 (m, 1H), 3.74 (d, 2H), 3.58 (d, 2H), 3.52 (m, 1H), 3.33 (s, 2H), 3.24 (m, 2H), 2.56 (m, 1H), 1.78 (m, 1H), 1.62 (m, 1H), 1.28 (m, 2H).

¹H NMR (400 MHz, DMSO-d₆) of Example 93: δ 12.13 (brs, 1H), 8.82 (s, 1H), 8.69 (s, 1H), 8.42 (s, 1H), 8.40 (d, 1H), 7.84 (d, 1H), 7.65 (d, 1H), 7.62 (dd, 2H), 7.06 (d, 1H), 3.95 (m, 1H), 3.76 (d, 2H), 3.58 (d, 2H), 3.54 (m, 1H), 3.33 (s, 2H), 3.31 (m, 2H), 2.57 (m, 1H), 1.74 (m, 2H), 1.29 (m, 2H).

¹H NMR (400 MHz, DMSO-d₆) of Example 94: δ 12.13 (brs, 1H), 8.82 (s, 1H), 8.69 (s, 1H), 8.56 (s, 1H), 8.42 (s, 1H), 8.11 (d, 1H), 7.82 (s, 1H), 7.74 (dd, 1H), 7.60 (d, 1H), 7.06 (d, 1H), 4.00 (m, 1H), 3.76 (d, 2H), 3.59 (d, 2H), 3.56 (m, 1H), 3.33 (s, 2H), 3.31 (m, 2H), 2.58 (m, 1H), 1.76 (m, 2H), 1.30 (m, 2H).

¹H NMR (400 MHz, DMSO-d₆) of Example 95: δ 12.12 (brs, 1H), 8.83 (s, 1H), 8.69 (s, 1H), 8.42 (s, 1H), 8.24 (d, 1H), 7.89 (s, 1H), 7.87 (d, 1H), 7.65 (dd, 1H), 7.60 (d, 1H), 7.06 (d, 1H), 4.04 (m, 1H), 3.77 (d, 2H), 3.59 (d, 2H), 3.56 (m, 1H), 3.33 (s, 2H), 3.31 (m, 2H), 2.58 (m, 1H), 1.77 (m, 2H), 1.31 (m, 2H).

¹H NMR (300 MHz, DMSO-d₆) of Example 96: δ 8.76 (s, 1H), 8.63 (s, 1H), 8.36 (s, 1H), 7.99 (m, 1H), 7.86 (s, 1H), 7.66 (m, 1H), 7.54 (d, J=3.60 Hz, 1H), 7.37 (m, 2H), 7.00 (d, J=3.90 Hz, 1H), 4.12 (m, 1H), 3.69 (m, 2H), 3.52 (m, 2H), 3.48 (s, 2H), 3.08 (m, 3H), 2.48 (m, 1H), 1.69 (m, 2H), 1.16 (m, 2H).

¹H NMR (400 MHz, CDCl₃) of Example 100: δ 10.14 (s, 1H), 8.83 (s, 1H), 8.40 (s, 1H), 8.31 (s, 1H), 7.41 (dd, J₁=3.5 Hz, J₂=2.4 Hz, 1H), 6.78 (dd, J₁=2.4 Hz, J₂=1.8 Hz, 1H), 4.16 (d, J=14.4 Hz, 1H), 3.78 (m, 1H), 3.75 (d, J=7.9 Hz, 2H), 3.37 (s, 2H), 3.16 (t, J=11.5 Hz, 1H), 3.02 (t, J=10.8 Hz, 1H), 2.54 (m, 1H), 2.47 (m, 1H), 2.18 (m, 2H), 1.74 (9m, 2H), 1.71-1.60 (m, 6H), 1.31 (m, 2H).

¹H NMR (400 MHz, DMSO-d₆) of Example 129 (TFA salt): δ 12.50 (s, 1H), 9.12 (s, 1H), 9.04 (dd, 1H), 8.81 (s, 1H), 8.59 (s, 1H), 8.18 (m, 2H), 7.95 (dd, 1H), 7.75 (dd, 1H), 7.68 (dd, 1H), 7.64 (dd, 1H), 7.60 (dd, 1H), 7.41 (dd, 1H), 7.40 (dd, 1H), 7.18 (dd, 1H), 5.00 (d, 2H), 4.76 (m, 2H), 4.59 (m, 1H), 3.85 (m, 2H), 3.69 (m, 2H), 3.17 (m, 1H), 2.85 (m, 1H), 2.10 (m, 2H), 1.43 (m, 2H).

¹H NMR (400 MHz, DMSO-d₆) of Example 130 (TFA salt): δ 12.50 (s, 1H), 9.72 (s, 1H), 9.12 (s, 1H), 8.81 (s, 1H), 8.59 (m, 2H), 8.45 (d, 1H), 8.00 (m, 2H), 7.75 (m, 2H), 7.61 (t, 1H), 7.48 (dd, 1H), 7.46 (dd, 1H), 7.18 (d, 1H), 5.00 (d, 2H), 4.75 (m, 2H), 4.59 (m, 1H), 3.83 (m, 2H), 3.69 (m, 2H), 3.16 (m, 1H), 2.85 (m, 1H), 2.12 (m, 1H), 2.02 (m, 1H), 1.43 (m, 2H).

¹H NMR (400 MHz, DMSO-d₆) of Example 131 (TFA salt): δ 12.35 (s, 1H), 9.12 (s, 1H), 9.07 (s, 1H), 8.77 (d, 1H), 8.62 (m, 2H), 8.57 (s, 1H), 8.19 (m, 1H), 8.15 (m, 1H), 8.01 (m, 1H), 7.76 (m, 1H), 7.71 (m, 1H), 7.65 (t, 1H), 7.47 (dd, 1H), 7.13 (s, 1H), 4.96 (d, 2H), 4.75 (m, 2H), 4.59 (m, 1H), 3.85 (m, 2H), 3.67 (m, 2H), 3.16 (m, 1H), 2.85 (m, 1H), 2.22 (m, 1H), 2.00 (m, 1H), 1.42 (m, 2H).

¹H NMR (400 MHz, DMSO-d₆) of Example 132 (TFA salt): δ 12.40 (s, 1H), 9.12 (s, 1H), 9.08 (s, 1H), 8.87 (dd, 1H), 8.78 (s, 1H), 8.46 (dd, 1H), 8.01 (dd, 1H), 7.78 (dd, 1H), 7.72 (m, 2H), 7.58 (m, 2H), 7.73 (m, 2H), 7.13 (m, 1H), 4.96 (d, 2H), 4.75 (m, 2H), 4.59 (m, 1H), 3.85 (m, 2H), 3.67 (m, 2H), 3.16 (m, 1H), 2.85 (m, 1H), 2.05 (m, 2H), 1.40 (m, 2H).

¹H NMR (400 MHz, DMSO-d₆) of Example 133 (TFA salt): δ 12.33 (s, 1H), 9.62 (s, 1H), 9.05 (s, 1H), 8.75 (s, 1H), 8.64 (d, 1H), 8.55 (s, 1H), 8.51 (s, 1H), 8.23 (d, 1H), 8.15 (d, 2H), 7.79 (t, 1H), 7.68 (t, 1H), 7.45 (dd, 1H), 7.38 (dd, 1H), 7.11 (dd, 1H), 4.94 (d, 2H), 4.69 (m, 2H), 4.55 (m, 1H), 3.75 (m, 2H), 3.63 (m, 2H), 3.14 (m, 1H), 2.83 (m, 1H), 2.20 (m, 1H), 1.96 (m, 1H), 1.39 (m, 2H).

¹H NMR (400 MHz, DMSO-d₆) of Example 134 (TFA salt): δ 12.42 (s, 1H), 9.09 (s, 1H), 9.04 (dd, 1H), 8.79 (s, 1H), 8.58 (m, 2H), 8.26 (s, 1H), 8.18 (d, 1H), 7.88 (d, 1H), 7.81 (t, 1H), 7.73 (dd, 1H), 7.68 (dd, 1H), 7.45 (dd, 1H), 7.38 (dd, 1H), 7.15 (dd, 1H), 4.98 (d, 2H), 4.73 (m, 2H), 4.56 (m, 1H), 3.78 (m, 2H), 3.67 (m, 2H), 3.24 (m, 1H), 2.68 (m, 1H), 2.20 (m, 1H), 1.98 (m, 1H), 1.40 (m, 2H).

¹H NMR (400 MHz, DMSO-d₆) of Example 136 (TFA salt): δ 12.31 (brs, 1H), 9.06 (s, 1H), 8.75 (s, 1H), 8.56 (s, 1H), 8.27 (d, 2H), 7.78 (m, 2H), 7.69 (dd, 1H), 7.53 (d, 2H), 7.46 (dd, 2H), 7.11 (dd, 1H), 4.94 (m, 2H), 4.73 (m, 2H), 4.56 (m, 1H), 3.74 (s, 2H), 3.67 (m, 2H), 3.13 (m, 1H), 2.84 (m, 1H), 2.09 (m, 1H), 1.96 (m, 1H), 1.37 (m, 2H).

¹H NMR (400 MHz, DMSO-d₆) of Example 137 (TFA salt): δ 12.32 (brs, 1H), 9.07 (s, 1H), 8.76 (s, 1H), 8.56 (s, 1H), 8.30 (dd, 1H), 7.87 (dd, 2H), 7.70 (dd, 1H), 7.55 (dd, 2H), 7.45 (dd, 2H), 7.12 (dd, 1H), 4.94 (m, 2H), 4.73 (m, 2H), 4.54 (m, 1H), 3.74 (s, 2H), 3.67 (m, 2H), 3.13 (m, 1H), 2.84 (m, 1H), 2.10 (m, 1H), 1.96 (m, 1H), 1.37 (m, 2H).

Example 138

3-[(3-{3-(Cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)carbonyl]-5-fluorobenzonitrile

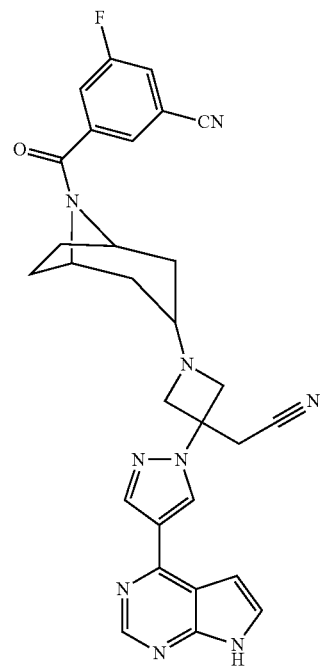 [SMILES: N#CCC1(n2cc(-c3ncnc4[nH]ccc34)cn2)CN(C2CC3CCC(C2)N3C(=O)c2cc(F)cc(C#N)c2)C1]

127

Step A: tert-Butyl 3-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-8-azabicyclo[3.2.1]octane-8-carboxylate

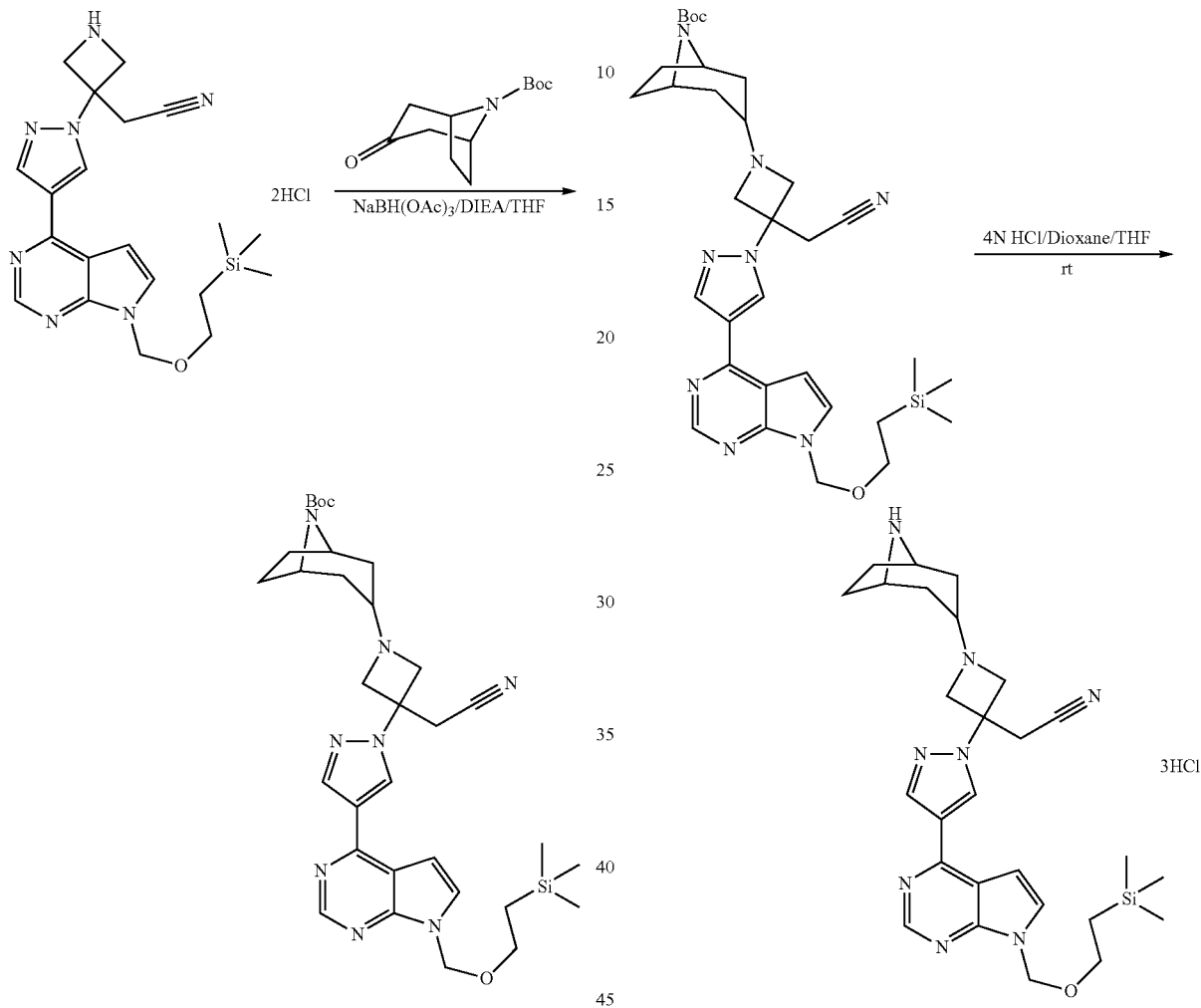

128

Step B: {1-(8-Azabicyclo[3.2.1]oct-3-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride To a solution of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (2.6 g, 6.3 mmol) in THF (30 mL) were added tert-butyl 3-oxo-8-azabicyclo[3.2.1]octane-8-carboxylate (1.3 g, 6.3 mmol), N,N-diisopropylethylamine (4.4 mL, 25 mmol) and sodium triacetoxyborohydride (2.2 g, 10 mmol). The mixture was stirred at room temperature overnight and quenched by addition of 20 mL of brine. The solution was extracted with EtOAc. The extract was dried over anhydrous Na$_2$SO$_4$. After removing solvent, the residue was purified by combiflash column eluting with 30-80% EtOAc in hexanes to give the desired product tert-butyl 3-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-8-azabicyclo[3.2.1]octane-8-carboxylate. LC-MS: 619.3 (M+H)$^+$.

To a solution of tert-butyl 3-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-8-azabicyclo[3.2.1]octane-8-carboxylate (123 mg, 0.2 mmol) in THF (3 mL) was added a 4 N solution of HCl in dioxane (3 mL). After being stirred at room temperature for 2 hours, the solution was concentrated. The residue obtained was used for the next reaction. LC-MS: 519.3 (M+H)$^+$.

Step C: 3-[(3-{3-(Cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)carbonyl]-5-fluorobenzonitrile A mixture of {1-(8-azabicyclo[3.2.1]oct-3-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (100.0 mg, 0.193 mmol), 3-cyano-5-fluorobenzoic acid (31.8 mg, 0.193 mmol), benzotriazol-1-yloxytris(dimethylamino)phosphonium hexafluorophosphate (93.8 mg, 0.212 mmol), and triethylamine(0.108 mL, 0.771 mmol) in DMF (3.0 mL) was stirred at room temperature for 2 hours. Purification by HPLC afforded the coupling product as a white powder. LCMS found: 666.3 (M+1)⁺. The white powder was dissolved in trifluoroacetic acid (2 mL) and methylene chloride (2 mL). The resulting solution was stirred at room temperature for 1 hour. The solvents were evaporated to dryness. The residue was treated with methanol (3 mL) and ethylenediamine (0.3 mL, 4 mmol) for 1 hour at room temperature. Purification using HPLC method A gave the title compound 3-[(3-{3-(cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)carbonyl]-5-fluorobenzonitrile as a TFA salt. LCMS found: 536.3 (M+H)⁺. ¹H NMR (400 MHz, DMSO-$d_6$): δ 8.93 (s, 1H), 8.81 (s, 1H), 8.51 (s, 1H), 7.97 (s, 1H), 7.81 (s, 1H), 7.72 (m, 3H), 7.18 (s, 1H), 4.53 (m, 2H), 3.80 (m, 1H), 3.57 (m, 6H), 1.55-2.08 (m, 8H).

The following compounds were prepared by a method analogous to that for Example 138.

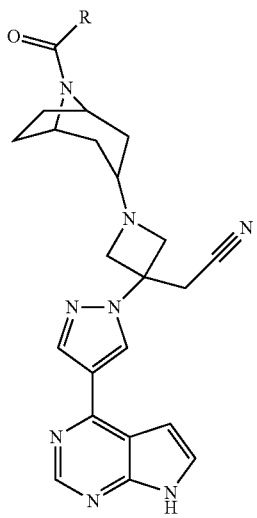

| Example # | R | Compound | LC-MS (M + H)⁺ |
|---|---|---|---|
| 139 | 3,4-difluorophenyl | {1-[8-(3,4-difluorobenzoyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile | 529.2 |
| 140 | 2-fluoro-4-cyanophenyl | 4-[(3-{3-(cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)carbonyl]-2-fluorobenzonitrile | 536.2 |
| 141 | 4-chloro-3-fluorophenyl | {1-[8-(4-chloro-3-fluorobenzoyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile | 545.1 |
| 142 | 3-fluoro-2-(trifluoromethyl)pyridin-4-yl | {1-{8-[3-fluoro-2-(trifluoromethyl)isonicotinoyl]-8-azabicyclo[3.2.1]oct-3-yl}-3-[4-(7H-pyrrolo[2,3-d]pyrimidin-4-yl)-1H-pyrazol-1-yl]azetidin-3-yl}acetonitrile | 580.2 |
| 143 | 6-(trifluoromethyl)pyridin-3-yl | [3-[4-(7H-pyrrolo[2,3-d]pyrimidin-4-yl)-1H-pyrazol-1-yl]-1-(8-{[6-(trifluoromethyl)pyridin-3-yl]carbonyl}-8-azabicyclo[3.2.1]oct-3-yl)azetidin-3-yl]acetonitrile | 562.2 |

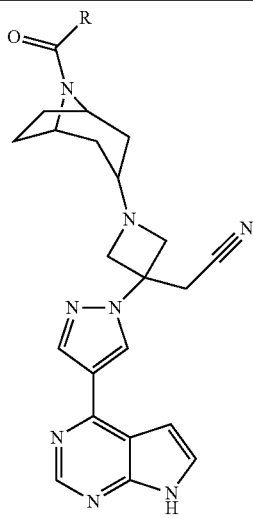

| Example # | R | Compound | LC-MS (M + H)+ |
|---|---|---|---|
| 144 | 4-pyridyl with 2-CF3 | (3-[4-(7H-pyrrolo[2,3-d]pyrimidin-4-yl)-1H-pyrazol-1-yl]-1-{8-[2-(trifluoromethyl)isonicotinoyl]-8-azabicyclo[3.2.1]oct-3-yl}azetidin-3-yl)acetonitrile | 562.2 |
| 145 | cyclopentyl | {1-[8-(cyclopentylcarbonyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile | 485.2 |
| 146 | tetrahydro-2H-pyran-4-yl | {3-[4-(7H-pyrrolo[2,3-d]pyrimidin-4-yl)-1H-pyrazol-1-yl]-1-[8-(tetrahydro-2H-pyran-4-ylcarbonyl)-8-azabicyclo[3.2.1]oct-3-yl]azetidin-3-yl}acetonitrile | 501.2 |
| 147 | cyclohexyl | {1-[8-(cyclohexylcarbonyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile | 499.2 |
| 148 | 4,4-difluorocyclohexyl | {1-{8-[(4,4-difluorocyclohexyl)carbonyl]-8-azabicyclo[3.2.1]oct-3-yl}-3-[4-(7H-pyrrolo[2,3-d]pyrimidin-4-yl)-1H-pyrazol-1-yl]azetidin-3-yl}acetonitrile | 535.2 |

$^1$H NMR (400 MHz, DMSO-$d_6$) of Example 139 (TFA salt): δ 8.93 (s, 1H), 8.80 (s, 1H), 8.51 (s, 1H), 7.74 (s, 1H), 7.54 (m, 3H), 7.34 (s, 1H), 7.17 (s, 1H), 4.50-5.00 (m, 2H), 3.88 (m, 1H), 3.57 (m, 6H), 1.55-2.08 (m, 8H).

$^1$H NMR (300 MHz, DMSO-$d_6$) of Example 143: δ 12.18 (brs, 1H), 8.80 (s, 1H), 8.73 (s, 1H), 8.63 (s, 1H), 8.33 (s, 1H), 8.11 (d, 1H), 7.91 (d, 1H), 7.55 (d, 1H), 6.99 (d, 1H), 4.50 (s, 1H), 3.78 (s, 1H), 3.43 (s, 2H), 3.23 (s, 4H), 2.62 (m, 1H), 2.05 (m, 2H), 1.91-1.59 (m, 4H), 1.50 (m, 1H).

$^1$H NMR (300 MHz, DMSO-$d_6$) of Example 144: δ 12.11 (brs, 1H), 8.81 (dd, 1H), 8.73 9 (s, 1H), 8.62 (s, 1H), 8.33 (s, 1H), 7.89 (s, 1H), 7.22 (dd, 1H), 7.03 (d, 1H), 6.99 (d, 1H), 4.49 (m, 1H), 3.70 (m, 1H), 3.50 (d, 4H), 3.28 (s, 2H), 2.64 (m, 1H), 2.05 (m, 2H), 1.90-1.60 (m, 4H), 1.49 (m, 2H).

Examples 149 and 150

Diastereomers of {1-[1-(3-fluorobenzoyl)-2-methyl-piperidin-4-yl]-3-[4-(7H-pyrrolo[2,3-d]pyrimidin-4-yl)-1H-pyrazol-1-yl]azetidin-3-yl}acetonitrile

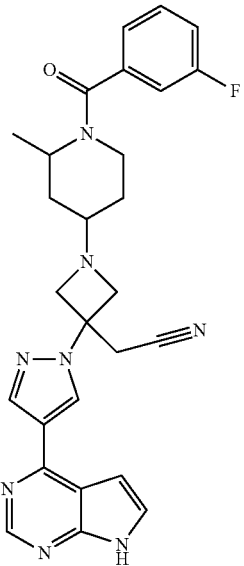 [SMILES: CC1CC(N2CC(CC#N)(n3cc(-c4ncnc5[nH]ccc45)cn3)C2)CCN1C(=O)c1cccc(F)c1]

Step A: tert-Butyl 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-methylpiperidine-1-carboxylate

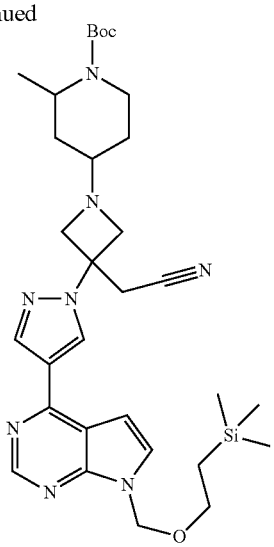

To a solution of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (2.6 g, 6.3 mmol) and tert-butyl 2-methyl-4-oxopiperidine-1-carboxylate (1.3 g, 6.3 mmol) in THF (30 mL) were added N,N-diisopropylethylamine (4.4 mL, 25 mmol) and sodium triacetoxyborohydride (2.2 g, 10 mmol). The mixture was stirred at room temperature overnight. After addition of 20 mL of brine, the solution was extracted with EtOAc. The extract was dried over anhydrous Na$_2$SO$_4$ and filtered. After removing the solvent, the residue was purified by combiflash chromatography eluting with 30-80% EtOAc in hexanes to give 2.6 g (81%) of the desired product tert-butyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-methylpiperidine-1-carboxylate. LC-MS: 607.3 (M+H)$^+$.

Step B: {1-(2-Methylpiperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

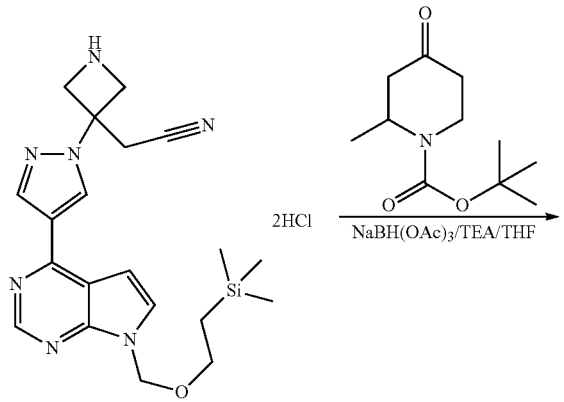

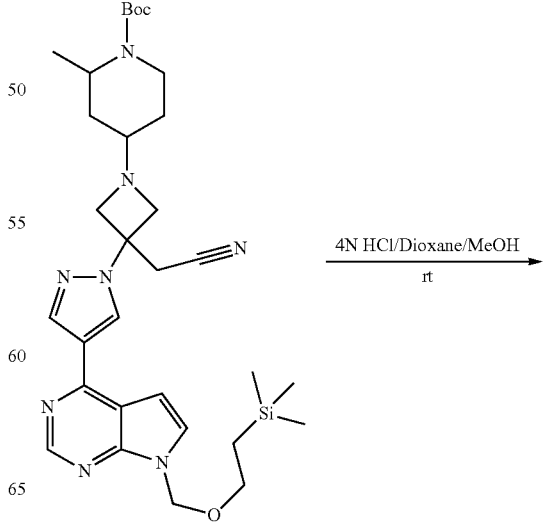

-continued

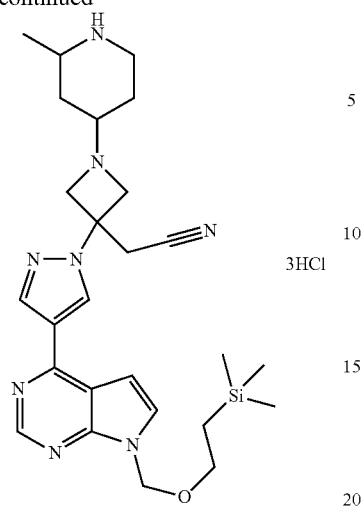

To a solution of tert-butyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-methylpiperidine-1-carboxylate (0.5 g) in methanol (2 mL) was added 10 mL of a 4.0 N solution of hydrogen chloride in 1,4-dioxane (40 mmol). The resulting solution was stirred at room temperature for an hour. The solvents were removed under reduced pressure to give 0.5 g (99%) of {1-(2-methylpiperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile as a white solid. LC-MS: 507.1 (M+H)$^+$.

Step C: {1-[1-(3-Fluorobenzoyl)-2-methylpiperidin-4-yl]-3-[4-(H-pyrrolo[2, 3-d]pyrimidin-4-yl)-1H-pyrazol-1-yl]azetidin-3-yl}acetonitrile To a solution of {1-(2-methylpiperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (40 mg, 0.08 mmol) in DMF (3 mL) were added 3-fluorobenzoic acid (12.51 mg, 0.0893 mmol), benzotriazol-1-yloxytris(dimethylamino)phosphonium hexafluorophosphate (53.86 mg, 0.122 mmol) and triethylamine (0.0396 mL, 0.284 mmol). The mixture was stirred at room temperature overnight and purified by prep-LC-MS to give 20 mg of {1-[1-(3-fluorobenzoyl)-2-methylpiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile as a white powder. LC/MS found: 629.3 (M+H)$^+$.

The above white powder (20 mg, 0.03 mmol) was dissolved in 2 mL of trifluoroacetic acid and 2 mL of methylene chloride. The mixture was stirred at room temperature for an hour. The solvents were removed under reduced pressure. The residue was dissolved in methanol (2 mL) and ethylenediamine (0.03 mL, 0.4 mmol). The mixture was stirred at room temperature for an hour. Purification by HPLC (method B) gave 4.5 mg of diastereomer 1 (Example 149) and 4.5 mg of diastereomer 2 (Example 150) as a white solid. Both diastereomers were mixture of 2 enantiomers. LC/MS found: 499.3 (M+H)$^+$ for both diastereomers.

Example 151

{1-{1-[(4,4-difluorocyclohexyl)carbonyl]-2-methylpiperidin-4-yl}-3-[4-(7H-pyrrolo[2,3-d]pyrimidin-4-yl)-1H-pyrazol-1-yl]azetidin-3-yl}acetonitrile The title compound was prepared as a mixture of 4 isomers by a method analogous to that for Examples 149 and 150. LC-MS: 523.2 (M+H)$^+$.

Example 152

{1-[1-(3-Fluorobenzoyl)-4-methylpiperidin-4-yl]-3-[4-(7H-pyrrolo[2,3-d]pyrimidin-4-yl)-1H-pyrazol-1-yl]azetidin-3-yl}acetonitrile

Step A: tert-Butyl 4-[3-(Cyanomethylene)azetidin-1-yl]-4-methylpiperidine-1-carboxylate

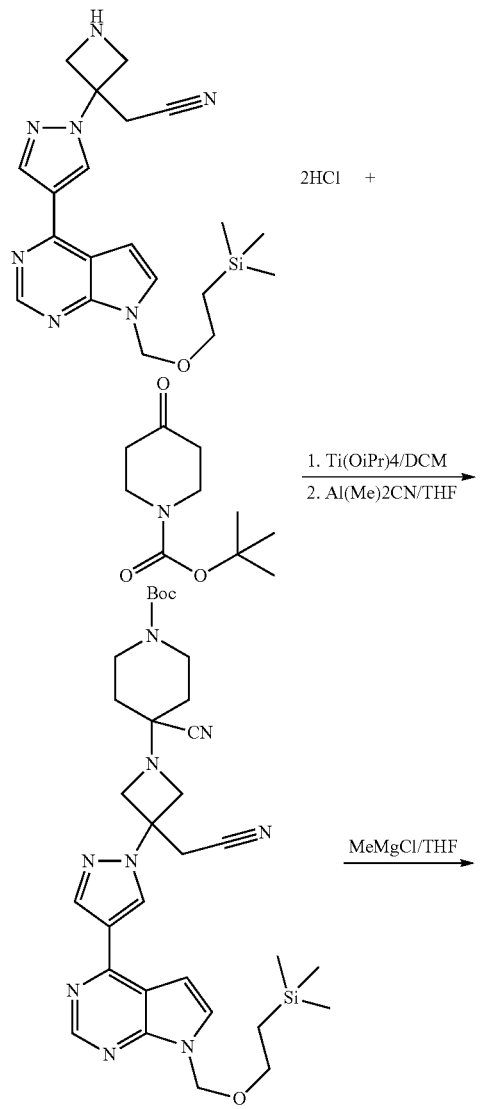

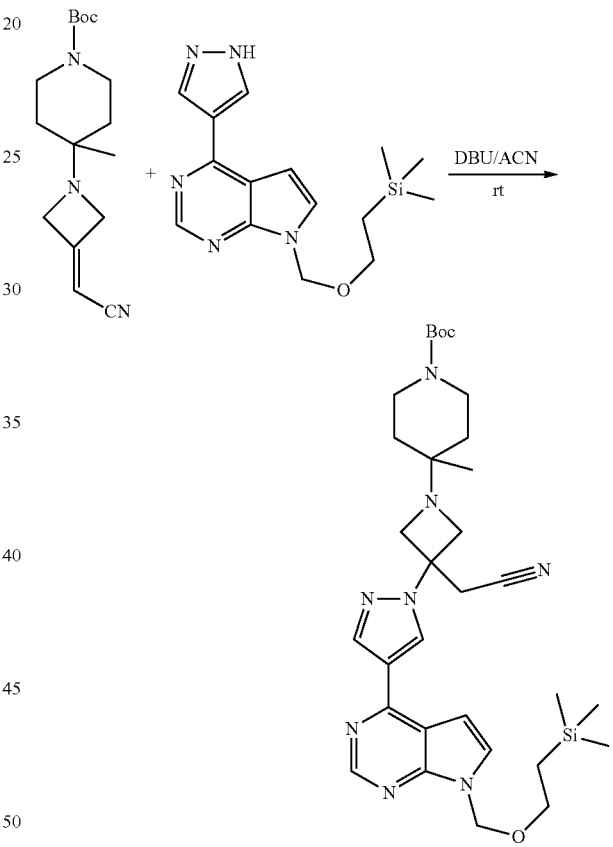

A round-bottom flask was charged with {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride (1.0 g, 2.4 mmol), tert-butyl 4-oxo-1-piperidinecarboxylate (0.49 g, 2.4 mmol), titanium tetraisopropoxide (0.72 mL, 2.4 mmol), triethylamine (1.0 mL, 7.3 mmol), and 10 mL of dichloromethane. The reaction mixture was stirred at room temperature overnight and then rotovaped to dryness to give an oil residue which was used directly for the next step.

The above residue was dissolved in 25 mL of THF. To the resulting solution was added a 1.0 M solution of diethylaluminum cyanide in toluene (8.4 mL, 8.4 mmol). The mixture was stirred at 30° C. for 5 hours. The reaction was quenched with 1 mL of water and 20 mL of EtOAc, stirred for 30 min and filtered through celite. The celite was washed with 20 mL of EtOAc. The filtrate was dried over Na$_2$SO$_4$ and concentrated to dryness to give 1.3 g of the desired product as a colorless oil. MS found: 618 (M+H)$^+$.

The colorless oil was dissolved in THF (20 mL) and a 3 M solution of methylmagnesium bromide in THF (0.45 mL, 1.3 mmol) was added. The mixture was stirred at room temperature overnight. The reaction was quenched by addition of 15 mL of water and 25 mL of EtOAc. After being stirred for 30 min, the solution was flittered through a celite bed. The organic layer was separated, dried over anhydrous Na$_2$SO$_4$, and evaporated under reduced pressure. Purification by HPLC afforded the desired product tert-butyl 4-[3-(cyanomethylene)azetidin-1-yl]-4-methylpiperidine-1-carboxylate. LC-MS: 292.1 (M+H)$^+$.

Step B: tert-Butyl 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-4-methylpiperidine-1-carboxylate A 2 L round bottom flask fitted with overhead stirring, septa and nitrogen inlet was charged with tert-butyl 4-[3-(cyanomethylene)azetidin-1-yl]-4-methylpiperidine-1-carboxylate (9.17 g, 0.0472 mol), 4-(1H-pyrazol-4-yl)-7-{[2-(trimethylsilyl)ethoxy]methyl}-7H-pyrrolo[2,3-d]pyrimidine (14.9 g, 0.0472 mol) and acetonitrile (300 mL). The resulting solution was heterogeneous. To the solution was added 1,8-diazabicyclo[5.4.0]undec-7-ene (8.48 mL, 0.0567 mol) portionwise via a syringe over 3 minutes at room temperature. The solution slowly became homogeneous and yellow in color. The reaction was allowed to stir at room temperature for 3 hours. The solution was concentrated on a rotovap to remove ~150 mL of acetonitrile. After addition of 100 mL of EtOAc and 100 mL of 20% brine, the organic phase was separated. The aqueous layer was extracted with 150 mL of EtOAc. The combined organic phase was dried over MgSO₄, filtered and concentrated to yield an orange oil. Purification by flash chromatography (150 grams of silica, 60% EtOAc/hexanes, loaded with CH₂Cl₂) yielded the title compound as a white foam. LC-MS: 607.2 (M+H)⁺.

Step C: {1-(4-Methylpiperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

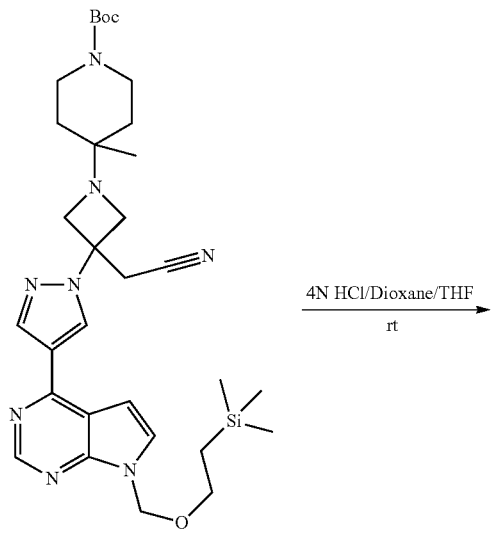

To a solution of tert-butyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-4-methylpiperidine-1-carboxylate (30 mg, 0.05 mmol) in THF (2 mL) was added a 4 N solution of HCl in dioxane (2 mL). After being stirred at room temperature for 2 hours, the reaction mixture was evaporated under reduced pressure to give the title compound (31 mg, 99%), which was used for the next reaction. LC-MS found: 507.2 (M+H)⁺.

Step D: {1-[1-(3-Fluorobenzoyl)-4-methylpiperidin-4-yl]-3-[4-(7H-pyrrolo[2, 3-d]pyrimidin-4-yl)-1H-pyrazol-1-yl]azetidin-3-yl}acetonitrile To a solution of {1-(4-methylpiperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (40 mg, 0.08 mmol) in DMF (3 mL) were added benzotriazol-1-yloxytris(dimethylamino)phosphonium hexafluorophosphate (45 mg, 0.10 mmol), N,N-diisopropylethylamine (0.041 mL, 0.24 mmol), and 3-fluorobenzoic acid (11 mg, 0.079 mmol). The reaction mixture was stirred at room temperature overnight. Purification by HPLC afforded the desired intermediate as a white powder, which was then treated with TFA (1 mL) and DCM (1 mL) for 1 hour at room temperature. After removing the solvents, the residue was treated with ethylenediamine (1 mL) in methanol (5 mL) for 2 hours. Purification using HPLC method A provided A provided the final product {1-[1-(3-fluorobenzoyl)-4-methylpiperidin-4-yl]-3-[4-(7H-pyrrolo[2,3-d]pyrimidin-4-yl)-1H-pyrazol-1-yl]azetidin-3-yl}acetonitrile as a TFA salt. LC-MS found: 499.3 (M+H)⁺. ¹H NMR (400 MHz, DMSO-d₆): δ 12.36 (s, 1H), 8.81-9.11 (m, 2H), 8.77 (s, 1H), 8.57 (s, 1H), 7.71 (t, 1H), 7.31 (m, 1H), 7.25 (dd, 2H), 7.17 (s, 1H), 4.5-4.85 (m, 4H), 3.82 (m, 2H), 3.56 (s, 4H), 3.21 (m, 1H), 2.60 (m, 1H), 1.55-1.75 (m, 2H), 1.37 (s, 3H).

Example 153

{1-[1-(Cyclohexylcarbonyl)-4-methylpiperidin-4-yl]-3-[4-(7H-pyrrolo[2,3-d]pyrimidin-4-yl)-1H-pyrazol-1-yl]azetidin-3-yl}acetonitrile

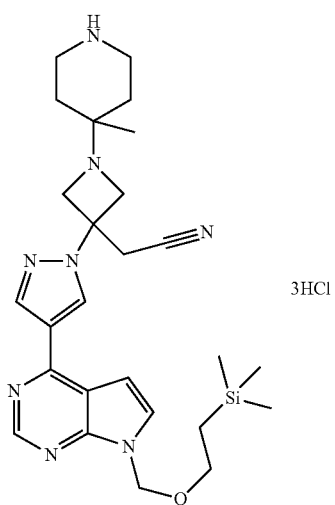

3HCl

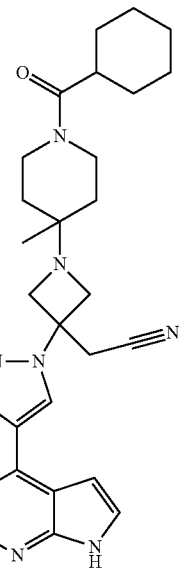

The title compound was prepared by a method analogous to that for Example 152 and was obtained as a TFA salt using HPLC method A for purification. LC-MS: 487.2 (M+H)⁺. ¹H NMR (400 MHz, DMSO-d₆): δ 12.28 (s, 1H), 8.81-9.11 (m, 1H), 8.74 (s, 1H), 8.55 (s, 1H), 7.68 (t, 1H), 7.11 (m, 1H), 4.40-4.85 (m, 4H), 3.80-3.95 (m, 1H), 3.56 (s, 2H), 3.15 (m, 1H), 2.60 (m, 1H), 1.63 (m, 10H), 1.43 (s, 3H), 1.12-1.28 (m, 6H).

Example 154

4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide

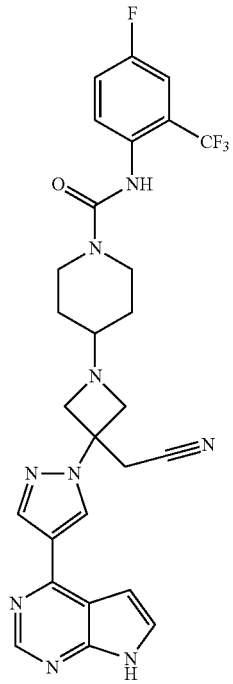 [SMILES: N#CCC1(n2cc(-c3ncnc4[nH]ccc34)cn2)CN(C2CCN(C(=O)Nc3ccc(F)cc3C(F)(F)F)CC2)C1]

Step A: 4-{3-(Cyanomethyl)-3-[4-(7-{[2-(trimethylsilyl)ethoxy]methyl}-7H-pyrrolo[2, 3-d]pyrimidin-4-yl)-1H-pyrazol-1-yl]azetidin-1-yl}-N-[4-fluoro-2-(trifluoromethyl)phenyl]piperidine-1-carboxamide

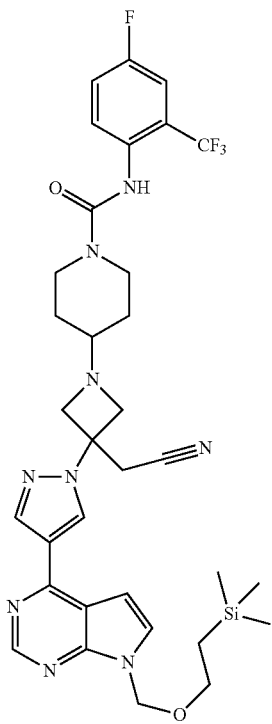 [SMILES: C[Si](C)(C)CCOCn1ccc2c(-c3cnn(C4(CC#N)CN(C5CCN(C(=O)Nc6ccc(F)cc6C(F)(F)F)CC5)C4)c3)ncnc21]

To a solution of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride (500 mg, 1 mmol) in tetrahydrofuran (30 mL) were added triethylamine (0.29 g, 2.8 mmol) and 4-fluoro-1-isocyanato-2-(trifluoromethyl)benzene (190 mg, 0.95 mmol). The mixture was stirred at room temperature for 1 hour. The solvent was removed under reduced pressure. Purification by combiflash using 30-100% EtOAc/hexanes gave 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide as a powder. LC-MS: 698.1 (M+H)$^+$.

Step B: 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide (210 mg, 0.3 mmol) was dissolved in a 50 M solution of trifluoroacetic acid in methylene chloride (20 mL). After being stirred at room temperature for one hour, the solvents were removed under reduced pressure. The residue was dissolved in methanol (20 mL) and ethylenediamine (1.0 g, 17 mmol). After being stirred at room temperature for one hour, the mixture was purified by HPLC (method B) to give 4-{3-(cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide as a white powder. LC-MS: 568.1 (M+H)$^+$. $^1$H NMR (400 MHz, DMSO-d$_6$): δ 12.10 (s, 1H), 8.76 (s, 1H), 8.63 (s, 1H), 8.36 (s, 1H), 8.18 (s, 1H), 7.55 (d, J=3.6 Hz, 1H), 7.50 (m, 1H), 7.43 (m, 1H), 7.34 (m, 1H), 7.01 (d, J=3.6 Hz, 1H), 3.79 (m, 2H), 3.67 (d, J=8 Hz, 2H), 3.51 (m, 4H), 2.92 (m, 2H), 2.38 (m, 1H), 1.62 (m, 2H), 1.09 (m, 2H).

Example 155

4-{3-(Cyanomethyl)-3-[4-(7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide

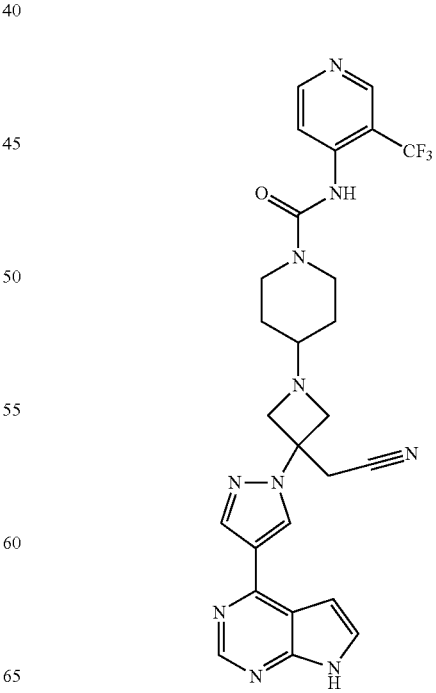

Step A: 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide

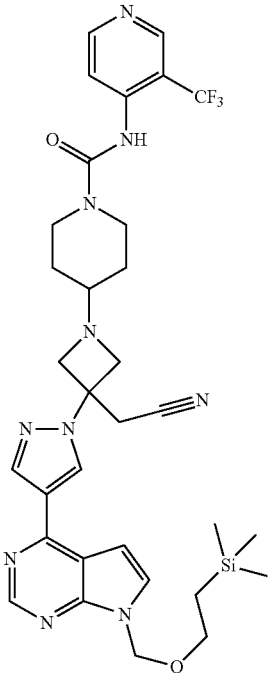 [SMILES: C[Si](C)(C)CCOCn1ccc2c(-c3cnn(C4(CC#N)CN(C5CCN(C(=O)Nc6ccncc6C(F)(F)F)CC5)C4)c3)ncnc21]

A 20 mL vial was charged with 4-(trifluoromethyl)pyridin-3-amine (15.6 mg, 0.0963 mmol), THF (2 mL), a 20 M solution of phosgene in toluene (0.50 mL, 1 mmol) and triethylamine (0.017 mL, 0.12 mmol). The mixture was stirred at room temperature for one hour and concentrated. To the vial were added {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride (40 mg, 0.08 mmol), THF (2 mL) and triethylamine (0.025 g, 0.24 mmol). The mixture was stirred for two hours and purified with HPLC to give 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide as a white solid. LC-MS: 681.3 (M+H)$^+$.

Step B: 4-{3-(Cyanomethyl)-3-[4-(7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide A 20 mL vial was charged with 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide (56 mg, 0.1 mmol), trifluoroacetic acid (1.5 mL, 19 mmol) and methylene chloride (1.5 mL). The mixture was stirred at room temperature for 1 hour and concentrated in vacuum. The residue was dissolved in 3 mL of a methanol solution containing 20% ethylenediamine. After being stirred at room temperature for 1 hour, HPLC purification (method B) gave the title compound 4-{3-(cyanomethyl)-3-[4-(7H-pyrrolo[2,3-d]pyrimidin-4-yl)-1H-pyrazol-1-yl]azetidin-1-yl}-N-[3-(trifluoromethyl)pyridin-4-yl]piperidine-1-carboxamide. LC-MS: 551.2 (M+H)$^+$.

The following compounds were prepared by a method analogous to that for Example 154 or Example 155.

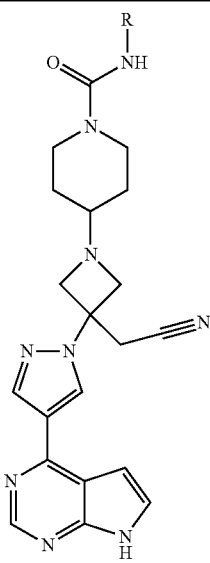

| Example # | R | Compound | LC-MS (M + H)$^+$ |
|---|---|---|---|
| 156 | ![2,6-difluorophenyl] | 4-{3-(cyanomethyl)-3-[4-(7H-pyrrolo[2,3-d]pyrimidin-4-yl)-1H-pyrazol-1-yl]azetidin-1-yl}-N-(2,6-difluorophenyl)piperidine-1-carboxamide | 518.2 |

-continued

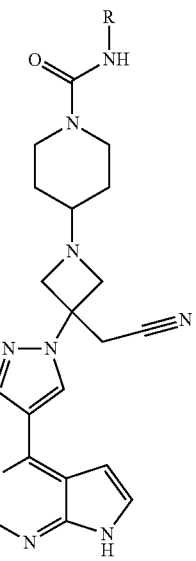

| Example # | R | Compound | LC-MS (M + H)+ |
|---|---|---|---|
| 157 | 2-(trifluoromethyl)phenyl | 4-{3-(cyanomethyl)-3-[4-(7H-pyrrolo[2,3-d]pyrimidin-4-yl)-1H-pyrazol-1-yl]azetidin-1-yl}-N-[2-(trifluoromethyl)phenyl]piperidine-1-carboxamide | 550.2 |
| 158 | 2-(trifluoromethoxy)phenyl | 4-{3-(cyanomethyl)-3-[4-(7H-pyrrolo[2,3-d]pyrimidin-4-yl)-1H-pyrazol-1-yl]azetidin-1-yl}-N-[2-(trifluoromethoxy)phenyl]piperidine-1-carboxamide | 566.2 |
| 159 | 4-bromo-3-thienyl | N-(4-bromo-3-thienyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 566.1 568.1 |
| 160 | 2,6-dichlorophenyl | 4-{3-(cyanomethyl)-3-[4-(7H-pyrrolo[2,3-d]pyrimidin-4-yl)-1H-pyrazol-1-yl]azetidin-1-yl}-N-(2,6-dichlorophenyl)piperidine-1-carboxamide | 550.1 |
| 161 | 2-chloro-6-methylphenyl | N-(2-chloro-6-methylphenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 530.1 |
| 162 | 2-chloro-4-fluorophenyl | N-(2-chloro-4-fluorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 534.1 |

-continued

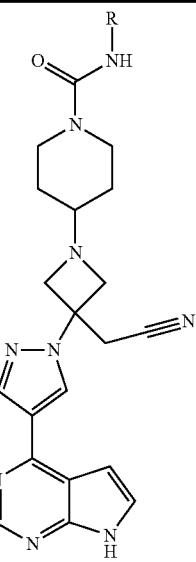

| Example # | R | Compound | LC-MS (M + H)+ |
|---|---|---|---|
| 163 | 2-chlorophenyl | N-(2-chlorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 516.2 |
| 164 | 2-(F₂HCO)phenyl | 4-{3-(cyanomethyl)-3-[4-(7H-pyrrolo[2,3-d]pyrimidin-4-yl)-1H-pyrazol-1-yl]azetidin-1-yl}-N-[2-(difluoromethoxy)phenyl]piperidine-1-carboxamide | 548.2 |
| 165 | 4-(F₃C)pyridin-3-yl | 4-{3-(cyanomethyl)-3-[3-(7H-pyrrolo[2,3-d]pyrimidin-4-yl)-1H-pyrrol-1-yl]azetidin-1-yl}-N-[4-(trifluoromethyl)pyridin-3-yl]piperidine-1-carboxamide | 551.2 |
| 166 | 3-(CF₃)phenyl | 4-{3-(cyanomethyl)-3-[4-(7H-pyrrolo[2,3-d]pyrimidin-4-yl)-1H-pyrazol-1-yl]azetidin-1-yl}-N-[3-(trifluoromethyl)phenyl]piperidine-1-carboxamide | 550.2 |
| 167 | 4-(CF₃)phenyl | 4-{3-(cyanomethyl)-3-[4-(7H-pyrrolo[2,3-d]pyrimidin-4-yl)-1H-pyrazol-1-yl]azetidin-1-yl}-N-[4-(trifluoromethyl)phenyl]piperidine-1-carboxamide | 550.2 |
| 168 | 5-chloro-2-methylphenyl | N-(5-chloro-2-methylphenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 530.2 |
| 169 | 2-fluorophenyl | 4-{3-(cyanomethyl)-3-[4-(7H-pyrrolo[2,3-d]pyrimidin-4-yl)-1H-pyrazol-1-yl]azetidin-1-yl}-N-(2-fluorophenyl)piperidine-1-carboxamide | 500.2 |

-continued

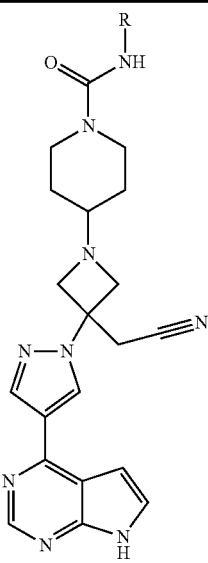

| Example # | R | Compound | LC-MS (M + H)+ |
|---|---|---|---|
| 170 | 2-fluoro-3-(trifluoromethyl)phenyl | 4-{3-(cyanomethyl)-3-[4-(7H-pyrrolo[2,3-d]pyrimidin-4-yl)-1H-pyrazol-1-yl]azetidin-1-yl}-N-[2-fluoro-3-(trifluoromethyl)phenyl]piperidine-1-carboxamide | 568.2 |
| 171 | 2,4-difluorophenyl | 4-{3-(cyanomethyl)-3-[4-(7H-pyrrolo[2,3-d]pyrimidin-4-yl)-1H-pyrazol-1-yl]azetidin-1-yl}-N-(2,4-difluorophenyl)piperidine-1-carboxamide | 518.2 |
| 172 | 2,3,4-trifluorophenyl | 4-{3-(cyanomethyl)-3-[4-(7H-pyrrolo[2,3-d]pyrimidin-4-yl)-1H-pyrazol-1-yl]azetidin-1-yl}-N-(2,3,4-trifluorophenyl)piperidine-1-carboxamide | 536.2 |
| 173 | 2,3,5-trifluorophenyl | 4-{3-(cyanomethyl)-3-[4-(7H-pyrrolo[2,3-d]pyrimidin-4-yl)-1H-pyrazol-1-yl]azetidin-1-yl}-N-(2,3,5-trifluorophenyl)piperidine-1-carboxamide | 536.2 |
| 174 | 2,5-difluorophenyl | 4-{3-(cyanomethyl)-3-[4-(7H-pyrrolo[2,3-d]pyrimidin-4-yl)-1H-pyrazol-1-yl]azetidin-1-yl}-N-(2,5-difluorophenyl)piperidine-1-carboxamide | 518.2 |
| 175 | 3,5-difluorophenyl | 4-{3-(cyanomethyl)-3-[4-(7H-pyrrolo[2,3-d]pyrimidin-4-yl)-1H-pyrazol-1-yl]azetidin-1-yl}-N-(3,5-difluorophenyl)piperidine-1-carboxamide | 518.2 |

-continued

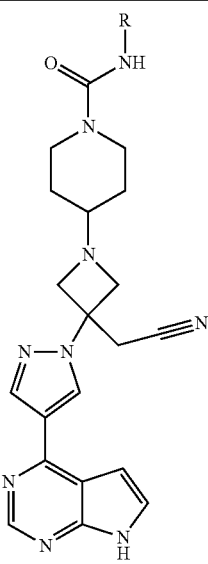

| Example # | R | Compound | LC-MS (M + H)+ |
|---|---|---|---|
| 176 | 3,4-difluorophenyl | 4-{3-(cyanomethyl)-3-[4-(7H-pyrrolo[2,3-d]pyrimidin-4-yl)-1H-pyrazol-1-yl]azetidin-1-yl}-N-(3,4-difluorophenyl)piperidine-1-carboxamide | 518.2 |
| 177 | 3-chloro-2-fluorophenyl | N-(3-chloro-2-fluorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 534.1 |
| 178 | 4-chloro-2-fluorophenyl | N-(4-chloro-2-fluorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 534.1 |
| 179 | 3-thienyl | 4-{3-(cyanomethyl)-3-[4-(7H-pyrrolo[2,3-d]pyrimidin-4-yl)-1H-pyrazol-1-yl]azetidin-1-yl}-N-3-thienylpiperidine-1-carboxamide | 488.1 |
| 180 | 2-methoxyphenyl | 4-{3-(cyanomethyl)-3-[4-(7H-pyrrolo[2,3-d]pyrimidin-4-yl)-1H-pyrazol-1-yl]azetidin-1-yl}-N-(2-methoxyphenyl)piperidine-1-carboxamide | 512.2 |
| 181 | 3-methoxyphenyl | 4-{3-(cyanomethyl)-3-[4-(7H-pyrrolo[2,3-d]pyrimidin-4-yl)-1H-pyrazol-1-yl]azetidin-1-yl}-N-(3-methoxyphenyl)piperidine-1-carboxamide | 512.2 |
| 182 | 4-(trifluoromethoxy)phenyl | 4-{3-(cyanomethyl)-3-[4-(7H-pyrrolo[2,3-d]pyrimidin-4-yl)-1H-pyrazol-1-yl]azetidin-1-yl}-N-[4-(trifluoromethoxy)phenyl]piperidine-1-carboxamide | 566.2 |

-continued

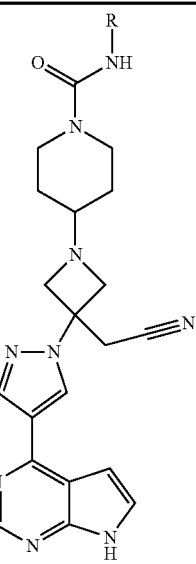

| Example # | R | Compound | LC-MS (M + H)+ |
|---|---|---|---|
| 183 | 3-chlorophenyl | N-(3-chlorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 516.1 |
| 184 | 4-chlorophenyl | N-(4-chlorophenyl)-4-{3-(cyanomethyl)-3-[4-(7H-pyrrolo[2,3-d]pyrimidin-4-yl)-1H-pyrazol-1-yl]azetidin-1-yl}piperidine-1-carboxamide | 516.1 |
| 185 | 2-methylphenyl | 4-{3-(cyanomethyl)-3-[4-(7H-pyrrolo[2,3-d]pyrimidin-4-yl)-1H-pyrazol-1-yl]azetidin-1-yl}-N-(2-methylphenyl)piperidine-1-carboxamide | 496.2 |
| 186 | 2,5-dimethoxyphenyl | 4-{3-(cyanomethyl)-3-[4-(7H-pyrrolo[2,3-d]pyrimidin-4-yl)-1H-pyrazol-1-yl]azetidin-1-yl}-N-(2,5-dimethoxyphenyl)piperidine-1-carboxamide | 542.2 |
| 187 | 4-fluoro-2-methylphenyl | 4-{3-(cyanomethyl)-3-[4-(7H-pyrrolo[2,3-d]pyrimidin-4-yl)-1H-pyrazol-1-yl]azetidin-1-yl}-N-(4-fluoro-2-methylphenyl)piperidine-1-carboxamide | 514.2 |
| 188 | 6-(trifluoromethyl)pyridin-2-yl | 4-{3-(cyanomethyl)-3-[4-(7H-pyrrolo[2,3-d]pyrimidin-4-yl)-1H-pyrazol-1-yl]azetidin-1-yl}-N-[6-(trifluoromethyl)pyridin-2-yl]piperidine-1-carboxamide | 551.2 |
| 189 | 2,6-dimethylpyridin-3-yl | 4-{3-(cyanomethyl)-3-[4-(7H-pyrrolo[2,3-d]pyrimidin-4-yl)-1H-pyrazol-1-yl]azetidin-1-yl}-N-(2,6-dimethylpyridin-3-yl)piperidine-1-carboxamide | 511.2 |

-continued

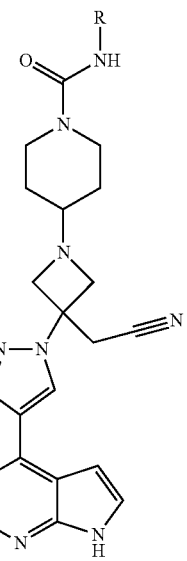

| Example # | R | Compound | LC-MS (M + H)+ |
|---|---|---|---|
| 190 | thiazol-2-yl | 4-{3-(cyanomethyl)-3-[4-(7H-pyrrolo[2,3-d]pyrimidin-4-yl)-1H-pyrazol-1-yl]azetidin-1-yl}-N-1,3-thiazol-2-ylpiperidine-1-carboxamide | 489.1 |
| 191 | 4-methylthiazol-2-yl | 4-{3-(cyanomethyl)-3-[4-(7H-pyrrolo[2,3-d]pyrimidin-4-yl)-1H-pyrazol-1-yl]azetidin-1-yl}-N-(4-methyl-1,3-thiazol-2-yl)piperidine-1-carboxamide | 503.1 |
| 192 | 4,5-dimethylthiazol-2-yl | 4-{3-(cyanomethyl)-3-[4-(7H-pyrrolo[2,3-d]pyrimidin-4-yl)-1H-pyrazol-1-yl]azetidin-1-yl}-N-(4,5-dimethyl-1,3-thiazol-2-yl)piperidine-1-carboxamide | 517.2 |
| 193 | benzothiazol-2-yl | N-1,3-benzothiazol-2-yl-4-{3-(cyanomethyl)-3-[4-(7H-pyrrolo[2,3-d]pyrimidin-4-yl)-1H-pyrazol-1-yl]azetidin-1-yl}piperidine-1-carboxamide | 539.1 |
| 194 | 1-methylbenzimidazol-2-yl | 4-{3-(cyanomethyl)-3-[4-(7H-pyrrolo[2,3-d]pyrimidin-4-yl)-1H-pyrazol-1-yl]azetidin-1-yl}-N-(1-methyl-1H-benzimidazol-2-yl)piperidine-1-carboxamide | 536.2 |
| 195 | 4-(4-chlorophenyl)-1,3-thiazol-2-yl | N-[4-(4-chlorophenyl)-1,3-thiazol-2-yl]-4-{3-(cyanomethyl)-3-[4-(7H-pyrrolo[2,3-d]pyrimidin-4-yl)-1H-pyrazol-1-yl]azetidin-1-yl}piperidine-1-carboxamide | 599.1 |
| 196 | 1-ethyl-1H-pyrazol-5-yl | 4-{3-(cyanomethyl)-3-[4-(7H-pyrrolo[2,3-d]pyrimidin-4-yl)-1H-pyrazol-1-yl]azetidin-1-yl}-N-(1-ethyl-1H-pyrazol-5-yl)piperidine-1-carboxamide | 500.2 |

-continued

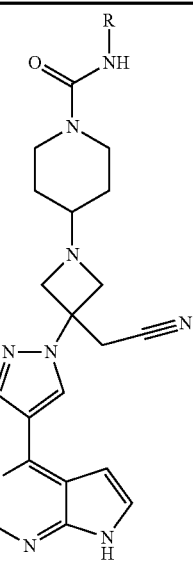

| Example # | R | Compound | LC-MS (M + H)+ |
|---|---|---|---|
| 197 | 1,5-dimethylpyrazol-3-yl (1,3-dimethyl-1H-pyrazol-5-yl) | 4-{3-(cyanomethyl)-3-[4-(7H-pyrrolo[2,3-d]pyrimidin-4-yl)-1H-pyrazol-1-yl]azetidin-1-yl}-N-(1,3-dimethyl-1H-pyrazol-5-yl)piperidine-1-carboxamide | 500.2 |
| 198 | 2-methylpyridin-3-yl | 4-{3-(cyanomethyl)-3-[4-(7H-pyrrolo[2,3-d]pyrimidin-4-yl)-1H-pyrazol-1-yl]azetidin-1-yl}-N-(2-methylpyridin-3-yl)piperidine-1-carboxamide | 497.2 |
| 199 | 6-fluoro-2-methylpyridin-3-yl | 4-{3-(cyanomethyl)-3-[4-(7H-pyrrolo[2,3-d]pyrimidin-4-yl)-1H-pyrazol-1-yl]azetidin-1-yl}-N-(6-fluoro-2-methylpyridin-3-yl)piperidine-1-carboxamide | 515.2 |
| 200 | 2-fluoro-6-methylpyridin-3-yl | 4-{3-(cyanomethyl)-3-[4-(7H-pyrrolo[2,3-d]pyrimidin-4-yl)-1H-pyrazol-1-yl]azetidin-1-yl}-N-(2-fluoro-6-methylpyridin-3-yl)piperidine-1-carboxamide | 515.2 |
| 201 | 3-(trifluoromethyl)pyridin-2-yl | 4-{3-(cyanomethyl)-3-[4-(7H-pyrrolo[2,3-d]pyrimidin-4-yl)-1H-pyrazol-1-yl]azetidin-1-yl}-N-[3-(trifluoromethyl)pyridin-2-yl]piperidine-1-carboxamide | 551.2 |
| 202 | 3-fluoropyridin-2-yl | 4-{3-(cyanomethyl)-3-[4-(7H-pyrrolo[2,3-d]pyrimidin-4-yl)-1H-pyrazol-1-yl]azetidin-1-yl}-N-(3-fluoropyridin-2-yl)piperidine-1-carboxamide | 501.2 |
| 203 | 3,5-difluoropyridin-2-yl | 4-{3-(cyanomethyl)-3-[4-(7H-pyrrolo[2,3-d]pyrimidin-4-yl)-1H-pyrazol-1-yl]azetidin-1-yl}-N-(3,5-difluoropyridin-2-yl)piperidine-1-carboxamide | 519.2 |

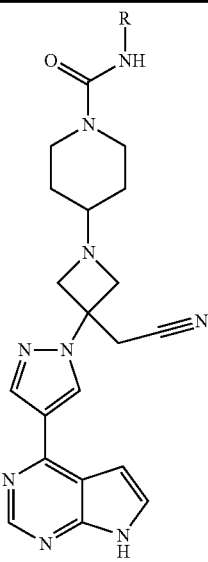

| Example # | R | Compound | LC-MS (M + H)+ |
|---|---|---|---|
| 204 | MeO, pyridin-3-yl (2-methoxy) | 4-{3-(cyanomethyl)-3-[4-(7H-pyrrolo[2,3-d]pyrimidin-4-yl)-1H-pyrazol-1-yl]azetidin-1-yl}-N-(2-methoxypyridin-3-yl)piperidine-1-carboxamide | 513.2 |
| 205 | 2-methyl-6-(trifluoromethyl)pyridin-3-yl | 4-{3-(cyanomethyl)-3-[4-(7H-pyrrolo[2,3-d]pyrimidin-4-yl)-1H-pyrazol-1-yl]azetidin-1-yl}-N-[2-methyl-6-(trifluoromethyl)pyridin-3-yl]piperidine-1-carboxamide | 565.2 |
| 206 | MeO$_2$C-phenyl | methyl 2-{[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]amino}benzoate | 540.2 |
| 207 | MeO$_2$C, F-phenyl | methyl 2-{[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]amino}-5-fluorobenzoate | 558.2 |
| 208 | F, CO$_2$Me-phenyl | methyl 4-{[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]amino}-3-fluorobenzoate | 558.2 |

$^1$H NMR (400 MHz, DMSO-d$_6$) of Example 156: δ 12.10 (br, 1H), 8.76 (s, 1H), 8.63 (s, 1H), 8.36 (s, 1H), 8.15 (s, 1H), 7.55 (d, 1H), 7.21 (m, 1H), 7.01 (m, 3H), 3.82 (dd, 2H), 3.70 (d, 2H), 3.54 (m, 4H), 2.94 (t, 2H), 2.38 (m, 1H), 1.64 (m, 2H), 1.11 (m, 2H).

$^1$H NMR (400 MHz, DMSO-d$_6$) of Example 157: δ 12.10 (s, 1H), 8.76 (s, 1H), 8.63 (s, 1H), 8.36 (s, 1H), 8.13 (s, 1H), 7.60 (d, J=8 Hz, 1H), 7.55 (m, 2H), 7.34 (m, 2H), 7.01 (d, J=3.6 Hz, 1H), 3.80 (m, 2H), 3.69 (d, J=8.4 Hz, 2H), 3.51 (m, 4H), 2.92 (m, 2H), 2.38 (m, 1H), 1.62 (m, 2H), 1.09 (m, 2H).

$^1$H NMR (400 MHz, DMSO-d$_6$) of Example 158: δ 12.10 (br, 1H), 8.76 (s, 1H), 8.63 (s, 1H), 8.36 (s, 1H), 8.26 (s, 1H), 7.55 (d, 1H), 7.43 (dd, 1H), 7.26 (dd, 2H), 7.12 (t, 1H), 7.01 (d, 1H), 3.81 (dd, 2H), 3.67 (d, 2H), 3.51 (m, 4H), 2.95 (t, 2H), 2.40 (m, 1H), 1.64 (m, 2H), 1.11 (m, 2H).

$^1$H NMR (400 MHz, DMSO-d$_6$) of Example 159: δ 12.10 (br, 1H), 8.76 (s, 1H), 8.63 (s, 1H), 8.36 (s, 1H), 8.07 (s, 1H), 7.55 (d, 1H), 7.43 (dd, 1H), 7.00 (d, 1H) 6.96 (d, 1H), 3.80 (dd, 2H), 3.67 (d, 2H), 3.51 (m, 4H), 2.95 (t, 2H), 2.38 (m, 1H), 1.64 (m, 2H), 1.11 (m, 2H).

¹H NMR (400 MHz, DMSO-d₆) of Example 160: δ 12.10 (br, 1H), 8.76 (s, 1H), 8.63 (s, 1H), 8.36 (s, 1H), 8.31 (s, 1H), 7.55 (d, 1H), 7.43 (d, 2H), 7.21 (t, 1H), 7.01 (d, 1H), 3.85 (dd, 2H), 3.70 (d, 2H), 3.52 (m, 4H), 2.94 (t, 2H), 2.40 (m, 1H), 1.65 (m, 2H), 1.12 (m, 2H).

¹H NMR (400 MHz, DMSO-d₆) of Example 161: δ 12.10 (br, 1H), 8.76 (s, 1H), 8.63 (s, 1H), 8.37 (s, 1H), 8.02 (s, 1H), 7.55 (d, 1H), 7.24 (dd, 1H), 7.05-7.13 (m, 2H), 7.01 (d, 1H), 3.87 (dd, 2H), 3.70 (d, 2H), 3.52 (m, 4H), 2.92 (t, 2H), 2.40 (m, 1H), 2.11 (s, 3H), 1.65 (m, 2H), 1.11 (m, 2H).

¹H NMR (400 MHz, DMSO-d₆) of Example 162: δ 12.10 (br, 1H), 8.76 (s, 1H), 8.63 (s, 1H), 8.36 (s, 1H), 8.17 (s, 1H), 7.55 (d, 1H), 7.38 (m, 2H), 7.12 (t, 1H), 7.01 (d, 1H), 3.82 (dd, 2H), 3.70 (d, 2H), 3.52 (m, 4H), 2.94 (t, 2H), 2.40 (m, 1H), 1.65 (m, 2H), 1.12 (m, 2H).

¹H NMR (400 MHz, DMSO-d₆) of Example 163: δ 12.10 (s, 1H), 8.76 (s, 1H), 8.63 (s, 1H), 8.36 (s, 1H), 8.10 (s, 1H), 7.55 (d, J=3.6 Hz, 1H), 7.40 (m, 4H), 7.21 (m, 1H), 7.05 (m, 1H), 7.01 (d, J=3.2 Hz, 1H), 3.81 (m, 2H), 3.69 (d, J=8.4 Hz, 2H), 3.51 (m, 4H), 2.95 (m, 2H), 2.37 (m, 1H), 1.62 (m, 2H), 1.10 (m, 2H).

¹H NMR (400 MHz, DMSO-d₆) of Example 164: δ 12.10 (s, 1H), 8.80 (s, 1H), 8.68 (s, 1H), 8.40 (s, 1H), 8.07 (s, 1H), 7.60 (t, 1H), 7.46 (m, 1H), 7.15 (m, 3H), 7.06 (m, 1H), 6.96 (s, 1H), 3.83 (m, 2H), 3.74 (d, J=8 Hz, 2H), 3.55 (m, 4H), 3.00 (m, 2H), 2.40 (m, 1H), 1.65 (m, 2H), 1.15 (m, 2H).

¹H NMR (400 MHz, DMSO-d₆) of Example 166: δ 12.10 (br, 1H), 8.76 (s, 2H), 8.63 (s, 1H), 8.36 (s, 1H), 7.85 (s, 1H), 7.67 (d, 1H), 7.55 (d, 1H), 7.38 (t, 1H), 7.19 (d, 1H), 7.01 (d, 1H), 3.85 (dd, 2H), 3.70 (d, 2H), 3.52 (m, 4H), 2.97 (t, 2H), 2.39 (m, 1H), 1.66 (m, 2H), 1.13 (m, 2H).

¹H NMR (400 MHz, DMSO-d₆) of Example 167: δ 12.10 (br, 1H), 8.82 (s, 1H), 8.76 (s, 1H), 8.63 (s, 1H), 8.36 (s, 1H), 7.62 (d, 2H), 7.55 (d, 1H), 7.51 (d, 2H), 7.01 (d, 1H), 3.86 (dd, 2H), 3.70 (d, 2H), 3.52 (m, 4H), 2.97 (t, 2H), 2.39 (m, 1H), 1.66 (m, 2H), 1.13 (m, 2H).

¹H NMR (400 MHz, DMSO-d₆) of Example 168: δ 12.10 (br, 1H), 8.76 (s, 1H), 8.63 (s, 1H), 8.36 (s, 1H), 8.03 (s, 1H), 7.55 (d, 1H), 7.22 (d, 1H), 7.12 (d, 1H), 6.99 (m, 2H), 3.82 (dd, 2H), 3.70 (d, 2H), 3.51 (m, 4H), 2.94 (t, 2H), 2.39 (m, 1H), 2.06 (s, 3H), 1.65 (m, 2H), 1.12 (m, 2H).

¹H NMR (400 MHz, DMSO-d₆) of Example 169: δ 12.10 (br, 1H), 8.76 (s, 1H), 8.63 (s, 1H), 8.36 (s, 1H), 8.20 (s, 1H), 7.55 (d, 1H), 7.33 (m, 1H), 7.11 (m, 1H), 7.03 (m, 3H), 3.83 (dd, 2H), 3.70 (d, 2H), 3.52 (m, 4H), 2.93 (t, 2H), 2.39 (m, 1H), 1.65 (m, 2H), 1.13 (m, 2H).

¹H NMR (400 MHz, DMSO-d₆) of Example 170: δ 12.10 (br, 1H), 8.76 (s, 1H), 8.63 (s, 1H), 8.52 (br, 1H), 8.36 (s, 1H), 7.65 (t, 1H), 7.55 (d, 1H), 7.39 (t, 1H), 7.24 (t, 1H), 7.01 (d, 1H), 3.83 (dd, 2H), 3.70 (d, 2H), 3.52 (m, 4H), 2.97 (t, 2H), 2.40 (m, 1H), 1.66 (m, 2H), 1.13 (m, 2H).

¹H NMR (400 MHz, DMSO-d₆) of Example 171: δ 12.10 (br, 1H), 8.76 (s, 1H), 8.63 (s, 1H), 8.36 (s, 1H), 8.21 (s, 1H), 7.55 (d, 1H), 7.30 (m, 1H), 7.18 (m, 1H), 7.01 (d, 1H), 6.95 (m, 1H), 3.80 (dd, 2H), 3.70 (d, 2H), 3.51 (m, 4H), 2.95 (t, 2H), 2.39 (m, 1H), 1.64 (m, 2H), 1.11 (m, 2H).

¹H NMR (400 MHz, DMSO-d₆) of Example 172: δ 12.10 (br, 1H), 8.76 (s, 1H), 8.63 (s, 1H), 8.45 (br, 1H), 8.36 (s, 1H), 7.55 (d, 1H), 7.12 (m, 2H), 7.01 (d, 1H), 3.81 (dd, 2H), 3.70 (d, 2H), 3.51 (m, 4H), 2.95 (t, 2H), 2.39 (m, 1H), 1.65 (m, 2H), 1.12 (m, 2H).

¹H NMR (400 MHz, DMSO-d₆) of Example 173: δ 12.10 (br, 1H), 8.76 (s, 1H), 8.63 (s, 1H), 8.40 (br, 1H), 8.36 (s, 1H), 7.55 (d, 1H), 7.12 (m, 2H), 7.01 (d, 1H), 3.80 (dd, 2H), 3.70 (d, 2H), 3.53 (m, 4H), 2.97 (t, 2H), 2.39 (m, 1H), 1.64 (m, 2H), 1.12 (m, 2H).

¹H NMR (400 MHz, DMSO-d₆) of Example 174: δ 12.10 (br, 1H), 8.76 (s, 1H), 8.63 (s, 1H), 8.36 (s, 1H), 8.30 (br, 1H), 7.55 (d, 1H), 7.32 (m, 1H), 7.16 (m, 1H), 701 (d, 1H), 6.82 (m, 1H), 3.80 (dd, 2H), 3.70 (d, 2H), 3.53 (m, 4H), 2.98 (t, 2H), 2.39 (m, 1H), 1.63 (m, 2H), 1.13 (m, 2H).

¹H NMR (400 MHz, DMSO-d₆) of Example 175: δ 12.10 (br, 1H), 8.80 (s, 1H), 8.76 (s, 1H), 8.63 (s, 1H), 8.36 (s, 1H), 7.55 (d, 1H), 7.16 (m, 2H), 701 (d, 1H), 6.64 (m, 1H), 3.82 (dd, 2H), 3.70 (d, 2H), 3.53 (m, 4H), 2.96 (t, 2H), 2.39 (m, 1H), 1.63 (m, 2H), 1.12 (m, 2H).

¹H NMR (400 MHz, DMSO-d₆) of Example 176: δ 12.10 (br, 1H), 8.76 (s, 1H), 8.63 (d, 2H), 8.36 (s, 1H), 7.55 (m, 2H), 7.20 (m, 2H), 701 (d, 1H), 3.83 (dd, 2H), 3.70 (d, 2H), 3.53 (m, 4H), 2.96 (t, 2H), 2.39 (m, 1H), 1.63 (m, 2H), 1.12 (m, 2H).

¹H NMR (400 MHz, DMSO-d₆) of Example 181: δ 12.15 (s, 1H), 8.81 (s, 1H), 8.68 (s, 1H), 8.41 (s, 1H), 7.60 (m, 3H), 7.06 (d, J=3.6 Hz, 1H), 6.96 (s, 2H), 6.81 (m, 1H), 3.83 (m, 2H), 3.78 (s, 3H), 3.74 (d, J=8 Hz, 2H), 3.56 (m, 4H), 3.01 (m, 2H), 2.42 (m, 1H), 1.68 (m, 2H), 1.17 (m, 2H).

¹H NMR (400 MHz, DMSO-d₆) of Example 184: δ 12.10 (br, 1H), 8.81 (s, 1H), 8.68 (s, 1H), 8.66 (s, 1H), 8.41 (s, 1H), 7.62 (m, 2H), 7.38 (d, 1H), 7.22 (m, 1H), 7.06 (d, 1H), 6.95 (m, 1H), 3.88 (m, 2H), 3.75 (d, 2H), 3.58 (m, 4H), 2.99 (t, 2H), 2.39 (m, 1H), 1.67 (m, 2H), 1.12 (m, 2H).

¹H NMR (400 MHz, DMSO-d₆) of Example 185: δ 12.10 (s, 1H), 8.76 (s, 1H), 8.63 (s, 1H), 8.36 (s, 1H), 7.96 (s, 1H), 7.55 (d, J=3.6 Hz, 1H), 7.10 (m, 3H), 7.05 (m, 1H), 6.95 (m, 1H), 3.81 (m, 2H), 3.68 (m, 2H), 3.50 (m, 4H), 2.90 (m, 2H), 2.45 (m, 1H), 2.05 (s, 3H), 1.62 (m, 2H), 1.10 (m, 2H).

¹H NMR (400 MHz, DMSO-d₆) of Example 186: δ 12.05 (s, 1H), 8.76 (s, 1H), 8.63 (s, 1H), 8.36 (s, 1H), 7.54 (d, J=7 Hz, 1H), 7.52 (s, 1H), 7.34 (d, J=3.2 Hz, 1H), 7.00 (d, J=3.6 Hz, 1H), 6.82 (d, J=8.8 Hz, 1H), 6.45 (d, J=8.8 Hz, 1H), 3.75 (m, 2H), 3.69 (s, 3H), 3.68 (m, 2H), 3.60 (s, 3H), 3.52 (m, 4H), 2.95 (m, 2H), 2.42 (m, 1H), 1.62 (m, 2H), 1.11 (m, 2H).

¹H NMR (400 MHz, DMSO-d₆) of Example 187: δ 12.05 (s, 1H), 8.76 (s, 1H), 8.63 (s, 1H), 8.36 (s, 1H), 7.98 (s, 1H), 7.54 (d, J=3.6 Hz, 1H), 7.06 (m, 1H), 7.01 (m, 1H), 6.90 (m, 1H), 6.84 (m, 1H), 3.81 (m, 2H), 3.69 (m, 2H), 3.52 (m, 4H), 2.90 (m, 2H), 2.42 (m, 1H), 2.07 (s, 3H), 1.62 (m, 2H), 1.10 (m, 2H).

¹H NMR (400 MHz, DMSO-d₆) of Example 188: δ 8.81 (s, 1H), 8.68 (s, 1H), 8.41 (s, 1H), 7.95 (d, J=8.4 Hz, 1H), 7.90 (dd, J₁=3.6 Hz, J₂=8.4 Hz, 1H), 7.60 (d, J=3.6 Hz, 1H), 7.40 (d, J=7.2 Hz, 1H), 7.05 (d, J=3.6 Hz, 1H), 3.90 (m, 2H), 3.75 (m, 2H), 3.55 (m, 4H), 3.02 (m, 2H), 2.42 (m, 1H), 1.65 (m, 2H), 1.10 (m, 2H).

¹H NMR (400 MHz, DMSO-d₆) of Example 189: δ 12.10 (br, 1H), 8.76 (s, 1H), 8.63 (s, 1H), 8.36 (s, 1H), 8.04 (s, 1H), 7.55 (d, 1H), 7.32 (d, 1H), 7.01 (d, 1H), 6.94 (d, 1H), 3.83 (dd, 2H), 3.70 (d, 2H), 3.53 (m, 4H), 2.92 (t, 2H), 2.39 (m, 1H), 2.35 (s, 3H), 2.20 (s, 3H), 1.63 (m, 2H), 1.12 (m, 2H).

¹H NMR (400 MHz, DMSO-d₆) of Example 190: δ 12.10 (br, 1H), 8.75 (s, 1H), 8.63 (s, 1H), 8.36 (s, 1H), 8.30 (br, 1H), 7.55 (d, 1H), 7.33 (s, 1H), 7.00 (d, 1H), 6.93 (s, 1H), 3.86 (dd, 2H), 3.69 (d, 2H), 3.53 (m, 4H), 2.98 (t, 2H), 2.39 (m, 1H), 1.64 (m, 2H), 1.11 (m, 2H).

¹H NMR (400 MHz, DMSO-d₆) of Example 191: δ 12.10 (br, 1H), 8.75 (s, 1H), 8.63 (s, 1H), 8.36 (s, 1H), 7.55 (d, 1H), 7.00 (d, 1H), 6.50 (s, 1H), 3.86 (dd, 2H), 3.69 (d, 2H), 3.53 (m, 4H), 2.98 (t, 2H), 2.39 (m, 1H), 2.10 (s, 3H), 1.64 (m, 2H), 1.11 (m, 2H).

¹H NMR (400 MHz, DMSO-d₆) of Example 196: δ 12.10 (s, 1H), 8.76 (s, 1H), 8.63 (s, 1H), 8.36 (s, 1H), 8.33 (s, 1H), 7.55 (dd, 1H), 7.24 (s, 1H), 7.00 (dd, 1H), 5.90 (s, 1H), 3.83 (m, 4H), 3.76 (d, 2H), 3.52 (m, 4H), 2.96 (m, 2H), 2.42 (m, 1H), 1.67 (m, 2H), 1.20 (t, 3H), 1.10 (m, 2H).

¹H NMR (400 MHz, DMSO-d₆) of Example 197: δ 12.08 (s, 1H), 8.76 (s, 1H), 8.63 (s, 1H), 8.36 (s, 1H), 8.34 (s, 1H), 7.55 (dd, 1H), 7.00 (dd, 1H), 5.68 (s, 1H), 3.78 (m, 2H), 3.76 (d, 2H), 3.52 (m, 4H), 3.39 (s, 3H), 2.92 (m, 2H), 2.42 (m, 1H), 2.00 (s, 3H), 1.62 (m, 2H), 1.10 (m, 2H).

¹H NMR (400 MHz, DMSO-d₆) of Example 198: δ 12.06 (s, 1H), 8.76 (s, 1H), 8.63 (s, 1H), 8.36 (s, 1H), 8.13 (t, 2H), 7.55 (m, 1H), 7.45 (m, 1H), 7.09 (m, 1H), 7.00 (t, 1H), 3.83 (m, 2H), 3.70 (d, 2H), 3.52 (m, 4H), 2.92 (m, 2H), 2.42 (m, 1H), 2.28 (s, 3H), 1.64 (m, 2H), 1.11 (m, 2H).

¹H NMR (400 MHz, DMSO-d₆) of Example 199: δ 12.08 (s, 1H), 8.76 (s, 1H), 8.63 (s, 1H), 8.36 (s, 1H), 8.18 (s, 1H), 7.62 (t, 1H), 7.55 (m, 1H), 7.00 (m, 1H), 6.85 (m, 1H), 3.83 (m, 2H), 3.69 (d, 2H), 3.50 (m, 4H), 2.94 (m, 2H), 2.42 (m, 1H), 2.20 (s, 3H), 1.64 (m, 2H), 1.11 (m, 2H).

¹H NMR (400 MHz, DMSO-d₆) of Example 200: δ 12.09 (s, 1H), 8.76 (s, 1H), 8.63 (s, 1H), 8.36 (s, 1H), 8.28 (s, 1H), 7.70 (m, 1H), 7.55 (m, 1H), 7.04 (m, 1H), 7.00 (m, 1H), 3.80 (m, 2H), 3.68 (d, 2H), 3.50 (m, 4H), 2.92 (m, 2H), 2.45 (m, 1H), 2.30 (s, 3H), 1.63 (m, 2H), 1.11 (m, 2H).

¹H NMR (400 MHz, DMSO-d₆) of Example 204: δ 12.09 (s, 1H), 8.76 (s, 1H), 8.63 (s, 1H), 8.36 (s, 1H), 7.87 (m, 1H), 7.74 (m, 1H), 7.70 (s, 1H), 7.55 (m, 1H), 7.01 (m, 1H), 6.85 (m, 1H), 3.82 (s, 3H), 3.80 (m, 2H), 3.68 (d, 2H), 3.51 (m, 4H), 2.94 (m, 2H), 2.40 (m, 1H), 1.63 (m, 2H), 1.11 (m, 2H).

¹H NMR (400 MHz, DMSO-d₆) of Example 205: δ 12.08 (s, 1H), 8.76 (s, 1H), 8.63 (s, 1H), 8.36 (s, 2H), 7.81 (d, J=8 Hz, 1H), 7.60 (d, J=8.4 Hz, 1H), 7.55 (m, 1H), 7.01 (m, 1H), 3.83 (m, 2H), 3.70 (d, J=8 Hz, 2H), 3.52 (m, 4H), 3.00 (m, 2H), 2.42 (m, 1H), 2.36 (s, 3H), 1.66 (m, 2H), 1.14 (m, 2H).

¹H NMR (400 MHz, DMSO-d₆) of Example 206: δ 12.07 (s, 1H), 10.33 (s, 1H), 8.76 (s, 1H), 8.63 (s, 1H), 8.36 (s, 1H), 8.25 (dd, 1H), 7.85 (dd, 1H), 7.55 (m, 1H), 7.50 (m, 1H), 7.00 (m, 1H), 6.98 (m, 1H), 3.80 (s, 3H), 3.76 (m, 2H), 3.70 (d, 2H), 3.52 (m, 4H), 3.05 (m, 2H), 2.44 (m, 1H), 1.68 (m, 2H), 1.17 (m, 2H).

¹H NMR (400 MHz, DMSO-d₆) of Example 207: δ 12.06 (s, 1H), 10.05 (s, 1H), 8.76 (s, 1H), 8.63 (s, 1H), 8.36 (s, 1H), 8.20 (m, 1H), 7.60 (m, 2H), 7.40 (m, 1H), 7.00 (m, 1H), 3.80 (s, 3H), 3.76 (m, 2H), 3.70 (d, 2H), 3.52 (m, 4H), 3.05 (m, 2H), 2.43 (m, 1H), 1.68 (m, 2H), 1.16 (m, 2H).

¹H NMR (400 MHz, DMSO-d₆) of Example 208: δ 12.08 (s, 1H), 8.76 (s, 1H), 8.63 (s, 1H), 8.54 (s, 1H), 8.36 (s, 1H), 7.60 (m, 3H), 7.55 (m, 1H), 7.00 (m, 1H), 3.81 (m, 2H), 3.77 (s, 3H), 3.70 (d, 2H), 3.52 (m, 4H), 3.00 (m, 2H), 2.40 (m, 1H), 1.64 (m, 2H), 1.15 (m, 2H).

Example 209

3-[(4-{3-(Cyanomethyl)-3-[4-(7H-pyrrolo[2,3-d]pyrimidin-4-yl)-1H-pyrazol-1-yl]azetidin-1-yl}piperidin-1-yl)methyl]-6-(dimethylamino)-2-fluorobenzonitrile

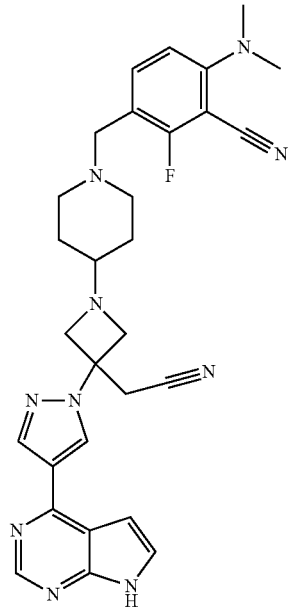 [SMILES: CN(C)c1ccc(CN2CCC(N3CC(CC#N)(n4cc(-c5ncnc6[nH]ccc56)cn4)C3)CC2)c(F)c1C#N]

Step A: 3-[(4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)methyl]-6-(dimethylamino)-2-fluorobenzonitrile

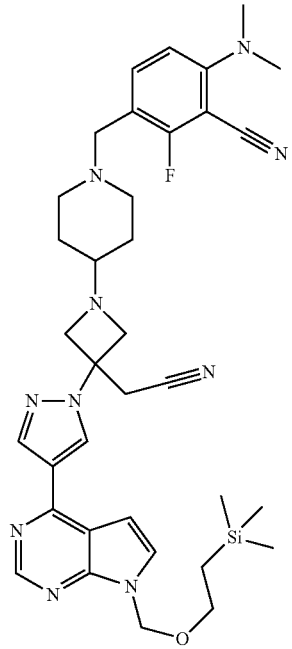 [SMILES: CN(C)c1ccc(CN2CCC(N3CC(CC#N)(n4cc(-c5ncnc6c5ccn6COCC[Si](C)(C)C)cn4)C3)CC2)c(F)c1C#N]

To a solution of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride (200 mg, 0.4 mmol) in THF (10 mL) and triethylamine (0.1643 mL, 1.179 mmol) was added 6-(dimethylamino)-2-fluoro-3-formylbenzonitrile (75.52 mg, 0.3929 mmol). The solution was stirred at room temperature for 30 minutes before the addition of sodium triacetoxyborohydride (249.8 mg, 1.179 mmol). The mixture was stirred at room temperature overnight. After addition of aqueous NaHCO$_3$, and EtOAc, the organic layer was separated, washed with brine, dried over anhydrous Na$_2$SO$_4$ and concentrated.

Purification by HPLC afforded 150 mg of the product 3-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)methyl]-6-(dimethylamino)-2-fluorobenzonitrile as a white solid. LC/MS: 669.2 (M+H)$^+$.

Step B: 3-[(4-{3-(Cyanomethyl)-3-[4-(7H-pyrrolo[2,3-d]pyrimidin-4-yl)-1H-pyrazol-1-yl]azetidin-1-yl}piperidin-1-yl)methyl]-6-(dimethylamino)-2-fluorobenzonitrile Into a reaction vial were added 3-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)methyl]-6-(dimethylamino)-2-fluorobenzonitrile (56 mg, 0.1 mmol), trifluoroacetic acid (1.5 mL) and methylene chloride (1.5 mL). The mixture was stirred at room temperature for 1 hour and concentrated in vacuum. The residue was dissolved in 5 mL of a methanol solution containing 20% ethylenediamine. After being stirred at room temperature for 1 hour, the mixture was purified by HPLC (method B) to give the title compound. LC-MS: 539.2 (M+H)$^+$. $^1$H NMR (400 MHz, DMSO-d$_6$): δ 12.10 (s, 1H), 8.79 (s, 1H), 8.67 (s, 1H), 8.39 (s, 1H), 7.59 (d, J=3.6 Hz, 1H), 7.42 (t, J=8.8 Hz, 1H), 7.05 (d, J=3.6 Hz, 1H), 6.78 (d, J=8.8 Hz, 1H), 3.68 (d, J=8.4 Hz, 2H), 3.51 (m, 4H), 3.38 (s, 2H), 3.01 (s, 6H), 2.67 (m, 2H), 2.17 (m, 1H), 1.97 (m, 2H), 1.63 (m, 2H), 1.15 (m, 2H).

The following compounds were prepared by a method analogous to that for Example 209.

| Example # | R | Compound | LC-MS (M + H)$^+$ |
|---|---|---|---|
| 210 | 3,5-dichlorophenyl | {1-[1-(3,5-dichlorobenzyl)piperidin-4-yl]-3-[4-(7H-pyrrolo[2,3-d]pyrimidin-4-yl)-1H-pyrazol-1-yl]azetidin-3-yl}acetonitrile | 521.1 |
| 211 | 2-chloro-5-(trifluoromethyl)phenyl | {1-{1-[2-chloro-5-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile | 555.1 |

-continued

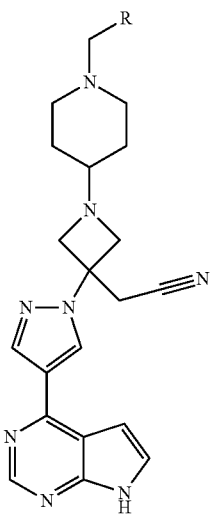

| Example # | R | Compound | LC-MS (M + H)+ |
|---|---|---|---|
| 212 | 2-fluoro-3-(trifluoromethyl)phenyl | {1-{-[2-fluoro-3-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile | 539.2 |
| 213 | 2-fluoro-6-(trifluoromethyl)phenyl | {1-{1-[2-fluoro-6-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile | 539.2 |
| 214 | 2-chloroquinolin-3-yl | {1-{1-[(2-chloroquinolin-3-yl)methyl]piperidin-4-yl}-3-[4-(7H-pyrrolo[2,3-d]pyrimidin-4-yl)-1H-pyrazol-1-yl]azetidin-3-yl}acetonitrile | 538.2 |
| 215 | 3,5-difluorophenyl | {1-[1-(3,5-difluorobenzyl)piperidin-4-yl]-3-[4-(7H-pyrrolo[2,3-d]pyrimidin-4-yl)-1H-pyrazol-1-yl]azetidin-3-yl}acetonitrile | 489.2 |
| 216 | 2-fluoro-4-(trifluoromethyl)phenyl | {1-{1-[2-fluoro-4-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile | 539.2 |
| 217 | 2,5-difluorophenyl | {1-[1-(2,4-difluorobenzyl)piperidin-4-yl]-3-[4-(7H-pyrrolo[2,3-d]pyrimidin-4-yl)-1H-pyrazol-1-yl]azetidin-3-yl}acetonitrile | 489.2 |

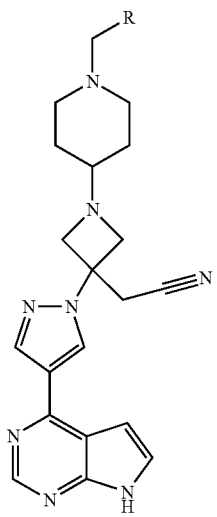

| Example # | R | Compound | LC-MS (M + H)+ |
|---|---|---|---|
| 218 | 2-MeO, 6-F phenyl | {1-[1-(2-fluoro-6-methoxybenzyl)piperidin-4-yl]-3-[4-(7H-pyrrolo[2,3-d]pyrimidin-4-yl)-1H-pyrazol-1-yl]azetidin-3-yl}acetonitrile | 501.2 |
| 219 | 2,3-diCl phenyl | {1-[1-(2,3-dichlorobenzyl)piperidin-4-yl]-3-[4-(7H-pyrrolo[2,3-d]pyrimidin-4-yl)-1H-pyrazol-1-yl]azetidin-3-yl}acetonitrile | 521.1 |
| 220 | 3-CN, 4-F phenyl | 5-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]-2-fluorobenzonitrile | 496.2 |
| 221 | 4-(1,2,3-oxadiazol-4-yl)phenyl | {1-{1-[4-(1,2,3-oxadiazol-4-yl)benzyl]piperidin-4-yl}-3-[4-(7H-pyrrolo[2,3-d]pyrimidin-4-yl)-1H-pyrazol-1-yl]azetidin-3-yl}acetonitrile | 521.2 |
| 222 | 2-CN phenyl | 2-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]benzonitrile | 478.2 |
| 223 | 3-CN phenyl | 3-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]benzonitrile | 478.2 |
| 224 | 2-OMe, 3-CN pyridin-6-yl | 6-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]-2-methoxynicotinonitrile | 509.2 |

-continued

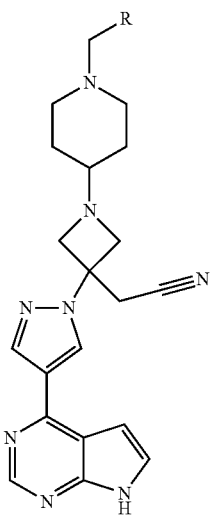

| Example # | R | Compound | LC-MS (M + H)+ |
|---|---|---|---|
| 225 | 2,6-dibromopyridin-4-yl | {1-{1-[(2,6-dibromopyridin-4-yl)methyl]piperidin-4-yl}-3-[4-(7H-pyrrolo[2,3-d]pyrimidin-4-yl)-1H-pyrazol-1-yl]azetidin-3-yl}acetonitrile | 610.0 612.0 614.0 |
| 226 | 2-bromopyridin-4-yl | {1-{1-[(2-bromopyridin-4-yl)methyl]piperidin-4-yl}-3-[4-(7H-pyrrolo[2,3-d]pyrimidin-4-yl)-1H-pyrazol-1-yl]azetidin-3-yl}acetonitrile | 532.0 534.0 |
| 227 | 2-chloro-6-fluorophenyl | {1-[1-(2-chloro-6-fluorobenzyl)piperidin-4-yl]-3-[4-(7H-pyrrolo[2,3-d]pyrimidin-4-yl)-1H-pyrazol-1-yl]azetidin-3-yl}acetonitrile | 505.1 |
| 228 | 3-chloro-2,6-difluorophenyl | {1-[1-(3-chloro-2,6-difluorobenzyl)piperidin-4-yl]-3-[4-(7H-pyrrolo[2,3-d]pyrimidin-4-yl)-1H-pyrazol-1-yl]azetidin-3-yl}acetonitrile | 523.1 |
| 229 | 4-cyano-3-fluorophenyl | 4-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]-2-fluorobenzonitrile | 496.2 |

-continued

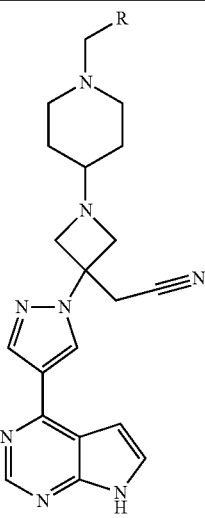

| Example # | R | Compound | LC-MS (M + H)+ |
|---|---|---|---|
| 230 | | {1-{1-[(5-methyl-3-phenylisoxazol-4-yl)methyl]piperidin-4-yl}-3-[4-(7H-pyrrolo[2,3-d]pyrimidin-4-yl)-1H-pyrazol-1-yl]azetidin-3-yl}acetonitrile | 534.2 |
| 231 | | {1-(1-{[3-fluoro-2-(trifluoromethyl)pyridin-4-yl]methyl}piperidin-4-yl)-3-[4-(7H-pyrrolo[2,3-d]pyrimidin-4-yl)-1H-pyrazol-1-yl]azetidin-3-yl}acetonitrile | 540.2 |
| 232 | | {1-[1-(1-benzofuran-2-ylmethyl)piperidin-4-yl]-3-[4-(7H-pyrrolo[2,3-d]pyrimidin-4-yl)-1H-pyrazol-1-yl]azetidin-3-yl}acetonitrile | 493.2 |
| 233 | | {1-[1-(3-phenoxybenzyl)piperidin-4-yl]-3-[4-(7H-pyrrolo[2,3-d]pyrimidin-4-yl)-1H-pyrazol-1-yl]azetidin-3-yl}acetonitrile | 545.2 |
| 234 | | {1-[1-(2,3-dihydro-1,4-benzodioxin-6-ylmethyl)piperidin-4-yl]-3-[4-(7H-pyrrolo[2,3-d]pyrimidin-4-yl)-1H-pyrazol-1-yl]azetidin-3-yl}acetonitrile | 511.2 |
| 235 | | N-{4-[(4-{3-(cyanomethyl)-3-[4-(7H-pyrrolo[2,3-d]pyrimidin-4-yl)-1H-pyrazol-1-yl]azetidin-1-yl}piperidin-1-yl)methyl]pyridin-2-yl}-2,2-dimethylpropanamide | 553.2 |

-continued

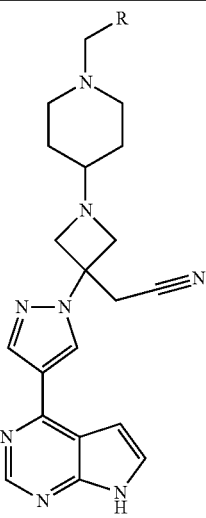

| Example # | R | Compound | LC-MS (M + H)+ |
|---|---|---|---|
| 236 | 3-chloro-2-fluoro-6-(trifluoromethyl)phenyl | {1-{1-[3-chloro-2-fluoro-6-(trifluoromethyl)benzyl]piperidin-4-yl}-3-[4-(7H-pyrrolo[2,3-d]pyrimidin-4-yl)-1H-pyrazol-1-yl]azetidin-3-yl}acetonitrile | 573.1 |
| 237 | 3,5-dichloropyridin-4-yl | {1-{1-[(3,5-dichloropyridin-4-yl)methyl]piperidin-4-yl}-3-[4-(7H-pyrrolo[2,3-d]pyrimidin-4-yl)-1H-pyrazol-1-yl]azetidin-3-yl}acetonitrile | 522.1 |
| 238 | 2-chloro-6-methoxyquinolin-3-yl | {1-{1-[(2-chloro-6-methoxyquinolin-3-yl)methyl]piperidin-4-yl}-3-[4-(7H-pyrrolo[2,3-d]pyrimidin-4-yl)-1H-pyrazol-1-yl]azetidin-3-yl}acetonitrile | 568.2 |
| 239 | 2-chloro-3,4-dimethoxyphenyl | {1-[1-(2-chloro-3,4-dimethoxybenzyl)piperidin-4-yl]-3-[4-(7H-pyrrolo[2,3-d]pyrimidin-4-yl)-1H-pyrazol-1-yl]azetidin-3-yl}acetonitrile | 547.2 |

$^1$H NMR (400 MHz, DMSO-$d_6$) of Example 210: δ 12.15 (br, 1H), 8.73 (s, 1H), 8.62 (s, 1H), 8.34 (s, 1H), 8.0 (s, 1H), 7.60 (s, 1H), 7.55 (d, 1H), 7.34 (s, 1H), 7.00 (d, 1H), 3.70 (dd, 2H), 3.68 (d, 2H), 3.53 (m, 4H), 2.74 (s, 2H), 2.20 (m, 1H), 2.07 (m, 2H), 1.64 (m, 2H), 1.11 (m, 2H).

$^1$H NMR (400 MHz, DMSO-$d_6$) of Example 211: δ 12.15 (br, 1H), 8.80 (s, 1H), 8.62 (s, 1H), 8.34 (s, 1H), 8.0 (s, 1H), 7.60 (d, 1H), 7.55 (d, 1H), 7.34 (s, 1H), 7.00 (d, 1H), 3.70 (dd, 2H), 3.68 (d, 2H), 3.53 (m, 4H), 2.74 (s, 2H), 2.20 (m, 1H), 2.07 (m, 2H), 1.645 (m, 2H), 1.12 (m, 2H).

$^1$H NMR (400 MHz, DMSO-$d_6$) of Example 212: δ 12.10 (br, 1H), 8.80 (s, 1H), 8.68 (s, 1H), 8.40 (s, 1H), 7.73 (m, 1H), 7.67 (m, 1H), 7.60 (d, 1H), 7.38 (s, 1H), 7.04 (d, 1H), 3.68 (dd, 2H), 3.57 (m, 2H), 3.52 (m, 4H), 2.71 (s, 2H), 2.20 (m, 1H), 2.07 (m, 2H), 1.645 (m, 2H), 1.12 (m, 2H).

$^1$H NMR (400 MHz, DMSO-$d_6$) of Example 213: δ 12.17 (br, 1H), 8.94 (s, 1H), 8.69 (s, 1H), 8.47 (s, 1H), 7.77 (m, 1H), 7.61 (m, 3H), 7.06 (d, 1H), 3.68 (dd, 2H), 3.57 (m, 2H), 3.52 (m, 4H), 2.71 (s, 2H), 2.20 (m, 1H), 2.07 (m, 2H), 1.70 (m, 2H), 1.14 (m, 2H).

$^1$H NMR (400 MHz, DMSO-$d_6$) of Example 214: δ 12.10 (br, 1H), 8.81 (s, 1H), 8.68 (s, 1H), 8.42 (s, 1H), 8.07 (m, 2H), 7.93 (m, 1H), 7.80 (m, 1H), 7.64 (m, 1H), 7.60 (d, 1H), 7.06 (d, 1H), 3.71 (m, 2H), 3.67 (m, 2H), 3.55 (m, 4H), 2.82 (s, 2H), 2.22 (m, 1H), 2.15 (m, 2H), 1.73 (m, 2H), 1.15 (m, 2H).

¹H NMR (400 MHz, DMSO-d₆) of Example 215: δ 12.13 (br, 1H), 8.80 (s, 1H), 8.68 (s, 1H), 8.40 (s, 1H), 7.60 (m, 1H), 7.02 (m, 4H), 3.71 (m, 2H), 3.52 (m, 6H), 2.72 (s, 2H), 2.22 (m, 1H), 2.05 (m, 2H), 1.68 (m, 2H), 1.21 (m, 2H).

¹H NMR (400 MHz, DMSO-d₆) of Example 216: δ 12.15 (br, 1H), 8.80 (s, 1H), 8.67 (s, 1H), 8.40 (s, 1H), 7.60 (m, 4H), 7.04 (m, 1H), 3.70 (d, 2H), 3.53 (m, 6H), 2.74 (d, 2H), 2.20 (m, 1H), 2.07 (t, 2H), 1.67 (m, 2H), 1.22 (m, 2H).

¹H NMR (400 MHz, DMSO-d₆) of Example 218: δ 12.10 (br, 1H), 8.73 (s, 1H), 8.62 (s, 1H), 8.34 (s, 1H), 7.54 (d, 1H), 7.22 (m, 1H), 7.00 (d, 1H), 6.79 (d, 1H), 6.79 (t, 1H), 3.72 (s, 3H), 3.62 (d, 2H), 3.43 (m, 6H), 2.67 (m, 2H), 2.22 (m, 1H), 1.95 (m, 2H), 1.56 (m, 2H), 1.08 (m, 2H).

¹H NMR (400 MHz, DMSO-d₆) of Example 220: δ 12.14 (br, 1H), 8.79 (s, 1H), 8.68 (s, 1H), 8.40 (s, 1H), 7.78 (m, 1H), 7.71 (m, 1H), 7.59 (m, 1H), 7.46 (m, 1H), 7.04 (m, 1H), 3.70 (d, 2H), 3.51 (m, 6H), 2.67 (m, 2H), 2.21 (m, 1H), 2.00 (m, 2H), 1.67 (m, 2H), 1.21 (m, 2H).

¹H NMR (400 MHz, DMSO-d₆) of Example 221: δ 12.10 (br, 1H), 9.53 (s, 1H), 8.75 (s, 1H), 8.63 (s, 1H), 8.35 (s, 1H), 8.03 (d, 1H), 7.71 (m, 1H), 7.55 (m, 1H), 7.39 (m, 2H), 7.00 (m, 1H), 3.64 (d, 2H), 3.45 (m, 6H), 2.68 (m, 2H), 2.17 (m, 1H), 1.96 (m, 2H), 1.63 (m, 2H), 1.18 (m, 2H).

¹H NMR (400 MHz, DMSO-d₆) of Example 222: δ 12.13 (br, 1H), 8.80 (s, 1H), 8.68 (s, 1H), 8.40 (s, 1H), 7.79 (m, 1H), 7.67 (m, 1H), 7.59 (m, 1H), 7.55 (m, 1H), 7.42 (m, 1H), 7.05 (m, 1H), 3.70 (d, 2H), 3.61 (s, 2H), 3.52 (m, 4H), 2.72 (m, 2H), 2.23 (m, 1H), 2.09 (m, 2H), 1.63 (m, 2H), 1.19 (m, 2H).

¹H NMR (400 MHz, DMSO-d₆) of Example 223: δ 12.14 (br, 1H), 8.79 (s, 1H), 8.68 (s, 1H), 8.40 (s, 1H), 7.71 (m, 2H), 7.60 (m, 2H), 7.54 (m, 1H), 7.05 (m, 1H), 3.70 (d, 2H), 3.52 (m, 6H), 2.70 (m, 2H), 2.20 (m, 1H), 1.99 (m, 2H), 1.63 (m, 2H), 1.19 (m, 2H).

¹H NMR (400 MHz, DMSO-d₆) of Example 227: δ 12.13 (br, 1H), 8.80 (s, 1H), 8.67 (s, 1H), 8.65 (s, 1H), 8.49 (d, 1H), 8.40 (s, 1H), 7.60 (d, 1H), 7.48 (d, 1H), 7.05 (d, 1H), 3.72 (d, 2H), 3.54 (m, 6H), 2.75 (d, 2H), 2.25 (m, 1H), 2.14 (t, 2H), 1.69 (d, 2H), 1.26 (m, 2H).

¹H NMR (400 MHz, DMSO-d₆) of Example 228: δ 12.13 (br, 1H), 8.78 (s, 1H), 8.67 (s, 1H), 8.39 (s, 1H), 7.59 (d, 1H), 7.32 (m, 1H), 7.19 (t, 1H), 7.04 (d, 1H), 3.69 (d, 2H), 3.55 (m, 6H), 2.74 (d, 2H), 2.19 (m, 1H), 2.10 (t, 2H), 1.63 (d, 2H), 1.15 (m, 2H).

¹H NMR (400 MHz, DMSO-d₆) of Example 229: δ 12.12 (s, 1H), 8.79 (s, 1H), 8.68 (s, 1H), 8.40 (s, 1H), 7.85 (t, 1H), 7.59 (dd, 1H), 7.40 (d, 1H), 7.33 (d, 1H), 7.05 (dd, 1H), 3.69 (d, 2H), 3.52 (m, 4H), 3.50 (s, 2H), 2.68 (m, 2H), 2.20 (m, 1H), 2.00 (m, 2H), 1.65 (m, 2H), 1.20 (m, 2H).

¹H NMR (400 MHz, DMSO-d₆) of Example 230: δ 12.10 (br, 1H), 8.79 (s, 1H), 8.67 (s, 1H), 8.40 (s, 1H), 7.88 (m, 3H), 7.60 (m, 1H), 7.48 (m, 2H), 7.05 (m, 1H), 3.70 (d, 2H), 3.51 (m, 4H), 3.23 (s, 2H), 2.72 (d, 2H), 2.41 (s, 3H), 2.22 (m, 1H), 2.01 (t, 2H), 1.68 (d, 2H), 1.19 (m, 2H).

¹H NMR (400 MHz, DMSO-d₆) of Example 232: δ 12.05 (brs, 1H), 8.74 (s, 1H), 8.62 (s, 1H), 8.34 (s, 1H), 7.54 (d, 1H), 7.51 (m, 1H), 7.49 (d, 1H), 7.18 (m, 2H), 7.00 (d, 1H), 6.70 (s, 1H), 3.64 (d, 2H), 3.57 (s, 2H), 3.48 (m, 4H), 2.75 (m, 2H), 2.12 (m, 1H), 2.03 (m, 2H), 1.61 (m, 2H), 1.15 (m, 2H).

¹H NMR (400 MHz, DMSO-d₆) of Example 233: δ 12.06 (brs, 1H), 8.74 (s, 1H), 8.62 (s, 1H), 8.34 (s, 1H), 7.54 (d, 1H), 7.36 (m, 2H), 7.27 (t, 1H), 7.06 (d, 1H), 7.00 (m, 2H), 6.92 (d, 2H), 6.85 (s, 1H), 6.80 (d, 1H), 3.64 (d, 2H), 3.46 (m, 4H), 3.36 (s, 2H), 2.62 (m, 2H), 2.14 (m, 1H), 1.90 (m, 2H), 1.58 (m, 2H), 1.10 (m, 2H).

¹H NMR (400 MHz, DMSO-d₆) of Example 234: δ 12.06 (brs, 1H), 8.74 (s, 1H), 8.62 (s, 1H), 8.34 (s, 1H), 7.54 (d, 1H), 7.00 (d, 1H), 6.63 (m, 3H), 4.14 (s, 4H), 3.62 (d, 2H), 3.46 (m, 4H), 3.24 (s, 2H), 2.62 (m, 2H), 2.12 (m, 1H), 1.88 (m, 2H), 1.58 (m, 2H), 1.10 (m, 2H).

¹H NMR (400 MHz, DMSO-d₆) of Example 235: δ 12.08 (s, 1H), 10.08 (s, 1H), 8.74 (s, 1H), 8.62 (s, 1H), 8.35 (s, 1H), 8.22 (dd, 1H), 7.62 (dd, 1H), 7.54 (d, 1H), 7.05 (dd, 1H), 7.00 (d, 1H), 3.65 (d, 2H), 3.46 (m, 4H), 3.38 (s, 2H), 2.62 (m, 2H), 2.20 (m, 1H), 1.90 (m, 2H), 1.62 (m, 2H), 1.17 (m, 2H), 1.15 (s, 9H).

¹H NMR (400 MHz, DMSO-d₆) of Example 236: δ 12.10 (s, 1H), 8.78 (s, 1H), 8.67 (s, 1H), 8.39 (s, 1H), 7.77 (m, 1H), 7.62 (m, 2H), 7.05 (d, 1H), 3.67 (d, 2H), 3.60 (s, 2H), 3.50 (m, 4H), 2.65 (m, 2H), 2.20 (m, 1H), 2.10 (m, 2H), 1.62 (m, 2H), 1.11 (m, 2H).

¹H NMR (400 MHz, DMSO-d₆) of Example 237: δ 12.06 (brs, 1H), 8.74 (s, 1H), 8.62 (s, 1H), 8.54 (s, 2H), 8.34 (s, 1H), 7.54 (d, J=3.6 Hz, 1H), 7.00 (d, J=3.6 Hz, 1H), 3.62 (d, J=8.4 Hz, 2H), 3.59 (s, 2H), 3.46 (m, 4H), 2.65 (m, 2H), 2.16 (m, 3H), 1.55 (m, 2H), 1.10 (m, 2H).

Example 240

3-[(3-{3-(Cyanomethyl)-3-[4-(7H-pyrrolo[2,3-d]pyrimidin-4-yl)-1H-pyrazol-1-yl]azetidin-1-yl}-8-azabicyclo[3.2.1]oct-8-yl)methyl]-6-(dimethylamino)-2-fluorobenzonitrile

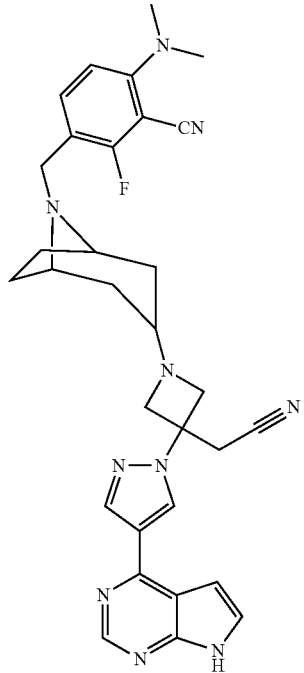 [SMILES: CN(C)c1ccc(CN2C3CCC2CC(N2CC(CC#N)(n4cc(-c5ncnc6[nH]ccc56)cn4)C2)C3)c(F)c1C#N]

To a solution of {1-(8-azabicyclo[3.2.1]oct-3-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (40 mg, 0.08 mmol) in THF (2 mL) were added 6-(dimethylamino)-2-fluoro-3-formylbenzonitrile (17.2 mg, 0.089 mmol), and triethylamine (0.034 mL, 0.24 mmol). The mixture was stirred at room temperature for 30 minutes before the addition of sodium triacetoxyborohydride (51.6 mg, 0.24 mmol). The mixture was stirred at room temperature overnight. The resulting solution was worked up with aqueous NaHCO₃ and EtOAc. The organic layer was washed with brine, dried over Na₂SO₄ and concentrated under reduced pressure. Purification with acidic prep-LCMS afforded 25 mg (41.6%) of the desired intermediate 3-[(3-{3-(cyanomethyl)-3-[4-(7-{[2-(trimethylsilyl)ethoxy]methyl}-7H-pyrrolo[2, 3-]pyrimidin-4-yl)-1H-pyrazol-1-yl]azetidin-1-yl}-8-azabicyclo[3.2.1]oct-8-yl)methyl]-6-(dimethylamino)-2-fluorobenzonitrile. LC/MS found: 695.3 (M+H)⁺.

The above white solid (25 mg, 0.036 mmol) was dissolved in a 50 M solution of trifluoroacetic acid in methylene chloride (2 mL, 100 mmol). The mixture was stirred at room temperature for an hour and concentrated under reduced pressure. The residue was dissolved in methanol (2 mL, 50 mmol) and ethylenediamine (0.03 mL, 0.4 mmol). After being stirred at room temperature for an hour, the mixture was purified with HPLC (method B) to give about 10 mg (50%) of the title compound as a white solid. LC/MS found: 565.3 (M+H)⁺. ¹H NMR (400 MHz, DMSO-d₆): δ 12.20 (s, 1H), 8.90 (s, 1H), 8.79 (s, 1H), 8.50 (s, 1H), 7.71 (d, J=3.2 Hz, 1H), 7.67 (t, J=8.8 Hz, 1H), 7.15 (d, J=3.2 Hz, 1H), 6.90 (d, J=8.8 Hz, 1H), 3.65 (m, 6H), 3.48 (s, 2H), 3.12 (s, 6H), 3.07 (m, 2H), 2.60 (m, 1H), 2.05 (m, 2H), 1.96 (m, 2H), 1.80 (m, 2H), 1.57 (m, 2H).

Example 241

{1-[8-(2-Chloro-3,6-difluorobenzyl)-8-azabicyclo[3.2.1]oct-3-yl]-3-[4-(7H-pyrrolo[2,3-d]pyrimidin-4-yl)-1H-pyrazol-1-yl]azetidin-3-yl}acetonitrile

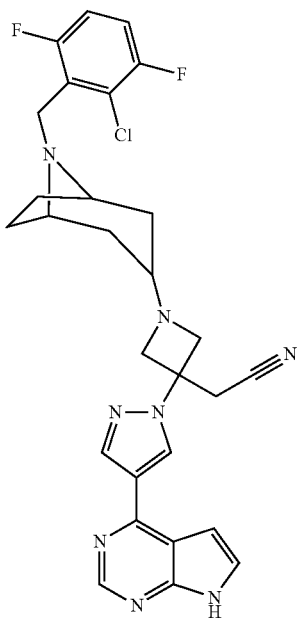 [SMILES: N#CCC1(n2cc(-c3ncnc4[nH]ccc34)cn2)CN(C2CC3CCC(C2)N3Cc2c(F)ccc(F)c2Cl)C1]

The title compound was prepared by a method analogous to that for Example 240. LC-MS: 549.1 (M+H)⁺.

Examples 242 and 243

Diastereomers of 3-[(4-{3-(cyanomethyl)-3-[4-(7H-pyrrolo[2,3-d]pyrimidin-4-yl)-1H-pyrazol-1-yl]azetidin-1-yl}-2-methylpiperidin-1-yl)methyl]-6-(dimethylamino)-2-fluorobenzonitrile

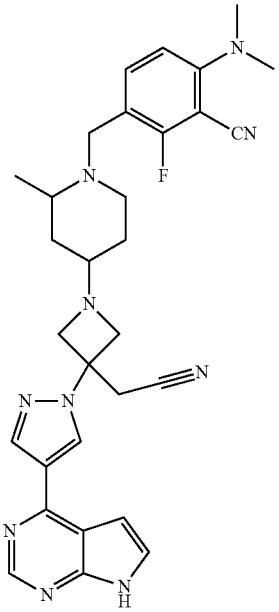 [SMILES: CC1CC(N2CC(CC#N)(n3cc(-c4ncnc5[nH]ccc45)cn3)C2)CCN1Cc1ccc(N(C)C)c(C#N)c1F]

To a solution of {1-(2-methylpiperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (40 mg, 0.08 mmol) in THF (2 mL) were added 6-(dimethylamino)-2-fluoro-3-formylbenzonitrile (17.16 mg, 0.0893 mmol) and triethylamine (0.034 mL, 0.244 mmol). The solution was stirred at room temperature for 30 min before the addition of sodium triacetoxyborohydride (51.62 mg, 0.244 mmol). The mixture was stirred at room temperature overnight. The resulting mixture was quenched with aqueous NaHCO₃ and EtOAc. The organic layer was separated and washed with brine, dried over Na₂SO₄ and concentrated under reduced pressure. The residue was purified with acidic prep-LCMS to afford 25 mg (47%) of the intermediate 3-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-methylpiperidin-1-yl)methyl]-6-(dimethylamino)-2-fluorobenzonitrile as a white solid. LC/MS found: 683.2 (M+H)⁺.

The above white solid powder (25 mg, 0.037 mmol) was dissolved in 2 mL of trifluoroacetic acid and 2 mL of methylene chloride. The mixture was stirred at room temperature for an hour. The solvents were removed under reduced pressure. The residue was dissolved in methanol (2 mL) and ethylenediamine (0.03 mL, 0.4 mmol). After being stirred at room temperature for an hour, the mixture was purified with HPLC (method B) to give the desired two products Example 245 and Example 246 as a white solid: Example 245 (7 mg) was the fast moving diastereomer on HPLC and Example 246 (7 mg) was the slow moving diatereomer on HPLC. LC/MS found: 553.2 (M+H)⁺ for both isomers.

Examples 244 and 245

Distereomers of {1-[1-(2-chloro-6-fluorobenzyl)-2-methylpiperidin-4-yl]-3-[4-(7H-pyrrolo[2,3-d]pyrimidin-4-yl)-1H-pyrazol-1-yl]azetidin-3-yl}acetonitrile

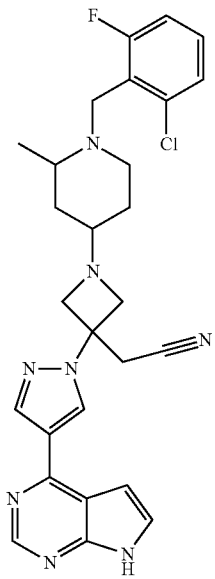 [SMILES: CC1CC(N2CC(CC#N)(n3cc(-c4ncnc5[nH]ccc45)cn3)C2)CCN1Cc1c(F)cccc1Cl]

The title compounds were prepared by a method analogous to that for Examples 242 and 243. Example 247 was the fast moving diastereomer on HPLC and Example 248 was the slow moving diatereomer on HPLC. LC/MS found: 519.2 (M+H)+ for both isomers.

Example 246

{1-{1-[(1-Methyl-1H-pyrazol-5-yl)sulfonyl]piperidin-4-yl}-3-[4-(7H-pyrrolo[2,3-d]pyrimidin-4-yl)-1H-pyrazol-1-yl]azetidin-3-yl}acetonitrile

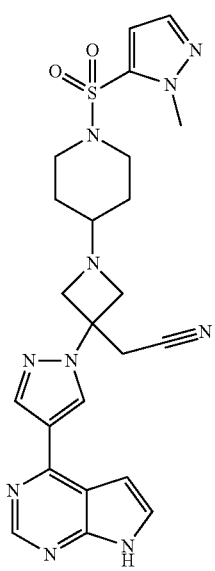 [SMILES: Cn1nccc1S(=O)(=O)N1CCC(N2CC(CC#N)(n3cc(-c4ncnc5[nH]ccc45)cn3)C2)CC1]

Step A: {1-{1-[(1-Methyl-1H-pyrazol-5-yl)sulfonyl]piperidin-4-yl}-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

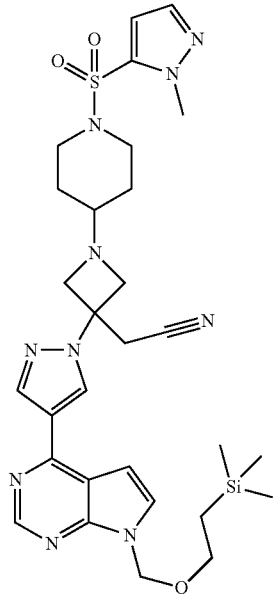 [SMILES: Cn1nccc1S(=O)(=O)N1CCC(N2CC(CC#N)(n3cc(-c4ncnc5c4ccn5COCC[Si](C)(C)C)cn3)C2)CC1]

A mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride (44.4 mg, 0.108 mmol), 1-methyl-1H-pyrazole-5-sulfonyl chloride (19.6 mg, 0.108 mmol) and triethylamine (0.0412 mL, 0.296 mmol) in THF (10.0 mL) was stirred at room temperature for 2 hours. Purification on silica gel column afforded the desired product {1-{1-[(1-methyl-1H-pyrazol-5-yl)sulfonyl]piperidin-4-yl}-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile. Yield: 58.8%. LC-MS: 637.3 (M+H)+.

Step B: {1-{1-[(1-Methyl-1H-pyrazol-5-yl)sulfonyl]piperidin-4-yl}-3-[4-(7H-pyrrolo[2, 3-d]pyrimidin-4-yl)-1H-pyrazol-1-yl]azetidin-3-yl}acetonitrile To a solution of {1-{1-[(1-methyl-1H-pyrazol-5-yl)sulfonyl]piperidin-4-yl}-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (56 mg, 0.1 mmol) in methylene chloride (1.5 mL) was added trifluoroacetic acid (1.5 mL). The mixture was stirred at room temperature for 2 hours and concentrated in vacuo. The residue was dissolved in 2 mL of a methanol solution containing 20% ethylenediamine. After being stirred at room temperature for 1 hour, the mixture was purified by HPLC (method B) to give 20 mg (64.5%) of {1-{1-[(1-methyl-1H-pyrazol-5-yl)sulfonyl]piperidin-4-yl}-3-[4-(7H-pyrrolo[2,3-d]pyrimidin-4-yl)-1H-pyrazol-1-yl]azetidin-3-yl}acetonitrile. LC-MS: 507.2 (M+H)+. $^1$H NMR (300 MHz, DMSO-$d_6$): δ 12.08 (brs, 1H), 8.72 (d, 1H), 8.62 (s, 1H), 8.34 (s, 1H), 7.55 (d, 2H), 6.99 (d, 1H), 6.75 (s, 1H), 3.95 (s, 3H), 3.62 (dd, 2H), 3.45 (dd, 2H), 3.40 (m, 2H), 3.25 (s, 2H), 3.19 (m, 1H), 2.75 (m, 2H), 1.70 (m, 2H), 1.25 (m, 2H).

The following compounds were prepared by a method analogous to that for Example 246.

| Example # | R | Compound | LC-MS (M + H)+ |
|---|---|---|---|
| 247 | 2-cyanophenyl | 2-[(4-{3-(cyanomethyl)-3-[4-(7H-pyrrolo[2,3-d]pyrimidin-4-yl)-1H-pyrazol-1-yl]azetidin-1-yl}piperidin-1-yl)sulfonyl]benzonitrile | 528.1 |
| 248 | 3-cyanophenyl | 3-[(4-{3-(cyanomethyl)-3-[4-(7H-pyrrolo[2,3-d]pyrimidin-4-yl)-1H-pyrazol-1-yl]azetidin-1-yl}piperidin-1-yl)sulfonyl]benzonitrile | 528.1 |
| 249 | 4-cyanophenyl | 4-[(4-{3-(cyanomethyl)-3-[4-(7H-pyrrolo[2,3-d]pyrimidin-4-yl)-1H-pyrazol-1-yl]azetidin-1-yl}piperidin-1-yl)sulfonyl]benzonitrile | 528.1 |
| 250 | 3-cyano-4-(dimethylamino)phenyl | 5-[(4-{3-(cyanomethyl)-3-[4-(7H-pyrrolo[2,3-d]pyrimidin-4-yl)-1H-pyrazol-1-yl]azetidin-1-yl}piperidin-1-yl)sulfonyl]-2-(dimethylamino)benzonitrile | 571.2 |
| 251 | 1-methyl-1H-pyrazol-3-yl | {1-{1-[(1-methyl-1H-pyrazol-3-yl)sulfonyl]piperidin-4-yl}-3-[4-(7H-pyrrolo[2,3-d]pyrimidin-4-yl)-1H-pyrazol-1-yl]azetidin-3-yl}acetonitrile | 507.2 |
| 252 | cyclohexyl | {1-[1-(cyclohexylsulfonyl)piperidin-4-yl]-3-[4-(7H-pyrrolo[2,3-d]pyrimidin-4-yl)-1H-pyrazol-1-yl]azetidin-3-yl}acetonitrile | 509.2 |
| 253 | cyclopentyl | {1-[1-(cyclopentylsulfonyl)piperidin-4-yl]-3-[4-(7H-pyrrolo[2,3-d]pyrimidin-4-yl)-1H-pyrazol-1-yl]azetidin-3-yl}acetonitrile | 495.2 |
| 254 | Me | {1-[1-(methylsulfonyl)piperidin-4-yl]-3-[4-(7H-pyrrolo[2,3-d]pyrimidin-4-yl)-1H-pyrazol-1-yl]azetidin-3-yl}acetonitrile | 441.1 |
| 255 | Et | {1-[1-(ethylsulfonyl)piperidin-4-yl]-3-[4-(7H-pyrrolo[2,3-d]pyrimidin-4-yl)-1H-pyrazol-1-yl]azetidin-3-yl}acetonitrile | 455.1 |
| 256 | cyclopropyl | {1-[1-(cyclopropylsulfonyl)piperidin-4-yl]-3-[4-(7H-pyrrolo[2,3-d]pyrimidin-4-yl)-1H-pyrazol-1-yl]azetidin-3-yl}acetonitrile | 467.1 |
| 257 | isopropyl | {1-[1-(isopropylsulfonyl)piperidin-4-yl]-3-[4-(7H-pyrrolo[2,3-d]pyrimidin-4-yl)-1H-pyrazol-1-yl]azetidin-3-yl}acetonitrile | 469.2 |
| 258 | 1-methyl-1H-imidazol-4-yl | {1-{1-[(1-methyl-1H-imidazol-4-yl)sulfonyl]piperidin-4-yl}-3-[4-(7H-pyrrolo[2,3-d]pyrimidin-4-yl)-1H-pyrazol-1-yl]azetidin-3-yl}acetonitrile | 507.2 |
| 259 | 1,2-dimethyl-1H-imidazol-4-yl | {1-{1-[(1,2-dimethyl-1H-imidazol-4-yl)sulfonyl]piperidin-4-yl}-3-[4-(7H-pyrrolo[2,3-d]pyrimidin-4-yl)-1H-pyrazol-1-yl]azetidin-3-yl}acetonitrile | 521.2 |
| 260 | 3,5-dimethylisoxazol-4-yl | {1-{1-[(3,5-dimethylisoxazol-4-yl)sulfonyl]piperidin-4-yl}-3-[4-(7H-pyrrolo[2,3-d]pyrimidin-4-yl)-1H-pyrazol-1-yl]azetidin-3-yl}acetonitrile | 522.2 |

¹H NMR (400 MHz, DMSO-d₆) of Example 250 (TFA salt): δ 12.27 (s, 1H), 9.00 (s, 1H), 8.73 (s, 1H), 8.53 (s, 1H), 7.67 (t, 1H), 7.19 (t, 1H), 7.09 (s, 1H), 7.01 (d, 1H), 6.83 (t, 1H), 4.9 (m, 1H), 3.68 (s, 3H), 3.17 (s, 6H), 2.5 (m, 2H), 2.27 (m, 3H), 2.05 (m, 3H), 1.39 (m, 3H).

¹H NMR (300 MHz, DMSO-d₆) of Example 251: 12.28 (brs, 1H), 8.67 (s, 1H), 8.41 (s, 1H), 8.19 (s, 1H), 7.62 (d, 1H), 7.32 (d, 1H), 6.75 (d, 1H), 6.32 (s, 1H), 4.55 (m, 2H), 4.30 (m, 2H), 3.58 (s, 3H), 3.39 (m, 4H), 3.02 (m, 1H), 2.12 (m, 2H), 1.63 (m, 2H), 1.08 (m, 2H).

¹H NMR (300 MHz, DMSO-d₆) of Example of 252: δ 12.03 (brs, 1H), 8.74 (s, 1H), 8.62 (s, 1H), 8.34 (s, 1H), 7.55 (d, 1H), 7.00 (d, 1H), 3.68 (d, 2H), 3.51 (d, 2H), 3.52-3.38 (m, 3H), 3.27 (s, 2H), 3.35-3.20 (m, 1H), 3.06-2.87 (m, 3H), 2.35 (m, 1H), 1.89 (d, 2H), 1.70-1.49 (m, 4H), 1.35-0.95 (m, 6H).

¹H NMR (300 MHz, DMSO-d₆) of Example 253: δ 12.13 (brs, 1H), 8.81 (s, 1H), 8.69 (s, 1H), 8.41 (s, 1H), 7.60 (d, 1H), 7.06 (d, 1H), 3.70 (d, 2H), 3.55 (d, 2H), 3.45 (m, 3H), 3.35 (s, 2H), 3.40-3.30 (m, 4H), 2.95 (t, 2H), 2.41 (m, 1H), 1.89 (m, 2H), 1.80-1.40 (m, 4H), 1.22 (m, 2H).

¹H NMR (300 MHz, DMSO-d₆) of Example of 254: δ 12.13 (brs, 1H), 8.81 (s, 1H), 8.69 (s, 1H), 8.42 (s, 1H), 7.60 (d, 1H), 7.05 (d, 1H), 3.72 (d, 2H), 3.55 (d, 2H), 3.52 (m, 1H), 3.36 (m, 1H), 3.31 (s, 2H), 2.85 (m, 2H), 2.81 (s, 3H), 2.35 (m, 1H), 1.73 (m, 2H), 1.30 (m, 2H).

Example 261

{1-{1-[3-Fluoro-2-(trifluoromethyl)isonicotinoyl] piperidin-4-yl}-3-[3-(7H-pyrrolo[2,3-d]pyrimidin-4-yl)-1H-pyrrol-1-yl]azetidin-3-yl}acetonitrile

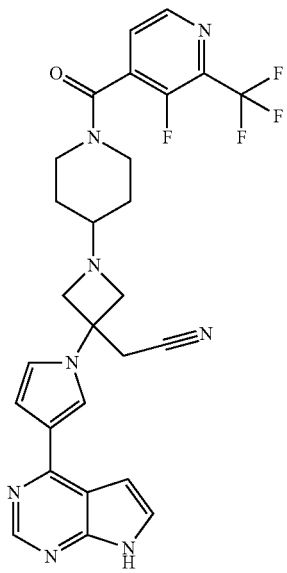 [SMILES: N#CCC1(n2ccc(-c3ncnc4[nH]ccc34)c2)CN(C2CCN(C(=O)c3ccnc(C(F)(F)F)c3F)CC2)C1]

Step A: 4-(1H-Pyrrol-3-yl)-7-{[2-(trimethylsilyl) ethoxy]methyl}-7H-pyrrolo[2, 3-d]pyrimidine

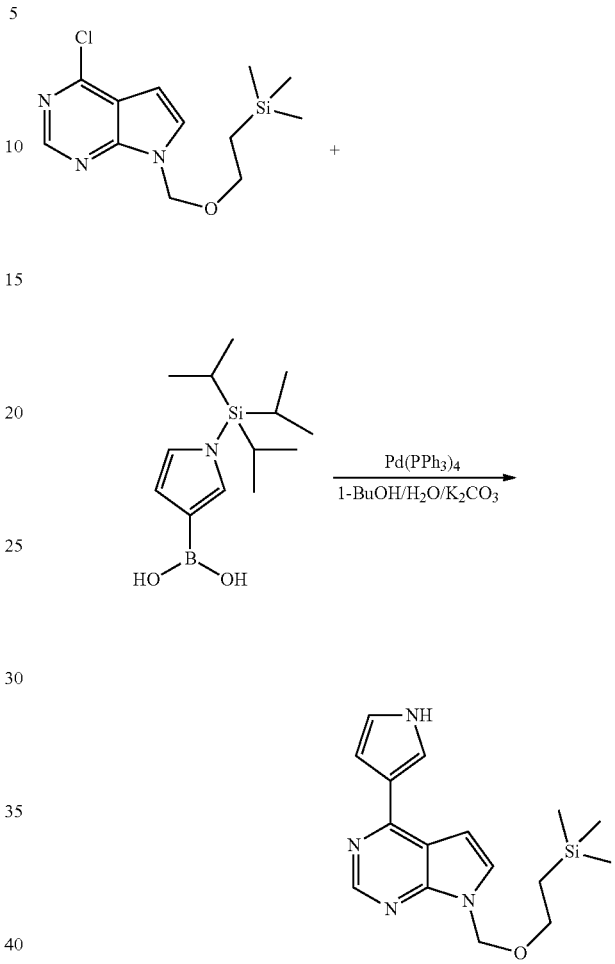

A 100 mL round bottom flask was charged with 4-chloro-7-{[2-(trimethylsilyl)ethoxy]methyl}-7H-pyrrolo[2,3-d]pyrimidine (1.00 g, 3.52 mmol), 1-butanol (25.0 mL), [1-(triisopropylsilyl)-1H-pyrrol-3-yl]boronic acid (1.41 g, 5.28 mmol), water (25.0 mL) and potassium carbonate (1.27 g, 8.8 mmol). This solution was degased 4 times, filling with nitrogen each time. Tetrakis(triphenylphosphine)-palladium (0) (0.41 g, 0.35 mmol) was added and the mixture was degased 4 times, filling with nitrogen each time. The reaction was stirred overnight at 100° C. and cooled to room temperature. The mixture was filtered through a bed of celite and the celite was rinsed with ethyl acetate (42 mL). The filtrate was combined and the organic layer was separated. The aqueous layer was extracted with ethyl acetate. The organic extracts were combined and concentrated under vacuum with a bath temperature of 30-70° C. to give the title compound 4-(1H-pyrrol-3-yl)-7-{[2-(trimethylsilyl)ethoxy] methyl}-7H-pyrrolo[2,3-d]pyrimidine. Yield: 83%; LC-MS: 315.2 (M+H)⁺.

Step B: tert-Butyl 3-(Cyanomethyl)-3-[3-(7-{[2-(trimethylsilyl)ethoxy]methyl}-7H-pyrrolo[2,3-d]pyrimidin-4-yl)-1H-pyrrol-1-yl]azetidine-1-carboxylate

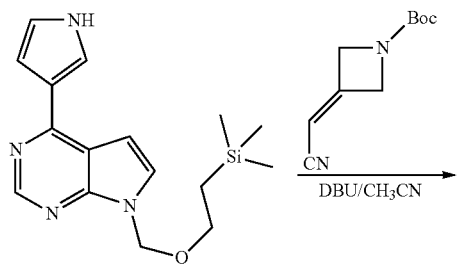

Step C: {3-[3-(7-{[2-(Trimethylsilyl)ethoxy]methyl}-7H-pyrrolo[2,3-d]pyrimidin-4-yl)-1H-pyrrol-1-yl]azetidin-3-yl}acetonitrile dihydrochloride

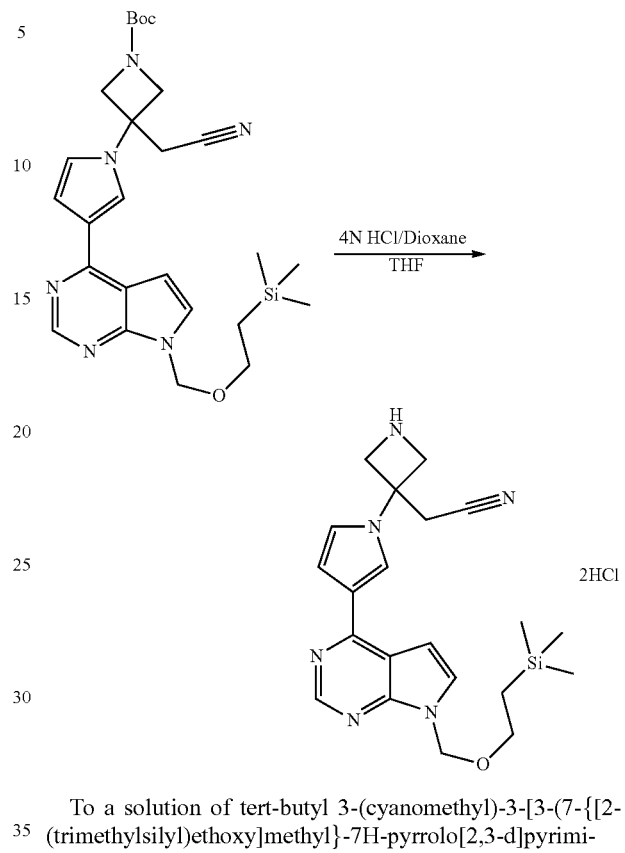

A 100 mL round bottom flask fitted with overhead stirring, septa and nitrogen inlet was charged with tert-butyl-3-(cyanomethylene)azetidine-1-carboxylate (1.8 g, 9.5 mmol), 4-(1H-pyrrol-3-yl)-7-{[2-(trimethylsilyl)ethoxy]methyl}-7H-pyrrolo[2,3-d]pyrimidine (3.0 g, 9.5 mmol) and acetonitrile (60 mL). The resulting solution was heterogeneous. 1,8-Diazabicyclo[5.4.0]undec-7-ene (1.4 mL, 9.5 mmol) was added portionwise via a syringe over 3 minutes at room temperature. The solution slowly becomes homogeneous and yellow in color. The reaction was allowed to stir at room temperature for 3 hours. The solution was concentrated by rotary evaporation to remove acetonitrile. EtOAc (100 mL) and brine (100 mL) were added. The organic phase was separated and the aqueous layer was extracted with 3×30 mL EtOAc. The combined extracts were dried over anhydrous MgSO₄, filtered and concentrated in vacuo to yield an orange oil which was purified by flash chromatography (120 grams silica, 30-55% EtOAc/hexane, loaded with CH₂Cl₂). Desired fractions were combined and concentrated to yield a yellow oil which was placed on a high vacuum pump to give 4 g (83%) of tert-butyl 3-(cyanomethyl)-3-[3-(7-{[2-(trimethylsilyl)ethoxy]methyl}-7H-pyrrolo[2,3-d]pyrimidin-4-yl)-1H-pyrrol-1-yl]azetidine-1-carboxylate as a white foam. LC-MS: [M+H]+=509.3.

To a solution of tert-butyl 3-(cyanomethyl)-3-[3-(7-{[2-(trimethylsilyl)ethoxy]methyl}-7H-pyrrolo[2,3-d]pyrimidin-4-yl)-1H-pyrrol-1-yl]azetidine-1-carboxylate (4 g, 7.87 mmol) in 20 mL of THF was added 20 mL of 4 N HCl in dioxane. After being stirred at room temperature for 1 hour, the solvents were removed in vacuo to give 3.9 g (99%) of the desired product {3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile dihydrochloride, which was used for the next reaction. LC-MS: [M+H]+=409.3.

Step D: tert-Butyl 4-{3-(Cyanomethyl)-3-[3-(7-{[2-(trimethylsilyl)ethoxy]methyl}-7H-pyrrolo[2,3-d]pyrimidin-4-yl)-1H-pyrrol-1-yl]azetidin-1-yl}piperidine-1-carboxylate

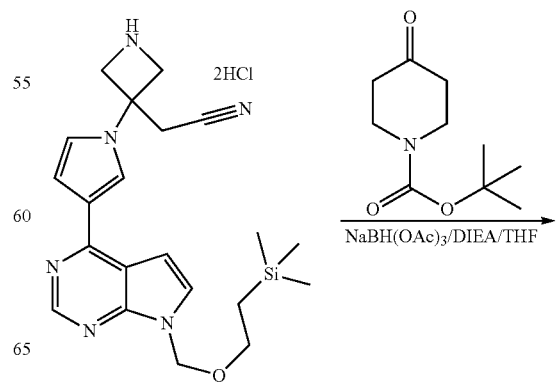

-continued

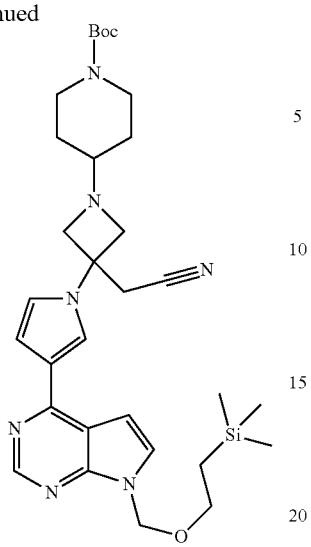

To a suspension of {3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile dihydrochloride (3.0 g, 7.3 mmol) in THF (30 mL) were added tert-butyl 4-oxo-1-piperidinecarboxylate (1.4 g, 7.3 mmol), N,N-diisopropylethylamine (6.4 mL, 37 mmol) and sodium triacetoxyborohydride (3.1 g, 15 mmol). The reaction mixture was stirred at room temperature overnight. Brine (20 mL) and EtOAc (20 mL) were added. The organic phase was separated and the aqueous layer was extracted with EtOAc. The combined extracts were dried over sodium sulfate, filtered, and evaporated in vacuo. The residue was purified using combiflash column eluting with 20-50% EtOAc in hexanes to generate tert-butyl 4-{3-(cyanomethyl)-3-[3-(7-{[2-(trimethylsilyl)ethoxy]methyl}-7H-pyrrolo[2,3-d]pyrimidin-4-yl)-1H-pyrrol-1-yl]azetidin-1-yl}piperidine-1-carboxylate as an oil. Yield: 3.37 g (78%); LC-MS: [M+H]+=592.3.

Step E: {1-Piperidin-4-yl-3-[3-(7-{[2-(trimethylsilyl)ethoxy]methyl}-H-pyrrolo[2, 3-d]pyrimidin-4-yl)-1H-pyrrol-1-yl]azetidin-3-yl}acetonitrile trihydrochloride

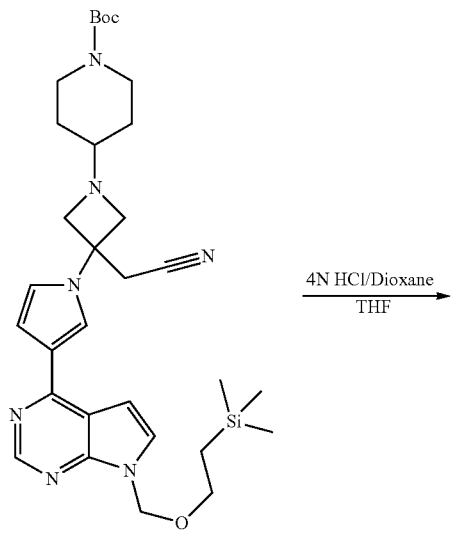

-continued

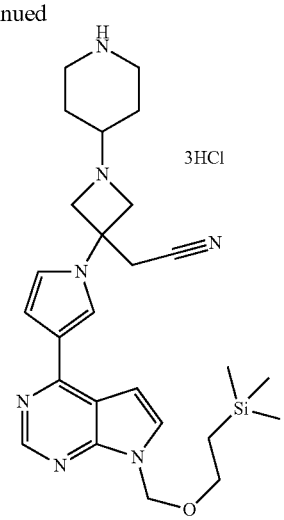

To a solution of tert-butyl 4-{3-(cyanomethyl)-3-[3-(7-{[2-(trimethylsilyl)ethoxy]methyl}-7H-pyrrolo[2,3-d]pyrimidin-4-yl)-1H-pyrrol-1-yl]azetidin-1-yl}piperidine-1-carboxylate (3.3 g, 5.6 mmol) in THF (17 mL) was added a 4 N solution of HCl in dioxane (17 mL). The mixture was stirred at room temperature for 2 hours and concentrated to afford {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride as a white powder solid, which was used for the next reaction. Yield: 99%; LC-MS: [M+H]+=492.3.

Step F: {1-{1-[3-Fluoro-2-(trifluoromethyl)isonicotinoyl]piperidin-4-yl}-3-[3-(7H-pyrrolo[2,3-d]pyrimidin-4-yl)-1H-pyrrol-1-yl]azetidin-3-yl}acetonitrile A mixture of {1-piperidin-4-yl-3-[4-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride (1.22 g, 2.03 mmol), 3-fluoro-2-(trifluoromethyl)isonicotinic acid (460 mg, 2.2 mmol), benzotriazol-1-yloxytris(dimethylamino)phosphonium hexafluorophosphate (1.07 g, 2.42 mmol) and triethylamine (2.0 mL, 14 mmol) in DMF (20.0 mL) was stirred at room temperature overnight. LS-MS showed the reaction was complete. EtOAc (60 mL) and saturated NaHCO₃ aqueous solution (60 mL) were added to the reaction mixture. After stirring at room temperature for 10 minutes, the organic phase was separated and the aqueous layer was extracted with EtOAc three times. The combined extracts were washed with brine, dried over anhydrous Na₂SO₄, filtered and evaporated under reduced pressure. Purification by flash chromatography provided {1-{1-[3-fluoro-2-(trifluoromethyl)isonicotinoyl]piperidin-4-yl}-3-[4-(7-{[2-(trimethylsilyl)ethoxy]methyl}-7H-pyrrolo[2,3-d]pyrimidin-4-yl)-1H-pyrrol-1-yl]azetidin-3-yl}acetonitrile as a white powder.

The white powder was dissolved in trifluoroacetic acid (5 mL) and methylene chloride (5 mL). The mixture was stirred at room temperature for 2 hours and concentrated in vacuo. The residue was dissolved in 10 mL of a methanol solution containing 20% ethylenediamine. After being stirred at room temperature for 1 hour, HPLC purification (method B) gave the title compound {1-{1-[3-fluoro-2-(trifluoromethyl)isonicotinoyl]piperidin-4-yl}-3-[3-(7H-pyrrolo[2,3-d]pyrimidin-4-yl)-1H-pyrrol-1-yl]azetidin-3-yl}acetonitrile. LC-MS: 553.3 (M+H)+. 1H NMR (400 MHz, CDCl3): δ 9.10 (m, 1H), 8.77 (s, 1H), 8.57 (d, J=4.8 Hz, 1H), 7.57 (s, 1H), 7.53 (t, J=4.7 Hz, 1H), 7.31 (dd, J1=3.6 Hz, J2=2.2 Hz, 1H), 6.97 (dd, J1=2.9 Hz, J2=1.5 Hz, 1H), 6.83 (dd, J1=3.8 Hz, J2=2.1 Hz, 1H), 6.81 (t, J=2.6 Hz, 1H), 4.17 (m, 1H), 3.76 (m, 2H), 3.50 (dd, J1=9.1 Hz, J2=7.4 Hz, 2H), 3.44 (m, 2H), 3.21 (s, 2H), 3.09 (m, 1H), 2.52 (m, 1H), 1.81 (m, 1H), 1.69 (m, 1H), 1.51 (m, 1H), 1.23 (m, 1H).

The following compounds were prepared by a method analogous to that for Example 261.

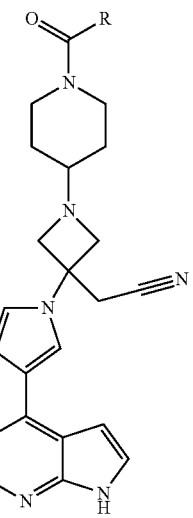

| Example # | R | Compound | LC-MS (M + H)+ |
|---|---|---|---|
| 262 | (3-cyanophenyl) | 3-[(4-{3-(cyanomethyl)-3-[3-(7H-pyrrolo[2,3-d]pyrimidin-4-yl)-1H-pyrrol-1-yl]azetidin-1-yl}piperidin-1-yl)carbonyl]benzonitrile | 491.2 |
| 263 | (3-fluoro-5-cyanophenyl) | 3-[(4-{3-(cyanomethyl)-3-[3-(7H-pyrrolo[2,3-d]pyrimidin-4-yl)-1H-pyrrol-1-yl]azetidin-1-yl}piperidin-1-yl)carbonyl]-5-fluorobenzonitrile | 509.2 |
| 264 | (2-fluoro-4-cyanophenyl) | 4-[(4-{3-(cyanomethyl)-3-[3-(7H-pyrrolo[2,3-d]pyrimidin-4-yl)-1H-pyrrol-1-yl]azetidin-1-yl}piperidin-1-yl)carbonyl]-3-fluorobenzonitrile | 509.2 |
| 265 | (2,6-difluoro-4-cyanophenyl) | 4-[(4-{3-(cyanomethyl)-3-[3-(7H-pyrrolo[2,3-d]pyrimidin-4-yl)-1H-pyrrol-1-yl]azetidin-1-yl}piperidin-1-yl)carbonyl]-3,5-difluorobenzonitrile | 527.2 |
| 266 | (2-trifluoromethyl-5-fluorophenyl) | {1-{1-[5-fluoro-2-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 552.2 |

-continued

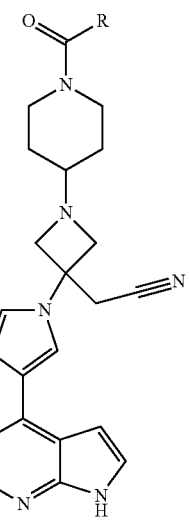

| Example # | R | Compound | LC-MS (M + H)+ |
|---|---|---|---|
| 267 | 4-CF3, 3-F phenyl | {1-{1-[3-fluoro-4-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 552.2 |
| 268 | 3-CF3 phenyl | (3-[3-(7H-pyrrolo[2,3-d]pyrimidin-4-yl)-1H-pyrrol-1-yl]-1-{1-[3-(trifluoromethyl)benzoyl]piperidin-4-yl}azetidin-3-yl)acetonitrile | 534.2 |
| 269 | 4-F, 3-OCF3 phenyl | {1-{1-[2-fluoro-5-(trifluoromethoxy)benzoyl]piperidin-4-yl}-3-[3-(7H-pyrrolo[2,3-d]pyrimidin-4-yl)-1H-pyrrol-1-yl]azetidin-3-yl}acetonitrile | 568.2 |
| 270 | 2,3,6-trifluorophenyl | {3-[3-(7H-pyrrolo[2,3-d]pyrimidin-4-yl)-1H-pyrrol-1-yl]-1-[1-(2,3,6-trifluorobenzoyl)piperidin-4-yl]azetidin-3-yl}acetonitrile | 520.2 |
| 271 | 2-thienyl | {3-[3-(7H-pyrrolo[2,3-d]pyrimidin-4-yl)-1H-pyrrol-1-yl]-1-[1-(2-thienylcarbonyl)piperidin-4-yl]azetidin-3-yl}acetonitrile | 472.1 |
| 272 | 2-F, 4-CF3 phenyl | {1-{1-[2-fluoro-4-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 552.2 |

-continued

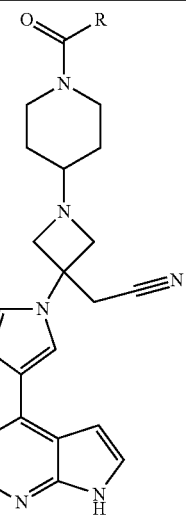

| Example # | R | Compound | LC-MS (M + H)+ |
|---|---|---|---|
| 273 | F, CF3 (2-fluoro-5-CF3 phenyl) | {1-{1-[2-fluoro-5-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 552.2 |
| 274 | F, CF3 (3-fluoro-5-CF3 phenyl) | {1-{1-[3-fluoro-5-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 552.2 |
| 275 | F, CF3 (4-fluoro-3-CF3 phenyl) | {1-{1-[4-fluoro-3-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 552.2 |
| 276 | 2,3-difluorophenyl | {1-[1-(2,3-difluorobenzoyl)piperidin-4-yl]-3-[3-(7H-pyrrolo[2,3-d]pyrimidin-4-yl)-1H-pyrrol-1-yl]azetidin-3-yl}acetonitrile | 502.2 |
| 277 | 3,4-difluorophenyl | {1-[1-(3,4-difluorobenzoyl)piperidin-4-yl]-3-[3-(7H-pyrrolo[2,3-d]pyrimidin-4-yl)-1H-pyrrol-1-yl]azetidin-3-yl}acetonitrile | 502.2 |
| 278 | 2,5-difluorophenyl | {1-[1-(2,5-difluorobenzoyl)piperidin-4-yl]-3-[3-(7H-pyrrolo[2,3-d]pyrimidin-4-yl)-1H-pyrrol-1-yl]azetidin-3-yl}acetonitrile | 502.2 |

-continued

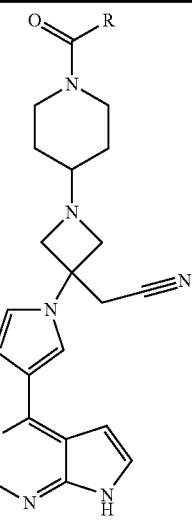

| Example # | R | Compound | LC-MS (M + H)⁺ |
|---|---|---|---|
| 279 | 2,6-difluorophenyl | {1-[1-(2,6-difluorobenzoyl)piperidin-4-yl]-3-[3-(7H-pyrrolo[2,3-d]pyrimidin-4-yl)-1H-pyrrol-1-yl]azetidin-3-yl}acetonitrile | 502.2 |
| 280 | 2,3,4-trifluorophenyl | {3-[3-(7H-pyrrolo[2,3-d]pyrimidin-4-yl)-1H-pyrrol-1-yl]-1-[1-(2,3,4-trifluorobenzoyl)piperidin-4-yl]azetidin-3-yl}acetonitrile | 520.2 |
| 281 | 2-fluoro-3-(trifluoromethoxy)phenyl | {1-{1-[2-fluoro-3-(trifluoromethoxy)benzoyl]piperidin-4-yl}-3-[3-(7H-pyrrolo[2,3-d]pyrimidin-4-yl)-1H-pyrrol-1-yl]azetidin-3-yl}acetonitrile | 568.2 |
| 282 | 4-hydroxy-3-(trifluoromethyl)phenyl | {1-{1-[4-hydroxy-3-(trifluoromethyl)benzoyl]piperidin-4-yl}-3-[3-(7H-pyrrolo[2,3-d]pyrimidin-4-yl)-1H-pyrrol-1-yl]azetidin-3-yl}acetonitrile | 550.2 |

¹H NMR (400 MHz, DMSO-d₆) of Example 262: δ 11.98 (s, 1H), 8.60 (s, 1H), 7.90 (m, 1H), 7.86 (m, 1H), 7.82 (m, 1H), 7.69 (m, 1H), 7.63 (t, 1H), 7.50 (d, 1H), 7.07 (t, 1H), 6.93 (m, 2H), 4.10 (m, 1H), 3.56 (m, 5H), 3.45 (m, 3H), 3.17 (m, 1H), 3.05 (m, 1H), 1.74 (m, 1H), 1.62 (m, 1H), 1.25 (m, 2H).

¹H NMR (400 MHz, DMSO-d₆) of Example 263: δ 11.97 (s, 1H), 8.60 (s, 1H), 7.95 (m, 1H), 7.82 (t, 1H), 7.76 (t, 1H), 7.68 (m, 1H), 7.50 (d, 1H), 7.07 (t, 1H), 6.93 (m, 2H), 4.05 (m, 1H), 3.56 (m, 5H), 3.45 (m, 3H), 3.18 (m, 1H), 3.05 (m, 1H), 1.74 (m, 1H), 1.62 (m, 1H), 1.25 (m, 2H).

¹H NMR (400 MHz, DMSO-d₆) of Example 264: δ 11.97 (s, 1H), 8.60 (s, 1H), 7.98 (dd, 1H), 7.81 (t, 1H), 7.77 (dd, 1H), 7.61 (t, 1H), 7.50 (d, 1H), 7.07 (t, 1H), 6.93 (d, 2H), 4.05 (m, 1H), 3.56 (m, 5H), 3.47 (s, 2H), 3.35 (m, 1H), 3.21 (m, 1H), 3.02 (m, 1H), 1.74 (m, 1H), 1.60 (m, 1H), 1.25 (m, 2H).

¹H NMR (400 MHz, DMSO-d₆) of Example 265: δ 11.96 (s, 1H), 8.59 (s, 1H), 7.96 (s, 1H), 7.94 (s, 1H), 7.81 (t, 1H), 7.49 (s, 1H), 7.06 (t, 1H), 6.92 (t, 2H), 4.06 (m, 1H), 3.56 (m, 4H), 3.47 (s, 2H), 3.40 (m, 1H), 3.30 (m, 2H), 3.20 (m, 1H), 1.74 (m, 1H), 1.60 (m, 1H), 1.20 (m, 2H).

¹H NMR (400 MHz, DMSO-d₆) of Example 266: δ 11.96 (brs, 1H), 8.60 (s, 1H), 7.82 (s, 1H), 7.71 (dd, 1H), 7.50 (d, 1H), 7.35 (dd, 1H), 7.09 (dd, 1H), 7.07 (dd, 1H), 6.94 (s, 1H), 6.93 (s, 1H), 3.97 (d, 2H), 3.60 (d, 2H), 3.57 (d, 2H), 3.47 (m, 1H), 3.32 (s, 2H), 3.24 (m, 2H), 1.72 (m, 2H), 1.23 (m, 2H).

¹H NMR (400 MHz, DMSO-d₆) of Example 267: δ 11.96 (brs, 1H), 8.60 (s, 1H), 7.81 (s, 1H), 7.50 (dd, 1H), 7.49 (dd, 1H), 7.47 (dd, 1H), 7.45 (d, 1H), 7.06 (d, 1H), 6.93 (s, 1H), 6.92 (s, 1H), 4.02 (m, 1H), 3.58 (d, 2H), 3.53 (d, 2H), 3.46 (m, 1H), 3.32 (s, 2H), 3.30 (m, 1H), 3.21 (m, 1H), 3.02 (m, 1H), 1.70 (m, 2H), 1.21 (m, 2H).

¹H NMR (400 MHz, DMSO-d₆) of Example 269: δ 11.96 (brs, 1H), 8.60 (s, 1H), 7.84 (d, 1H), 7.82 (s, 1H), 7.57 (d, 1H), 7.50 (d, 1H), 7.39 (d, 1H), 7.07 (d, 1H), 6.93 (s, 1H), 6.92 (s, 1H), 4.02 (m, 1H), 3.53 (m, 1H), 3.55 (d, 2H), 3.46 (d, 2H), 3.41 (m, 1H), 3.32 (s, 2H), 3.18 (m, 1H), 3.04 (m, 1H), 1.73 (m, 1H), 1.60 (m, 1H), 1.21 (m, 2H).

¹H NMR (400 MHz, DMSO-d₆) of Example 270: δ 11.91 (brs, 1H), 8.54 (s, 1H), 7.76 (s, 1H), 7.56 (dd, 1H), 7.45 (d, 1H), 7.22 (s, 1H), 7.01 (s, 1H), 6.88 (s, 1H), 6.87 (s, 1H), 4.02 (m, 1H), 3.53 (d, 2H), 3.50 (m, 1H), 3.46 (d, 2H), 3.39 (m, 1H), 3.27 (s, 2H), 3.20 (m, 1H), 3.04 (m, 1H), 1.69 (m, 1H), 1.57 (m, 1H), 1.13 (m, 2H).

Example 283

4-{3-(Cyanomethyl)-3-[3-(7H-pyrrolo[2,3-d]pyrimidin-4-yl)-1H-pyrrol-1-yl]azetidin-1-yl}-N-[4-fluoro-2-(trifluoromethyl)phenyl]piperidine-1-carboxamide

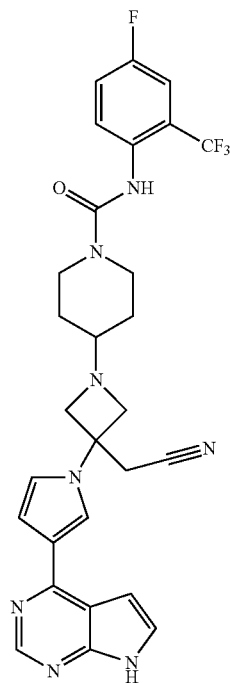 [SMILES: N#CCC1(n2ccc(-c3ncnc4[nH]ccc34)c2)CN(C2CCN(C(=O)Nc3ccc(F)cc3C(F)(F)F)CC2)C1]

To a solution of {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride (500 mg, 1 mmol) in THF (30 mL) were added triethylamine (0.29 g, 2.8 mmol), and 4-fluoro-1-isocyanato-2-(trifluoromethyl)benzene (190 mg, 0.95 mmol). The mixture was stirred at room temperature for one hour. The solvent was removed under reduced pressure. Purification with combiflash using 30-100% EtOAc/hexanes gave the product as a powder. LC-MS: 697.1 (M+H)⁺.

Into the above solid was added a 50 M solution of trifluoroacetic acid in methylene chloride (20 mL, 1000 mmol). After being stirred at room temperature for one hour, the solvent was removed. The residue was dissolved in methanol (20 mL) and ethylenediamine (1.0 g, 17 mmol). After being stirred at room temperature for one hour, the mixture was purified with HPLC (method B) to give 4-{3-(cyanomethyl)-3-[3-(7H-pyrrolo[2,3-d]pyrimidin-4-yl)-1H-pyrrol-1-yl]azetidin-1-yl}-N-[4-fluoro-2-(trifluoromethyl)phenyl]piperidine-1-carboxamide as a white powder. LC-MS: 567.2 (M+H)⁺. ¹H NMR (400 MHz, DMSO-d₆): δ 11.95 (s, 1H), 8.60 (s, 1H), 8.22 (s, 1H), 7.82 (s, 1H), 7.55 (m, 1H), 7.49 (m, 2H), 7.40 (m, 1H), 7.07 (m, 1H), 6.94 (m, 2H), 3.83 (m, 2H), 3.60 (d, J=8.0 Hz, 2H), 3.54 (d, J=8.0 Hz, 2H), 3.47 (s, 2H), 2.97 (t, J=10.4 Hz, 2H), 2.39 (m, 1H), 1.65 (m, 2H), 1.14 (m, 2H).

The following compounds were prepared by a method analogous to that for Example 283.

| Example # | R | Compound | LC-MS (M + H)⁺ |
|---|---|---|---|
| 284 | ![pyridine with OMe] | 4-{3-(cyanomethyl)-3-[3-(7H-pyrrolo[2,3-d]pyrimidin-4-yl)-1H-pyrrol-1-yl]azetidin-1-yl}-N-(2-methoxypyridin-3-yl)piperidine-1-carboxamide | 512.2 |
| 285 | ![pyridine with CF₃ and methyl] | 4-{3-(cyanomethyl)-3-[3-(7H-pyrrolo[2,3-d]pyrimidin-4-yl)-1H-pyrrol-1-yl]azetidin-1-yl}-N-[2-methyl-6-(trifluoromethyl)pyridin-3-yl]piperidine-1-carboxamide | 564.2 |

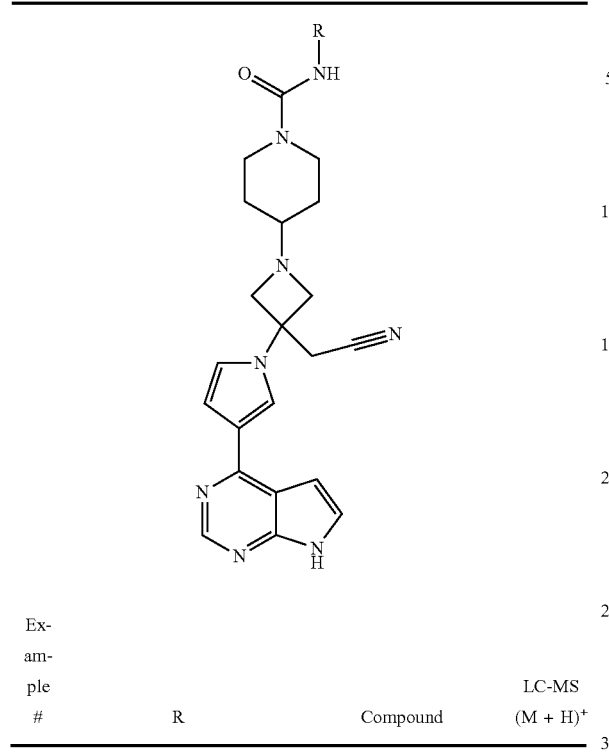

| Example # | R | Compound | LC-MS (M + H)+ |
|---|---|---|---|
| 286 | 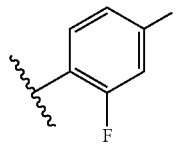 | 4-{3-(cyanomethyl)-3-[3-(7H-pyrrolo[2,3-d]pyrimidin-4-yl)-1H-pyrrol-1-yl]azetidin-1-yl}-N-(2,4-difluorophenyl)piperidine-1-carboxamide | 517.2 |
| 287 | 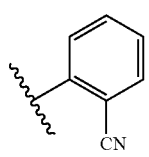 [SMILES: *c1ccccc1C#N] | 4-{3-(cyanomethyl)-3-[3-(7H-pyrrolo[2,3-d]pyrimidin-4-yl)-1H-pyrrol-1-yl]azetidin-1-yl}-N-(2-cyanophenyl)piperidine-1-carboxamide | 506.2 |
| 288 | 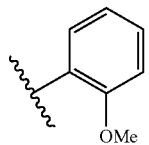 [SMILES: *c1ccccc1OC] | 4-{3-(cyanomethyl)-3-[3-(7H-pyrrolo[2,3-d]pyrimidin-4-yl)-1H-pyrrol-1-yl]azetidin-1-yl}-N-(2-methoxyphenyl)piperidine-1-carboxamide | 511.2 |
| 289 | 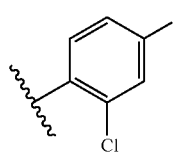 | N-(2-chloro-4-fluorophenyl)-4-{3-(cyanomethyl)-3-[3-(7H-pyrrolo[2,3-d]pyrimidin-4-yl)-1H-pyrrol-1-yl]azetidin-1-yl}piperidine-1-carboxamide | 533.2 |
| 290 | 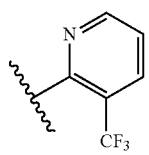 | 4-{3-(cyanomethyl)-3-[3-(7H-pyrrolo[2,3-d]pyrimidin-4-yl)-1H-pyrrol-1-yl]azetidin-1-yl}-N-[3-(trifluoromethyl)pyridin-2-yl]piperidine-1-carboxamide | 550.2 |

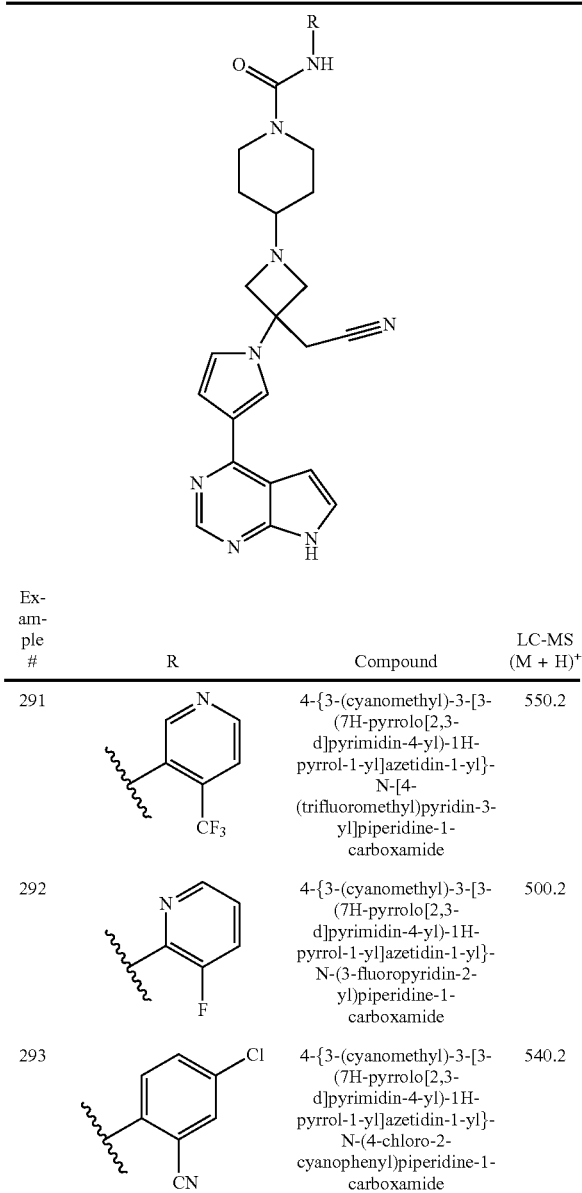

| Example # | R | Compound | LC-MS (M + H)+ |
|---|---|---|---|
| 291 | 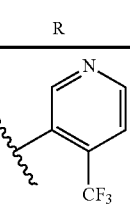 | 4-{3-(cyanomethyl)-3-[3-(7H-pyrrolo[2,3-d]pyrimidin-4-yl)-1H-pyrrol-1-yl]azetidin-1-yl}-N-[4-(trifluoromethyl)pyridin-3-yl]piperidine-1-carboxamide | 550.2 |
| 292 | 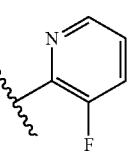 | 4-{3-(cyanomethyl)-3-[3-(7H-pyrrolo[2,3-d]pyrimidin-4-yl)-1H-pyrrol-1-yl]azetidin-1-yl}-N-(3-fluoropyridin-2-yl)piperidine-1-carboxamide | 500.2 |
| 293 | 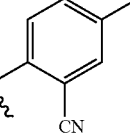 | 4-{3-(cyanomethyl)-3-[3-(7H-pyrrolo[2,3-d]pyrimidin-4-yl)-1H-pyrrol-1-yl]azetidin-1-yl}-N-(4-chloro-2-cyanophenyl)piperidine-1-carboxamide | 540.2 |

$^1$H NMR (400 MHz, DMSO-$d_6$) of Example 284: δ 11.85 (br, 1H), 8.55 (s, 1H), 7.87 (dd, 1H), 7.77 (m, 2H), 7.69 (s, 1H), 7.45 (d, 1H), 7.03 (m, 1H), 6.87 (m, 3H), 3.82 (s, 3H), 3.77 (m, 2H), 3.55 (d, 2H), 3.48 (d, 2H), 3.42 (s, 2H), 2.95 (t, 2H), 2.34 (m, 1H), 1.62 (m, 2H), 1.13 (m, 2H).

$^1$H NMR (400 MHz, DMSO-$d_6$) of Example 285: δ 11.95 (br, 1H), 8.60 (s, 1H), 8.41 (s, 1H), 7.83 (m, 2H), 7.66 (d, 1H), 7.50 (m, 1H), 7.07 (m, 1H), 6.94 (m, 2H), 3.87 (m, 2H), 3.61 (d, 2H), 3.56 (d, 2H), 3.47 (s, 2H), 3.05 (t, 2H), 2.42 (s, 4H), 1.70 (m, 2H), 1.20 (m, 2H).

$^1$H NMR (400 MHz, DMSO-$d_6$) of Example 286: δ 11.99 (s, 1H), 8.56 (s, 1H), 8.20 (s, 1H), 7.77 (t, J=5 Hz, 1H), 7.45 (d, J=9 Hz, 1H), 7.30 (m, 1H), 7.18 (m, 1H), 7.05 (m, 1H), 6.95 (m, 1H), 6.88 (m, 2H), 3.80 (m, 2H), 3.55 (m, 2H), 3.50 (m, 2H), 3.42 (s, 2H), 2.95 (m, 2H), 2.35 (m, 1H), 1.62 (m, 2H), 1.05 (m, 2H).

$^1$H NMR (400 MHz, DMSO-$d_6$) of Example 288: δ 11.91 (br, 1H), 8.55 (s, 1H), 7.76 (m, 1H), 7.57 (m, 2H), 7.45 (m, 1H), 7.02 (m, 1H), 6.90 (m, 4H), 6.79 (m, 1H), 3.78 (m, 2H), 3.73 (s, 3H), 3.55 (d, 2H), 3.50 (d, 2H), 3.42 (s, 2H), 2.94 (t, 2H), 2.34 (m, 1H), 1.62 (m, 2H), 1.13 (m, 2H).

$^1$H NMR (400 MHz, DMSO-d$_6$) of Example 289: δ 11.90 (br, 1H), 8.55 (s, 1H), 8.20 (br, 1H), 7.77 (m, 1H), 7.44 (m, 1H), 7.35 (m, 2H), 7.11 (m, 1H), 7.02 (m, 1H), 6.88 (m, 2H), 3.79 (m, 2H), 3.55 (d, 2H), 3.50 (d, 2H), 3.42 (s, 2H), 2.94 (t, 2H), 2.35 (m, 1H), 1.62 (m, 2H), 1.12 (m, 2H).

$^1$H NMR (400 MHz, DMSO-d$_6$) of Example 290: δ 12.10 (s, 1H), 10.30 (s, 1H), 8.77 (s, 1H), 8.63 (s, 1H), 8.36 (s, 1H), 8.25 (d, J=9 Hz, 1H), 7.86 (d, J=10 Hz, 1H), 7.55 (m, 1H), 7.48 (m, 1H), 7.01 (m, 1H), 6.98 (m, 1H), 3.80 (m, 2H), 3.75 (m, 2H), 3.55 (m, 4H), 3.03 (m, 2H), 2.40 (m, 1H), 1.65 (m, 2H), 1.08 (m, 2H).

$^1$H NMR (400 MHz, DMSO-d$_6$) of Example 291: δ 12.05 (s, 1H), 10.05 (s, 1H), 8.77 (s, 1H), 8.63 (s, 1H), 8.36 (s, 1H), 8.20 (m, 1H), 7.58 (m, 2H), 7.38 (m, 1H), 7.01 (m, 1H), 3.80 (m, 2H), 3.75 (m, 2H), 3.54 (m, 4H), 3.03 (m, 2H), 2.40 (m, 1H), 1.65 (m, 2H), 1.08 (m, 2H).

$^1$H NMR (400 MHz, DMSO-d$_6$) of Example 292: δ 12.05 (s, 1H), 8.76 (s, 1H), 8.63 (s, 1H), 8.55 (s, 1H), 8.36 (s, 1H), 7.60 (m, 4H), 7.00 (d, J=9 Hz, 1H), 3.80 (m, 2H), 3.75 (m, 2H), 3.54 (m, 4H), 3.00 (m, 2H), 2.40 (m, 1H), 1.62 (m, 2H), 1.08 (m, 2H).

Example 294

{1-{1-[3-Fluoro-2-(trifluoromethyl)isonicotinoyl]piperidin-4-yl}-3-[3-(7H-pyrrolo[2,3-d]pyridin-4-yl)-1H-pyrazol-1-yl]azetidin-3-yl}acetonitrile

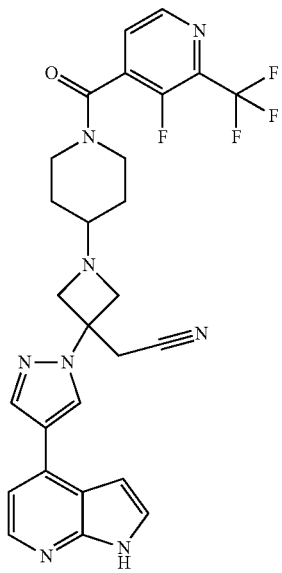 [SMILES: N#CCC1(n2cc(-c3ccnc4[nH]ccc34)cn2)CN(C2CCN(C(=O)c3ccnc(C(F)(F)F)c3F)CC2)C1]

Step A: 4-Bromo-1-{[2-(trimethylsilyl)ethoxy]methyl}-1H-pyrrolo[2, 3-b]pyridine

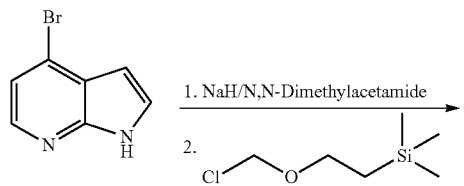

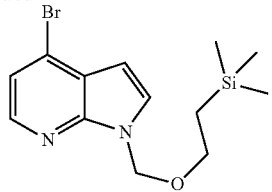

A solution of 4-bromo-1H-pyrrolo[2,3-b]pyridine (10.0 g, 0.0508 mol) in DMF (40 mL) was cooled under nitrogen to 0° C. Sodium hydride (3.0 g, 0.075 mol) was added portionwise. The reaction was stirred for 1 hour. To this mixture, [2-(trimethylsilyl)ethoxy]methyl chloride (10.8 mL, 0.061 mol) was added slowly. After being stirred at 0° C. for 1 hour, the reaction was quenched with water and extracted with EtOAc twice. The combined extracts were washed with water, brine, dried over anhydrous sodium sulfate, filtered and concentrated under reduced pressure. The residue was purified by silica gel chromatography, eluting with 0-25% EtOAc/hexanes to afford 15.7 g (94.5%) of the desired product as a yellowish oil. LC/MS found: 327.1, 329.1 (M+H)$^+$.

Step B: 4-(1H-Pyrazol-4-yl)-1-{[2-(trimethylsilyl)ethoxy]methyl}-1H-pyrrolo[2, 3-b]pyridine

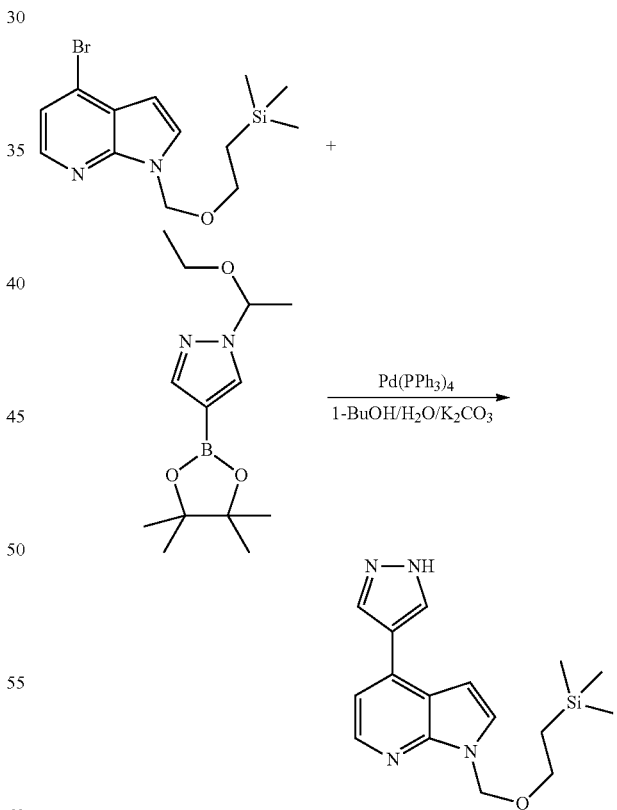

A mixture of 4-bromo-1-{[2-(trimethylsilyl)ethoxy]methyl}-1H-pyrrolo[2,3-b]pyridine (15.70 g, 47.97 mmol), 1-(1-ethoxyethyl)-4-(4,4,5,5-tetramethyl-1,3,2-dioxaborolan-2-yl)-1H-pyrazole (14.04 g, 52.77 mmol), tetrakis(triphenylphosphine)palladium(0) (2.772 g, 2.398 mmol) and sodium carbonate (15.25 g, 143.9 mmol) in 1,4-dioxane (150 mL) and water (75 mL) was stirred at 110° C. for 1 hour. After being cooled to room temperature, the mixture was diluted with EtOAc, and washed with water and brine, dried over Na₂SO₄ and concentrated. The residue was purified by flash chromatography on silica gel eluting with 10-30% EtOAc/hexanes. The purified intermediate was dissolved in THF (21 mL), water (90 mL) and hydrogen chloride (75 mL, 240 mmol). The resulting suspension was stirred at room temperature for 2 hours. The mixture was adjusted to pH=9-10 with 6 N NaOH. Hexanes (150 mL) were added. The solids formed was filtered and washed with water (3×) to provide 12.9 g (85%) of 4-(1H-pyrazol-4-yl)-1-{[2-(trimethylsilyl)ethoxy]methyl}-1H-pyrrolo[2,3-b]pyridine as a white solid. LC/MS found: 315.2 (M+H)⁺.

Step C: tert-Butyl 3-(Cyanomethyl)-3-[4-(1-{[2 (trimethylsilyl)ethoxy]methyl}-1H-pyrrolo[2, 3-b] pyridin-4-yl)-1H-pyrazol-1-yl]azetidine-1-carboxylate

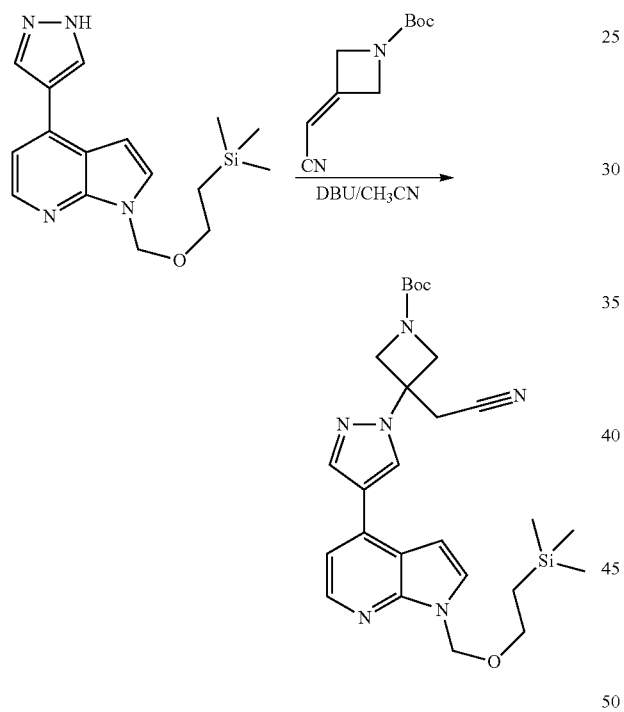

To a solution of 4-(1H-pyrazol-4-yl)-1-{[2-(trimethylsilyl)ethoxy]methyl}-1H-pyrrolo[2,3-b]pyridine (230 mg, 0.73 mmol) and tert-butyl 3-(cyanomethylene)azetidine-1-carboxylate (142 mg, 0.73 mmol) in acetonitrile (5 mL) was added 1,8-diazabicyclo[5.4.0]undec-7-ene (0.11 mL, 0.73 mmol). After being stirred for 5 minutes at room temperature, the mixture became a solution. LC-MS indicated that the reaction was complete. Acetonitrile was evaporated and ethyl acetate was added. The mixture was washed with 1 N HCl, brine, dried over sodium sulfate, filtered and concentrated. The residue was purified by silica gel chromatography (0-80% EtOAc/hexanes) to give 341 mg of tert-butyl 3-(cyanomethyl)-3-[4-(1-{[2-(trimethylsilyl)ethoxy]methyl}-1H-pyrrolo[2,3-b]pyridin-4-yl)-1H-pyrazol-1-yl]azetidine-1-carboxylate as a colorless oil. LC/MS found: 509.2 (M+H)⁺.

Step D: {3-[4-(1-{[2-(Trimethylsilyl)ethoxy] methyl}-1H-pyrrolo[2, 3-b]pyridin-4-yl)-1H-pyrazol-1-yl]azetidin-3-yl}acetonitrile. 2[HCl]

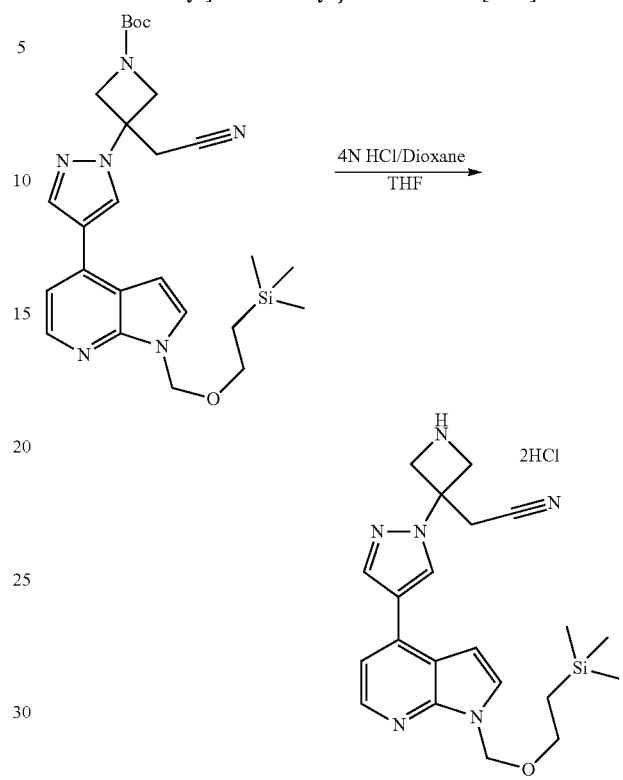

A solution of tert-butyl 3-(cyanomethyl)-3-[4-(1-{[2-(trimethylsilyl)ethoxy]methyl}-1H-pyrrolo[2,3-b]pyridin-4-yl)-1H-pyrazol-1-yl]azetidine-1-carboxylate (341 mg, 0.67 mmol) in THF (5 mL) and methanol (5 mL) was added a 4.0 M solution of hydrogen chloride in 1,4-dioxane (5 mL, 20 mmol). The mixture was stirred at room temperature for 2 hours and concentrated to give 347 mg (100%) of {3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile.2[HCl] as a yellowish solid. LC/MS found: 409.2 (M+H)⁺.

Step E: {1-Piperidin-4-yl-3-[4-(1-{[2-(trimethylsilyl)ethoxy]methyl}-1H-pyrrolo[2, 3-b]pyridin-4-yl)-1H-pyrazol-1-yl]azetidin-3-yl}acetonitrile trihydrochloride

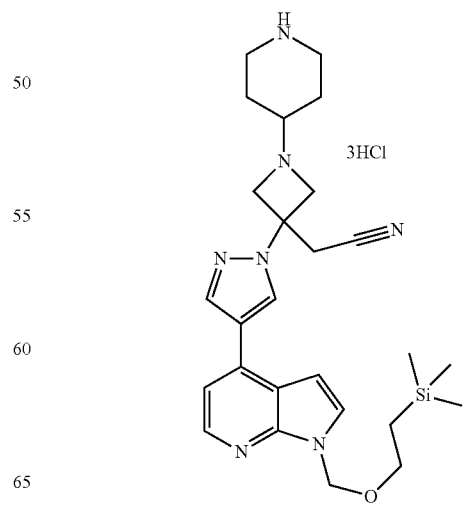

To a mixture of {3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile.2[HCl] (347 mg, 0.70 mmol), tert-butyl 4-oxo-1-piperidinecarboxylate (134 mg, 0.70 mmol) and N,N-diisopropylethylamine (0.467 mL, 2.68 mmol) in THF (10.0 mL) was added sodium triacetoxyborohydride (284 mg, 1.34 mmol). The mixture was stirred at room temperature for 2 hours and quenched with brine. The resulting solution was extracted with EtOAc (2 times). The combined extracts were washed with water, brine and dried over Na$_2$SO$_4$. After filtration and evaporation, the residue was purified by flash chromatography on silica gel eluting with 50-100% EtOAc/hexanes. The purified intermediate (MS: [M+H]$^+$=592.3) was dissolved in THF (6 mL). To the solution was added a 4.0 M solution of HCl in 1,4-dioxane (6 mL, 24 mmol). The mixture was stirred at room temperature for 2 hours and concentrated to give 260 mg of {1-piperidin-4-yl-3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile trihydrochloride as a yellowish solid. LC/MS found: 492.0 (M+H)$^+$. $^1$H NMR (400 MHz, DMSO-d$_6$), δ 9.45 (s, 1H), 8.96 (s, 1H), 8.73 (s, 1H), 8.35 (d, 1H), 8.46 (s, 1H), 8.33 (d, 1H), 7.81 (d, 1H), 7.50 (d, 1H), 7.10 (m, 1H), 5.69 (s, 2H), 4.93 (d, 2H), 4.54 (d, 2H), 3.75-3.60 (m, 1H), 3.55 (s, 2H), 3.55 (s, 2H), 3.52 (t, 2H), 3.49-3.37 (m, 2H), 2.81 (m, 2H), 2.12 (d, 2H), 1.80 (m, 2H), 0.82 (t, 2H), −0.11 (s, 9H).

Step F: {1-{1-[3-Fluoro-2-(trifluoromethyl)isonicotinoyl]piperidin-4-yl}-3-[4-(1H-pyrrolo[2, 3-b]pyridin-4-yl)-1H-pyrazol-1-yl]azetidin-3-yl}acetonitrile A mixture of {1-piperidin-4-yl-3-[4-(7-{[2-(trimethylsilyl)ethoxy]methyl}-7H-pyrrolo[2,3-d]pyridin-4-yl)-1H-pyrazol-1-yl]azetidin-3-yl}acetonitrile trihydrochloride (1.22 g, 2.03 mmol), 3-fluoro-2-(trifluoromethyl)isonicotinic acid (460 mg, 2.2 mmol), benzotriazol-1-yloxytris(dimethylamino)phosphonium hexafluorophosphate (1.07 g, 2.42 mmol) and triethylamine (2.0 mL, 14 mmol) in DMF (10.0 mL) was stirred at room temperature overnight. LS-MS showed the reaction was complete. EtOAc (60 mL) and saturated NaHCO$_3$ aqueous solution (60 mL) were added to the reaction mixture. After stirring at room temperature for 10 minutes, the organic phase was separated and the aqueous layer was extracted with EtOAc three times. The combined extracts were washed with brine, dried over anhydrous Na$_2$SO$_4$, filtered and evaporated under reduced pressure. The residue was purified by flash chromatography to provide {1-{1-[3-fluoro-2-(trifluoromethyl)isonicotinoyl]piperidin-4-yl}-3-[4-(7-{[2-(trimethylsilyl)ethoxy]methyl}-7H-pyrrolo[2,3-d]pyrimidin-4-yl)-1H-pyrrol-1-yl]azetidin-3-yl}acetonitrile as a white powder. The powder was dissolved in 10 mL of TFA/DCM (1:1). After being stirred at room temperature for 2 hours, the solution was concentrated. The residue was dissolved in 10 mL of a solution of 20% ethylenediamine/MeOH. After being stirred at room temperature for 2 hours, the solution was concentrated. Purification by HPLC (method B) provided the final compound {1-{1-[3-fluoro-2-(trifluoromethyl)isonicotinoyl]piperidin-4-yl}-3-[3-(7H-pyrrolo[2,3-d]pyridin-4-yl)-1H-pyrazol-1-yl]azetidin-3-yl}acetonitrile. LC-MS: 553.3 (M+H)$^+$. $^1$H NMR (400 MHz, CDCl$_3$): δ 9.42 (s, 1H), 8.82 (s, 1H), 8.57 (d, J=4.7 Hz, 1H), 8.29 (d, J=5.2 Hz, 1H), 8.06 (d, J=5.8 Hz, 1H), 7.53 (t, J=4.5 Hz, 1H), 7.38 (dd, J$_1$=3.6 Hz, J$_2$=2.4 Hz, 1H), 7.16 (d, J=5.1 Hz, 1H), 6.69 (dd, J$_1$=3.7 Hz, J$_2$=2.1 Hz, 1H), 4.21 (m, 1H), 3.76 (m, 2H), 3.63 (dd, J$_1$=7.4 Hz, J$_2$=5.8 Hz, 2H), 3.46 (m, 2H), 3.35 (s, 2H), 3.11 (m, 1H), 2.56 (m, 1H), 1.84 (m, 1H), 1.71 (m, 1H), 1.49 (m, 1H), 1.40 (m, 1H).

The following compounds were prepared by a method analogous to that for Example 294.

| Example # | R | Compound | LC-MS (M + H)$^+$ |
|---|---|---|---|
| 295 | 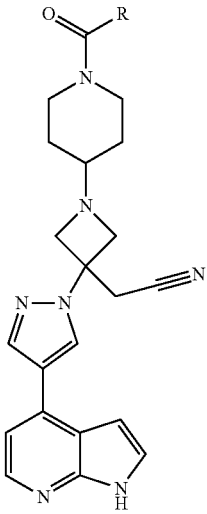 | 4-[(4-{3-(cyanomethyl)-3-[4-(1H-pyrrolo[2,3-b]pyridin-4-yl)-1H-pyrazol-1-yl]azetidin-1-yl}piperidin-1-yl)carbonyl]-3-fluorobenzonitrile | 509.2 |

-continued

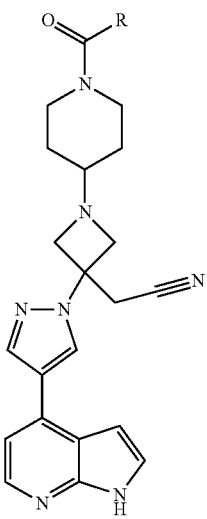

| Example # | R | Compound | LC-MS (M + H)+ |
|---|---|---|---|
| 296 | 2-F, 4-OH phenyl | {1-[1-(3-fluoro-4-hydroxybenzoyl)piperidin-4-yl]-3-[4-(1H-pyrrolo[2,3-b]pyridin-4-yl)-1H-pyrazol-1-yl]azetidin-3-yl}acetonitrile | 500.2 |
| 297 | 4-OH, 3-F phenyl | {1-[1-(2-fluoro-4-hydroxybenzoyl)piperidin-4-yl]-3-[4-(1H-pyrrolo[2,3-b]pyridin-4-yl)-1H-pyrazol-1-yl]azetidin-3-yl}acetonitrile | 500.2 |
| 298 | 5-Cl, 2-CF3 pyridin-4-yl | {1-{1-[5-chloro-2-(trifluoromethyl)isonicotinoyl]piperidin-4-yl}-3-[4-(1H-pyrrolo[2,3-b]pyridin-4-yl)-1H-pyrazol-1-yl]azetidin-3-yl}acetonitrile | 569.2 |
| 299 | 2-CF3 pyrimidin-4-yl | [3-[4-(1H-pyrrolo[2,3-b]pyridin-4-yl)-1H-pyrazol-1-yl]-1-(1-{[2-(trifluoromethyl)pyrimidin-4-yl]carbonyl}piperidin-4-yl)azetidin-3-yl]acetonitrile | 536.2 |
| 300 | 6-CF3 pyrazin-2-yl | [3-[4-(1H-pyrrolo[2,3-b]pyridin-4-yl)-1H-pyrazol-1-yl]-1-(1-{[6-(trifluoromethyl)pyrazin-2-yl]carbonyl}piperidin-4-yl)azetidin-3-yl]acetonitrile | 536.3 |
| 301 | 5-CF3 pyrazin-2-yl | [3-[4-(1H-pyrrolo[2,3-b]pyridin-4-yl)-1H-pyrazol-1-yl]-1-(1-{[5-(trifluoromethyl)pyrazin-2-yl]carbonyl}piperidin-4-yl)azetidin-3-yl]acetonitrile | 536.3 |

-continued

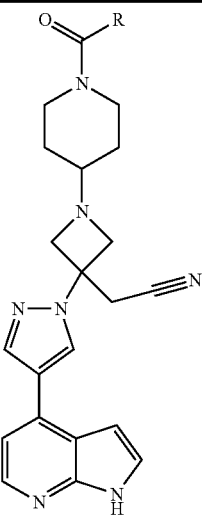

| Example # | R | Compound | LC-MS (M + H)+ |
|---|---|---|---|
| 302 | 4,4-difluorocyclohexyl | {1-{1-[(4,4-fluorocyclohexyl)carbonyl]piperidin-4-yl}-3-[4-(1H-pyrrolo[2,3-b]pyridin-4-yl)-1H-pyrazol-1-yl]azetidin-3-yl}acetonitrile | 508.2 |

$^1$H NMR (400 MHz, CDCl$_3$) of Example 296: δ 8.94 (s, 1H), 8.24 (d, J=5.1 Hz, 1H), 8.05 (d, J=5.3 Hz, 1H), 7.52 (dd, J=8.0 Hz, J$_2$=1.5 Hz, 1H), 7.49 (dd, J=8.1 Hz, J$_2$=6.1 Hz, 1H), 7.42 (dd, J$_1$=8.4 Hz, J$_2$=0.8 Hz, 1H), 7.36 (dd, J$_1$=3.6 Hz, J$_2$=2.3 Hz, 1H), 7.16 (d, J=5.0 Hz, 1H), 6.69 (dd, J$_1$=3.6 Hz, J$_2$=1.8 Hz, 1H), 4.25 (s, 1H), 3.74 (m, 2H), 3.62 (dd, J$_1$=7.6 Hz, J$_2$=3.5 Hz, 1H), 3.46 (m, 1H), 3.35 (s, 2H), 3.09 (m, 1H), 2.53 (m, 1H), 1.81 (m, 1H), 1.65 (m, 1H), 1.45 (m, 1H), 1.22 (m, 1H), 0.85 (m, 1H).

$^1$H NMR (300 MHz, DMSO-d$_6$) of Example 297: δ 11.64 (brs, 1H), 8.61 (s, 1H), 8.20 (s, 1H), 8.12 (d, J=5.1 Hz, 1H), 7.45 (d, J=3.60 Hz, 1H), 7.26 (d, J=5.10 Hz, 1H), 7.09 (t, J=8.40 Hz, 1H), 6.80 (d, J=3.30 Hz, 1H), 6.56 (m, 2H), 4.01 (m, 1H), 3.65 (m, 2H), 3.50 (m, 2H), 3.46 (s, 2H), 3.38 (m, 2H), 3.01 (m, 1H), 2.51 (m, 1H), 1.64 (m, 2H), 1.11 (m, 2H).

$^1$H NMR (300 MHz, DMSO-d$_6$) of Example 300: δ 12.09 (brs, 1H), 9.59 (s, 1H), 9.48 (s, 1H), 8.88 (s, 1H), 8.57 (s, 1H), 8.49 (d, 1H), 7.82 (dd, 1), 7.63 (dd, 1H), 7.16 (d, 1H), 4.39 (m, 1H), 4.02 (d, 2H), 3.90 (dd, 2H), 3.83 (m 1H), 3.61 (s, 2H), 3.58 (m, 1H), 3.45 (m, 1H), 2.86 (m, 1H), 2.02 (m, 2H), 1.59 (m, 2H).

$^1$H NMR (300 MHz, DMSO-d$_6$) of Example 301: δ 12.07 (brs, 1H), 8.82 (s, 1H), 8.76 (s, 1H), 8.68 (s, 2H), 8.41 (s, 2H), 7.61 (d, 1H), 7.06 (d, 1H), 4.55 (m, 1H), 4.05 (m, 1H), 3.75 (dd, 2H), 3.59 (dd, 2H), 3.55 (m, 2H), 3.32 (s, 2H), 3.30 (m, 1H), 1.80 (m, 2H), 1.30 (m, 2H).

Example 303

4-{3-(Cyanomethyl)-3-[4-(1H-pyrrolo[2,3-b]pyridin-4-yl)-1H-pyrazol-1-yl]azetidin-1-yl}-N-[4-fluoro-2-(trifluoromethyl)phenyl]piperidine-1-carboxamide

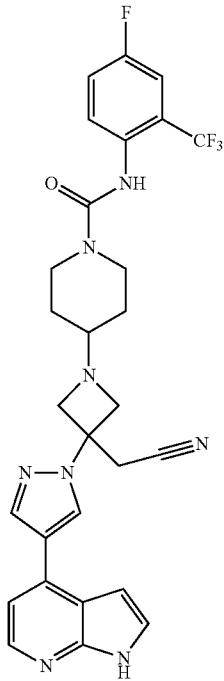 [SMILES: N#CCC1(n2cc(-c3ccnc4[nH]ccc34)cn2)CN(C2CCN(C(=O)Nc3ccc(F)cc3C(F)(F)F)CC2)C1]

To a solution of {1-piperidin-4-yl-3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile trihydrochloride (40 mg, 0.08 mmol) in THF (8 mL) were added triethylamine (0.025 g, 0.24 mmol), and 4-fluoro-1-isocyanato-2-(trifluoromethyl)benzene (18 mg, 0.086 mmol). The mixture was stirred at room temperature for one hour and concentrated. Purification with combi-flash chromatography using 30-100% EtOAc/hexanes gave a powder product. LC-MS: 697.1 (M+H)$^+$.

The above solid was dissolved in a 50 M solution of trifluoroacetic acid in methylene chloride (2 mL, 100 mmol). After being stirred at room temperature for one hour, the solvents were removed. The residue was dissolved in methanol (2 mL) and ethylenediamine (0.024 g, 0.40 mmol). After being stirred at room temperature for one hour, the solution was purified by HPLC (method B) to give 4-{3-(cyanomethyl)-3-[4-(1H-pyrrolo[2,3-b]pyridin-4-yl)-1H-pyrazol-1-yl]azetidin-1-yl}-N-[4-fluoro-2-(trifluoromethyl)phenyl]piperidine-1-carboxamide as a white powder. LC-MS: 567.2 (M+H). $^1$H NMR (400 MHz, DMSO-d$_6$): δ 11.70 (s, 1H), 8.68 (s, 1H), 8.26 (m, 1H), 8.23 (s, 1H), 8.18 (d, J=4.8 Hz, 1H), 7.57 (dd, J$_1$=7.2 Hz, J$_2$=3.2 Hz, 1H), 7.50 (m, 2H), 7.41 (m, 1H), 7.32 (d, J=7.2 Hz, 1H), 6.86 (d, J=3.6 Hz, 1H), 3.86 (m, 2H), 3.73 (d, J=8.0 Hz, 2H), 3.58 (d, J=8.4 Hz, 2H), 3.52 (s, 2H), 2.99 (t, J=10.6 Hz, 2H), 2.43 (m, 1H), 1.68 (m, 2H), 1.12 (m, 2H).

The following compounds were prepared by a method analogous to that for Example 303.

| Example # | R | Compound | LC-MS (M + H)$^+$ |
|---|---|---|---|
| 304 | 2,4-difluorophenyl | 4-{3-(cyanomethyl)-3-{4-(1H-pyrrolo[2,3-b]pyridin-4-yl)-1H-pyrazol-1-yl]azetidin-1-yl}-N-(2,4-difluorophenyl)piperidine-1-carboxamide | 517.2 |
| 305 | 2-chloro-4-fluorophenyl | N-(2-chloro-4-fluorophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide | 533.2 |
| 306 | 2-methoxypyridin-3-yl | 4-{3-(cyanomethyl)-3-[4-(1H-pyrrolo[2,3-b]pyridin-4-yl)-1H-pyrazol-1-yl]azetidin-1-yl}-N-(2-methoxypyridin-3-yl)piperidine-1-carboxamide | 512.3 |
| 307 | 3-(trifluoromethyl)pyridin-4-yl | 4-{3-(cyanomethyl)-3-[4-(1H-pyrrolo[2,3-b]pyridin-4-yl)-1H-pyrazol-1-yl]azetidin-1-yl}-N-[3-(trifluoromethyl)pyridin-4-yl]piperidine-1-carboxamide | 550.2 |

-continued

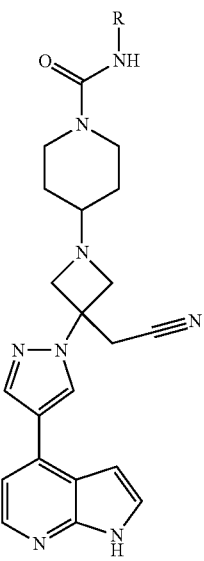

| Example # | R | Compound | LC-MS (M + H)+ |
|---|---|---|---|
| 308 | 3-pyridyl with 4-CF3 | 4-{3-(cyanomethyl)-3-[4-(1H-pyrrolo[2,3-b]pyridin-4-yl)-1H-pyrazol-1-yl]azetidin-1-yl}-N-[4-(trifluoromethyl)pyridin-3-yl]piperidine-1-carboxamide | 550.2 |
| 309 | 2-fluorophenyl | 4-{3-(cyanomethyl)-3-[4-(1H-pyrrolo[2,3-b]pyridin-4-yl)-1H-pyrazol-1-yl]azetidin-1-yl}-N-(2-fluorophenyl)piperidine-1-carboxamide | 499.3 |
| 310 | 2-chlorophenyl | N-(2-chlorophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide | 515.2 |
| 311 | 4-cyano-2-CF3-phenyl | 4-{3-(cyanomethyl)-3-[4-(1H-pyrrolo[2,3-b]pyridin-4-yl)-1H-pyrazol-1-yl]azetidin-1-yl}-N-[4-cyano-2-(trifluoromethyl)phenyl]piperidine-1-carboxamide | 574.2 |
| 312 | 4-cyano-2-fluorophenyl | N-(4-cyano-2-fluorophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide | 524.1 |
| 313 | 2-chloro-4-cyanophenyl | N-(2-chloro-4-cyanophenyl)-4-{3-(cyanomethyl)-3-[4-(1H-pyrrolo[2,3-b]pyridin-4-yl)-1H-pyrazol-1-yl]azetidin-1-yl}piperidine-1-carboxamide | 540.2 |

¹H NMR (400 MHz, DMSO-d₆) of Example 304: δ 11.65 (br, 1H), 8.62 (s, 1H), 8.21 (s, 2H), 8.13 (d, 1H), 7.46 (m, 1H), 7.28 (m, 2H), 7.16 (m, 1H), 6.93 (m, 1H), 6.81 (m, 1H), 3.80 (m, 2H), 3.68 (d, 2H), 3.53 (d, 2H), 3.48 (s, 2H), 2.93 (t, 2H), 2.40 (m, 1H), 1.64 (d, 2H), 1.12 (m, 2H).

¹H NMR (400 MHz, DMSO-d₆) of Example 305: δ 11.65 (br, 1H), 8.63 (s, 1H), 8.21 (s, 1H), 8.17 (s, 1H), 8.13 (d, 1H), 7.46 (m, 1H), 7.36 (m, 2H), 7.27 (d, 1H), 7.10 (m, 1H), 6.81 (m, 1H), 3.82 (m, 2H), 3.68 (d, 2H), 3.53 (d, 2H), 3.48 (s, 2H), 2.94 (t, 2H), 2.38 (m, 1H), 1.65 (d, 2H), 1.13 (m, 2H).

¹H NMR (400 MHz, DMSO-d₆) of Example 306: δ 11.65 (br, 1H), 8.63 (s, 1H), 8.21 (s, 1H), 8.17 (s, 1H), 8.13 (d, 1H), 7.88 (d, 1H), 7.75 (m, 1H), 7.70 (s, 1H), 7.45 (d, 1H), 6.87 (m, 1H), 6.81 (m, 1H), 3.82 (s, 3H), 3.79 (m, 2H), 3.68 (d, 2H), 3.53 (d, 2H), 3.48 (s, 2H), 2.95 (t, 2H), 2.38 (m, 1H), 1.65 (d, 2H), 1.13 (m, 2H).

¹H NMR (400 MHz, DMSO-d₆) of Example 307: δ 11.65 (br, 1H), 8.67 (s, 1H), 8.63 (s, 1H), 8.55 (s, 1H), 8.36 (m, 1H), 8.21 (d, 1H), 8.13 (d, 1H), 7.54 (s, 1H), 7.46 (m, 1H), 7.27 (d, 1H), 6.81 (m, 1H), 3.79 (m, 2H), 3.68 (m, 2H), 3.53 (d, 2H), 3.48 (s, 2H), 3.01 (t, 2H), 2.38 (m, 1H), 1.66 (d, 2H), 1.15 (m, 2H).

¹H NMR (400 MHz, DMSO-d₆) of Example 309: δ 11.65 (br, 1H), 8.63 (s, 1H), 8.21 (d, 2H), 8.13 (d, 1H), 7.46 (m, 1H), 7.35 (m, 1H), 7.27 (d, 1H), 7.11 (m, 1H), 7.03 (m, 2H), 6.81 (m, 1H), 3.82 (m, 2H), 3.68 (d, 2H), 3.53 (d, 2H), 3.48 (s, 2H), 2.94 (t, 2H), 2.38 (m, 1H), 1.65 (d, 2H), 1.12 (m, 2H).

¹H NMR (400 MHz, DMSO-d₆) of Example 310: δ 11.65 (br, 1H), 8.63 (s, 1H), 8.21 (s, 1H), 8.12 (m, 2H), 7.46 (m, 1H), 7.38 (m, 2H), 7.27 (d, 1H), 7.21 (t, 1H), 7.04 (t, 1H), 6.81 (m, 1H), 3.83 (m, 2H), 3.68 (d, 2H), 3.53 (d, 2H), 3.48 (m, 2H), 2.99 (t, 2H), 2.38 (m, 1H), 1.64 (m, 2H), 1.14 (m, 2H).

¹H NMR (400 MHz, DMSO-d₆) of Example 312: δ 11.65 (br, 1H), 8.65 (br, 1H), 8.62 (s, 1H), 8.21 (s, 1H), 8.12 (m, 1H), 7.67 (m, 2H), 7.51 (d, 1H), 7.46 (m, 1H), 7.27 (d, 1H), 6.81 (m, 1H), 3.83 (m, 2H), 3.68 (d, 2H), 3.53 (d, 2H), 3.48 (m, 2H), 2.98 (t, 2H), 2.39 (m, 1H), 1.64 (m, 2H), 1.14 (m, 2H).

¹H NMR (400 MHz, DMSO-d₆) of Example 313: δ 11.65 (br, 1H), 8.63 (s, 1H), 8.36 (br, 1H), 8.21 (s, 1H), 8.12 (m, 1H), 7.95 (s, 1H), 7.75 (d, 1H), 7.64 (m, 1H), 7.46 (m, 1H), 7.27 (d, 1H), 6.81 (m, 1H), 3.83 (m, 2H), 3.68 (m, 2H), 3.53 (d, 2H), 3.48 (m, 2H), 3.00 (t, 2H), 2.39 (m, 1H), 1.66 (m, 2H), 1.15 (m, 2H).

Example 314

(3-[4-(5-Fluoro-1H-pyrrolo[2,3-b]pyridin-4-yl)-1H-pyrazol-1-yl]-1-{1-[3-fluoro-2-(trifluoromethyl)isonicotinoyl]piperidin-4-yl}azetidin-3-yl)acetonitrile

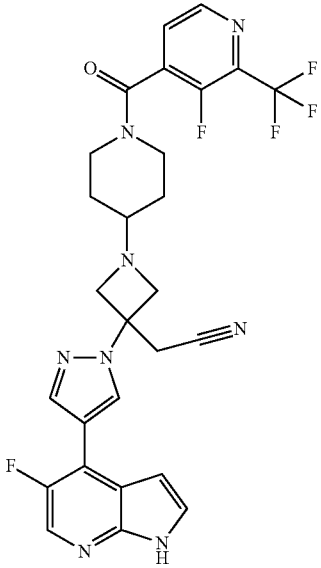 [SMILES: N#CCC1(n2cc(-c3c(F)cnc4[nH]ccc34)cn2)CN(C2CCN(C(=O)c3ccnc(C(F)(F)F)c3F)CC2)C1]

Step A: 5-fluoro-4-iodo-1-{[2-(trimethylsilyl)ethoxy]methyl}-1H-pyrrolo[2,3-b]pyridine

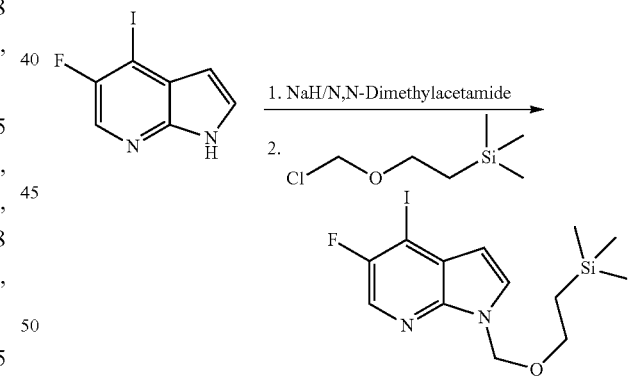

To a solution of 5-fluoro-4-iodo-1H-pyrrolo[2,3-b]pyridine (5.0 g, 0.019 mol) in DMF (30.0 mL) cooled at 0° C. under nitrogen was portionwise added sodium hydride (1.13 g, 0.0282 mol). The reaction was stirred for 1 hour. To the mixture was slowly added [β-(trimethylsilyl)ethoxy]methyl chloride (4.05 mL, 0.0229 mol). The reaction was stirred at 0° C. for 1 hour and quenched with water. The resulting solution was extracted with EtOAc (2 times). The combined extracts were washed with water, brine, dried over sodium sulfate and concentrated under reduced pressure. The residue was purified by silica gel chromatography, eluting with 0-25% EtOAc/hexanes to afford 7.1 g (95%) of 5-fluoro-4-iodo-1-{[2-(trimethylsilyl)ethoxy]methyl}-1H-pyrrolo[2,3-b]pyridine as a yellowish oil. LC/MS found: 393.0 (M+H)⁺.

219

Step B: 4-(1H-Pyrazol-4-yl)-5-fluoro-1-{[2-(trimethylsilyl)ethoxy]methyl}-1H-pyrrolo[2, 3-b]pyridine

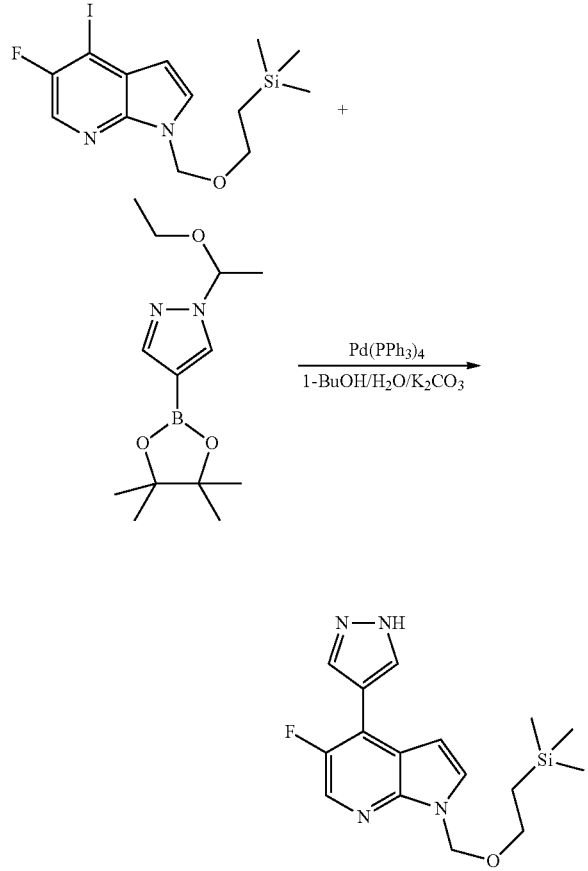

A mixture of 5-fluoro-4-iodo-1-{[2-(trimethylsilyl)ethoxy]methyl}-1H-pyrrolo[2,3-b]pyridine (7.20 g, 18.4 mmol), 1-(1-ethoxyethyl)-4-(4,4,5,5-tetramethyl-1,3,2-dioxaborolan-2-yl)-1H-pyrazole (5.36 g, 20.1 mmol), tetrakis(triphenylphosphine)palladium(0) (1.06 g, 0.918 mmol) and sodium carbonate (5.84 g, 55.1 mmol) in 1,4-dioxane (50 mL) and water (25 mL) was stirred at 110° C. under nitrogen for 1 hour. After being cooled to room temperature, the mixture was diluted with EtOAc, washed with water and brine, dried over Na$_2$SO$_4$ and concentrated under reduced pressure. The residue was purified by flash chromatography on silica gel eluting with 10-30% EtOAc/hexanes. The purified intermediate was added into a mixture solution of THF (8.0 mL), water (30 mL) and hydrogen chloride (30 mL, 100 mmol). The resulting suspension was stirred at room temperature for 2 hours. The mixture was adjusted to pH=9-10 with 6 N NaOH and extracted with EtOAc (2×). The combined extracts were washed with water, brine and dried over anhydrous Na$_2$SO$_4$. After filtration and concentration, the residue was added into a mixture solvents of hexane and EtOAc (9/1, 50 mL). The solid formed was filtered to give 4.2 g (69%) of 4-(1H-pyrazol-4-yl)-5fluoro-1-{[2-(trimethylsilyl)ethoxy]methyl}-1H-pyrrolo[2,3-b]pyridine as a light green solid. LC/MS found: 333.2 (M+H)$^+$.

220

Step C: {3-[4-(5-Fluoro-1-{[2-(trimethylsilyl)ethoxy]methyl}-1H-pyrrolo[2,3-b]pyridin-4-yl)-1H-pyrazol-1-yl]azetidin-3-yl}acetonitrile.2[HCl]

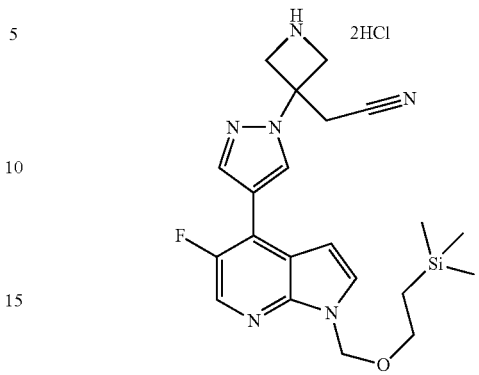

To a solution of 5-fluoro-4-(1H-pyrazol-4-yl)-1-{[2-(trimethylsilyl)ethoxy]methyl}-1H-pyrrolo[2,3-b]pyridine (2.00 g, 6.02 mmol) and tert-butyl 3-(cyanomethylene)azetidine-1-carboxylate (1.168 g, 6.02 mmol) in acetonitrile (20 mL) was added 1,8-diazabicyclo[5.4.0]undec-7-ene (0.8996 mL, 6.02 mmol). The mixture was stirred at room temperature overnight and concentrated. The residue was purified by silica gel chromatography (0-80% EtOAc/hexanes) to give 3.05 g (96.3%) of tert-butyl 3-(cyanomethyl)-3-[4-(5-fluoro-1-{[2-(trimethylsilyl)ethoxy]methyl}-1H-pyrrolo[2,3-b]pyridin-4-yl)-1H-pyrazol-1-yl]azetidine-1-carboxylate as a colorless oil. LC/MS found: 527.3 (M+H)$^+$.

To a solution of tert-butyl 3-(cyanomethyl)-3-[4-(5-fluoro-1-{[2-(trimethylsilyl)ethoxy]methyl}-1H-pyrrolo[2,3-b]pyridin-4-yl)-1H-pyrazol-1-yl]azetidine-1-carboxylate (3.05 g, 5.79 mmol) in THF (40 mL) was added a 4.0 M solution of hydrogen chloride in 1,4-dioxane (70 mL, 280 mmol). The mixture was stirred at room temperature for 2 hours and concentrated to give 3.08 g (99.2%) of {3-[4-(5-fluoro-1-{[2-(trimethylsilyl)ethoxy]methyl}-1H-pyrrolo[2,3-b]pyridin-4-yl)-1H-pyrazol-1-yl]azetidin-3-yl}acetonitrile.2[HCl] as a yellowish solid. LC/MS found: 427.2 (M+H)$^+$.

Step D: {3-[4-(5-Fluoro-1-{[2-(trimethylsilyl)ethoxy]methyl}-1H-pyrrolo[2, 3-b]pyridin-4-yl)-1H-pyrazol-1-yl]-1-piperidin-4-ylazetidin-3-yl}acetonitrile.3[HCl]

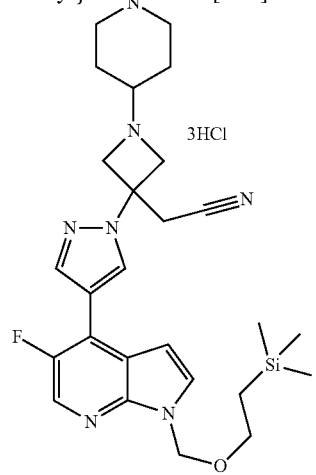

To a mixture of {3-[4-(5-fluoro-1-{[2-(trimethylsilyl)ethoxy]methyl}-1H-pyrrolo[2,3-b]pyridin-4-yl)-1H-pyrazol-1-yl]azetidin-3-yl}acetonitrile.2[HCl] (3.10 g, 5.78 mmol), tert-butyl 4-oxo-1-piperidinecarboxylate (1.152 g, 5.784 mmol) and N,N-diisopropylethylamine (3.022 mL, 17.35 mmol) in THF (100.0 mL) was added sodium triacetoxyborohydride (2.452 g, 11.57 mmol). The mixture was stirred at room temperature for 2 hours and quenched with brine. The resulting solution was extracted with EtOAc (2 times). The combined extracts were washed with water, brine and dried over $Na_2SO_4$. After filtration and evaporation, the residue was purified by flash chromatography on silica gel eluting with 50-100% EtOAc/hexanes. The purified intermediate ([M+H]$^+$=610.3) was dissolved in THF (50 mL). To the solution at 10° C. was added a 4.0 M solution of hydrogen chloride in 1,4-dioxane (50.0 mL, 200 mmol). The mixture was stirred at room temperature for 2 hours and concentrated to give 3.57 g of {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-yl}acetonitrile.3 [HCl] as an off-white solid. LC/MS found: 510.3 (M+H)$^+$. $^1$H NMR (400 MHz, DMSO-d$_6$), δ 9.41 (s, 1H), 8.81 (s, 1H), 8.72 (s, 1H), 8.35 (d, 1H), 8.32 (s, 1H), 7.85 (d, 1H), 7.00 (d, 1H), 5.63 (s, 2H), 4.93 (d, 2H), 4.55 (d, 2H), 3.78-3.60 (m, 1H), 3.55 (s, 2H), 3.51 (t, 2H), 3.47-3.37 (m, 2H), 2.79 (m, 2H), 2.11 (m, 2H), 1.80 (m, 2H), 0.81 (t, 2H), −0.12 (s, 9H).

Step E: (3-[4-(5-Fluoro-H-pyrrolo[2, 3-b]pyridin-4-yl)-1H-pyrazol-1-yl]-1-{1-[3-fluoro-2-(trifluoromethyl)isonicotinoyl]piperidin-4-yl}azetidin-3-yl)acetonitrile A solution of 3-fluoro-2-(trifluoromethyl)isonicotinic acid (70.0 mg, 0.335 mmol), {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-yl}acetonitrile.3 [HCl] (207 mg, 0.335 mmol), benzotriazol-1-yloxytris(dimethylamino)phosphonium hexafluorophosphate (148 mg, 0.335 mmol) and triethylamine (0.234 mL, 1.68 mmol) in methylene chloride (2 mL) was stirred at room temperature for 1 hour. To the mixture was added trifluoroacetic acid (2 mL, 20 mmol). The resulting solution was stirred at room temperature for 1 hour and concentrated. The residue was dissolved in methanol (2 mL) and ethylenediamine (0.5 mL, 7 mmol). After being stirred at room temperature for 2 hours, the mixture was purified by HPLC (method B) to give 11.2 mg of the title compound as a white solid. LC/MS found: 571.3 (M+H)$^+$. $^1$H NMR (400 MHz, CDCl$_3$): δ 11.85 (brs, 1H), 8.65 (d, J=4.4 Hz, 1H), 8.59 (s, 1H), 8.23 (d, J=3.2 Hz, 1H), 8.20 (s, 1H), 7.89 (s, 1H), 7.61 (s, 1H), 6.85 (s, 1H), 4.04 (m, 1H), 3.72 (m, 2H), 3.58 (m, 2H), 3.53 (m, 2H), 3.53 (m, 2H), 3.40 (m, 1H), 3.25 (m, 1H), 3.06 (t, J=9.2 Hz, 1H), 2.54 (m, 1H), 1.75 (m, 1H), 1.62 (m, 1H), 1.26 (m, 1H), 1.21 (m, 1H).

The following compounds were prepared following the procedures described for Example 314.

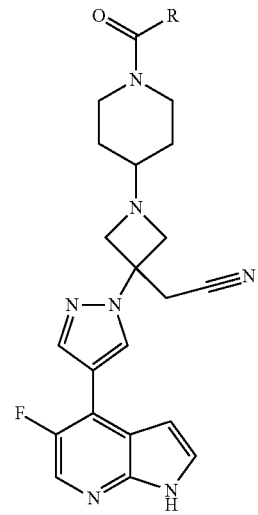

| Example # | R | Compound | LC-MS (M + H)$^+$ |
|---|---|---|---|
| 315 | 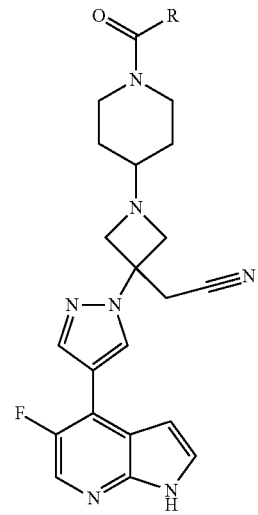CN, CN (3,5-dicyanophenyl) | 5-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]isophthalonitrile | 534.3 |

-continued

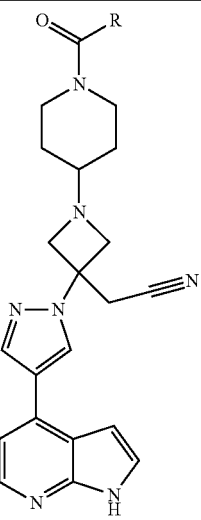

| Example # | R | Compound | LC-MS (M + H)+ |
|---|---|---|---|
| 316 | 3-fluoro-5-cyanophenyl | 3-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-5-fluorobenzonitrile | 527.2 |
| 317 | 4-cyano-2-fluorophenyl | 4-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-3-fluorobenzonitrile | 527.2 |
| 318 | 3-cyano-4-fluorophenyl | 5-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-2-fluorobenzonitrile | 527.2 |
| 319 | 5-fluoropyridin-2-yl | {1-{1-[(5-fluoropyridin-2-yl)carbonyl]piperidin-4-yl}-3-[4-(5-fluoro-1H-pyrrolo[2,3-b]pyridin-4-yl)-1H-pyrazol-1-yl]azetidin-3-yl}acetonitrile | 503.2 |
| 320 | 3-fluoropyridin-4-yl | {1-[1-(3-fluoroisonicotinoyl)piperidin-4-yl]-3-[4-(5-fluoro-1H-pyrrolo[2,3-b]pyridin-4-yl)-1H-pyrazol-1-yl]azetidin-3-yl}acetonitrile | 503.2 |
| 321 | 3,5-difluoropyridin-4-yl | {1-[1-(3,5-difluoroisonicotinoyl)piperidin-4-yl]-3-[4-(5-fluoro-1H-pyrrolo[2,3-b]pyridin-4-yl)-1H-pyrazol-1-yl]azetidin-3-yl}acetonitrile | 521.2 |

-continued

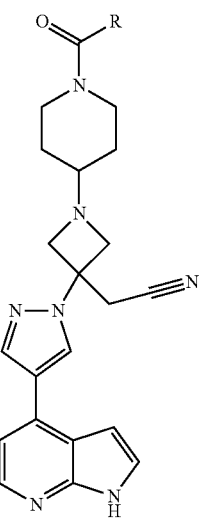

| Example # | R | Compound | LC-MS (M + H)+ |
|---|---|---|---|
| 322 | 2-fluoro-4-hydroxyphenyl | {1-[1-(3-fluoro-4-hydroxybenzoyl)piperidin-4-yl]-3-[4-(5-fluoro-1H-pyrrolo[2,3-b]pyridin-4-yl)-1H-pyrazol-1-yl]azetidin-3-yl}acetonitrile | 518.2 |
| 323 | 3-fluoro-4-hydroxyphenyl | {1-[1-(2-fluoro-4-hydroxybenzoyl)piperidin-4-yl]-3-[4-(5-fluoro-1H-pyrrolo[2,3-b]pyridin-4-yl)-1H-pyrazol-1-yl]azetidin-3-yl}acetonitrile | 518.2 |
| 324 | 2,5-dicyanophenyl | 2-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]terephthalonitrile | 534.3 |
| 325 | 2-fluoro-4-cyanophenyl | 4-[(4-{3-(cyanomethyl)-3-[4-(5-fluoro-1H-pyrrolo[2,3-b]pyridin-4-yl)-1H-pyrazol-1-yl]azetidin-1-yl}piperidin-1-yl)carbonyl]-2-fluorobenzonitrile | 527.2 |
| 326 | 5-chloro-2-(trifluoromethyl)pyridin-4-yl | {1-{1-[5-chloro-2-(trifluoromethyl)isonicotinoyl]piperidin-4-yl}-3-[4-(5-fluoro-1H-pyrrolo[2,3-b]pyridin-4-yl)-1H-pyrazol-1-yl]azetidin-3-yl}acetonitrile | 587.2 |

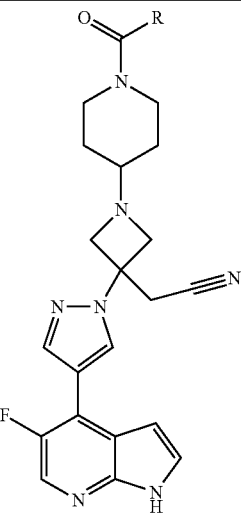

| Example # | R | Compound | LC-MS (M + H)+ |
|---|---|---|---|
| 327 | 4,4-difluorocyclohexyl-methyl | {1-{1-[(4,4-difluorocyclohexyl)carbonyl]piperidin-4-yl}-3-[4-(5-fluoro-1H-pyrrolo[2,3-b]pyridine-4-yl)-1H-pyrazol-1-yl]azetidin-3-yl}acetonitrile | 526.3 |

$^1$H NMR (300 MHz, DMSO-d$_6$) of Example 316: δ 11.81 (brs, 1H), 8.55 (s, 1H), 8.18 (d, J=3.00 Hz, 1H), 8.15 (s, 1H), 7.88 (d, J=8.1 Hz, 1H), 7.70 (s, 1H), 7.61 (d, J=7.80 Hz, 1H), 7.56 (d, J=3.30 Hz, 1H), 6.81 (d, J=3.30 Hz, 1H), 3.97 (m, 1H), 3.68 (m, 2H), 3.52 (m, 2H), 3.47 (s, 2H), 3.27 (m, 1H), 3.11 (m, 1H), 2.99 (m, 1H), 2.43 (m, 1H), 1.68 (m, 1H), 1.56 (m, 1H), 1.20 (m, 2H).

$^1$H NMR (300 MHz, DMSO-d$_6$) of Example 317: δ 11.81 (brs, 1H), 8.54 (s, 1H), 8.18 (d, J=3.30 Hz, 1H), 8.15 (d, J=2.1 Hz, 1H), 7.93 (dd, J$_1$=9.30 Hz, J$_2$=1.20 Hz, 1H), 7.72 (dd, J$_1$=7.80 Hz, J$_2$=1.20 Hz, 1H), 7.56 (m, 2H), 6.80 (d, J=3.30 Hz, 1H), 4.02 (m, 1H), 3.67 (m, 2H), 3.53 (m, 2H), 3.48 (s, 2H), 3.16 (m, 2H), 2.96 (m, 1H), 2.48 (m, 1H), 1.70 (m, 1H), 1.55 (m, 1H), 1.15 (m, 2H).

$^1$H NMR (300 MHz, DMSO-d$_6$) of Example 318: δ 11.81 (brs, 1H), 8.54 (s, 1H), 8.18 (d, J=3.30 Hz, 1H), 8.15 (d, J=2.1 Hz, 1H), 7.95 (dd, J$_1$=6.30 Hz, J$_2$=2.10 Hz, 1H), 7.74 (m, 1H), 7.54 (m, 2H), 6.81 (m, 1H), 4.00 (m, 1H), 3.68 (m, 2H), 3.52 (m, 2H), 3.47 (s, 2H), 3.01 (m, 3H), 2.45 (m, 1H), 1.64 (m, 2H), 1.20 (m, 2H).

$^1$H NMR (300 MHz, DMSO-d$_6$) of Example 319: δ 11.81 (brs, 1H), 8.54 (s, 1H), 8.52 (d, J=2.70 Hz, 1H), 8.18 (d, J=3.60 Hz, 1H) 8.15 (d, J=1.80 Hz, 1H), 7.78 (m, 1H), 7.58 (m, 2H), 6.81 (d, J=3.60 Hz, 1H), 4.04 (m, 1H), 3.67 (m, 2H), 3.52 (m, 2H), 3.50 (s, 2H), 3.08 (m, 3H), 2.46 (m, 1H), 1.70 (m, 1H), 1.58 (m, 1H), 1.16 (m, 2H).

$^1$H NMR (400 MHz, DMSO-d$_6$) of Example 321: δ 11.86 (brs, 1H), 8.65 (s, 2H), 8.59 (s, 1H), 8.23 (d, J=3.20 Hz, 1H), 8.20 (d, J=2.0 Hz, 1H), 7.61 (d, J=3.20 Hz, 1H), 6.86 (d, J=3.60 Hz, 1H), 4.07 (m, 1H), 3.72 (m, 2H), 3.58 (m, 2H), 3.54 (s, 2H), 3.42 (m, 1H), 3.28 (m, 1H), 3.10 (m, 1H), 2.54 (m, 1H), 1.76 (m, 1H), 1.64 (m, 1H), 1.20 (m, 2H).

$^1$H NMR (400 MHz, DMSO-d$_6$) of Example 322: δ 11.86 (brs, 1H), 8.59 (s, 1H), 8.23 (d, J=3.60 Hz, 1H), 8.20 (d, J=2.00 Hz, 1H), 7.61 (d, J=3.20 Hz, 1H), 7.14 (dd, J$_1$=11.60 Hz, J$_2$=1.60 Hz, 1H), 7.00 (d, J=8.00 Hz, 1H), 6.92 (t, J=8.00 Hz, 1H), 6.86 (d, J=3.60 Hz, 1H), 3.80 (m, 1H), 3.72 (m, 2H), 3.56 (m, 2H), 3.52 (s, 2H), 3.08 (m, 3H), 2.51 (m 1H), 1.67 (m, 2H), 1.19 (m, 2H).

$^1$H NMR (300 MHz, DMSO-d$_6$) of Example 323: δ 11.82 (brs, 1H), 8.54 (s, 1H), 8.18 (d, J=3.60 Hz, 1H), 8.15 (d, J=1.80 Hz, 1H), 7.56 (d, J=3.90 Hz, 1H), 7.09 (t, J=8.40 Hz, 1H), 6.81 (d, J=3.60 Hz, 1H), 6.54 (m, 2H), 4.00 (m, 1H), 3.66 (m, 2H), 3.51 (m, 2H), 3.48 (s, 2H), 3.35 (2H), 3.01 (m, 1H), 2.47 (m, 1H), 1.61 (m, 2H), 1.11 (m, 2H).

$^1$H NMR (300 MHz, DMSO-d$_6$) of Example 325: δ 11.81 (brs, 1H), 8.54 (s, 1H), 8.18 (d, J=3.30 Hz, 1H), 8.15 (d, J=2.1 Hz, 1H), 7.94 (t, J=6.90 Hz, 1H), 7.56 (m, 2H), 7.34 (dd, J$_1$=8.10 Hz, J$_2$=1.20 Hz, 1H), 6.81 (m, 1H), 3.99 (m, 1H), 3.68 (m, 2H), 3.52 (m, 2H), 3.47 (s, 2H), 3.05 (m, 3H), 2.47 (m, 1H), 1.68 (m, 1H), 1.16 (m, 1H), 1.18 (m, 2H).

$^1$H NMR (300 MHz, DMSO-d$_6$) of Example 326: δ 11.82 (brs, 1H), 8.88 (s, 1H), 8.54 (s, 1H), 8.18 (d, J=3.60 Hz, 1H), 8.15 (d, J=2.10 Hz, 1H), 8.06 (d, J=13.20 Hz, 1H), 7.56 (s, 1H), 6.81 (d, J=3.30 Hz, 1H), 4.02 (m, 1H), 3.68 (m, 2H), 3.50 (m, 4H), 3.19 (m, 2H), 2.94 (m, 1H), 2.48 (m, 1H), 1.67 (m, 2H), 1.20 (m, 2H).

$^1$H NMR (300 MHz, DMSO-d$_6$) of Example 327: δ 11.81 (brs, 1H), 8.54 (s, 1H), 8.18 (d, J=3.30 Hz, 1H), 8.15 (d, J=1.80 Hz, 1H), 7.56 (d, J=3.30 Hz, 1H), 6.81 (d, J=3.60 Hz, 1H), 3.93 (m, 1H), 3.75 (m, 1H), 3.66 (m, 2H), 3.52 (m, 2H), 3.48 (s, 2H), 3.09 (m, 1H), 2.83 (m, 1H), 2.72 (m, 1H), 2.42 (m, 1H), 1.90 (m, 4H), 1.61 (m, 6H), 1.06 (m, 2H).

Example 328

4-{3-(Cyanomethyl)-3-[4-(5-fluoro-1H-pyrrolo[2,3-b]pyridin-4-yl)-1H-pyrazol-1-yl]azetidin-1-yl}-N-[4-fluoro-2-(trifluoromethyl)phenyl]piperidine-1-carboxamide

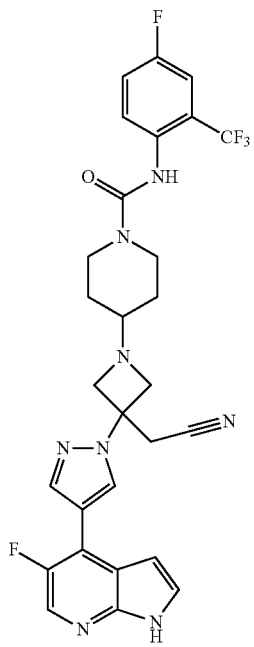 [SMILES: N#CCC1(n2cc(-c3c(F)cnc4[nH]ccc34)cn2)CN(C2CCN(C(=O)Nc3ccc(F)cc3C(F)(F)F)CC2)C1]

To a mixture of {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-1}acetonitrile.3 [HCl] (70.0 mg, 0.113 mmol) and triethylamine (41.3 uL, 0.296 mmol) in THF (4 mL) was added 4-fluoro-1-isocyanato-2-(trifluoromethyl)benzene (23.1 mg, 0.113 mmol). The mixture was stirred at room temperature for 1 hour and concentrated. The residue was diluted with acetonitrile (2 mL) and water (2 mL). The mixture was submitted to purification by HPLC to give 34 mg (49%) of the desired intermediate. LC-MS found: 715.3 (M+H)$^+$.

The purified intermediate was dissolved in methylene chloride (1 mL) and trifluoroacetic acid (1 mL, 10 mmol). The solution was stirred at room temperature for 1 hour and concentrated. The residue was treated with methanol (1 mL) and ethylenediamine (0.2 mL, 3 mmol). The solution was stirred at room temperature for 1 hour and purified by HPLC (method B) to give the title compound. LC-MS found: 585.1 (M+H)$^+$. $^1$H NMR (300 MHz, DMSO-d$_6$): δ 11.86 (brs, 1H), 8.60 (s, 1H), 8.24 (d, J=3.30 Hz, 1H), 8.21 (d, J=2.40 Hz, 1H), 7.61 (t, J=3.30 Hz, 1H), 7.49 (m, 3H), 6.86 (m, 1H), 3.83 (m, 2H), 3.72 (m, 2H), 3.58 (m, 2H), 3.54 (s, 2H), 2.97 (m, 2H), 2.44 (m, 1H), 1.66 (m, 2H), 1.13 (m, 2H).

The following compounds were prepared following the procedures described for Example 328.

| Example # | R | Compound | LC-MS (M + H)$^+$ |
|---|---|---|---|
| 329 | pyridin-2-yl with CF$_3$ at 3-position | 4-{3-(cyanomethyl)-3-[4-(5-fluoro-1H-pyrrolo[2,3-b]pyridin-4-yl)-1H-pyrazol-1-yl]azetidin-1-yl}-N-[3-(trifluoromethyl)pyridin-2-yl]piperidine-1-carboxamide | 568.2 |
| 330 | pyridin-3-yl with CF$_3$ at 4-position | 4-{3-(cyanomethyl)-3-[4-(5-fluoro-1H-pyrrolo[2,3-b]pyridin-4-yl)-1H-pyrazol-1-yl]azetidin-1-yl}-N-[4-(trifluoromethyl)pyridin-3-yl]piperidine-1-carboxamide | 568.2 |
| 331 | pyridin-4-yl with CF$_3$ at 3-position | 4-{3-(cyanomethyl)-3-[4-(5-fluoro-1H-pyrrolo[2,3-b]pyridin-4-yl)-1H-pyrazol-1-yl]azetidin-1-yl}-N-[3-(trifluoromethyl)pyridin-4-yl]piperidine-1-carboxamide | 568.2 |

$^1$H NMR (300 MHz, DMSO-d$_6$) of Example 330: δ 11.82 (brs, 1H), 8.60 (s, 2H), 8.49 (s, 1H), 8.23 (d, J=3.30 Hz, 1H), 8.20 (d, J=2.10 Hz, 1H), 7.68 (d, J=5.1 Hz, 1H), 7.61 (t, J=3.30 Hz, 1H), 6.86 (m, 1H), 3.84 (m, 2H), 3.72 (m, 2H), 3.58 (m, 2H), 3.54 (s, 2H), 3.01 (m, 2H), 2.49 (m, 1H), 1.68 (m, 2H), 1.15 (m, 2H).

$^1$H NMR (300 MHz, DMSO-d$_6$) of Example 331: δ 11.82 (brs, 1H), 8.64 (s, 1H), 8.55 (s, 1H), 8.51 (d, J=5.70 Hz, 1H), 8.19 (d, J=3.60 Hz, 1H), 8.16 (d, J=2.10 Hz, 1H), 7.56 (t, J=3.0 Hz, 1H), 7.53 (d, J=5.70 Hz, 1H), 6.81 (dt, J$_1$=3.30 Hz, J$_2$=1.00 Hz, 1H), 3.77 (m, 2H), 3.68 (m, 2H), 3.53 (m, 2H), 3.49 (s, 2H), 3.00 (m, 2H), 2.42 (m, 1H), 1.64 (m, 2H), 1.13 (m, 2H).

Example 332

4-[1-(3-(Cyanomethyl)-1-{1-[3-fluoro-2-(trifluoromethyl)isonicotinoyl]piperidin-4-yl}azetidin-3-yl)-1H-pyrazol-4-yl]-1H-pyrrolo[2,3-b]pyridine-5-carbonitrile

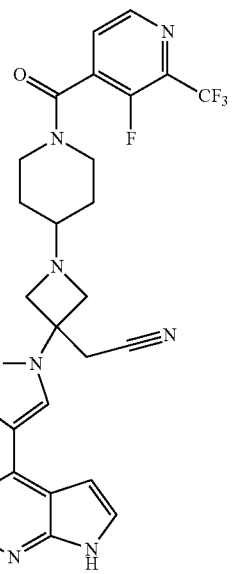

Step A: 4-Chloro-5-cyano-1-{[2-(trimethylsilyl)ethoxy]methyl}-1H-pyrrolo[2,3-b]pyridine

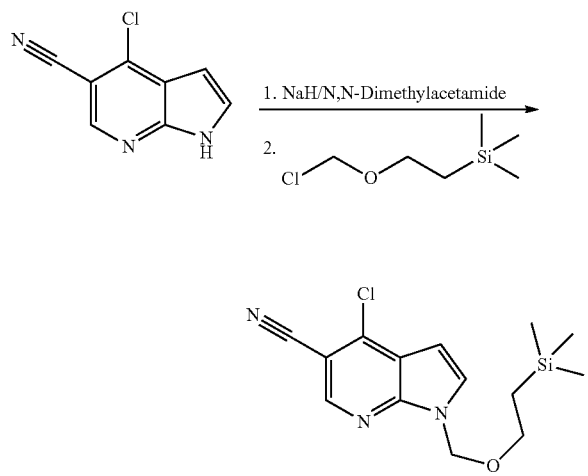

To a suspension of sodium hydride (1.8 g, 45.1 mmol) in N,N-dimethylacetamide (10 mL) at −5° C. (ice/salt bath) was added a dark solution of 4-chloro-5-cyano-pyrrolo[2,3-d]pyridine (6.0 g, 39 mmol) in N,N-dimethylacetamide (10 mL) slowly. The flask and addition funnel were rinsed with N,N-dimethylacetamide (5 mL). A large amount of gas was evolved immediately. The mixture turned to a slightly cloudy orange mixture and was stirred at 0° C. for 1 hour to give a light brown turbid mixture. To the mixture was slowly added [β-(trimethylsilyl)ethoxy]methyl chloride (7.6 g, 45 mmol). The reaction was stirred at 0° C. for 1 hour and quenched by addition of 12 mL of H$_2$O. After the reaction was quenched, H$_2$O (120 mL) was added. It was followed by MTBE (120 mL). The mixture was stirred for 10 minutes. The organic layer was separated. The aqueous layer was extracted with another portion of MTBE (120 mL). The organic extracts were combined, washed with brine, dried over sodium sulfate and concentrated under reduced pressure to give 10 g (95%) of the crude product 4-chloro-5-cyano-1-{[2-(trimethylsilyl)ethoxy]methyl}-1H-pyrrolo[2,3-b]pyridine as a dark oil. LC-MS: 308.1 (M+H)$^+$. The crude product was carried over to the next reaction without further purification.

Step B: 4-(1H-Pyrazol-4-yl)-5-cyano-1-{[2-(trimethylsilyl)ethoxy]methyl}-1H-pyrrolo[2, 3-b]pyridine

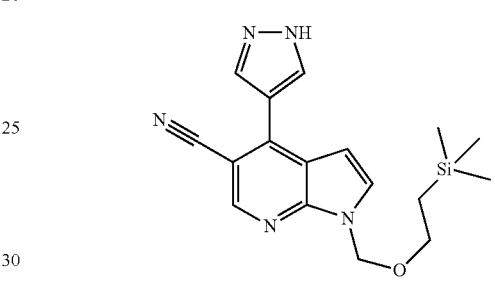

A 250 mL round bottom flask was charged with 4-chloro-5-cyano-1-{[2-(trimethylsilyl)ethoxy]methyl}-1H-pyrrolo[2,3-d]pyridine (5.00 g, 17.6 mmol), 1-butanol (25.0 mL), 1-(1-ethoxyethyl)-4-(4,4,5,5-tetramethyl-1,3,2-dioxaborolan-2-yl)-1H-pyrazole (7.06 g, 26.4 mmol), water (25.0 mL) and potassium carbonate (6.17 g, 44.08 mmol). This solution was degased 4 times with filling with nitrogen each time. To it was added tetrakis(triphenylphosphine)palladium(0) (2.071 g, 1.773 mmol). The solution was degassed 4 times, filling with nitrogen each time, and stirred at 100° C. for 3 hours. After being cooled to room temperature, the mixture was filtered through a bed of celite and the celite was rinsed with ethyl acetate (42 mL). The filtrate was combined and the organic layer was separated. The aqueous layer was extracted with ethyl acetate. The combined extracts were dried over anhydrous Na$_2$SO$_4$, filtered, evaporated under reduced pressure to give an oil residue which was purified by combiflash column to generate 3.8 g (53%) of the desired intermediate. LC-MS: 412.2 (M+H)$^+$.

A mixture of 3.8 g of the above intermediate in 20 mL of 2 N HCl aqueous solution and 20 mL of CHCl$_3$ was stirred ar room temperature over weekend. The organic layer was separated and the aqueous phase was extracted with EtOAc (3×50 mL). The combined extracts were dried over anhydrous Na$_2$SO$_4$, filtered, evaporated under reduced pressure to give 2.9 g (97%) of 4-(1H-pyrazol-4-yl)-5-cyano-1-{[2-(trimethylsilyl)ethoxy]methyl}-1H-pyrrolo[2,3-b]pyridine. LC-MS: 340.2 (M+H)$^+$.

Step C: 4-{1-[3-(Cyanomethyl)azetidin-3-yl]-1H-pyrazol-4-yl}-1-{[2-(trimethylsilyl)ethoxy]methyl}-1H-pyrrolo[2, 3-b]pyridine-5-carbonitrile.2[HCl]

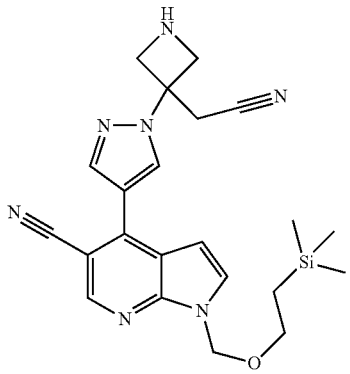 [SMILES: C[Si](C)(C)CCOCn1ccc2c(-c3cnn(C4(CC#N)CNC4)c3)c(C#N)cnc21]

To a solution of 4-(1H-pyrazol-4-yl)-1-{[2-(trimethylsilyl)ethoxy]methyl}-1H-pyrrolo[2,3-b]pyridine-5-carbonitrile (2.26 g, 6.66 mmol) and tert-butyl 3-(cyanomethylene)azetidine-1-carboxylate (1.293 g, 6.66 mmol) in acetonitrile (40 mL) was added 1,8-diazabicyclo[5.4.0]undec-7-ene (0.996 mL, 6.66 mmol). The mixture was stirred at room temperature overnight and concentrated. Purification by silica gel chromatography (0-80% EtOAc/hexanes) gave 2.20 g (62%) of the intermediate tert-butyl 3-(cyanomethyl)-3-[4-(5-cyano-1-{[2-(trimethylsilyl)ethoxy]methyl}-1H-pyrrolo[2,3-b]pyridin-4-yl)-1H-pyrazol-1-yl]azetidine-1-carboxylate as a colorless oil. LC-MS found: 534.3 (M+H)⁺.

To a solution of the above oil intermediate (2.20 g, 4.12 mmol) in THF (40 mL) was added a 4.0 M solution of hydrogen chloride in 1,4-dioxane (70 mL, 280 mmol). The mixture was stirred at room temperature for 2 hours and concentrated to give 2.23 g (99.6%) of the desired product as a yellowish solid. LC-MS found: 434.2 (M+H)⁺.

Step D: 4-{1-[3-(Cyanomethyl)-1-piperidin-4-ylazetidin-3-yl]-1H-pyrazol-4-yl}-1-{[2-(trimethylsilyl)ethoxy]methyl}-1H-pyrrolo[2, 3-b]pyridine-5-carbonitrile.3[HCl]

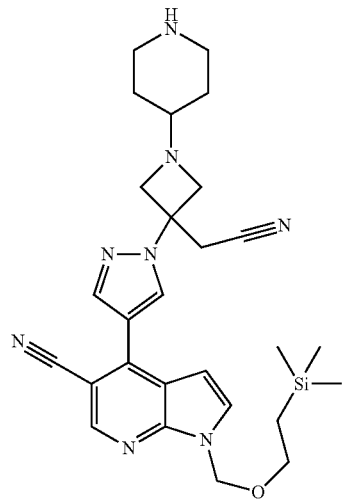 [SMILES: C[Si](C)(C)CCOCn1ccc2c(-c3cnn(C4(CC#N)CN(C5CCNCC5)C4)c3)c(C#N)cnc21]

To a mixture of 4-{1-[3-(cyanomethyl)azetidin-3-yl]-1H-pyrazol-4-yl}-1-{[2-(trimethylsilyl)ethoxy]methyl}-1H-pyrrolo[2,3-b]pyridine-5-carbonitrile.2[HCl] (2.0 g, 3.68 mmol), tert-butyl 4-oxo-1-piperidinecarboxylate (0.734 g, 3.68 mmol) and N,N-diisopropylethylamine (3.21 mL, 18.4 mmol) in THF (70.0 mL) was added sodium triacetoxyborohydride (1.56 g, 7.37 mmol). The mixture was stirred at room temperature for 2 hours and quenched with brine. The resulting solution was extracted with EtOAc (2 times). The combined extracts were washed with water, brine and dried over Na₂SO₄. After filtration and evaporation, the residue was purified by flash chromatography on silica gel eluting with 50-100% EtOAc/Hexanes. The purified intermediate was dissolved in THF (30 mL). To the solution at 10° C. was added a 4.0 M solution of hydrogen chloride in 1,4-dioxane (30.0 mL, 1.20 mmol). The mixture was stirred at room temperature for 2 hours and concentrated to give 2.01 g (87.2%) of the desired product as an off-white solid. LC/MS found: 517.3 (M+H)⁺. ¹H NMR (400 MHz, DMSO-d₆): δ 9.29 (s, 1H), 8.88 (s, 1H), 8.74 (s, 1H), 8.37 (s, 1H), 7.97 (d, 1H), 6.97 (s, 1H), 5.69 (s, 2H), 5.94 (m, 2H), 4.55 (m, 2H), 3.73-3.56 (m, 2H), 3.63 (t, 2H), 3.52 (m, 2H), 3.47-3.35 (m, 3H), 2.81 (m, 2H), 2.10 (m, 2H), 1.75 (m, 2H), 0.82 (t, 2H), −0.11 (s, 9H).

Step E: 4-[1-(3-(Cyanomethyl)-1-{1-[3-fluoro-2-(trifluoromethyl)isonicotinoyl]piperidin-4-yl}azetidin-3-yl)-1H-pyrazol-4-yl]-1-1H-pyrrolo[2, 3-b]pyridine-5-carbonitrile A mixture of 3-fluoro-2-(trifluoromethyl)isonicotinic acid (70.0 mg, 0.335 mmol), 4-{1-[3-(cyanomethyl)-1-piperidin-4-ylazetidin-3-yl]-1H-pyrazol-4-yl}-1-{[2-(trimethylsilyl)ethoxy]methyl}-1H-pyrrolo[2,3-b]pyridine-5-carbonitrile.3[HCl] (210 mg, 0.335 mmol), benzotriazol-1-yloxytris(dimethylamino)phosphonium hexafluorophosphate (149 mg, 0.335 mmol) and triethylamine (0.234 mL, 1.68 mmol) in DMF (2.0 mL) was stirred at room temperature for 2 hours. The mixture was diluted with water, then extracted with EtOAc (2 times). The combined extracts were washed with saturated NaHCO₃, water, brine, dried over Na₂SO₄. After filtration and evaporation, the residue was purified by flash chromatography on silica gel eluting with 0-10% MeOH/EtOAc to give 143 mg of the intermediate. LC-MS found: 708.1 (M+H)⁺.

The purified above intermediate (143 mg) was dissolved in methylene chloride (10 mL) and trifluoroacetic acid (10 mL, 100 mmol). The resulting solution was stirred at room temperature for 1 hour and concentrated. The residue was treated with methanol (10 mL) and ethylenediamine (5 mL, 70 mmol). The solution was stirred at room temperature for 1 hour. Purification with flash chromatography on silica gel eluting with 5-15% MeOH/EtOAc gave 63 mg (55%) of the title compound as an off-white solid. LC/MS found: 578.2 (M+1)⁺. ¹H NMR (400 MHz, CDCl₃): δ 12.34 (brs, 1H), 8.66 (s, 1H), 8.60 (d, J=4.80 Hz, 1H), 8.56 (s, 1H), 8.19 (s, 1H), 7.84 (t, J=4.80 Hz, 1H), 7.68 (d, J=3.60 Hz, 1H), 6.79 (d, J=3.60 Hz, 1H), 4.01 (m, 1H), 3.68 (m, 2H), 3.54 (m, 2H), 3.49 (m, 2H), 3.36 (m, 1H), 3.22 (m, 1H), 3.03 (m, 1H), 2.50 (m, 1H), 1.69 (m, 1H), 1.57 (m, 1H), 1.16 (m, 2H).

The following compounds were prepared following the procedures described for Example 332.

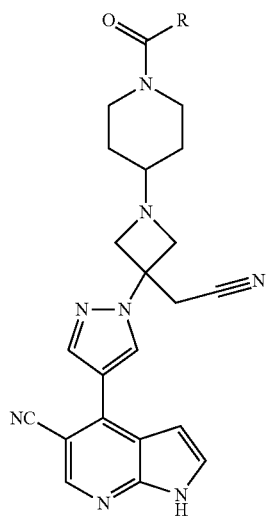

| Example # | R | Compound | LC-MS (M + H)+ |
|---|---|---|---|
| 333 | 3-CN-5-F-phenyl | 4-{1-[1-[1-(3-cyano-5-fluorobenzoyl)piperidin-4-yl]-3-(cyanomethyl)azetidin-3-yl]-1H-pyrazol-4-yl}-1H-pyrrolo[2,3-b]pyridine-5-carbonitrile | 534.2 |
| 334 | 4-CN-3-F-phenyl | 4-{1-[1-[1-(4-cyano-3-fluorobenzoyl)piperidin-4-yl]-3-(cyanomethyl)azetidin-3-yl]-1H-pyrazol-4-yl}-1H-pyrrolo[2,3-b]pyridine-5-carbonitrile | 534.2 |
| 335 | 2,5-dibromophenyl | 4-(1-{3-(cyanomethyl)-1-[1-(2,5-dibromobenzoyl)piperidin-4-yl]azetidin-3-yl}-1H-pyrazol-4-yl)-1H-pyrrolo[2,3-b]pyridine-5-carbonitrile | 649.1 |
| 336 | 3,5-dibromophenyl | 4-(1-{3-(cyanomethyl)-1-[1-(3,5-dibromobenzoyl)piperidin-4-yl]azetidin-3-yl}-1H-pyrazol-4-yl)-1H-pyrrolo[2,3-b]pyridine-5-carbonitrile | 649.1 |
| 337 | 2,5-dicyanophenyl | 2-[(4-{3-(cyanomethyl)-3-[4-(5-cyano-1H-pyrrolo[2,3-b]pyridin-4-yl)-1H-pyrazol-1-yl]azetidin-1-yl}piperidin-1-yl)carbonyl]terephthalonitrile | 541.2 |

-continued

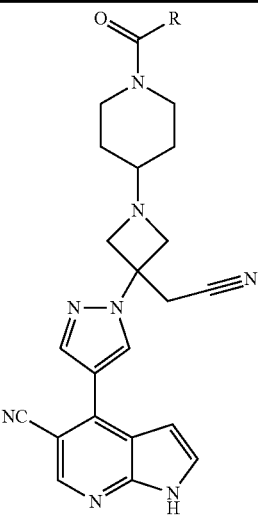

| Example # | R | Compound | LC-MS (M + H)+ |
|---|---|---|---|
| 338 | 3,5-dicyanophenyl (CN, CN) | 5-[(4-{3-(cyanomethyl)-3-[4-(5-cyano-1H-pyrrolo[2,3-b]pyridin-4-yl)-1H-pyrazol-1-yl]azetidin-1-yl}piperidin-1-yl)carbonyl]isophthalonitrile | 541.2 |
| 339 | 4-cyano-2-fluorophenyl | 4-{1-[1-[1-(4-cyano-2-fluorobenzoyl)piperidin-4-yl]-3-(cyanomethyl)azetidin-3-yl]-1H-pyrazol-4-yl}-1H-pyrrolo[2,3-b]pyridine-5-carbonitrile | 534.2 |
| 340 | 4-cyano-2,6-difluorophenyl | 4-{1-[1-[1-(4-cyano-2,6-difluorobenzoyl)piperidin-4-yl]-3-(cyanomethyl)azetidin-3-yl]-1H-pyrazol-4-yl}-1H-pyrrolo[2,3-b]pyridine-5-carbonitrile | 552.1 |
| 341 | 5-chloro-2-(trifluoromethyl)pyridin-4-yl | 4-{1-[1-{1-[5-chloro-2-(trifluoromethyl)isonicotinoyl]piperidin-4-yl}-3-(cyanomethyl)azetidin-3-yl]-1H-pyrazol-4-yl}-1H-pyrrolo[2,3-b]pyridine-5-carbonitrile | 594.2 |

$^1$H NMR (300 MHz, DMSO-$d_6$) of Example 339: δ 12.28 (brs, 1H), 8.66 (s, 1H), 8.55 (s, 1H), 8.19 (s, 1H), 7.92 (dd, $J_1$=9.30 Hz, $J_2$=1.20 Hz, 1H), 7.72 (dd, $J_1$=7.80 Hz, $J_2$=1.20 Hz, 1H), 7.67 (d, J=3.90 Hz, 1H), 7.56 (t, J=7.20 Hz, 1H), 6.78 (d, J=3.60 Hz, 1H), 4.00 (m, 1H), 3.67 (m, 2H), 3.54 (m, 2H), 3.49 (s, 2H), 3.21 (m, 2H), 2.96 (m, 1H), 2.49 (m, 1H), 1.63 (m, 2H), 1.18 (m, 2H).

$^1$H NMR (300 MHz, DMSO-$d_6$) of Example 340: δ 8.66 (s, 1H), 8.55 (s, 1H), 8.19 (s, 1H), 7.89 (d, J=7.80 Hz, 1H), 7.67 (d, J=3.90 Hz, 1H), 6.78 (d, J=3.60 Hz, 1H), 4.01 (m, 1H), 3.71 (m, 2H), 3.57 (m, 2H), 3.50 (s, 2H), 3.38 (m, 2H), 3.03 (m, 1H), 2.46 (m, 1H), 1.68 (m, 1H), 1.55 (m, 1H), 1.14 (m, 2H).

$^1$H NMR (300 MHz, DMSO-$d_6$) of example 341: δ 12.26 (brs, 1H), 8.87 (s, 1H), 8.66 (s, 1H), 8.56 (s, 1H), 8.19 (s, 1H), 8.06 (d, J=10.5 Hz, 1H), 7.67 (d, J=3.90 Hz, 1H), 6.79 (d, J=3.60 Hz, 1H), 4.02 (m, 1H), 3.68 (m, 2H), 3.55 (m, 2H), 3.47 (s, 2H), 3.23 (m, 2H), 2.95 (m, 1H), 2.49 (m, 1H), 1.60 (m, 2H), 1.21 (m, 2H).

Example 342

{1-{1-[5-Chloro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile

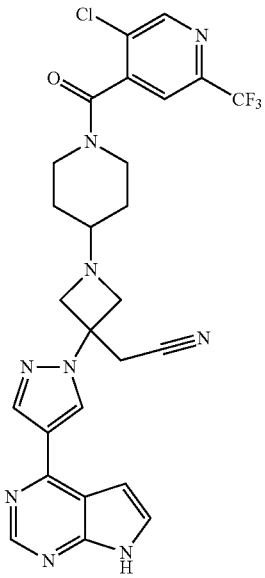 [SMILES: N#CCC1(n2cc(-c3ncnc4[nH]ccc34)cn2)CN(C2CCN(C(=O)c3cc(C(F)(F)F)ncc3F)CC2)C1]

Reaction of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride with 5-chloro-2-trifluoromethylisonicotinoic acid following the procedure described for Example 1, followed by HPLC purification (method B) provided the title compound. LC-MS: 570.2 (M+H)+. 1H NMR (300 MHz, DMSO-d6): δ 12.08 (brs, 1H), 8.92 (1H), 8.80 (s, 1H), 8.67 (s, 1H), 8.40 (s, 1H), 8.11 (d, J=14.09 Hz, 1H), 7.59 (d, J=3.30 Hz, 1H), 7.04 (d, J=3.30 Hz, 1H), 4.07 (m, 1H), 3.73 (m, 2H), 3.56 (m, 2H), 3.52 (s, 2H), 3.26 (m, 2H), 2.98 (m, 1H), 2.53 (m, 1H), 1.69 (m, 2H), 1.25 (m, 2H).

Example 343

{1-{1-[5-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile

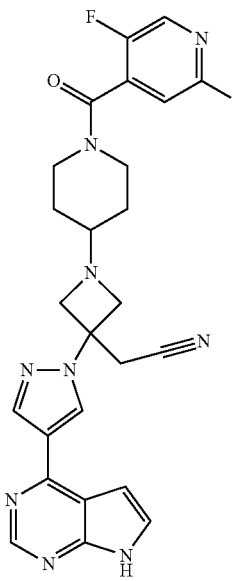

Reaction of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride with 5-fluoro-2-trifluoromethylisonicotinoic acid following the procedure described for Example 1, followed by HPLC purification (method B) provided the title compound. LC-MS: 554.2 (M+H). 1H NMR (400 MHz, DMSO-d6): δ 12.08 (brs, 1H), 8.84 (s, 1H), 8.76 (s, 1H), 8.63 (s, 1H), 8.36 (s, 1H), 8.09 (d, J=4.80 Hz, 1H), 7.55 (d, J=3.60 Hz, 1H), 7.00 (d, J=3.60 Hz, 1H), 4.02 (m, 1H), 3.69 (m, 2H), 3.52 (m, 2H), 3.49 (s, 2H), 3.34 (m, 1H), 3.20 (m, 1H), 3.00 (m, 1H), 2.49 (m, 1H), 1.70 (m, 1H), 1.57 (m, 1H), 1.22 (m, 2H).

Example 344

[3-[4-(7H-Pyrrolo[2,3-d]pyrimidin-4-yl)-1H-pyrazol-1-yl]-1-(1-{[4-(trifluoromethyl)-1,3-thiazol-2-yl]carbonyl}piperidin-4-yl)azetidin-3-yl]acetonitrile

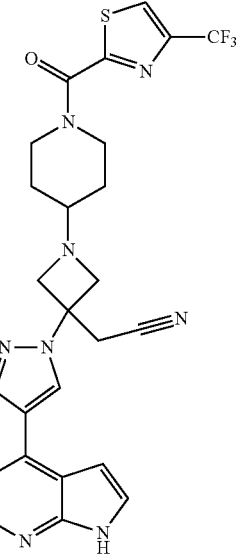

Reaction of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile trihydrochloride with 4-trifluoromethylthiazol-2-ylcarboxylic acid following the procedure described for Example 1, followed by HPLC purification (method B) provided the title compound. LC-MS: 542.2 (M+H)+.

Example 345

[3-[3-(7H-Pyrrolo[2,3-d]pyrimidin-4-yl)-1H-pyrrol-1-yl]-1-(1-{[2-(trifluoromethyl)pyrimidin-4-yl]carbonyl}piperidin-4-yl)azetidin-3-yl]acetonitrile

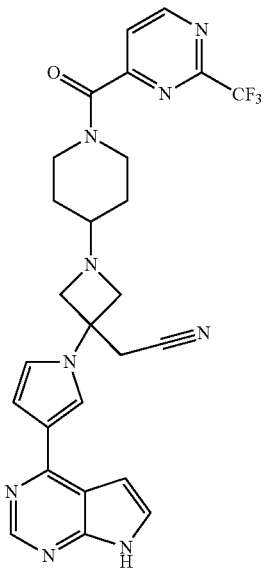 [SMILES: N#CCC1(n2ccc(-c3ncnc4[nH]ccc34)c2)CN(C2CCN(C(=O)c3ccnc(C(F)(F)F)n3)CC2)C1]

Reaction of {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride with 2-trifluoromethylpyrimidin-4-carboxylic acid following the procedure described for Example 261, followed by purification with HPLC (method B) provided the title compound. LC-MS: 536.2 (M+H)$^+$. $^1$H NMR (300 MHz, DMSO-d$_6$): δ 11.93 (brs, 1H), 9.18 (d, 1H), 8.59 (s, 1H), 7.95 (d, 1H), 7.79 (s, 1H), 7.48 (d, 1H), 7.05 (d, 1H), 6.91 (d, 2H), 4.00 (m, 1H), 3.55 (d, 2H), 3.40 (d, 2H), 3.35 (m, 1H), 3.30 (s 2H), 3.23 (m, 2H), 3.11 (m, 1H), 2.58 (m, 1H), 1.80-1.52 (m, 2H), 1.22 (m, 2H).

Example 346

[3-[3-(7H-Pyrrolo[2,3-d]pyrimidin-4-yl)-1H-pyrrol-1-yl]-1-(1-{[4-(trifluoromethyl)-1,3-thiazol-2-yl]carbonyl}piperidin-4-yl)azetidin-3-yl]acetonitrile

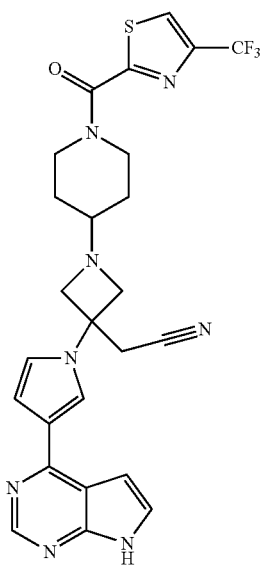 [SMILES: N#CCC1(n2ccc(-c3ncnc4[nH]ccc34)c2)CN(C2CCN(C(=O)c3nc(C(F)(F)F)cs3)CC2)C1]

Reaction of {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride with 4-trifluoromethylthiazol-2-ylcarboxylic acid following the procedure described for Example 261, followed by purification with HPLC (method B) provided the title compound. LC-MS: 541.2 (M+H)$^+$. $^1$H NMR (300 MHz, DMSO-d$_6$): δ 11.92 (brs, 1H), 8.75 (s, 1H), 8.57 (s, 1H), 7.78 (s, 1H), 7.43 (d, 2H), 7.02 (s, 1H), 6.90 (s, 1H), 4.45 (m, 1H), 3.95 (m, 1H), 3.70 (m, 1H), 3.55 (d, 2H), 3.45 (d, 2H), 3.37 (s, 2H), 3.20 (m, 2H), 1.80-1.60 (m, 2H), 1.25 (m, 2H).

Example 347

[3-[3-(7H-Pyrrolo[2,3-d]pyrimidin-4-yl)-1H-pyrrol-1-yl]-1-(1-{[5-(trifluoromethyl)pyrazin-2-yl]carbonyl}piperidin-4-yl)azetidin-3-yl]acetonitrile

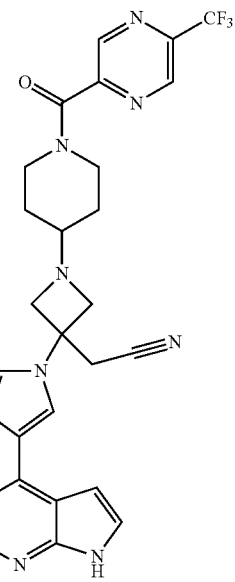

Reaction of {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride with 5-trifluoromethylpyrazin-2-ylcarboxylic acid following the procedure described for Example 261, followed by purification with HPLC (method B) provided the title compound. LC-MS: 536.1 (M+H)$^+$. $^1$H NMR (300 MHz, DMSO-d$_6$): δ 11.99 (brs, 1H), 9.23 (s, 1H), 9.07 (s, 1H), 8.62 (s, 1H), 7.84 (s, 1H), 7.55 (d, 1H), 7.11 (s, 1H), 6.98 (d, 2H), 4.12 (m 1H), 3.65 (d, 2H), 3.55 (d, 2H), 3.41 (m, 1H), 3.31 (s, 2H), 3.15 (m, 2H), 2.60 (m, 1H), 1.90-1.60 (m, 2H), 1.30 (m, 2H).

Example 348

{1-[1-(Methylsulfonyl)piperidin-4-yl]-3-[3-(7H-pyrrolo[2,3-d]pyrimidin-4-yl)-1H-pyrrol-1-yl]azetidin-3-yl}acetonitrile

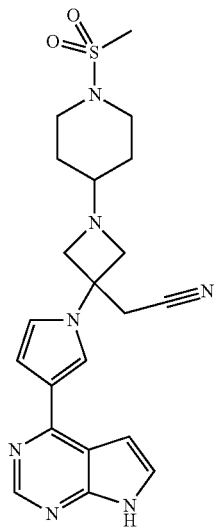 [SMILES: CS(=O)(=O)N1CCC(N2CC(CC#N)(n3ccc(-c4ncnc5[nH]ccc45)c3)C2)CC1]

Reaction of {1-piperidin-4-yl-3-[3-(7-{[2-(trimethylsilyl)ethoxy]methyl}-7H-pyrrolo[2,3-d]pyrimidin-4-yl)-1H-pyrrol-1-yl]azetidin-3-yl}acetonitrile trihydrochloride with methanesulfonyl chloride following the procedure described for Example 246, followed by purification with HPLC (method B) provided the title compound. LC-MS: 440.1 (M+H)$^+$. $^1$H NMR (300 MHz, DMSO-d$_6$): δ 11.91 (brs, 1H), 8.55 (s, 1H), 7.76 (s, 1H), 7.43 (d, 1H), 7.01 (d, 1H), 6.88 (d, 2H), 3.52 (d, 2H), 3.47 (d, 2H), 3.30 (m, 2H), 3.27 (s, 2H), 2.80 (m, 2H), 2.75 (s, 3H), 2.27 (m, 1H), 1.65 (m, 2H), 1.23 (m, 2H).

Example 349

[3-[4-(1H-Pyrrolo[2,3-b]pyridin-4-yl)-1H-pyrazol-1-yl]-1-(1-{[5-(trifluoromethyl)pyrazin-2-yl]carbonyl}piperidin-4-yl)azetidin-3-yl]acetonitrile

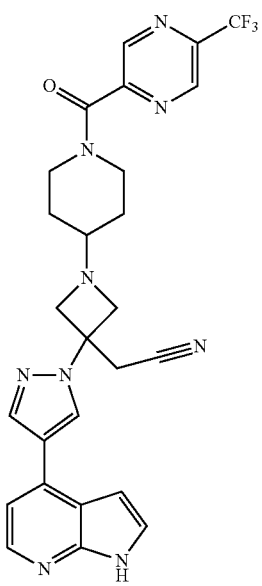 [SMILES: N#CCC1(n2cc(-c3ccnc4[nH]ccc34)cn2)CN(C2CCN(C(=O)c3cnc(C(F)(F)F)cn3)CC2)C1]

Reaction of {1-piperidin-4-yl-3-[4-(7-{[2-(trimethylsilyl)ethoxy]methyl}-7H-pyrrolo[2,3-d]pyridin-4-yl)-1H-pyrazol-1-yl]azetidin-3-yl}acetonitrile trihydrochloride with 5-trifluoromethylpyrazin-2-carboxylic acid following the procedure described for Example 294, followed by HPLC purification (method B) provided the title compound. LC-MS: 536.2 (M+H)$^+$. $^1$H NMR (300 MHz, DMSO-d$_6$): δ 12.07 (brs, 1H), 8.82 (s, 1H), 8.76 (s, 1H), 8.68 (s, 2H), 8.41 (s, 2H), 7.61 (d, 1H), 7.06 (d, 1H), 4.55 (m, 1H), 4.05 (m, 1H), 3.75 (dd, 2H), 3.59 (dd, 2H), 3.55 (m, 2H), 3.32 (s, 2H), 3.30 (m, 1H), 1.80 (m, 2H), 1.30 (m, 2H).

Example 350

[3-[4-(1H-Pyrrolo[2,3-b]pyridin-4-yl)-1H-pyrazol-1-yl]-1-(1-{[4-(trifluoromethyl)-1,3-thiazol-2-yl]carbonyl})piperidin-4-yl)azetidin-3-yl]acetonitrile

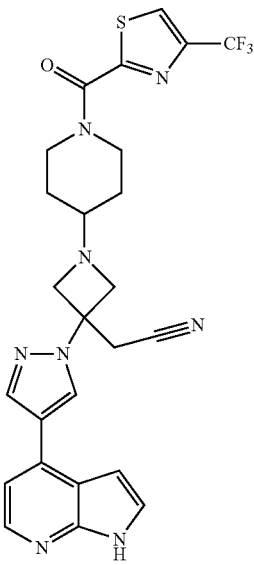 [SMILES: N#CCC1(n2cc(-c3ccnc4[nH]ccc34)cn2)CN(C2CCN(C(=O)c3nc(C(F)(F)F)cs3)CC2)C1]

Reaction of {1-piperidin-4-yl-3-[4-(7-{[2-(trimethylsilyl)ethoxy]methyl}-7H-pyrrolo[2,3-d]pyridin-4-yl)-1H-pyrazol-1-yl]azetidin-3-yl}acetonitrile trihydrochloride with 4-trifluoromethylthiazol-2-carboxylic acid following the procedure described for Example 294, followed by HPLC purification (method B) provided the title compound. LC-MS: 541.2 (M+H)$^+$. $^1$H NMR (300 MHz, DMSO-d$_6$): δ 12.01 (brs, 1H), 9.09 (s, 1H), 8.99 (s, 1H), 8.59 (s, 1H), 8.48 (d, 1H), 7.82 (dd, 1H), 7.62 (d, 1H), 7.16 (d, 1H), 4.85 (m, 1H), 4.35 (m, 1H), 4.05 (d, 2H), 4.03 (m, 1H), 3.90 (d, 1H), 3.80 (m, 1H), 3.62 (s, 2H), 3.58 (m, 1H), 2.90 (m, 1H), 2.08 (m, 2H), 1.62 (m, 2H).

Example 351

{1-[1-(Methylsulfonyl)piperidin-4-yl]-3-[4-(1H-pyrrolo[2,3-b]pyridin-4-yl)-1H-pyrazol-1-yl]azetidin-3-yl}acetonitrile

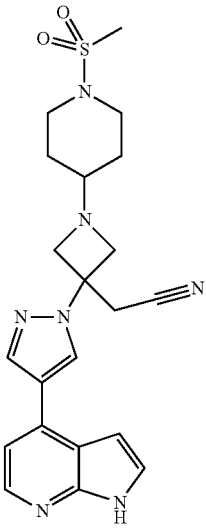 [SMILES: CS(=O)(=O)N1CCC(N2CC(CC#N)(n3cc(-c4ccnc5[nH]ccc45)cn3)C2)CC1]

Reaction of {1-piperidin-4-yl-3-[4-(7-{[2-(trimethylsilyl)ethoxy]methyl}-7H-pyrrolo[2,3-d]pyridin-4-yl)-1H-pyrazol-1-yl]azetidin-3-yl}acetonitrile trihydrochloride with methanesulfonyl chloride following the procedure described for Example 246, followed by HPLC purification (method B) provided the title compound. LC-MS: 440.1 (M+H)⁺. ¹H NMR (300 MHz, DMSO-d₆): δ 11.91 (brs, 1H), 8.55 (s, 1H), 7.76 (s, 1H), 7.43 (d, 1H), 7.01 (d, 1H), 6.88 (d, 2H), 3.52 (d, 2H), 3.47 (d, 2H), 3.30 (m, 2H), 3.27 (s, 2H), 2.80 (m, 2H), 2.75 (s, 3H), 2.27 (m, 1H), 1.65 (m, 2H), 1.23 (m, 2H).

Example 352

[3-[4-(5-Fluoro-1H-pyrrolo[2,3-b]pyridin-4-yl)-1H-pyrazol-1-yl]-1-(1-{[6-(trifluoromethyl)pyrazin-2-yl]carbonyl}piperidin-4-yl)azetidin-3-yl]acetonitrile

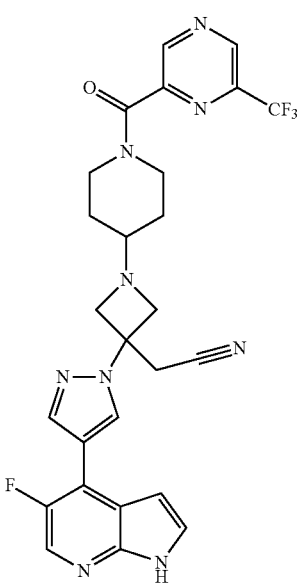 [SMILES: N#CCC1(n2cc(-c3c(F)cnc4[nH]ccc34)cn2)CN(C2CCN(C(=O)c3cncc(C(F)(F)F)n3)CC2)C1]

Reaction of {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-yl}acetonitrile.3 [HCl] with 6-trifluoromethylpyrazin-2-carboxylic acid following the procedure described for Example 314, followed by HPLC purification (method B) provided the title compound. LC-MS: 554.1 (M+H)⁺. ¹H NMR (300 MHz, DMSO-d₆): δ 12.11 (brs, 1H), 9.23 (s, 1H), 9.12 (s, 1H), 8.56 (s, 1H), 8.19 (d, 1H), 8.15 (d, 1H), 7.58 (d, 1H), 6.82 (d, 1H), 4.03 (m, 1H), 3.68 (d, 2H), 3.55 (d, 2H), 3.45 (m, 1H), 3.26 (s 2H), 3.24 (m, 1H), 3.11 (m, 1H), 2.55 (m, 1H), 1.80-1.57 (m, 2H), 1.25 (m, 2H).

Example 353

[3-[4-(5-Fluoro-1H-pyrrolo[2,3-b]pyridin-4-yl)-1H-pyrazol-1-yl]-1-(1-{[2-(trifluoromethyl)pyrimidin-4-yl]carbonyl}piperidin-4-yl)azetidin-3-yl]acetonitrile

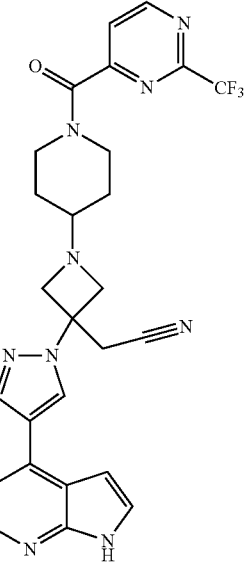

Reaction of {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-yl}acetonitrile.3 [HCl] with 2-trifluoromethylpyrimidin-4-carboxylic acid following the procedure described for Example 314, followed by HPLC purification (method B) provided the title compound. LC-MS: 554.1 (M+H)⁺. ¹H NMR (300 MHz, DMSO-d₆): δ 11.83 (brs, 1H), 9.15 (d, 1H), 8.56 (s, 1H), 8.21 (d, 1H), 8.18 (d, 1H), 7.94 (d, 1H), 7.58 (d, 1H), 6.82 (d, 1H), 4.00 (m, 1H), 3.70 (d, 2H), 3.55 (d, 2H), 3.45 (m, 1H), 3.40 (s, 2H), 3.15 (m, 1H), 3.08 (m, 1H), 2.52 (m, 1H), 1.80-1.52 (m, 2H), 1.23 (m, 2H).

Example 354

[3-[4-(5-Fluoro-1H-pyrrolo[2,3-b]pyridin-4-yl)-1H-pyrazol-1-yl]-1-(1-{[5-(trifluoromethyl)pyrazin-2-yl]carbonyl}piperidin-4-yl)azetidin-3-yl]acetonitrile

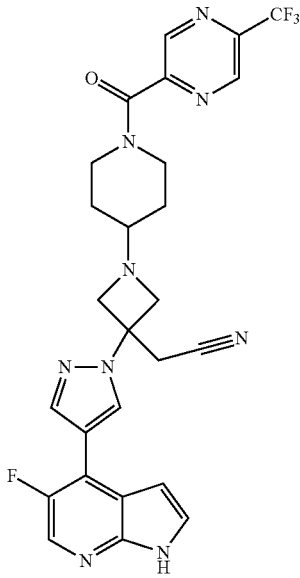 [SMILES: N#CCC1(n2cc(-c3c(F)cnc4[nH]ccc34)cn2)CN(C2CCN(C(=O)c3cnc(C(F)(F)F)cn3)CC2)C1]

Reaction of {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-yl}acetonitrile.3 [HCl] with 5-trifluoromethylpyrazin-2-carboxylic acid following the procedure described for Example 314, followed by HPLC purification (method B) provided the title compound. LC-MS: 554.1 (M+H)$^+$. $^1$H NMR (300 MHz, DMSO-d$_6$): δ 11.82 (brs, 1H), 9.16 (s, 1H), 8.99 (s, 1H), 8.59 (s, 1H), 8.20 (d, 2H), 7.59 (s, 1H), 6.82 (s, 1H), 4.05 (m, 1H), 3.70 (d, 2H), 3.55 (d, 2H), 3.45 (m, 1H), 3.35 (s, 2H), 3.15 (m, 2H), 2.59 (m, 1H), 1.80-1.55 (m, 2H), 1.22 (m, 2H).

Example 355

{3-[4-(5-Fluoro-1H-pyrrolo[2,3-b]pyridin-4-yl)-1H-pyrazol-1-yl]-1-[1-(methylsulfonyl)piperidin-4-yl]azetidin-3-yl}acetonitrile

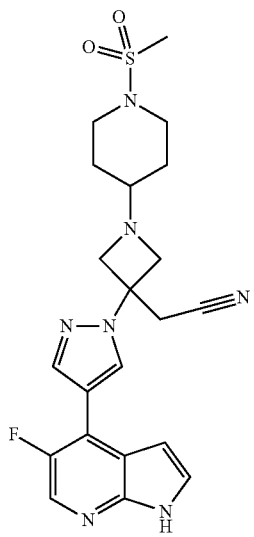 [SMILES: CS(=O)(=O)N1CCC(N2CC(CC#N)(n3cc(-c4c(F)cnc5[nH]ccc45)cn3)C2)CC1]

Reaction of {3-[4-(5-fluoro-1-{[2-(trimethylsilyl)ethoxy]methyl}-1H-pyrrolo[2,3-b]pyridin-4-yl)-1H-pyrazol-1-yl]-1-piperidin-4-ylazetidin-3-yl}acetonitrile.3 [HCl] with methanesulfonyl chloride following the procedure described for Example 246, followed by HPLC purification (method B) provided the title compound. LC-MS: 458.1 (M+H)$^+$. $^1$H NMR (300 MHz, DMSO-d$_6$): δ 11.87 (brs, 1H), 8.59 (s, 1H), 8.23 (d, J=3.60 Hz, 1H), 8.20 (d, J=2.10 Hz, 1H), 7.61 (d, J=3.60 Hz, 1H), 6.86 (d, J=3.30 Hz, 1H), 3.71 (m, 2H), 3.57 (m, 2H), 3.54 (s, 2H), 3.36 (m, 2H), 2.86 (m, 2H), 2.83 (s, 3H), 2.37 (m, 1H), 1.73 (m, 2H), 1.30 (m, 2H).

Example 356

4-[1-(3-(Cyanomethyl)-1-{1-[5-fluoro-2-(trifluoromethyl)isonicotinoyl]piperidin-4-yl}azetidin-3-yl)-1H-pyrazol-4-yl]-1H-pyrrolo[2,3-b]pyridine-5-carbonitrile

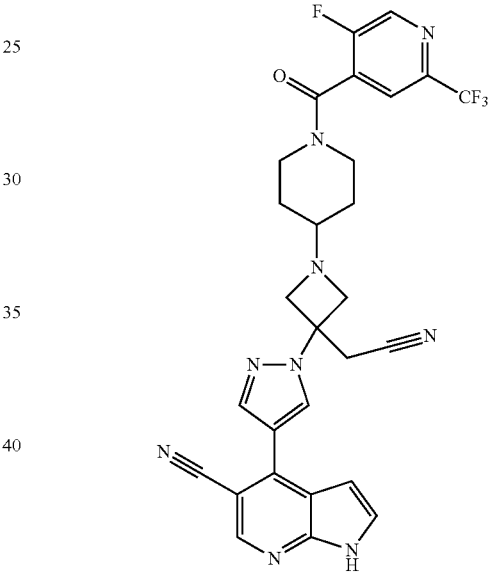

Reaction of 4-{1-[3-(cyanomethyl)-1-piperidin-4-ylazetidin-3-yl]-1H-pyrazol-4-yl}-1-{[2-(trimethylsilyl)ethoxy]methyl}-1H-pyrrolo[2,3-b]pyridine-5-carbonitrile.3 [HCl] with 5-fluoro-2-trifluoromethylisonicotinoic acid following the procedure described for Example 332, followed by HPLC purification (method B) provided the title compound. LC-MS: 578.2 (M+H)$^+$. $^1$H NMR (300 MHz, DMSO-d$_6$): δ 8.84 (s, 1H), 8.67 (s, 1H), 8.55 (s, 1H), 8.19 (s, 1H), 8.09 (d, J=4.80 Hz, 1H), 7.68 (d, J=3.60 Hz, 1H), 6.79 (d, J=3.60 Hz, 1H), 3.99 (m, 1H), 3.69 (m, 2H), 3.54 (m, 2H), 3.49 (s, 2H), 3.42 (m, 2H), 3.00 (m, 1H), 2.51 (m, 1H), 1.69 (m, 1H), 1.57 (m, 1H), 1.20 (m, 2H).

Example 357

4-(1-{3-(Cyanomethyl)-1-[1-(methylsulfonyl)piperidin-4-yl]azetidin-3-yl}-1H-pyrazol-4-yl)-1H-pyrrolo[2,3-b]pyridine-5-carbonitrile

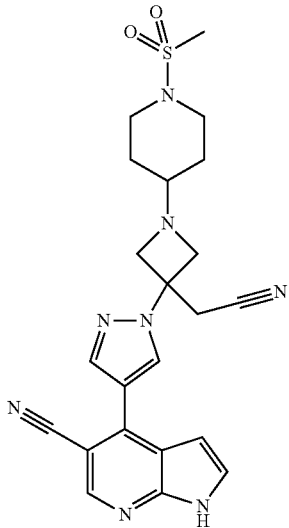 [SMILES: CS(=O)(=O)N1CCC(N2CC(CC#N)(n3cc(-c4c(C#N)cnc5[nH]ccc45)cn3)C2)CC1]

Reaction of 4-{1-[3-(cyanomethyl)-1-piperidin-4-ylazetidin-3-yl]-1H-pyrazol-4-yl}-1-{[2-(trimethylsilyl)ethoxy]methyl}-1H-pyrrolo[2,3-b]pyridine-5-carbonitrile.3 [HCl] with methanesulfonyl chloride following the procedure described for Example 246, followed by HPLC purification (method B) provided the title compound. LC-MS: 465.1 (M+H)$^+$. $^1$H NMR (300 MHz, DMSO-d$_6$): δ 12.28 (brs, 1H), 8.66 (s, 1H), 8.55 (s, 1H), 8.20 (s, 1H), 7.68 (d, J=3.60 Hz, 1H), 6.79 (d, J=3.90 Hz, 1H), 3.67 (m, 2H), 3.53 (m, 2H), 3.50 (s, 2H), 3.31 (m, 2H), 2.81 (m, 2H), 2.78 (s, 3H), 2.35 (m, 1H), 1.68 (m, 2H), 1.26 (m, 2H).

Example 358

{1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt

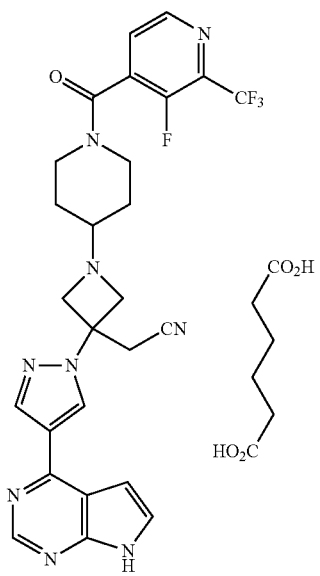 [SMILES: N#CCC1(n2cc(-c3ncnc4[nH]ccc34)cn2)CN(C2CCN(C(=O)c3ccnc(C(F)(F)F)c3F)CC2)C1 ; O=C(O)CCCCC(=O)O]

Screening: 1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (Example 1) free base is an amorphous substance. A salt screening study was performed using pharmaceutically acceptable acids for the formation of crystalline Example 1 salts. Adipic acid was identified to give a crystalline Example 1 adipic acid salt. The initially obtained solid form (Form I) of Example 1 adipic acid salt with a melting point of 178° C. has been selected for optimization. This form is a crystalline form as verified by X-ray powder diffractometry (XRPD), differential scanning calorimetry (DSC), and thermal gravimetric analysis (TGA). The stoichiometry of the salt was determined to be 1:1 (freebase to adipic acid) by $^1$H NMR spectroscopy and elemental analysis.

A polymorph screening study was performed on Example 1 adipate salt. Phase equilibration studies were carried out by slurrying the Form I crystals in a variety of solvents (MeCN, CHCl$_3$, CH$_2$Cl$_2$, MIBK, MEK, acetone, toluene, hexane, heptane, THF, MTBE, EtOH, i-PrOH, n-BuOH, EtOAc, i-PrOAc at 25° C. or 50° C. At 25° C., all the solvents tested gave the same crystalline Form I after slurrying. At 50° C., the same results were observed with the exception of ethanol. The XRPD pattern of the solid obtained from ethanol slurry showed the presence of free base which can be explained by a simple salt dissociation. The results of the phase equilibration studies suggest Form I is a stable crystalline form. Moreover, multiple lots (from gram to kilogram scales) of Example 1 adipic acid salt made to date have been determined to be the same crystalline form (Form I). Seeding had been used to induce the formation of Form I in the crystallization. However, it was also observed that Form I was obtained even without seeding in the crystallization.

Preparation: Adipic acid (790 g, 5.406 mol) was dissolved in methanol (29 L) at 16° C. 2-(3-(4-(7H-Pyrrolo[2,3-d]pyrimidin-4-yl)-1H-pyrazol-1-yl)-1-(1-(3-fluoro-2-(trifluoromethyl)-isonicotinoyl)piperidin-4-yl)azetidin-3-yl)acetonitrile free base (2.85 kg, 5.149 mol) was added to the adipic acid solution in methanol at 16° C. The reaction mixture was heated under reflux for 2 hours. The resulting reaction mixture was cooled to ambient temperature and the solvent was removed by distillation under reduced pressure to give the crude adipic acid salt. The crude adipic acid salt was dissolved in acetone (14 L) at ambient temperature. n-Heptane (20 L) was added over 2 hours to the crude adipic acid salt solution in acetone at 18° C. to precipitate the salt. The resultant slurry was stirred at 18° C. for 1 hour. The salt was isolated by filtration. The wet cake was washed with n-heptane (6 L). The product was dried on the filter funnel under suction for 18 hours to afford the crude 2-(3-(4-(7H-pyrrolo[2,3-d]pyrimidin-4-yl)-1H-pyrazol-1-yl)-1-(1-(3-fluoro-2-(trifluoromethyl)-isonicotinoyl)piperidin-4-yl)azetidin-3-yl)acetonitrile adipic acid salt (3.572 kg, 5.105 mol, 99.2% yield) as a white crystalline solid.

The crude adipic acid salt can be further purified by recrystallization. The crude adipic acid salt (3.378 kg, 4.828 mol) was suspended in acetone (24 L) at ambient temperature. The resulting suspension was heated to 55° C. and stirred at 50-60° C. to give a clear solution. The solution was filtered through an in-line filter to remove particulates. n-Heptane (24 L) was added to the solution at 55° C. over 2 hours to precipitate the salt. Upon complete addition of n-heptane, the slurry was cooled to 30° C. over 3 hours. The pure adipic acid salt was isolated by filtration. The wet cake was washed with a mixture of n-heptane and acetone (2:1 v/v, 6.8 L). The product was dried on the filter funnel under suction for 15 hours and was further dried in a vacuum oven at 55° C. for 42 hours to give pure 2-(3-(4-(7H-pyrrolo[2,3-d]pyrimidin-4-yl)-1H-pyrazol-1-yl)-1-(1-(3-fluoro-2-(trifluoromethyl)isonicotinoyl)piperidin-4-yl)azetidin-3-yl)acetonitrile adipic acid salt, 3.116 kg, 92.2% yield) as a white crystalline solid.

For adipic acid salt: mp 178° C.; $^1$H NMR (400 MHz, DMSO-d$_6$) δ 12.14 (s, 1H), 12.02 (br s, 2H), 8.81 (s, 1H), 8.69 (s, 1H), 8.66 (d, J=4.7 Hz, 1H), 8.42 (s, 1H), 7.90 (dd, J=4.7, 4.7, 1H), 7.60 (dd, J=2.3, 3.5 Hz, 1H), 7.06 (dd, J=1.8, 3.6 Hz, 1H), 4.08 (m, 1H), 3.74 (m, 2H), 3.57 (m, 2H), 3.55 (m, 2H), 3.39 (m, 1H), 3.25 (m, 1H), 3.07 (m, 1H), 2.56 (m, 1H), 2.19 (m, 4H), 1.77 (m, 1H), 1.62 (m, 1H), 1.48 (m, 4H), 1.36-1.12 (m, 2H); $^{13}$C NMR (100 MHz, DMSO-d$_6$) δ 174.4, 160.3, 152.2 ($^1J_{CF}$=265.7 Hz), 152.2, 150.9, 149.6, 146.3 ($^4J_{CF}$=5.8 Hz), 139.5, 135.0 ($^2J_{CF}$=17.3 Hz), 134.5 ($^2J_{CF}$=35.3, 11.9 Hz), 129.2, 127.6, 126.8, 121.7, 120.6 ($^1J_{CF}$=274.0 Hz, $^3J_{CF}$=4.8 Hz), 117.4, 113.0, 100.0, 61.4, 60.5 57.0, 44.2, 33.4, 28.6, 27.9, 27.2, 24.0; $^{19}$F NMR (376 MHz, DMSO-d$_6$) δ −64.54 (d, J=15.8 Hz, 3F), −129.34 (m, 1F); Anal. Calcd for: $C_{32}H_{33}F_4N_9O_5$: C, 54.93; H, 4.75; F, 10.86; N, 18.02. found: C, 54.68; H, 4.56; F, 10.94; N, 17.90. LCMS calculated for $C_{26}H_{24}F_4N_9O$ (M+H)$^+$ for the free base: m/z 554.2. found: 554.2.

The chemical purity was determined by reverse-phase HPLC to be 99.57 area %; the DSC thermogram revealed one major endothermic event with an onset of the peak at 175.9° C. which is believed to relate to the compound melting with the peak at 177.9° C. (see FIG. 1). The DSC was scanned from an initial temperature of 30° C. to a final temperature of 280° C. using a heating rate of 10° C./min. The TGA thermogram showed a small weight loss of 0.29% observed from 20° C. to 100° C., and a significant weight loss of 62% was observed upon further heating from 100° C. to 600° C. (see FIG. 2). The TGA thermogram was obtained when the sample was heated from 20° C. to 600° C. at a heating rate of 20° C./min. The XRPD pattern indicated crystalline nature of the adipic acid salt (see FIG. 3). The DSC, TGA, and XRPD data were consistent with those of Form I.

DSC parameters: Mettler Toledo Differential Scanning Calorimetry (DSC) instrument, Model No. 822; Aluminum sample pan (40 μL); general condition: 30-280° C. at 10° C./min.

TGA parameters: TA Instrument, Model No. Q500. The general starting method condition is: ramp at 20° C./min. to 600° C.

XRPD conditions: Rigaku MiniFlex X-ray Powder Diffractometer (XRPD) instrument; X-ray radiation is from Copper Cu at 1.054056 Å with K$_β$ filter; sample powder is dispersed on a zero-background sample holder; and general measurement conditions are:
Start Angle—3
Stop Angle—45
Sampling—0.02
Scan speed—2

TABLE 1

| 2-Theta (°) | d (Å) | BG | Height | H % | Area | A % | FWHM |
|---|---|---|---|---|---|---|---|
| 3.84 | 22.9919 | 7 | 341 | 24.4 | 19142 | 100 | 0.955 |
| 6.92 | 12.7638 | 169 | 461 | 33 | 6796 | 35.5 | 0.25 |
| 8.78 | 10.0638 | 164 | 52 | 3.7 | 1571 | 8.2 | 0.513 |
| 9.28 | 9.5227 | 161 | 47 | 3.4 | 760 | 4 | 0.275 |
| 10.4 | 8.4994 | 203 | 1399 | 100 | 15230 | 79.6 | 0.185 |

TABLE 1-continued

XRPD Data

| 2-Theta (°) | d (Å) | BG | Height | H % | Area | A % | FWHM |
|---|---|---|---|---|---|---|---|
| 10.981 | 8.0506 | 208 | 135 | 9.6 | 3688 | 19.3 | 0.465 |
| 11.74 | 7.532 | 179 | 302 | 21.6 | 6396 | 33.4 | 0.36 |
| 14.92 | 5.933 | 165 | 723 | 51.7 | 15980 | 83.5 | 0.376 |
| 15.4 | 5.7492 | 179 | 377 | 27 | 6733 | 35.2 | 0.303 |
| 16.859 | 5.2547 | 295 | 123 | 8.8 | 843 | 4.4 | 0.117 |
| 17.52 | 5.058 | 249 | 316 | 22.6 | 12179 | 63.6 | 0.655 |
| 18.68 | 4.7463 | 238 | 482 | 34.4 | 7294 | 38.1 | 0.257 |
| 19.861 | 4.4668 | 240 | 361 | 25.8 | 5072 | 26.5 | 0.239 |
| 20.98 | 4.2309 | 261 | 547 | 39.1 | 11823 | 61.8 | 0.368 |
| 22.12 | 4.0153 | 267 | 273 | 19.5 | 6037 | 31.5 | 0.377 |
| 22.46 | 3.9553 | 280 | 414 | 29.6 | 8893 | 46.5 | 0.365 |
| 23.28 | 3.8178 | 300 | 546 | 39 | 10395 | 54.3 | 0.324 |
| 23.74 | 3.7449 | 254 | 216 | 15.5 | 9220 | 48.2 | 0.725 |
| 24.38 | 3.6481 | 270 | 256 | 18.3 | 2926 | 15.3 | 0.194 |
| 25.062 | 3.5503 | 219 | 54 | 3.9 | 791 | 4.1 | 0.249 |
| 25.979 | 3.427 | 247 | 212 | 15.1 | 3384 | 17.7 | 0.272 |
| 26.901 | 3.3116 | 241 | 60 | 4.3 | 1124 | 5.9 | 0.32 |
| 27.76 | 3.2111 | 213 | 78 | 5.6 | 1985 | 10.4 | 0.431 |
| 28.839 | 3.0933 | 203 | 170 | 12.1 | 2489 | 13 | 0.249 |
| 29.841 | 2.9917 | 205 | 98 | 7 | 1115 | 5.8 | 0.194 |
| 30.94 | 2.8879 | 184 | 127 | 9.1 | 5062 | 26.4 | 0.677 |
| 31.562 | 2.8324 | 184 | 66 | 4.7 | 623 | 3.3 | 0.161 |
| 32.92 | 2.7185 | 181 | 125 | 8.9 | 3846 | 20.1 | 0.522 |
| 35.14 | 2.5518 | 182 | 147 | 10.5 | 4215 | 22 | 0.488 |
| 35.62 | 2.5185 | 173 | 83 | 6 | 5361 | 28 | 1.093 |
| 36.96 | 2.4302 | 178 | 52 | 3.7 | 1724 | 9 | 0.559 |
| 37.359 | 2.4051 | 178 | 89 | 6.4 | 2358 | 12.3 | 0.45 |
| 38.86 | 2.3156 | 173 | 72 | 5.2 | 3599 | 18.8 | 0.846 |
| 39.279 | 2.2918 | 177 | 77 | 5.5 | 2214 | 11.6 | 0.486 |

Example 359 cis-{1-{3-Methoxy-1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile

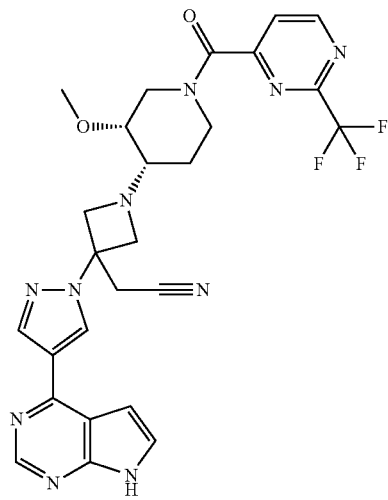 [SMILES: CO[C@@H]1CN(C(=O)c2ccnc(C(F)(F)F)n2)CC[C@@H]1N1CC(CC#N)(n2cc(-c3ncnc4[nH]ccc34)cn2)C1]

Step 1. tert-Butyl cis-4-[3-(cyanomethylene)azetidin-1-yl]-3-methoxypiperidine-1-carboxylate

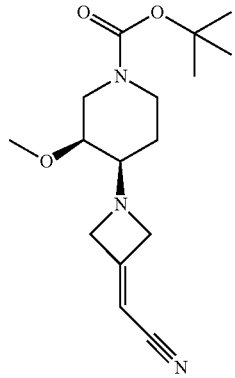 [SMILES: CO[C@H]1CN(C(=O)OC(C)(C)C)CC[C@H]1N1CC(=CC#N)C1]

To a solution of tert-butyl 3-(cyanomethylene)azetidine-1-carboxylate (3.0 g, 15 mmol) in tetrahydrofuran (8 mL) was added a 4.0 M solution of hydrogen chloride in 1,4-dioxane (10 mL, 40 mmol). After being stirred at room temperature for two hours, the reaction mixture was concentrated under reduced pressure. The residue was dissolved in tetrahydrofuran (20 mL), and tert-butyl 3-methoxy-4-oxopiperidine-1-carboxylate (3.58 g, 15.62 mmol) and triethylamine (3.126 g, 30.89 mmol) were added. After being stirred at room temperature for 30 minutes, sodium triacetoxyborohydride (8.184 g, 38.61 mmol) was added. The mixture was stirred at room temperature overnight. The resulting solution was diluted with aqueous NaHCO$_3$ and EtOAc. The organic layer was separated and washed with brine, dried over Na$_2$SO$_4$ and concentrated. Purification with combi-flash (20-100% EtOAc in hexanes) afforded 2.8 g (60% yield) of the desired product. LC/MS found: 308.1 (M-56)+.

Step 2. cis-{1-[3-Methoxypiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

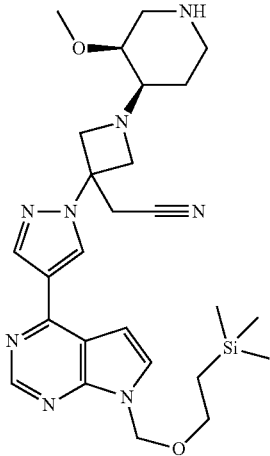 [SMILES: CO[C@H]1CNCC[C@H]1N1CC(CC#N)(n2cc(-c3ncnc4c3ccn4COCC[Si](C)(C)C)cn2)C1]

To a solution of 4-(1H-pyrazol-4-yl)-7-{[2-(trimethylsilyl)ethoxy]methyl}-7H-pyrrolo[2,3-d]pyrimidine (0.256 g, 0.812 mmol) in acetonitrile (10 mL) were added tert-butyl cis-4-[3-(cyanomethylene)azetidin-1-yl]-3-methoxypiperidine-1-carboxylate (0.20 g, 0.68 mmol) and 1,8-diazabicyclo[5.4.0]undec-7-ene (0.152 mL, 1.02 mmol). After being stirred at room temperature for 5 minutes, the reaction mixture became a clear solution. Stirring was continued at room temperature overnight. LC-MS indicated the reaction was complete. The solution was concentrated under reduced pressure and ethyl acetate was added. The resulting solution was washed with 1 N HCl and brine, dried over sodium sulfate, filtered and concentrated. Purification by silica gel chromatography (20-100% EtOAc/hexanes) afforded an oily product. The product was dissolved in THF (5 mL). To it was added 4 N HCl in dioxane (5 mL). After being stirred at room temperature for 2 hours, the solution was concentrated under reduced pressure to give 0.30 g (86%) of the title compound as a solid. LCMS: 511.1 (M+1)+.

Step 3. cis-{1-{3-Methoxy-1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile Into a 20 mL vial were added 3-fluoro-2-(trifluoromethyl)isonicotinic acid (18.67 mg, 0.0893 mmol) in DMF (3 mL), {1-[cis-3-methoxypiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (50.17 mg, 0.098 mmol), benzotriazol-1-yloxytris(dimethylamino)phosphonium hexafluorophosphate (59.25 mg, 0.134 mmol) and triethylamine (0.037 mL, 0.268 mmol). The mixture was stirred at room temperature overnight and purified with prep-LCMS to give 20 mg of the desired intermediate as a white solid. The white solid was dissolved in methylene chloride (1 mL) and trifluoroacetic acid (1 mL) was added. After being stirred at room temperature for one hour, the solution was concentrated. The residue was dissolved in methanol (2 mL) and ethylene diamine (0.1 g, 2 mmol) was added. The mixture was stirred at room temperature for two hours. Purification by prep-LCMS (pH=10, Method C) gave the title compound as a white powder. LCMS: 584.3 (M+1)+. $^1$H NMR (400 MHz, CD$_3$OD): δ 12.93 (s, 1H), 9.60 (d, J=2 Hz, 1H), 9.48 (d, J=7.2 Hz, 1H), 9.46 (d, J=4.4 Hz, 1H), 9.21 (d, J=1.2 Hz, 1H), 8.64 (s, 1H), 8.40 (d, J=3.6 Hz, 1H), 7.85 (d, J=3.2 Hz, 1H), 4.81 (m, 1H), 4.60 (m, 1H), 4.55 (m, 1H), 4.40 (m, 4H), 4.28 (m, 1H), 4.10 (m, 1H), 3.95 (m, 1H), 3.90 (s, 3H), 3.56 (m, 1H), 2.40 (m, 2H), 2.25 (m, 1H).

Example 360

{1-(cis-3-Methoxy-1-{[2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

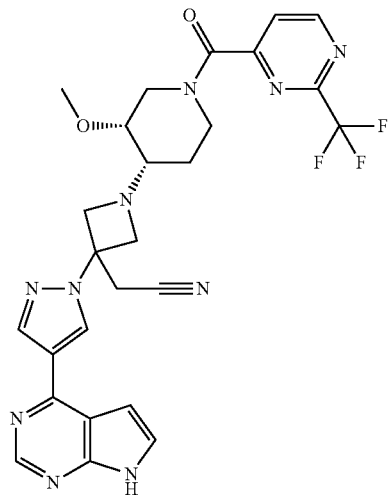 [SMILES: CO[C@@H]1CN(C(=O)c2ccnc(C(F)(F)F)n2)CC[C@@H]1N1CC(CC#N)(n2cc(-c3ncnc4[nH]ccc34)cn2)C1]

Into a 20 mL vial were added {1-[cis-3-methoxypiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (660 mg, 1.3 mmol) in DMF (10 mL), 2-(trifluoromethyl)pyrimidine-4-carboxylic acid (270 mg, 1.4 mmol), benzotriazol-1-yloxytris(dimethylamino)phosphonium hexafluorophosphate (610 mg, 1.4 mmol) and triethylamine (0.48 mL, 3.4 mmol). The mixture was stirred at room temperature overnight and purified with combi-flash using 5% methanol (MeOH)/50% EtOAc/hexanes to give 400 mg of the desired intermediate as a white solid. LC/MS found: 697.2 (M+1)$^+$.

The above residue was dissolved in methylene chloride (2 mL) and trifluoroacetic acid (2 mL) was added. After being stirred at room temperature for one hour, the solution was concentrated. The residue was dissolved in methanol (5 mL) and ethylenediamine (0.4 g, 7 mmol) was added. The resulting mixture was stirred at room temperature for two hours. Purification by prep-LCMS (pH=10, Method C) gave 210 mg of the title compound as a white powder. LCMS found: 567.2 (M+1)$^+$. $^1$H NMR (400 MHz, CD$_3$OD): δ 12.93 (s, 1H), 10.00 (dd, J=5.6 & 5.2 Hz, 1H), 9.60 (s, 1H), 9.48 (s, 1H), 9.21 (s, 1H), 8.73 (dd, J=5.6 & 5.6 Hz, 1H), 8.40 (d, J=3.6 Hz, 1H), 7.85 (d, J=3.2 Hz, 1H), 4.78 (m, 1H), 4.60 (m, 1H), 4.56 (m, 1H), 4.40 (m, 4H), 4.25 (m, 1H), 4.08 (m, 1H), 3.95 (m, 1H), 3.90 (s, 3H), 3.60 (m, 1H), 2.40 (m, 2H), 2.25 (m, 1H).

Example 361

{1-{cis-3-Fluoro-1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile

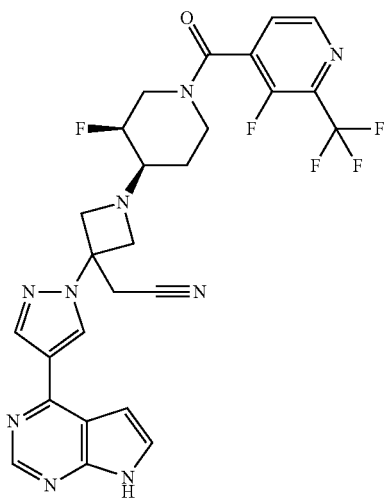 [SMILES: N#CCC1(n2cc(-c3ncnc4[nH]ccc34)cn2)CN([C@@H]2CCN(C(=O)c3ccnc(C(F)(F)F)c3F)C[C@@H]2F)C1]

Step 1. tert-Butyl cis-4-[3-(Cyanomethylene)azetidin-1-yl]-3-fluoropiperidine-1-carboxylate

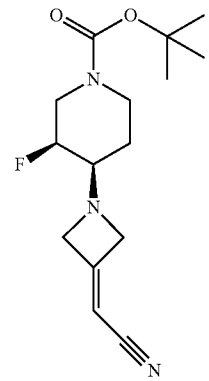 [SMILES: CC(C)(C)OC(=O)N1CC[C@@H](N2CC(=CC#N)C2)[C@@H](F)C1]

To a solution of tert-butyl 3-(cyanomethylene)azetidine-1-carboxylate (3.0 g, 15 mmol) in tetrahydrofuran (8 mL) was added a 4.0 M solution of hydrogen chloride in 1,4-dioxane (10 mL, 40 mmol). After being stirred at room temperature for two hours, the solution was concentrated under reduced pressure. The residue was dissolved in tetrahydrofuran (20 mL). To it were added tert-butyl 3-fluoro-4-oxopiperidine-1-carboxylate (3.392 g, 15.62 mmol) and triethylamine (3.126 g, 30.89 mmol). After being stirred at room temperature for 30 minutes, sodium triacetoxyborohydride (8.184 g, 38.61 mmol) was added. The mixture was stirred at room temperature overnight and diluted with aqueous NaHCO$_3$ and EtOAc. The organic layer was separated and washed with brine, dried over Na$_2$SO$_4$ and concentrated under reduced pressure. Purification with combi-flash (20-100% EtOAc in hexanes) afforded 0.5 g (66% yield) of the desired product. LC/MS found: 240.1 (M−56)$^+$.

Step 2. {1-[cis-3-Fluoropiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

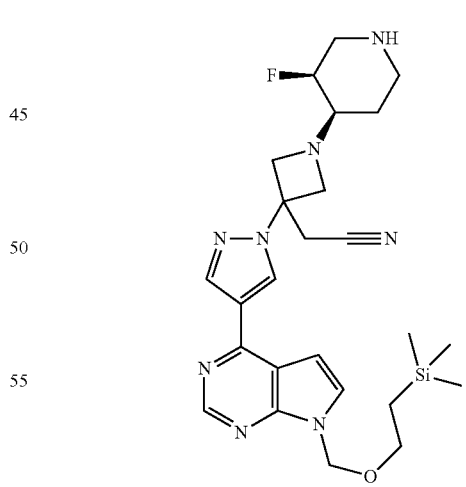

To a solution of tert-butyl cis-4-[3-(cyanomethylene)azetidin-1-yl]-3-fluoropiperidine-1-carboxylate (0.24 g, 0.81 mmol) and 4-(1H-pyrazol-4-yl)-7-{[2-(trimethylsilyl)ethoxy]methyl}-7H-pyrrolo[2,3-d]pyrimidine (0.31 g, 0.98 mmol) in acetonitrile (8 mL) was added 1,8-diazabicyclo[5.4.0]undec-7-ene (0.15 g, 0.98 mmol) by syringe. The resulting solution was stirred at room temperature for 6 hours and concentrated. Purification with combi-flash using 40-100% EtOAc/hexanew as eluent gave 0.30 g (61% yield) of the desired compound as a solid. LCMS found: 611.1 (M+1)⁺.

The above solid was dissolved in tetrahydrofuran (4 mL). To it was added a solution of 4.0 M HCl in dioxane (4 mL). The solution was stirred at room temperature for 2 hours and concentrated to give the title compound: LCMS: 511.1 (M+1)⁺.

Step 3. {1-{cis-3-Fluoro-1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile Into a 20 mL vial were added {1-[cis-3-fluoropiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (200 mg, 0.4 mmol) in DMF (3 mL), 3-fluoro-2-(trifluoromethyl)isonicotinic acid (99 mg, 0.47 mmol), benzotriazol-1-yloxytris(dimethylamino)phosphonium hexafluorophosphate (225 mg, 0.509 mmol) and triethylamine (0.14 mL, 1.0 mmol). The mixture was stirred at room temperature overnight and purified with prep-LCMS to give 50 mg of the desired compound as a white solid. LC/MS found: 702.2 (M+1)⁺.

The above product was dissolved in methylene chloride (2 mL). To it was added trifluoroacetic acid (2 mL). The resulting mixture was stirred at room temperature for an hour and concentrated. The residue was taken up in methanol (5 mL) and ethylenediamine (0.5 g, 8 mmol) was added. The mixture was stirred at room temperature for two hours. Purification with prep-LCMS (pH=10, Method C) gave the title compound as a white powder. LCMS found: 572.2 (M+1)⁺. ¹H NMR (400 MHz, CD₃OD): δ 12.93 (s, 1H), 9.62 (s, 1H), 9.49 (s, 1H), 9.48 (d, J=4.8 Hz, 1H), 9.22 (s, 1H), 8.60 (m, 1H), 8.40 (d, J=4.0 Hz, 1H), 7.85 (d, J=3.2 Hz, 1H), 5.60 (m, 1H), 5.20 (m, 1H), 4.60 (m, 2H), 4.42 (m, 2H), 4.38 (m, 2H), 4.20 (m, 1H), 3.90 (m, 1H), 3.58 (m, 1H), 2.52 (m, 1H), 2.35 (m, 2H).

Example 362

{1-(cis-3-Fluoro-1-{[2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

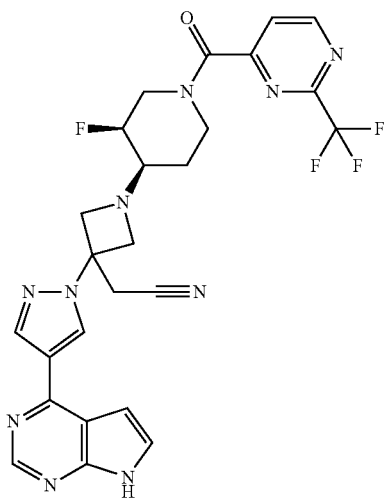 [SMILES: N#CCC1(n2cc(-c3ncnc4[nH]ccc34)cn2)CN([C@@H]2CCN(C(=O)c3ccnc(C(F)(F)F)n3)C[C@@H]2F)C1]

To a solution of {1-[cis-3-fluoropiperidin-4-yl]-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (200 mg, 0.4 mmol) and 2-(trifluoromethyl)pyrimidine-4-carboxylic acid (83 mg, 0.43 mmol) in DMF (10 mL) were added benzotriazol-1-yloxytris(dimethylamino)phosphonium hexafluorophosphate (5.20E2 mg, 1.17 mmol) and triethylamine (0.14 mL, 0.98 mmol). The mixture was stirred at room temperature overnight and purified with prep-LCMS to give 100 mg (36% yield) of the desired compound as a white solid.

The above residue was dissolved in methylene chloride (2 mL). To it was added trifluoroacetic acid (2 mL). After being stirred at room temperature for an hour, the solution was concentrated. The residue was dissolved in methanol (5 mL) and ethylenediamine (1 mL) was added. After being stirred at room temperature for two hours, the mixture was purified with prep-LCMS (pH=10, Method C) to give 41 mg (51% yield) of the title compound as a white powder. LCMS found: 555.3 (M+H)⁺. ¹H NMR (400 MHz, CD₃OD): δ 12.93 (s, 1H), 10.01 (dd, J=5.2 & 1.2 Hz, 1H), 9.62 (s, 1H), 9.49 (s, 1H), 9.22 (s, 1H), 8.71 (dd, J=22.4 & 4.8 Hz, 1H), 8.40 (dd, J=3.4 & 2.4 Hz, 1H), 7.85 (dd, J=3.6 & 1.2 Hz, 1H), 5.60 (m, 1H), 5.20 (m, 1H), 4.62 (m, 2H), 4.42 (m, 2H), 4.38 (m, 2H), 4.20 (m, 1H), 3.96 (m, 1H), 3.60 (m, 1H), 2.56 (m, 1H), 2.40 (m, 2H).

Example 363

{1-{1-[3-Fluoro-2-(trifluoromethyl)isonicotinoyl]-4-deuteropiperidin-4-yl}-3-[4-(7H-pyrrolo[2,3-d]pyrimidin-4-yl)-1H-pyrazol-1-yl]azetidin-3-yl}acetonitrile

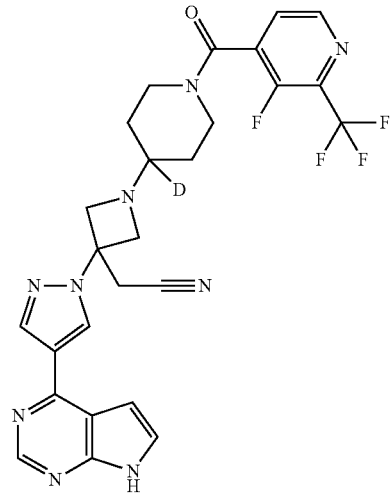 [SMILES: [2H]C1(N2CC(CC#N)(n3cc(-c4ncnc5[nH]ccc45)cn3)C2)CCN(C(=O)c2ccnc(C(F)(F)F)c2F)CC1]

Step 1. 1-(3-Fluoro-2-(trifluoromethyl)isonicotinoyl)piperidin-4-one

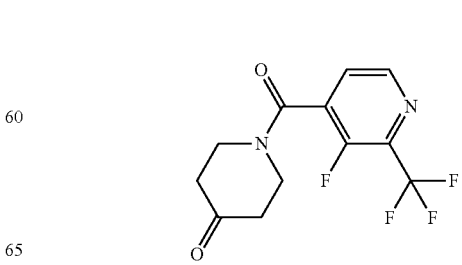

To a solution of piperidin-4-one (1 g, 10 mmol) and 3-fluoro-2-(trifluoromethyl)isonicotinic acid (2.32 g, 11.1 mmol) in DMF (20 mL) were added benzotriazol-1-yloxytris(dimethylamino)phosphonium hexafluorophosphate (5.62 g, 12.7 mmol) and triethylamine (4.43 mL, 31.8 mmol). The mixture was stirred at room temperature overnight and diluted with EtOAc. The solution was washed with brine, dried with sodium sulfate, filtered and concentrated. Purification on silica gel with 50-100% EtOAc/hexanes gave 2.1 g (70% yield) of the title compound. LC/MS found: 291.2 (M+1)$^+$.

Step 2. {1-{1-[3-Fluoro-2-(trifluoromethyl)isonicotinoyl]-4-deuteropiperidin-4-yl}-3-[4-(7H-pyrrolo[2,3-d]pyrimidin-4-yl)-1H-pyrazol-1-yl]azetidin-3-yl}acetonitrile To a solution of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (50 mg, 0.1 mmol) and 1-(3-fluoro-2-(trifluoromethyl)isonicotinoyl)piperidin-4-one (39 mg, 0.13 mmol) in tetrahydrofuran (3 mL, 40 mmol) was added sodium cyanoborodeuteride (0.024 g, 0.37 mmol). The mixture was stirred at room temperature overnight. The solvent was removed under reduced pressure. The resulting residue was taken up in EtOAc. The solution was washed with aqueous NaHCO$_3$ and brine, dried over Na$_2$SO$_4$ and concentrated under reduced pressure. Purification with prep-LCMS afforded 25 mg (36% yield) of the desired product as a solid. LC/MS found: 685.1 (M+1)$^+$.

The above solid was dissolved in CH$_2$Cl$_2$ (2 mL). To it was added trifluoroacetic acid (2 mL). After being stirred at room temperature for 1 hour, the solution was concentrated. The residue was taken up in methanol (2 mL). Ethylenediamine (0.1 g, 2 mmol) was added. The mixture was stirred at room temperature for two hours. Direct purification with prep-LCMS (Method C) gave the title compound as a white powder. LCMS found: 555.1 (M+1)$^+$. $^1$H NMR (400 MHz, CD$_3$OD): δ 12.93 (s, 1H), 9.61 (s, 1H), 9.49 (s, 1H), 9.48 (d, J=4.4 Hz, 1H), 9.21 (s, 1H), 8.70 (dd, J=4.8 & 4.8 Hz, 1H), 8.40 (dd, J=3.2 & 2.4 Hz, 1H), 7.86 (d, J=2.8 Hz, 1H), 4.85 (m, 1H), 4.58 (m, 2H), 4.38 (m, 4H), 4.21 (m, 1H), 4.08 (m, 1H), 3.90 (m, 1H), 2.58 (m, 1H), 2.40 (m, 1H), 2.02 (m, 2H).

Example 364

{1-{1-[3-Fluoro-2-(trifluoromethyl)isonicotinoyl]3,3,4,5,5-pentadeuteropiperidin-4-yl}-3-[4-(7H-pyrrolo[2,3-d]pyrimidin-4-yl)-1H-pyrazol-1-yl]azetidin-3-yl}acetonitrile

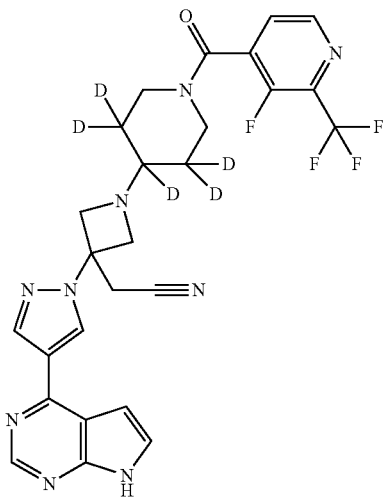 [SMILES: [2H]C1([2H])CN(C(=O)c2ccnc(C(F)(F)F)c2F)CC([2H])([2H])C1([2H])N1CC(CC#N)(n2cc(-c3ncnc4[nH]ccc34)cn2)C1]

A solution of 1-(3-fluoro-2-(trifluoromethyl)isonicotinoyl)piperidin-4-one (0.66 g, 2.3 mmol) and triethylamine (0.45 g, 4.4 mmol) in methanol-d$_4$ was stirred at room temperature overnight. To it were added {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (1.1 g, 2.7 mmol) and sodium cyanoborodeuteride (0.45 g, 6.8 mmol). The mixture was stirred at room temperature for 4 hours and concentrated. The residue was taken up in EtOAc. The solution was washed with aqueous NaHCO$_3$ and brine, dried over Na$_2$SO$_4$ and concentrated under reduced pressure. Purification with prep-LCMS afforded 80 mg (5% yield) of the desired compound. LC/MS found: 589.1, (M+1)$^+$.

The above product was dissolved in CH$_2$Cl$_2$ (2 mL). To it was added trifluoroacetic acid (2 mL). After being stirred for 1 hour, the solution was concentrated. The residue was dissolved in methanol (3 mL). To it was added ethylenediamine (0.5 g, 8 mmol). After being stirred for 2 hours, the mixture was separated by prep-HPLC (Method C) to give the title compound. LCMS found: 559.1 (M+1)$^+$. $^1$H NMR (400 MHz, CD$_3$OD): d 12.94 (s, 1H), 9.61 (s, 1H), 9.49 (s, 1H), 9.46 (d, J=4.4 Hz, 1H), 9.21 (s, 1H), 8.70 (dd, J=4.4 & 4.4 Hz, 1H), 8.40 (d, J=3.6 Hz, 1H), 7.86 (d, J=3.6 Hz, 1H), 4.82 (d, J=13.2 Hz, 1H), 4.54 (d, J=7.6 Hz, 2H), 4.39 (m, 4H), 4.20 (d, J=13.6 Hz, 1H), 4.05 (d, J=132. Hz, 1H), 3.85 (d, J=13.6 Hz, 1H).

Example 365

{1-{7-[3-Fluoro-2-(trifluoromethyl)isonicotinoyl]-3-oxa-7-azabicyclo[3.3.1]non-9-yl}-3-[4-(7H-pyrrolo[2,3-d]pyrimidin-4-yl)-1H-pyrazol-1-yl]azetidin-3-yl}acetonitrile

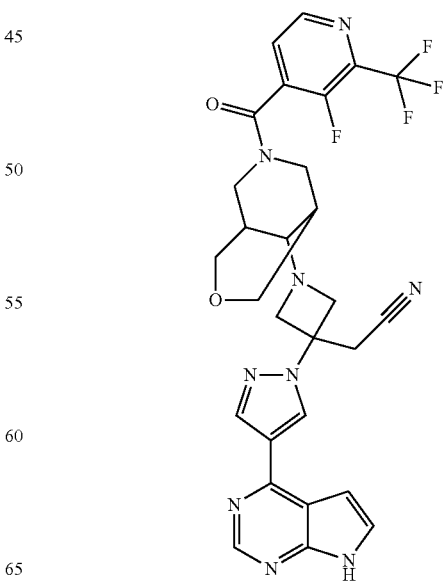

Step 1. {1-(3-Oxa-7-azabicyclo[3.3.1]non-9-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}

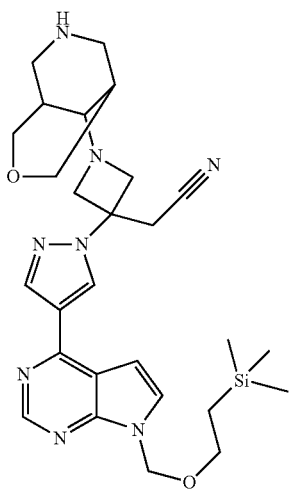 [SMILES: C[Si](C)(C)CCOCn1ccc2c(-c3cnn(C4(CC#N)CN(C5C6CNCC5COC6)C4)c3)ncnc21]

To a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.80 g, 1.95 mmol) and tert-butyl 9-oxo-3-oxa-7-azabicyclo[3.3.1]nonane-7-carboxylate (0.518 g, 2.148 mmol) in tetrahydrofuran (20.0 mL) were added triethylamine (1.62 mL, 11.7 mmol) and sodium triacetoxyborohydride (0.828 g, 3.91 mmol). After being stirred at room temperature for 2 hours, the reaction was quenched with 20 mL of water and 100 mL of EtOAc. The organic layer was washed with brine, dried over Na$_2$SO$_4$, filtered and concentrated under reduced pressure. Purification with combi-flash (5% MeOH/CH$_2$Cl$_2$) gave 0.8 g (65% yield) of the desired intermediate. LCMS found: 635.3 (M+1)$^+$.

The above product was dissolved in THF (5 mL) and a 4 M solution of HCl in dioxane (5 mL) was added. After being stirred for 1 hour, the solution was concentrated under reduced pressure to give the title compound. LCMS found: 535.2 (M+1)$^+$.

Step 2. {1-{7-[3-Fluoro-2-(trifluoromethyl)isonicotinoyl]-3-oxa-7-azabicyclo[3.3.1]non-9-yl}-3-[4-(7H-pyrrolo[2,3-d]pyrimidin-4-yl)-1H-pyrazol-1-yl]azetidin-3-yl}acetonitril To a mixture of 3-fluoro-2-(trifluoromethyl)isonicotinic acid (50.0 mg, 0.239 mmol) and {1-(3-oxa-7-azabicyclo[3.3.1]non-9-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (128 mg, 0.239 mmol) in DMF (2 mL) were added triethylamine (0.100 mL, 0.717 mmol) and benzotriazol-1-yloxytris(dimethylamino)phosphonium hexafluorophosphate (127 mg, 0.287 mmol). The mixture was stirred at room temperature for 2 hours. Direct purification with prep-LCMS (pH=10) afforded 50 mg (30% yield) of the desired product. LCMS found: 696.3 (M+1)$^+$.

The about product was dissolved in methylene chloride (2 mL). To it was added TFA (2 mL). After being stirred for 1 hour, the solution was concentrated. The residue was taken up in a solution of 20% ethylenediamine in MeOH (2 mL).

After being stirred for 2 hours, the mixture was separated with prep-HPLC (Method C) to give the title compound. LCMS found: 596.1 (M+1)$^+$. $^1$H NMR (300 MHz, DMSO-d$_6$): δ 12.10 (s, 1H), 8.82 (s, 1H), 8.68 (s, 1H), 8.66 (d, J=6.1 Hz, 1H), 8.41 (s, 1H), 7.63 (s, 1H), 7.59 (d, J=7.1 Hz, 1H), 7.05 (d, J=6.3 Hz, 1H), 4.79 (d, J=9.1 Hz, 1H), 4.44 (d, J=10.1 Hz, 1H), 4.00-3.80 (m, 2H), 3.77-3.41 (m, 4H), 3.60 (s, 2H), 3.39-3.18 (m, 4H), 3.01 (m, 1H), 1.60 (m, 2H).

Example 366

{1-(1-{[4-[(dimethylamino)methyl]-6-(trifluoromethyl)pyridin-2-yl]carbonyl}piperidin-4-yl)-3-[4-(7H-pyrrolo[2,3-d]pyrimidin-4-yl)-1H-pyrazol-1-yl]azetidin-3-yl}acetonitrile

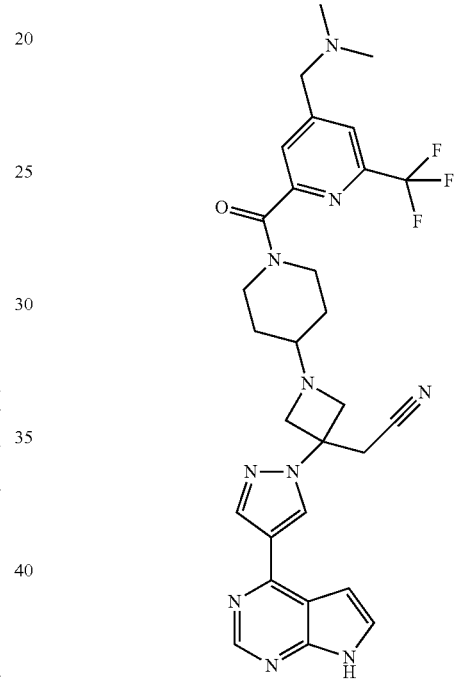

Step A. 4-[(dimethylamino)methyl]-6-(trifluoromethyl)pyridine-2-carboxylic acid

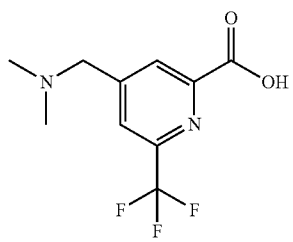 [SMILES: CN(C)Cc1cc(C(=O)O)nc(C(F)(F)F)c1]

A mixture of 4-bromo-6-(trifluoromethyl)pyridine-2-carboxylic acid (200 mg, 0.7 mmol, Anichem), cesium carbonate (724 mg, 2.22 mmol), dicyclohexyl(2',4',6'-triisopropylbiphenyl-2-yl)phosphine (42 mg, 0.089 mmol, Aldrich), potassium [(dimethylamino)methyl](trifluoro)borate(1−) (147 mg, 0.889 mmol, Aldrich), palladium acetate (10. mg, 0.044 mmol, Sigma-Aldrich) and THF:H$_2$O (10:1, 4.6 mL) was degassed by bubbling a stream of nitrogen through the solution for 15 minutes. The reaction vial was sealed and heated at 80° C. overnight. The crude mixture was purified via HPLC (Waters XBridge C18, 5 um particle size, 30×100 mm; 5 to 25% MeCN/H$_2$O containing 0.15% NH$_4$OH over 5 minutes) and the product was detected by UV absorbance and collected. Fractions containing the desired product were rotovapped and azeotroped once with methanol to afford product. Yield: 0.029 g (20%); LC-MS: 249.1 (M+H)$^+$.

Step B. {1-(1-{[4-[(dimethylamino)methyl]-6-(trifluoromethyl)pyridin-2-yl]carbonyl}piperidin-4-yl)-3-[4-(7H-pyrrolo[2,3-d]pyrimidin-4-yl)-1H-pyrazol-1-yl]azetidin-3-yl}acetonitrile To a solution of 4-[(dimethylamino)methyl]-6-(trifluoromethyl)pyridine-2-carboxylic acid (0.015 g, 0.060 mmol, from Step A) in N,N-dimethylformamide (1 mL) was added N,N,N',N'-tetramethyl-O-(7-azabenzotriazol-1-yl)uronium hexafluorophosphate (0.028 g, 0.072 mmol, Aldrich) and N,N-diisopropylethylamine (0.042 mL, 0.24 mmol). This mixture was prestirred for 15 minutes, followed by the addition of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.030 g, 0.061 mmol, prepared as described in Example 1, Step H, except worked up to provide the free base). The reaction was stirred overnight. Additional N,N-diisopropylethylamine (0.042 mL, 0.24 mmol), 4-[(dimethylamino)methyl]-6-(trifluoromethyl)pyridine-2-carboxylic acid (0.014 g, 0.056 mmol) in DMF (1 mL), and N,N,N',N'-tetramethyl-O-(7-azabenzotriazol-1-yl)uronium hexafluorophosphate (0.018 g, 0.048 mmol) were added and the reaction was stirred over an additional 48 hours. The reaction mixture was then partitioned between ethyl acetate and water and the layers were separated. Solid NaCl was added to saturate the aqueous layer and this was extracted with two further portions of ethyl acetate. The combined organic extracts were dried over sodium sulfate, decanted and concentrated. The crude product was deprotected by stirring with a 1:1 mixture of TFA:DCM for 1.5 hours, followed by evaporation and then stirring the resulting residue with ethylenediamine (0.2 mL) in methanol (4 mL). The mixture was filtered and purified by preparative HPLC-MS, (C18 eluting with a gradient of MeCN/H$_2$O containing 0.15% NH$_4$OH). Fractions containing product were frozen and lyophilized. Yield: 0.015 g (42%); LC-MS: 593.2 (M+H)$^+$. $^1$H NMR (400 MHz, CD$_3$OD): δ 8.70 (s, 1H), 8.67 (s, 1H), 8.40 (s, 1H), 7.88 (s, 1H), 7.80 (s, 1H), 7.51 (d, 1H), 6.99 (d, 1H), 4.32 (ddd, 1H), 3.86-3.70 (m, 5H), 3.64 (s, 2H), 3.50 (s, 2H), 3.36-3.16 (m, 2H), 2.69-2.61 (m, 1H), 2.28 (s, 6H), 1.98-1.88 (m, 1H), 1.86-1.77 (m, 1H), 1.51-1.39 (m, 2H). $^{19}$F NMR (400 MHz, CD$_3$OD): δ −69.82 (s, 3F).

Example 367

4-{3-(cyanomethyl)-3-[4-(7H-pyrrolo[2,3-d]pyrimidin-4-yl)-1H-pyrazol-1-yl]azetidin-1-yl}-N-isopropylpiperidine-1-carboxamide

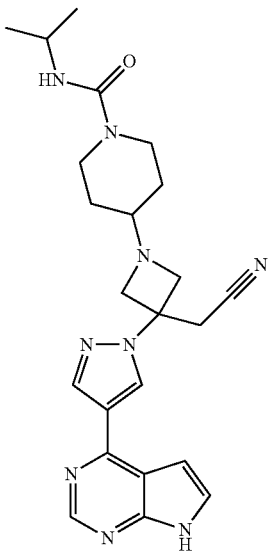 [SMILES: CC(C)NC(=O)N1CCC(N2CC(CC#N)(n3cc(-c4ncnc5[nH]ccc45)cn3)C2)CC1]

To a solution of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.075 g, 0.15 mmol, prepared as described in Example 1, Step H, except worked up to provide the free base) in methylene chloride (2 mL) was added N,N-diisopropylethylamine (0.026 mL, 0.15 mmol) followed by 2-isocyanatopropane (20 μL, 0.2 mmol, Aldrich). The reaction was continued for 2 hours. The crude product was deprotected by the addition of 1 mL TFA to the solution, which was stirred for 1 hour and evaporated. The deprotection was completed by stirring with ethylenediamine (0.2 mL) in methanol for 30 minutes. The product was purified by preparative HPLC-MS (C18 eluting with a gradient of MeCN/H$_2$O containing 0.15% NH$_4$OH). Fractions containing desired product were frozen and lyophilized. Yield: 0.025 g (37%); LC-MS: 448.2 (M+H)$^+$. $^1$H NMR (300 MHz, CDCl$_3$): δ 10.21 (br s, 1H), 8.85 (s, 1H), 8.41 (s, 1H), 8.32 (s, 1H), 7.41 (dd, 1H), 6.79 (dd, 1H), 4.22 (d, 1H), 4.04-3.87 (m, 1H), 3.81-3.69 (m, 4H), 3.61 (d, 2H), 3.40 (s, 2H), 3.00-2.86 (dq, 2H), 2.44-2.31 (m, 1H), 1.76-1.64 (m, 2H), 1.40-1.22 (m, 2H), 1.15 (d, 6H).

Example 368

{1-{1-[6-[(dimethylamino)methyl]-3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile

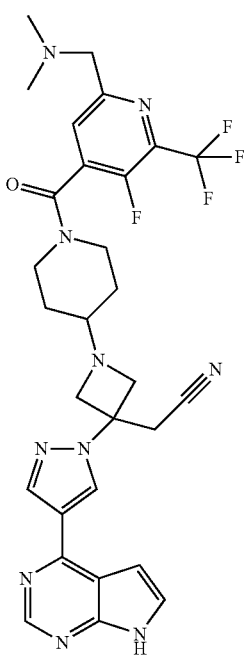 [SMILES: CN(C)Cc1cc(C(=O)N2CCC(N3CC(CC#N)(n4cc(-c5ncnc6[nH]ccc56)cn4)C3)CC2)c(F)c(C(F)(F)F)n1]

Step A. 3-fluoro-2-(trifluoromethyl)isonicotinic acid 1-oxide

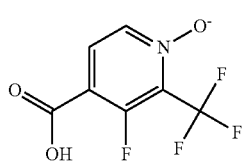

To a solution of 3-fluoro-2-(trifluoromethyl)isonicotinic acid (2.00 g, 9.56 mmol, Oakwood) and urea hydrogen peroxide addition compound (5.00 g, 53.2 mmol, Aldrich) in methylene chloride (50 mL) at 0° C. was added trifluoroacetic anhydride (7.51 mL, 53.2 mmol). The bath was removed and the reaction was allowed to warm to room temperature and stir overnight. The precipitate was filtered off. The filtrate was diluted with a small amount of water and ethyl acetate, the layers were separated and the aqueous was extracted with two further portions of ethyl acetate. The combined extracts were dried over sodium sulfate, filtered and concentrated. The solvent was removed in vacuo to afford a yellow solid which was used without further purification. LC-MS: 225.9 (M+H)$^+$. $^1$H NMR (300 MHz, CD$_3$OD): δ 8.20 (d, 1H), 8.04 (dd, 1H).

Step B. 6-chloro-3-fluoro-2-(trifluoromethyl)isonicotinic acid

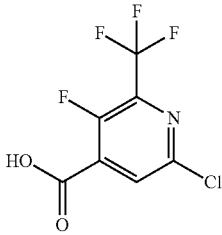 [SMILES: O=C(O)c1cc(Cl)nc(C(F)(F)F)c1F]

A solution of 3-fluoro-2-(trifluoromethyl)isonicotinic acid 1-oxide (1.0 g, 4.4 mmol from Step A) in phosphoryl chloride (4 mL, 40 mmol) was heated to 110° C. for 2 hours, then was left to stir at ambient temperature overnight. The POCl$_3$ was evaporated, the residue was treated with sodium bicarbonate solution, which was stirred for 1 hour. To this mixture was added tetrahydrofuran (20 mL) and lithium hydroxide monohydrate (0.24 g, 5.7 mmol). This was stirred for 3 hours. The pH of the mixture was then adjusted to the range of pH 4-5 by the addition of c.HCl. The product was extracted with three portions of ethyl acetate. The combined extracts were dried over sodium sulfate, filtered and concentrated. Yield: 0.54 g (50%); LC-MS: 244.1/245.9 (M+H)$^+$. $^1$H NMR (300 MHz, CDCl$_3$): δ 8.07 (d, 1H).

Step C. 6-[(dimethylamino)methyl]-3-fluoro-2-(trifluoromethyl)isonicotinic acid To a sealable vial was added 6-chloro-3-fluoro-2-(trifluoromethyl)isonicotinic acid (0.200 g, 0.821 mmol, from Step B), Palladium acetate (0.13 g, 0.57 mmol, Aldrich), dicyclohexyl(2',4',6'-triisopropylbiphenyl-2-yl)phosphine (0.55 g, 1.1 mmol, Aldrich), Cesium Carbonate (0.803 g, 2.46 mmol) and potassium [(dimethylamino)methyl](trifluoro)borate(1−) (0.163 g, 0.985 mmol, Aldrich) and THF:H$_2$O (10:1, 15 mL). The reaction was degassed by alternating vacuum and N$_2$ in three cycles. The vial was sealed and heated to 80° C. overnight. The mixture was filtered and the solvent was removed in vacuo. The product was purified by preparative HPLC-MS (C18 eluting with a gradient of MeCN/H$_2$O containing 0.1% TFA). Fractions containing product were rotovapped to afford a residue comprising product and DMF. The weight percent of each component was determined by NMR and the product used without further purification. Yield: 0.077 g (35%); $^1$H NMR (400 MHz, CD$_3$OD): δ 8.26 (d, 1H), 4.60 (s, 2H), 2.98 (s, 6H).

Step D. {1-{1-[6-[(dimethylamino)methyl]-3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile A solution of 6-[(dimethylamino)methyl]-3-fluoro-2-(trifluoromethyl)isonicotinic acid (0.0776 g, 0.291 mmol, from Step C) in N,N-dimethylformamide (1 mL) was treated with N,N-diisopropylethylamine (0.3 mL, 2 mmol) and benzotriazol-1-yloxytris(dimethylamino)phosphonium hexafluorophosphate (0.15 g, 0.35 mmol). This mixture was pre-stirred for 1 hour, followed by the addition of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.158 g, 0.320 mmol, prepared as described in Example 1, Step H, except worked up to provide the free base). After 3 hours, additional N,N-diisopropylethylamine (0.507 mL, 2.91 mmol) and benzotriazol-1-yloxytris(dimethylamino)phosphonium hexafluorophosphate (0.26 g, 0.58 mmol) were added and the mixture was stirred for 48 hours. The SEM-protected product was purified by preparative HPLC-MS (C18 eluting with a gradient of MeCN/$H_2O$ containing 0.15% $NH_4OH$). Solvent was removed from fractions containing desired product by rotary evaporation. The product was deprotected by stirring with a 1:1 mixture of TFA:DCM for 1 hour, followed by evaporation, and stirring with ethylenediamine (0.2 mL) in methanol for 30 minutes. The product was purified by preparative HPLC-MS (C18 eluting with a gradient of MeCN/$H_2O$ containing 0.15% $NH_4OH$). Fractions containing desired product were frozen and lyophilized. Yield: 0.006 g (3%); LC-MS: 611.2 $(M+H)^+$. $^1H$ NMR (300 MHz, $CD_3OD$): δ 8.69 (s, 1H), 8.67 (s, 1H), 8.40 (s, 1H), 7.77 (d, 1H), 7.51 (d, 1H), 6.98 (d, 1H), 4.33-4.21 (m, 1H), 3.87-3.71 (m, 4H), 3.68 (s, 2H), 3.59-3.45 (m, 3H), 3.44-3.10 (m, 2H), 2.71-2.58 (m, 1H), 2.31 (s, 6H), 1.97-1.85 (m, 1H), 1.85-1.72 (m, 1H), 1.56-1.24 (m, 2H). $^{19}F$ NMR (300 MHz, $CD_3OD$): δ −67.26 (d, 3F), −132.8 (m, 1F).

Example 369

3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-5-[(dimethylamino)methyl]benzonitrile

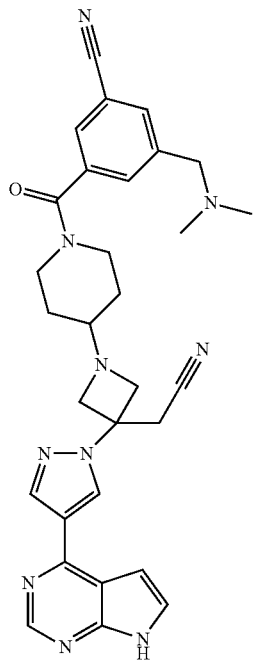 [SMILES: CN(C)Cc1cc(C#N)cc(C(=O)N2CCC(N3CC(CC#N)(n4cc(-c5ncnc6[nH]ccc56)cn4)C3)CC2)c1]

Step A. methyl 3-bromo-5-[(dimethylamino)methyl]benzoate

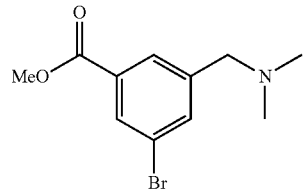

To a solution of methyl 3-bromo-5-formylbenzoate (1.8 g, 7.4 mmol, prepared as described in WO 2003048111 from dimethyl 5-bromoisophthalate, Alfa Aesar) in methylene chloride (20 mL) was added a solution of 2.0 M dimethylamine in tetrahydrofuran (7.4 mL, 15 mmol). This mixture was stirred for 15 minutes, followed by the addition of sodium triacetoxyborohydride (4.7 g, 22 mmol). The resulting mixture was stirred overnight. Saturated sodium bicarbonate solution was added and the product was extracted with ethyl acetate. The combined organic extracts were washed twice with water, once with brine, dried over sodium sulfate, filtered and concentrated to afford a light yellow oil. Yield: 1.87 g (93%); LC-MS: 272.0, 274.0 $(M+H)^+$. $^1H$ NMR (400 MHz, $CDCl_3$): δ 8.06 (dd, 1H), 7.89 (dd, 1H), 7.69 (dd, 1H), 3.91 (s, 3H), 3.42 (s, 2H), 2.24 (s, 6H).

Step B. 3-bromo-5-[(dimethylamino)methyl]benzoic acid

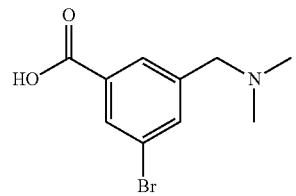

Methyl 3-bromo-5-[(dimethylamino)methyl]benzoate (0.30 g, 1.1 mmol, from Step A) was dissolved in tetrahydrofuran (20 mL) and lithium hydroxide monohydrate (0.555 g, 13.2 mmol) in water (6 mL) was added. After stirring for 3 hours, the mixture was rotovapped to remove THF and reduce the volume of water. The mixture was diluted with an equivalent volume of acetonitrile and filtered. The product was purified via preparative HPLC-MS (C18 eluting with a gradient of MeCN/$H_2O$ containing 0.15% $NH_4OH$). Solvent was removed from fractions containing desired product by rotary evaporation to afford a white solid. Yield: 0.26 g (91%); LC-MS: 258.0, 260.0 $(M+H)^+$. $^1H$ NMR (300 MHz, DMSO-$d_6$): δ 7.86 (dd, 1H), 7.76 (dd, 1H), 7.43 (dd, 1H), 3.38 (s, 2H), 2.14 (s, 6H).

Step C. 3-[(4-{3-(cyanomethyl)-3-[4-(7H-pyrrolo[2,3-d]pyrimidin-4-yl)-1H-pyrazol-1-yl]azetidin-1-yl}piperidin-1-yl)carbonyl]-5-[(dimethylamino)methyl]benzonitrile To a solution of 3-bromo-5-[(dimethylamino)methyl]benzoic acid (31.4 mg, 0.122 mmol, from Step B) in tetrahydrofuran (1.0 mL) was added triethylamine (0.045 mL, 0.32 mmol) and N,N,N',N'-tetramethyl-O-(7-azabenzotriazol-1- yl)uronium hexafluorophosphate (43.2 mg, 0.114 mmol). The mixture was pre-stirred for 15 minutes, followed by the addition of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (40. mg, 0.081 mmol, prepared as described in Example 1, Step H, except worked up to provide the free base). After stirring for two hours, the reaction mixture was partitioned between ethyl acetate and water. The organic layer was washed successively with water, 0.1N NaOH and sat. NaCl, dried over sodium sulfate and concentrated. The residue was dissolved in N,N-dimethylformamide (1.50 mL) and zinc cyanide (57 mg, 0.49 mmol) was added. The solution was degassed via a stream of nitrogen through the mixture for 10 minutes. Tetrakis(triphenylphosphine)palladium(0) (19 mg, 0.016 mmol) was added, and the reaction was heated to 120° C. in the microwave for 30 minutes. The reaction mixture was worked up by partition between water and ethyl acetate. The ethyl acetate layer was washed twice with water, once with brine, dried over sodium sulfate and concentrated. The residue was stirred in a 1:1 mixture of DCM:TFA for one hour, then concentrated. The residue was redissolved in methanol (1 mL), and ethylenediamine (0.2 mL) was added. Upon complete deprotection, the product was isolated via preparative HPLC-MS (C18 eluting with a gradient of MeCN/H₂O containing 0.15% NH₄OH). Yield: 11.7 mg (26%); LC-MS: 549.3 (M+H)⁺. ¹H NMR (400 MHz, DMSO-d₆): δ 12.15 (br s, 1H), 8.82 (s, 1H), 8.69 (s, 1H), 8.42 (s, 1H), 7.85 (s, 1H), 7.82 (s, 1H), 7.66 (s, 1H), 7.61 (dd, 1H), 7.07 (dd, 1H), 4.14-4.03 (m, 1H), 3.80-3.28 (m, 9H), 3.22-3.02 (m, 2H), 2.59-2.51 (m, 1H), 1.83-1.71 (m, 1H), 1.69-1.58 (m, 1H), 1.35-1.15 (m, 2H).

Example 370

{1-(1-{[6-[(dimethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

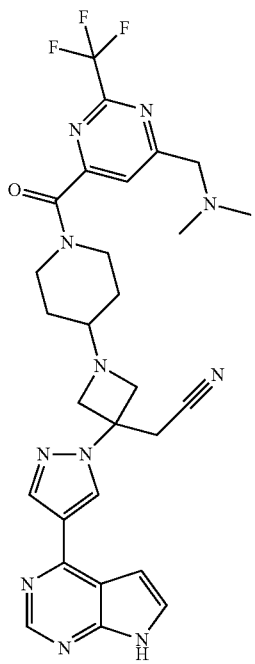 [SMILES: CN(C)Cc1cc(C(=O)N2CCC(N3CC(CC#N)(n4cc(-c5ncnc6[nH]ccc56)cn4)C3)CC2)nc(C(F)(F)F)n1]

Step A. ethyl 6-(bromomethyl)-2-(trifluoromethyl)pyrimidine-4-carboxylate

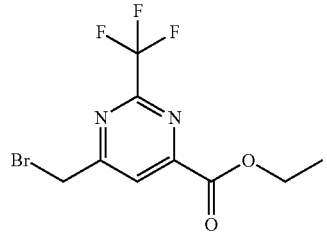 [SMILES: CCOC(=O)c1cc(CBr)nc(C(F)(F)F)n1]

A mixture of ethyl 6-methyl-2-(trifluoromethyl)pyrimidine-4-carboxylate (1.1 g, 4.5 mmol, prepared as described in WO 2007/090748), N-bromosuccinimide (2.86 g, 16.1 mmol) and benzoyl peroxide (0.21 g, 0.9 mmol) in carbon tetrachloride (9 mL) was heated in a sealed vessel to 100° C. overnight. The mixture was diluted with dichloromethane (DCM), filtered and the solvent was removed in vacuo. Purification via preparative HPLC-MS (C18 eluting with a gradient of MeCN/H₂O containing 0.15% NH₄OH) afforded the product, which on removal of solvent, was an oil.

Yield: 0.34 g (24%); LC-MS: 313.0, 315.0 (M+H)⁺. ¹H NMR (400 MHz, DMSO-d₆): δ 8.48 (s, 1H), 4.91 (s, 2H), 4.44 (q, 2H), 1.36 (t, 3H).

Step B. 6-[(dimethylamino)methyl]-2-(trifluoromethyl)pyrimidine-4-carboxylic acid

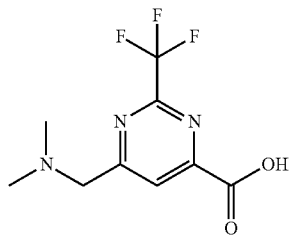 [SMILES: CN(C)Cc1cc(C(=O)O)nc(C(F)(F)F)n1]

To a solution of 2.0 M dimethylamine in THF (5.27 mL, 10.5 mmol) was added a solution of ethyl 6-(bromomethyl)-2-(trifluoromethyl)pyrimidine-4-carboxylate (0.33 g, 1.0 mmol, from Step A) in methylene chloride (5.0 mL). The reaction was stirred at room temperature for 2 hours, then concentrated. The residue was dissolved in tetrahydrofuran (20 mL), water (6 mL) was added, followed by lithium hydroxide monohydrate (0.4 g, 10 mmol). The mixture was stirred for one hour, then was rotovapped to remove most of the THF. The pH was adjusted to 7 by the addition of conc. HCl. Acetonitrile (10 mL) was added, the mixture was filtered and then purified via preparative HPLC-MS (C18 eluting with a gradient of MeCN/H₂O containing 0.15% NH₄OH) to afford product as a light yellow solid. Yield: 0.153 g (58%); LC-MS: 250.1 (M+H)⁺. ¹H NMR (400 MHz, DMSO-d₆): δ 8.02 (s, 1H), 3.70 (s, 2H), 2.27 (s, 6H).

Step C. {1-(1-{[6-[(dimethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile 6-[(Dimethylamino)methyl]-2-(trifluoromethyl)pyrimidine-4-carboxylic acid (22.8 mg, 0.0913 mmol, from Step B) was dissolved in tetrahydrofuran (0.67 mL), and triethylamine (33.9 µL, 0.244 mmol) and N,N,N',N'-tetramethyl-O-(7-azabenzotriazol-1-yl)uranium hexafluorophosphate (32.4 mg, 0.0852 mmol) were added. The mixture was stirred for 15 minutes, followed by the addition of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (30.0 mg, 0.0609 mmol, prepared as described in Example 1, Step H, except worked up to provide the free base). After two hours, the reaction mixture was partitioned between ethyl acetate and water. The organic layer was washed with water, 0.1N NaOH and sat. NaCl, dried over sodium sulfate and concentrated. The residue was stirred in a 1:1 mixture of DCM:TFA for 1 hour, concentrated, and stirred in methanol (1 mL) containing ethylenediamine (0.2 mL) until the deprotection was complete. Purification via preparative HPLC-MS (C18 eluting with a gradient of MeCN/H$_2$O containing 0.15% NH$_4$OH), afforded the desired compound as a white powder. Yield: 0.014 g (39%); LC-MS: 594.4 (M+H)$^+$. $^1$H NMR (400 MHz, DMSO-d$_6$): δ 12.14 (br s, 1H), 8.82 (s, 1H), 8.69 (s, 1H), 8.42 (s, 1H), 7.90 (s, 1H), 7.61 (dd, 1H), 7.07 (dd, 1H), 4.07 (ddd, 1H), 3.77-3.72 (m, 2H), 3.70 (s, 2H), 3.63-3.48 (m, 5H), 3.31-3.22 (m, 1H), 3.16-3.07 (m, 1H), 2.60-2.53 (m, 1H), 2.25 (s, 6H), 1.85-1.73 (m, 1H), 1.71-1.59 (m, 1H), 1.37-1.18 (m, 2H). $^{19}$F NMR (400 MHz, DMSO-d$_6$): δ −69.45 (s, 3F).

Example 371

{1-(1-{[6-[(methylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile trifluoroacetate salt

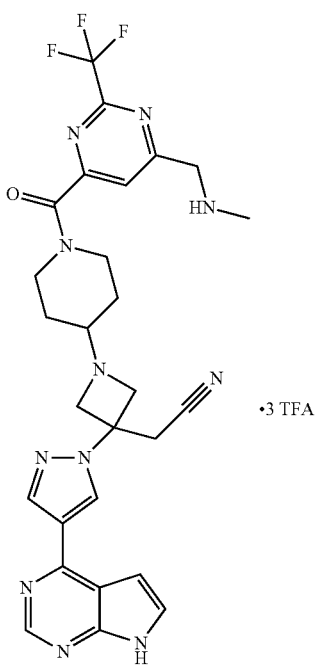 [SMILES: CNCc1cc(C(=O)N2CCC(N3CC(CC#N)(n4cc(-c5ncnc6[nH]ccc56)cn4)C3)CC2)nc(C(F)(F)F)n1]

Step A. 6-[(methylamino)methyl]-2-(trifluoromethyl)pyrimidine-4-carboxylic acid

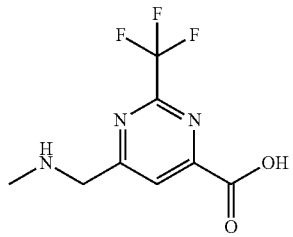 [SMILES: CNCc1cc(C(=O)O)nc(C(F)(F)F)n1]

A solution of methylamine (33 wt % in Ethanol, 1.12 mmol, Aldrich) was added portionwise to a solution of ethyl 6-(bromomethyl)-2-(trifluoromethyl)pyrimidine-4-carboxylate (0.150 g, 0.321 mmol, Example 5, Step A) in methylene chloride (3.0 mL), until reaction was complete. Solvent was removed in vacuo. The residue was dissolved in tetrahydrofuran (7.0 mL) and water (2.0 mL), and lithium hydroxide monohydrate (0.135 g, 3.21 mmol) was added. After a 5 minute reaction time, the mixture was treated with 1N HCl to adjust the pH to 7, then was purified using preparative HPLC-MS (C18 eluting with a gradient of MeCN/H$_2$O containing 0.15% NH$_4$OH). LC-MS: 236.1 (M+H)$^+$.

Step B. {1-(1-{[6-[(methylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile N,N,N',N'-Tetramethyl-O-(7-azabenzotriazol-1-yl)uranium hexafluorophosphate (32.4 mg, 0.0852 mmol) was added to a mixture of 6-[(methylamino)methyl]-2-(trifluoromethyl)pyrimidine-4-carboxylic acid (21.5 mg, 0.0913 mmol, from Step A), {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (30.0 mg, 0.0609 mmol, prepared as described in Example 1, Step H, except worked up to provide the free base) and triethylamine (33.9 µL, 0.244 mmol) in acetonitrile (0.30 mL) and THF (0.67 mL) and the reaction was stirred overnight. The reaction mixture was partitioned between ethyl acetate and water. The organic layer was separated and was washed successively with water, 0.1N NaOH and sat. NaCl, dried over sodium sulfate, filtered and concentrated. The residue was then stirred in a 1:1 mixture of DCM:TFA for 1 hour, concentrated, and subsequently stirred with ethylenediamine (0.2 mL) in methanol (1 mL) until deprotection was complete. Purification first via preparative HPLC-MS (C18 eluting with a gradient of MeCN/H$_2$O containing 0.15% NH$_4$OH) then again eluting with MeCN/H$_2$O containing 0.1% TFA afforded desired product as the trifluoroacetate salt. Yield: 0.0015 g (3%); LC-MS: 580.4 (M+H)$^+$.

Example 372

{1-(1-{[6-(azetidin-1-ylmethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

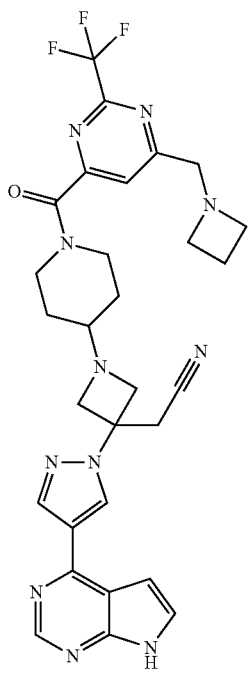 [SMILES: N#CCC1(n2cc(-c3ncnc4[nH]ccc34)cn2)CN(C2CCN(C(=O)c3cc(CN4CCC4)nc(C(F)(F)F)n3)CC2)C1]

Step A. Ethyl 6-(azetidin-1-ylmethyl)-2-(trifluoromethyl)pyrimidine-4-carboxylate

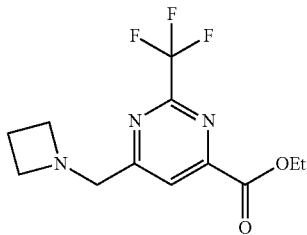 [SMILES: CCOC(=O)c1cc(CN2CCC2)nc(C(F)(F)F)n1]

Azetidine (0.110 mL, 1.6 mmol, Aldrich) was added to a solution of ethyl 6-(bromomethyl)-2-(trifluoromethyl)pyrimidine-4-carboxylate (0.78 g, 1.1 mmol, prepared as in Example 376, Step A) in DCM (11 mL). After stirring for 20 minutes, additional azetidine (0.10 mL, 1 mmol) was added. After 10 minutes, excess reagents and solvent were removed in vacuo. Flash chromatography, eluting with a gradient of 0-5% MeOH in DCM afforded purified product. Yield: 0.29 g (87%); LC-MS: 290.1 (M+H)$^+$. $^1$H NMR (400 MHz, CDCl$_3$): δ 8.24 (s, 1H), 4.52 (q, 2H), 3.90 (s, 2H), 3.39 (t, 4H), 2.19 (quin, 2H), 1.45 (t, 3H).

Step B. 6-(azetidin-1-ylmethyl)-2-(trifluoromethyl)pyrimidine-4-carboxylic acid hydrochloric acid salt

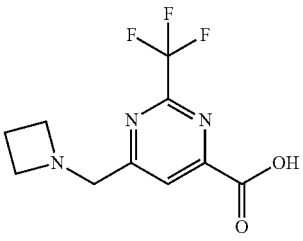

·HCl

Ethyl 6-(azetidin-1-ylmethyl)-2-(trifluoromethyl)pyrimidine-4-carboxylate (0.34 g, 1.2 mmol, from Step A) was dissolved in THF (6.0 mL) and water (1.5 mL) and lithium hydroxide monohydrate (0.108 g, 2.57 mmol) was added. After 15 minutes, THF was removed in vacuo and the mixture was treated with a solution of 1 N HCl (5.3 mL) and acetonitrile (7.0 mL). The mixture was then filtered and concentrated to afford a yellow solid, theoretical yield assumed. LC-MS: 262.1 (M+H)$^+$.

Step C. {1-(1-{[6-(azetidin-1-ylmethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile {1-Piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.150 g, 0.30 mmol, prepared as described in Example 1, Step H, except worked up to provide the free base) was added to a mixture of 6-(azetidin-1-ylmethyl)-2-(trifluoromethyl)pyrimidine-4-carboxylic acid (0.20 g, 0.46 mmol, as the hydrochloride salt from Step B), triethylamine (0.255 mL, 1.83 mmol) and N,N,N',N'-tetramethyl-O-(7-azabenzotriazol-1-yl)uronium hexafluorophosphate (0.150 g, 0.396 mmol) in tetrahydrofuran (3.0 mL) and DCM (3.0 mL) that was pre-stirred for 30 minutes. After stirring for 2 hours, the reaction mixture was diluted with ethyl acetate and washed successively with water, 0.1 N NaOH, and brine. The organic phase was dried over sodium sulfate, filtered and concentrated. The residue was dissolved in a 1:1 mixture of DCM:TFA, stirred for 1 hour, concentrated again, then stirred with methanol (3 mL) containing ethylenediamine (0.2 mL). After complete deprotection, the product was purified via preparative HPLC-MS (C18 eluting with a gradient of MeCN/H$_2$O containing 0.1% TFA) then again eluting with MeCN/H$_2$O containing 0.15% NH$_4$OH to afford desired product. Yield: 0.043 g (23%); LC-MS: 606.2 (M+H)$^+$. $^1$H NMR (400 MHz, DMSO-d$_6$): δ 12.15 (br s, 1H), 8.82 (s, 1H), 8.69 (s, 1H), 8.42 (s, 1H), 7.81 (s, 1H), 7.61 (d, 1H), 7.06 (d, 1H), 4.10-4.01 (m, 1H), 3.81 (s, 2H), 3.75 (dd, 2H), 3.62-3.44 (m, 5H), 3.31-3.21 (m, 5H), 3.14-3.05 (m, 1H), 2.60-2.52 (m, 1H), 2.04 (quin, 2H), 1.83-1.73 (m, 1H), 1.69-1.60 (m, 1H), 1.37-1.18 (m, 2H). $^{19}$F NMR (400 MHz, CD$_3$OD): δ −72.38 (s, 3F).

Example 373

{1-(1-{[6-[(diethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

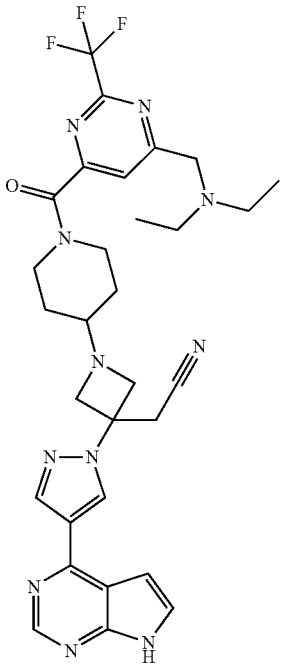 [SMILES: CCN(CC)Cc1cc(C(=O)N2CCC(N3CC(CC#N)(n4cc(-c5ncnc6[nH]ccc56)cn4)C3)CC2)nc(C(F)(F)F)n1]

Step A. 6-[(diethylamino)methyl]-2-(trifluoromethyl)pyrimidine-4-carboxylic acid

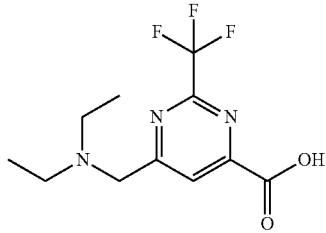 [SMILES: CCN(CC)Cc1cc(C(=O)O)nc(C(F)(F)F)n1]

To a solution of ethyl 6-(bromomethyl)-2-(trifluoromethyl)pyrimidine-4-carboxylate (0.15 g, 0.32 mmol, prepared as in Example 5, Step A) in methylene chloride (3.0 mL) was added N-ethylethanamine (0.13 mL, 1.3 mmol). After 30 minutes, the solvent was removed in vacuo. The ester was hydrolyzed by stirring with lithium hydroxide monohydrate (0.12 g, 3.0 mmol) in a mixture of tetrahydrofuran (5 mL) and water (2 mL). After 1 hour, 1N HCl was added dropwise to neutralize. Purification via preparative HPLC-MS (C18 eluting with a gradient of MeCN/H$_2$O containing 0.15% NH$_4$OH) afforded product as a light yellow solid. Yield: 0.050 g (60%); LC-MS: 278.0 (M+H)$^+$. $^1$H NMR (400 MHz, DMSO-d$_6$): δ 7.97 (s, 1H), 3.74 (s, 2H), 2.52 (q, 4H), 0.99 (t, 6H).

Step B. {1-(1-{[6-[(diethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile {1-Piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (30.0 mg, 0.0609 mmol, prepared as described in Example 1, Step H, except worked up to provide the free base) was added to a mixture of 6-[(diethylamino)methyl]-2-(trifluoromethyl)pyrimidine-4-carboxylic acid (22.8 mg, 0.0822 mmol, from Step A), triethylamine (33.9 µL, 0.244 mmol) and N,N,N',N'-tetramethyl-O-(7-azabenzotriazol-1-yl)uronium hexafluorophosphate (28.9 mg, 0.0761 mmol) in tetrahydrofuran (0.67 mL), that was prestirred for 30 minutes. After stirring overnight, the reaction mixture was partitioned between ethyl acetate and water. The organic layer was washed successively with water, 0.1N NaOH and sat. NaCl, dried over sodium sulfate, filtered and concentrated. The residue was stirred in a 1:1 mixture of DCM:TFA for 1 hour, and solvents were removed in vacuo. The residue was then stirred with ethylenediamine (0.2 mL) in methanol (1 mL) until deprotection was complete. Purification via preparative HPLC-MS (MeCN/H$_2$O containing 0.15% NH$_4$OH) afforded product. Yield: 0.0156 g (41%); LC-MS: 622.2 (M+H)$^+$. $^1$H NMR (400 MHz, DMSO-d$_6$): δ 12.14 (br s, 1H), 8.82 (s, 1H), 8.69 (s, 1H), 8.42 (s, 1H), 7.91 (s, 1H), 7.61 (d, 1H), 7.06 (d, 1H), 4.06 (ddd, 1H), 3.82 (s, 2H), 3.75 (d, 2H), 3.62-3.46 (m, 5H), 3.31-3.21 (m, 1H), 3.16-3.06 (m, 1H), 2.55 (q, 4H), 1.85-1.74 (m, 1H), 1.70-1.60 (m, 1H), 1.37-1.18 (m, 2H), 0.98 (t, 6H). $^{19}$F NMR (400 MHz, DMSO-d$_6$): δ −69.46 (s, 3F).

Example 374

{1-(1-{[6-{[ethyl(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

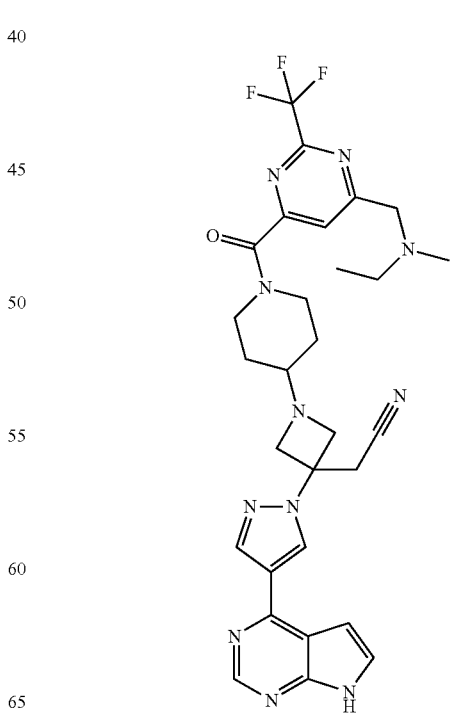

Step A. 6-{[yl(ethyl(methyl)amino]methyl}-2-(trifluoromethyl)pyrimidine-4-carboxylic acid

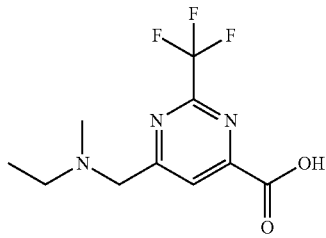 [SMILES: CCN(C)Cc1cc(C(=O)O)nc(C(F)(F)F)n1]

N-methylethanamine (96 µL, 1.1 mmol) was added to a solution of ethyl 6-(bromomethyl)-2-(trifluoromethyl)pyrimidine-4-carboxylate (0.13 g, 0.28 mmol, prepared as in Example 5, Step A) in methylene chloride (2.6 mL). After stirring for 30 minutes, solvent was removed in vacuo. The ester was hydrolyzed by stirring with lithium hydroxide monohydrate (0.12 g, 2.8 mmol) in tetrahydrofuran (4 mL) and water (2 mL) for 1 hour. 1N HCl was added dropwise to adjust the pH to 7. Purification via preparative HPLC-MS (C18 eluting with a gradient of MeCN/H$_2$O containing 0.15% NH$_4$OH) afforded product. Yield: 0.043 g (58%); LC-MS: 264.1 (M+H)$^+$. $^1$H NMR (300 MHz, DMSO-d$_6$): δ 8.03 (s, 1H), 3.75 (s, 2H), 2.51 (q, 2H), 2.22 (s, 3H), 1.05 (t, 3H).

Step B. {1-(1-{[6-{[ethyl(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile After prestirring a mixture of 6-{[ethyl(methyl)amino]methyl}-2-(trifluoromethyl)pyrimidine-4-carboxylic acid (40.1 mg, 0.152 mmol, from Step A), triethylamine (56.6 µL, 0.406 mmol) and N,N,N',N'-tetramethyl-O-(7-azabenzotriazol-1-yl)uranium hexafluorophosphate (54.0 mg, 0.142 mmol) in tetrahydrofuran (1.1 mL) for 30 minutes, {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (50.0 mg, 0.101 mmol, prepared as described in Example 1, Step H, except worked up to provide the free base) was added and the reaction stirred overnight. The reaction mixture was partitioned between ethyl acetate and water. The organic layer was successively washed with water, 0.1N NaOH and sat. NaCl, dried over sodium sulfate, filtered and concentrated. The product was deprotected by stirring first in a 1:1 mixture of DCM:TFA for 1 hour, followed by evaporation and stirring with ethylenediamine (0.2 mL) in methanol (1 mL) until deprotection was complete. Purification via preparative HPLC-MS (C18 eluting with a gradient of MeCN/H$_2$O containing 0.15% NH$_4$OH) afforded product. Yield: 0.025 g (41%); LC-MS: 608.2 (M+H)$^+$. $^1$H NMR (400 MHz, DMSO-d$_6$): δ 12.14 (br s, 1H), 8.82 (s, 1H), 8.69 (s, 1H), 8.42 (s, 1H), 7.89 (s, 1H), 7.61 (d, 1H), 7.06 (d, 1H), 4.11-4.02 (m, 1H), 3.78-3.71 (m, 4H), 3.63-3.48 (m, 5H), 3.32-3.21 (m, 1H), 3.17-3.07 (m, 1H), 2.62-2.53 (m, 1H), 2.48 (q, 2H), 2.21 (s, 3H), 1.84-1.74 (m, 1H), 1.70-1.61 (m, 1H), 1.37-1.18 (m, 2H), 1.03 (t, 3H). $^{19}$F NMR (400 MHz, DMSO-d$_6$): δ −69.45 (s, 3F).

Example 375

{1-(1-{3-(difluoromethyl)-5-[(dimethylamino)methyl]benzoyl}piperidin-4-yl)-3-[4-(7H-pyrrolo[2,3-d]pyrimidin-4-yl)-1H-pyrazol-1-yl]azetidin-3-yl}acetonitrile

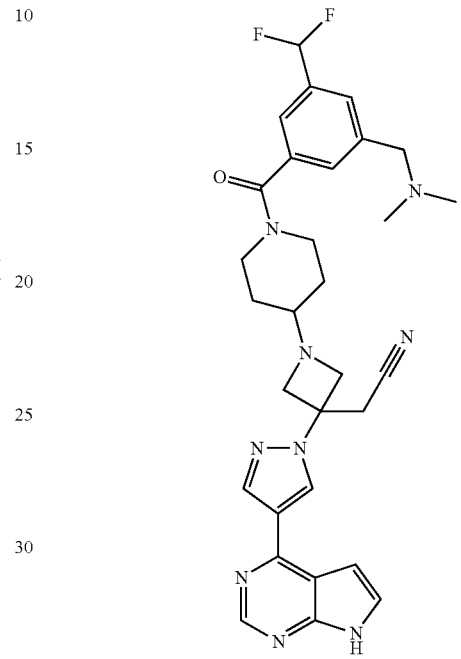

Step A. methyl 3-[(dimethylamino)methyl]-5-(hydroxymethyl)benzoate

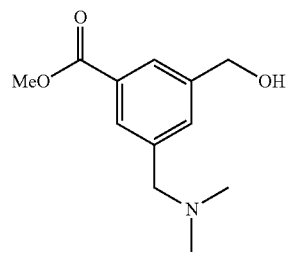

To a reaction vial was added methyl 3-bromo-5-(hydroxymethyl)benzoate (1.2 g, 4.9 mmol, prepared as described in WO 2003048111 from dimethyl 5-bromoisophthalate, Alfa Aesar), cesium carbonate (4.79 g, 14.7 mmol), dicyclohexyl(2',4',6'-triisopropylbiphenyl-2-yl)phosphine (280 mg, 0.59 mmol, Aldrich), potassium [(dimethylamino)methyl](trifluoro)borate(1−) (0.970 g, 5.88 mmol, Aldrich), palladium acetate (66 mg, 0.29 mmol) and THF:H$_2$O (10:1, 30 mL). The reaction mixture was degassed by purging with a stream of nitrogen for 10 minutes. The vial was sealed and heated at 80° C. for 17 hours. The reaction mixture was partitioned between water and ethyl acetate. The organic layer was was washed twice with water. The combined aqueous portions were then saturated with NaCl, and the product was extracted with eight portions of DCM.

The extracts were dried over sodium sulfate, filtered and concentrated to afford product as a colorless oil. Yield: 0.37 g (34%); LC-MS: 224.1 (M+H)+. 1H NMR (300 MHz, CDCl3): δ 7.94 (s, 1H), 7.88 (s, 1H), 7.56 (s, 1H), 4.74 (s, 2H), 3.91 (s, 3H), 3.46 (s, 2H), 2.24 (s, 6H).

Step B. methyl 3-[(dimethylamino)methyl]-5-form-ylbenzoate

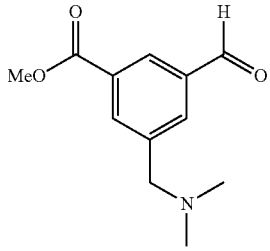 [SMILES: COC(=O)c1cc(C=O)cc(CN(C)C)c1]

Manganese(IV) oxide (0.72 g, 8.3 mmol) was added to methyl 3-[(dimethylamino)methyl]-5-(hydroxymethyl)benzoate (0.37 g, 1.6 mmol, from Step A) in Toluene (15 mL). The mixture was heated to 105° C. for 2 hours, then was cooled to room temperature and filtered. Solvent was removed from the filtrate in vacuo to afford the product as a colorless oil. Yield: 0.30 g (82%); LC-MS: 222.1 (M+H)+. 1H NMR (400 MHz, CDCl3): δ 10.07 (s, 1H), 8.43 (dd, 1H), 8.25 (dd, 1H), 8.05 (dd, 1H), 3.96 (s, 3H), 3.54 (s, 2H), 2.26 (s, 6H).

Step C. methyl 3-(difluoromethyl)-5-[(dimethylamino)methyl]benzoate

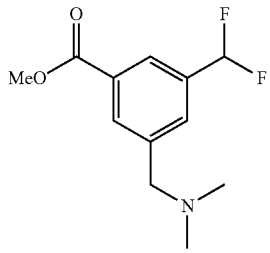 [SMILES: COC(=O)c1cc(CN(C)C)cc(C(F)F)c1]

Methyl 3-[(dimethylamino)methyl]-5-formylbenzoate (99 mg, 0.45 mmol, from Step B), was stirred in Deoxo-Fluor® (495 μL, 2.69 mmol) containing ethanol (5 μL, 0.09 mmol) for 24 hours. The mixture was quenched by dropwise addition into ice-cold saturated NaHCO3 solution. The product was isolated by extraction using DCM. The organic extract was washed twice with water, once with brine, was dried over sodium sulfate, filtered and concentrated to afford product as a light yellow oil which was used without further purification. Yield: 0.046 g (30%); LC-MS: 244.1 (M+H)+. 1H NMR (400 MHz, CDCl3): δ 8.09 (s, 2H), 7.69 (s, 1H), 6.68 (t, 1H), 3.94 (s, 3H), 3.36 (s, 2H), 2.25 (s, 6H).

Step D. 3-(difluoromethyl)-5-[(dimethylamino)methyl]benzoic acid

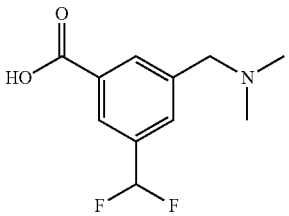 [SMILES: CN(C)Cc1cc(C(=O)O)cc(C(F)F)c1]

Lithium hydroxide monohydrate (65.2 mg, 1.55 mmol) in water (0.7 mL) was added to a solution of methyl 3-(difluoromethyl)-5-[(dimethylamino)methyl]benzoate (45 mg, 0.13 mmol, from Step C) in tetrahydrofuran (2 mL). Upon stirring for 3.5 hours, the mixture was treated with 1N HCl to adjust the pH to 7, then THF was removed by rotary evaporation. Acetonitrile was added to make a 1:1 ACN:water mixture, the mixture was filtered, and the filtrate was purified via preparative HPLC-MS (C18 eluting with a gradient of MeCN/H2O containing 0.15% NH4OH) to afford product as a white solid. Yield: 0.030 g (100%); LC-MS: 230.1 (M+H)+. 1H NMR (300 MHz, DMSO-d6): δ 7.95 (s, 2H), 7.50 (s, 1H), 7.05 (t, 1H), 3.44 (s, 2H), 2.15 (s, 6H).

Step E. {1-(1-{3-(difluoromethyl)-5-[(dimethylamino)methyl]benzoyl}piperidin-4-yl)-3-[4-(7H-pyrrolo[2,3-d]pyrimidin-4-yl)-1H-pyrazol-1-yl]azetidin-3-yl}acetonitrile A mixture of 3-(difluoromethyl)-5-[(dimethylamino)methyl]benzoic acid (14.0 mg, 0.0609 mmol, from Step D), Triethylamine (28.3 μL, 0.203 mmol) and N,N,N',N'-tetramethyl-O-(7-azabenzotriazol-1-yl)uronium hexafluorophosphate (21.2 mg, 0.0558 mmol) in tetrahydrofuran (0.56 mL) was stirred for 15 minutes. {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (25.0 mg, 0.0507 mmol, prepared as described in Example 1, Step H, except worked up to provide the free base) was added and the reaction was stirred for two hours. The reaction mixture was partitioned between ethyl acetate and water. The organic portion was washed with water, 0.1N NaOH and sat. NaCl, dried over sodium sulfate, filtered and concentrated. The residue was stirred in 1:1 DCM:TFA for 1 hour, solvents were removed in vacuo, and the resulting residue stirred in methanol (1 mL) containing ethylenediamine (0.2 mL) until deprotection was complete. Purification via preparative HPLC-MS (C18 eluting with a gradient of MeCN/H2O containing 0.15% NH4OH) afforded product as a white powder. Yield: 0.012 g (40%); LC-MS: 574.3 (M+H)+. 1H NMR (400 MHz, DMSO-d6): δ 12.09 (br s, 1H), 8.82 (s, 1H), 8.69 (s, 1H), 8.42 (s, 1H), 7.61 (d, 1H), 7.56 (s, 1H), 7.46-7.41 (m, 2H), 7.07 (t, 1H), 7.07 (d, 1H), 4.17-4.03 (m, 1H), 3.75 (d, 2H), 3.62-3.25 (m, 7H), 3.22-3.03 (m, 2H), 2.58-2.51 (m, 1H), 2.15 (s, 6H), 1.85-1.55 (m, 2H), 1.33-1.12 (m, 2H).

Example 376

{1-(1-{[6-(pyrrolidin-1-ylmethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile (trifluoroacetate salt: 4 TFA)

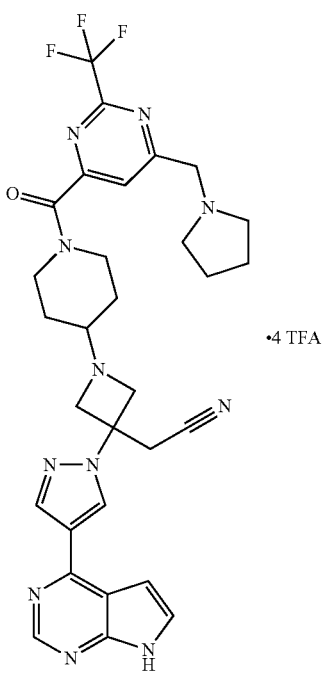 [SMILES: N#CCC1(n2cc(-c3ncnc4[nH]ccc34)cn2)CN(C2CCN(C(=O)c3cc(CN4CCCC4)nc(C(F)(F)F)n3)CC2)C1]

·4 TFA

Step A. ethyl 6-(bromomethyl)-2-(trifluoromethyl)pyrimidine-4-carboxylate

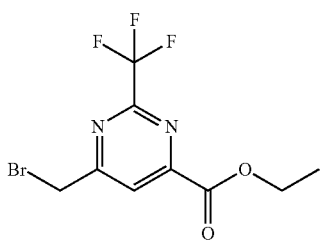

A solution of ethyl 6-methyl-2-(trifluoromethyl)pyrimidine-4-carboxylate (2.00 g, 8.54 mmol, prepared as described in WO2007/090748) in acetic acid (12 mL) was treated with bromine (1.36 g, 8.54 mmol) and the reaction was heated to 80° C. in a sealed vial for 30 minutes, at which time it was decolorized. The mixture containing unreacted starting material, desired product, and over brominated product, was rotovapped and azeotroped once with toluene. The percent by weight of desired component was determined by NMR and the mixture used without further purification. Yield: 1.62 g (61%); LC-MS: 313.0, 315.0 (M+H)$^+$. $^1$H NMR (300 MHz, CDCl$_3$): δ 8.32 (s, 1H), 4.60 (s, 2H), 4.54 (q, 2H), 1.46 (t, 3H).

Step B. ethyl 6-[(acetyloxy)methyl]-2-(trifluoromethyl)pyrimidine-4-carboxylate

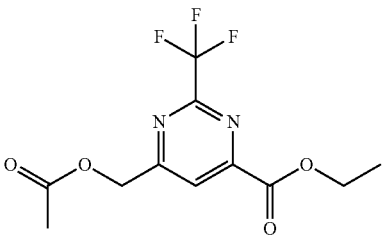 [SMILES: CCOC(=O)c1cc(COC(C)=O)nc(C(F)(F)F)n1]

Ethyl 6-(bromomethyl)-2-(trifluoromethyl)pyrimidine-4-carboxylate (1.62 g, 5.17 mmol, from Step A) was dissolved in acetonitrile (15 mL) and sodium acetate (2.8 g, 34 mmol) was added. The mixture was heated to 80° C. for 4 hours, then stood at room temperature overnight. Acetonitrile was removed in vacuo. The residue was partitioned between water and ethyl acetate and the aqueous layer was extracted with two further portions of ethyl acetate. The combined extracts were washed with water, then brine, dried over sodium sulfate, filtered and concentrated. Flash chromatography, eluting with a gradient from 0-60% ethyl acetate/hexane afforded purified product. Yield: 0.95 g (63%); LC-MS: 293.0 (M+H)$^+$. $^1$H NMR (300 MHz, CDCl$_3$): δ 8.15 (s, 1H), 5.36 (s, 2H), 4.53 (q, 2H), 2.25 (s, 3H), 1.46 (t, 3H).

Step C. 6-[(acetyloxy)methyl]-2-(trifluoromethyl)pyrimidine-4-carboxylic acid

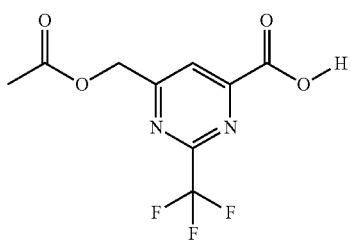 [SMILES: CC(=O)OCc1cc(C(=O)O)nc(C(F)(F)F)n1]

A solution of ethyl 6-[(acetyloxy)methyl]-2-(trifluoromethyl)pyrimidine-4-carboxylate (0.95 g, 3.2 mmol, from Step B) in tetrahydrofuran (8.7 mL) at 0° C. was treated with Lithium hydroxide, monohydrate (140 mg, 3.2 mmol) in water (1.3 mL). The reaction was stirred for 15 minutes, then was treated with 1N HCl to pH~4 while still in the ice bath. THF was removed from the mixture in vacuo. The product was extracted first with ethyl acetate, then with several portions of 10% isopropanol in CHCl$_3$, including periodic adjustment of pH as necessary. The extracts were combined and dried over sodium sulfate, filtered and concentrated to afford a yellow oil, which was used without further purification.

Yield: 0.86 g (100%); LC-MS: 265.0 (M+H)$^+$. $^1$H NMR (300 MHz, CDCl$_3$): δ 8.25 (s, 1H), 5.35 (s, 2H), 2.23 (s, 3H).

Step D. [6-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)carbonyl]-2-(trifluoromethyl)pyrimidin-4-yl]methyl acetate

Step E. {1-(1-{[6-(hydroxymethyl)-2-(trifluoromethyl)pyrimidin-4-yl]carbonyl}piperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile

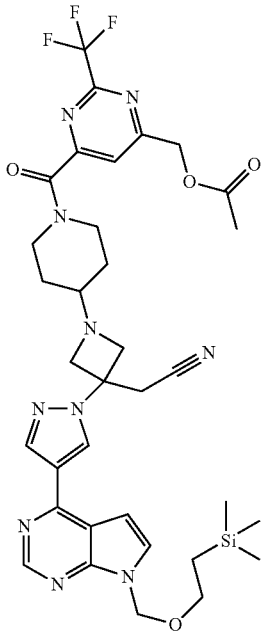 [SMILES: CC(=O)OCc1cc(C(=O)N2CCC(N3CC(CC#N)(n4cc(-c5ncnc6c5ccn6COCC[Si](C)(C)C)cn4)C3)CC2)nc(C(F)(F)F)n1]

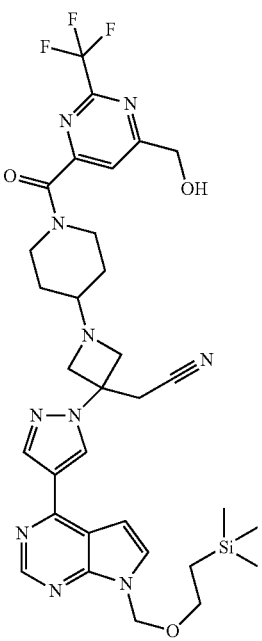 [SMILES: C[Si](C)(C)CCOCn1ccc2c(-c3cnn(C4(CC#N)CN(C5CCN(C(=O)c6cc(CO)nc(C(F)(F)F)n6)CC5)C4)c3)ncnc21]

{1-Piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.89 g, 1.8 mmol, prepared as described in Example 1, Step H, except worked up to provide the free base) and 6-[(acetyloxy)methyl]-2-(trifluoromethyl)pyrimidine-4-carboxylic acid (0.572 g, 2.16 mmol, from Step C) were dissolved in N,N-dimethylformamide (18 mL). Triethylamine (1.2 mL, 9.0 mmol) and benzotriazol-1-yloxytris(dimethylamino)phosphonium hexafluorophosphate (958 mg, 2.16 mmol) were added. The reaction was stirred overnight. The reaction mixture was partitioned between ethyl acetate and water. The aqueous was extracted with three portions of ethyl acetate. The combined extracts were washed twice with water and once with brine, dried over sodium sulfate, filtered and concentrated. Flash chromatography, eluting with a gradient from 0–5% methanol in ethyl acetate, afforded desired product. Yield: 0.85 g (64%); LC-MS: 739.2 (M+H)$^+$. $^1$H NMR (300 MHz, CDCl$_3$): δ 8.85 (s, 1H), 8.40 (s, 1H), 8.31 (s, 1H), 7.82 (s, 1H), 7.41 (d, 1H), 6.80 (d, 1H), 5.68 (s, 2H), 5.32 (s, 2H), 4.26-4.16 (m, 1H), 3.87-3.72 (m, 3H), 3.64 (dd, 2H), 3.55 (dd, 2H), 3.48-3.35 (m, 3H), 3.29 (ddd, 1H), 2.64-2.54 (m, 1H), 2.04 (s, 3H), 1.92-1.73 (m, 2H), 1.61-1.43 (m, 2H), 0.92 (dd, 2H), –0.06 (s, 9H).

To a solution of [6-[(4-{3-(cyanomethyl)-3-[4-(7-{[2-trimethylsilyl)ethoxy]methyl}-7H-pyrrolo[2,3-d]pyrimidin-4-yl)-1H-pyrazol-1-yl]azetidin-1-yl)carbonyl]-2-(trifluoromethyl)pyrimidin-4-yl]methyl acetate (0.85 g, 1.15 mmol, from Step D) in THF (16 mL) at room temperature was added a solution of lithium hydroxide, monohydrate (0.072 g, 1.7 mmol) in water (4 mL). The reaction was stirred for 45 minutes, then was neutralized by the addition of 1N HCl and the product was extracted with ethyl acetate. The extracts were combined and dried over sodium sulfate, decanted and concentrated to afford a yellow foam, which was used without further purification. Yield: 0.72 g (90%); LC-MS: 697.2 (M+H)$^+$. $^1$H NMR (300 MHz, CDCl$_3$): δ 8.86 (s, 1H), 8.44 (s, 1H), 8.31 (s, 1H), 7.92 (s, 1H), 7.42 (d, 1H), 6.81 (d, 1H), 5.68 (s, 2H), 4.92 (s, 2H), 4.28-4.17 (m, 1H), 3.89-3.71 (m, 3H), 3.71-3.61 (m, 2H), 3.55 (dd, 2H), 3.47-3.34 (m, 3H), 3.33-3.21 (m, 1H), 2.68-2.53 (m, 1H), 1.93-1.68 (m, 2H), 1.60-1.41 (m, 2H), 0.92 (dd, 2H), –0.06 (s, 9H).

Step F. {1-(1-{[6-(pyrrolidin-1-ylmethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile (trifluoroacetate salt: 4 TFA)

To a solution of {1-(1-{[6-(hydroxymethyl)-2-(trifluoromethyl)pyrimidin-4-yl]carbonyl}piperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.030 g, 0.043 mmol, from Step E) and triethylamine (0.015 mL, 0.11 mmol) in methylene chloride (1 mL) at 0° C. was added methanesulfonyl chloride (0.006 mL, 0.08 mmol). The reaction was allowed to warm to room temperature immediately after addition of mesyl chloride (MsCl). When mesylate formation was confirmed to be complete, the solution of mesylate was added to a mixture of pyrrolidine (0.017 mL, 0.20 mmol, Aldrich) and a few drops of triethylamine in DCM (0.2 mL). The displacement reaction was heated to 40° C. for 30 minutes. The reaction was cooled to room temperature and trifluoroacetic acid (1 mL) was added. After stirring for 1 hour, the solvents were removed in vacuo and replaced with methanol (1 mL) and ethylenediamine (0.2 mL). After stirring for 30 minutes, the product was purified by preparative HPLC-MS (Waters SunFire C18, 5 um particle size, 30×100 mm, eluting with a gradient of 5-23% MeCN in H$_2$O containing 0.1% TFA over 12 minutes). Yield: 0.012 g (25%); LC-MS: 620.2 (M+H)$^+$. $^1$H NMR (300 MHz, CD$_3$OD): δ 9.10 (s, 1H), 8.90 (s, 1H), 8.59 (s, 1H), 8.01 (s, 1H), 7.83 (d, 1H), 7.29 (d, 1H), 4.95 (d, 2H), 4.85 (s, 2H), 4.77-4.66 (m, 3H), 4.02 (d, 1H), 3.95-3.15 (m, 8H), 3.12-2.99 (m, 1H), 2.31-2.03 (m, 6H), 1.77-1.51 (m, 2H). $^{19}$F NMR (300 MHz, CD$_3$OD): δ -72.21 (s, 3F), -77.61 (s, 12F).

Example 377

{1-(1-{[6-{[(3S)-3-fluoropyrrolidin-1-yl]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile
(trifluoroacetate salt: 4 TFA)

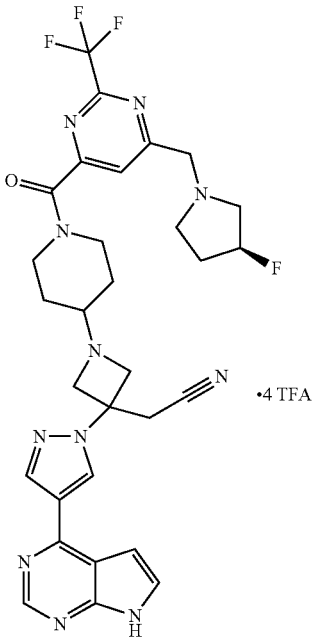 [SMILES: N#CCC1(n2cc(-c3ncnc4[nH]ccc34)cn2)CN(C2CCN(C(=O)c3cc(CN4CC[C@H](F)C4)nc(C(F)(F)F)n3)CC2)C1]

Prepared as in the manner of Example 376, using (3S)-3-fluoropyrrolidine hydrochloride (0.050 g, 0.40 mmol, Aldrich) and excess triethylamine in Step F, and was heated for 24 hours at 40° C. Yield: 0.012 g (26%); LC-MS: 638.3 (M+H)$^+$. $^1$H NMR (300 MHz, CD$_3$OD): δ 9.05 (s, 1H), 8.88 (s, 1H), 8.57 (s, 1H), 8.01 (s, 1H), 7.79 (d, 1H), 7.25 (d, 1H), 5.50 (d, 1H), 4.93 (s, 2H), 4.85 (d, 2H), 4.74-4.57 (m, 3H), 4.06-3.65 (m, 7H), 3.60-3.45 (m, 1H), 3.29-3.17 (m, 1H), 3.15-3.02 (m, 1H), 2.58-2.36 (m, 2H), 2.22 (d, 1H), 2.10 (d, 1H), 1.75-1.49 (m, 2H). $^{19}$F NMR (300 MHz, CD$_3$OD): δ -72.24 (s, 3F), -77.59 (s, 12F), -175.45 (br, 1F).

Example 378

{1-(1-{[6-{[(3R)-3-fluoropyrrolidin-1-yl]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile
(trifluoroacetate salt: 4 TFA)

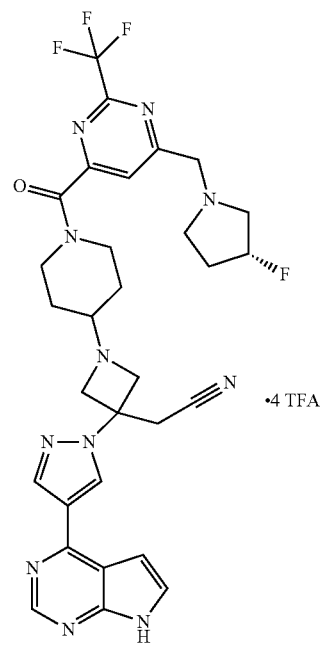 [SMILES: N#CCC1(n2cc(-c3ncnc4[nH]ccc34)cn2)CN(C2CCN(C(=O)c3cc(CN4CC[C@@H](F)C4)nc(C(F)(F)F)n3)CC2)C1]

Prepared as in the manner of Example 376, using (3R)-3-fluoropyrrolidine hydrochloride (0.025 g, 0.20 mmol, Oakwood). Yield: 0.012 g (26%); LC-MS: 638.3 (M+H)$^+$. $^1$H NMR (300 MHz, CD$_3$OD): δ 9.04 (s, 1H), 8.87 (s, 1H), 8.57 (s, 1H), 8.01 (s, 1H), 7.78 (d, 1H), 7.25 (d, 1H), 5.50 (d, 1H), 4.93 (s, 2H), 4.84 (d, 2H), 4.74-4.54 (m, 3H), 4.07-3.62 (m, 7H), 3.59-3.44 (m, 1H), 3.29-3.20 (m, 1H), 3.15-3.03 (m, 1H), 2.58-2.37 (m, 2H), 2.21 (d, 1H), 2.09 (d, 1H), 1.75-1.49 (m, 2H). $^{19}$F NMR (300 MHz, CD$_3$OD): δ -72.24 (s, 3F), -77.55 (s, 12F), -175.47 (br, 1F).

Example 379

{1-(1-{[6-[(3,3-difluoropyrrolidin-1-yl)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile (trifluoroacetate salt: 4 TFA)

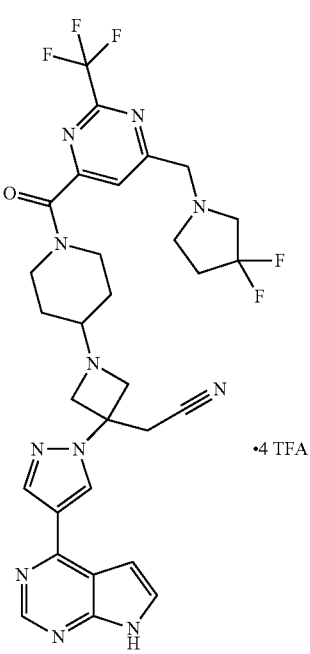 [SMILES: N#CCC1(n2cc(-c3ncnc4[nH]ccc34)cn2)CN(C2CCN(C(=O)c3cc(CN4CCC(F)(F)C4)nc(C(F)(F)F)n3)CC2)C1]

Example 380

{1-(1-{[6-[(tert-butylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile (trifluoroacetate salt: 3 TFA)

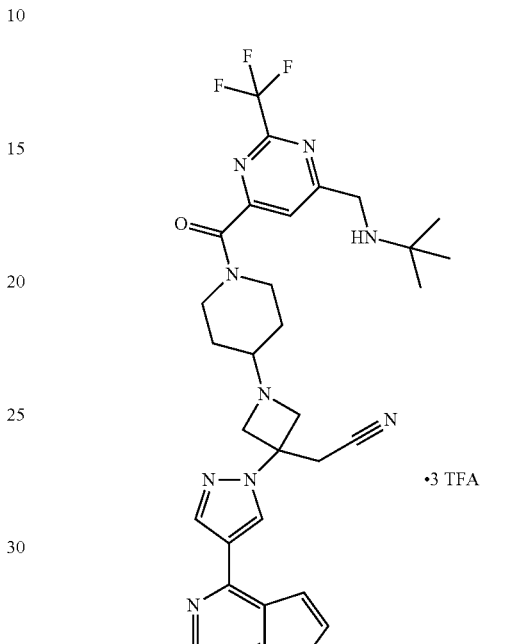

Prepared as in the manner of Example 376, using 3,3-difluoropyrrolidine hydrochloride (0.050 g, 0.40 mmol, Matrix) and excess triethylamine in Step F, and was heated for 24 hours at 40° C. Yield: 0.012 g (25%); LC-MS: 656.2 (M+H)$^+$. $^1$H NMR (300 MHz, CD$_3$OD): δ 9.07 (s, 1H), 8.89 (s, 1H), 8.58 (s, 1H), 7.99 (s, 1H), 7.81 (d, 1H), 7.26 (d, 1H), 4.95-4.87 (m, 2H), 4.76-4.62 (m, 3H), 4.24 (s, 2H), 4.04-3.92 (m, 1H), 3.71 (s, 2H), 3.65-3.50 (m, 1H), 3.40-3.14 (m, 5H), 3.12-2.99 (m, 1H), 2.44 (tt, 2H), 2.10 (d, 1H), 1.62 (dddd, 2H). $^{19}$F NMR (300 MHz, CD$_3$OD): δ −72.33 (s, 3F), −77.64 (s, 12F), −95.48 (tt, 2F).

Prepared as in the manner of Example 376, using tert-butylamine (0.050 mL, 0.48 mmol, Aldrich) and excess triethylamine in Step F, and was heated for 24 hours at 40° C. Yield: 0.012 g (28%); LC-MS: 622.3 (M+H)$^+$. $^1$H NMR (300 MHz, CD$_3$OD): δ 9.01 (s, 1H), 8.85 (s, 1H), 8.56 (s, 1H), 8.03 (s, 1H), 7.75 (d, 1H), 7.22 (d, 1H), 4.77 (d, 2H), 4.71-4.61 (m, 3H), 4.56 (d, 2H), 3.95 (br d, 1H), 3.69 (s, 2H), 3.56-3.39 (m, 1H), 3.30-3.20 (m, 1H), 3.17-3.04 (m, 1H), 2.19 (br d, 1H), 2.07 (br d, 1H), 1.73-1.52 (m, 2H), 1.49 (s, 9H). $^{19}$F NMR (300 MHz, CD$_3$OD): δ −72.02 (s, 3F), −77.47 (s, 9F).

Example 381

{1-(1-{[6-(hydroxymethyl)-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

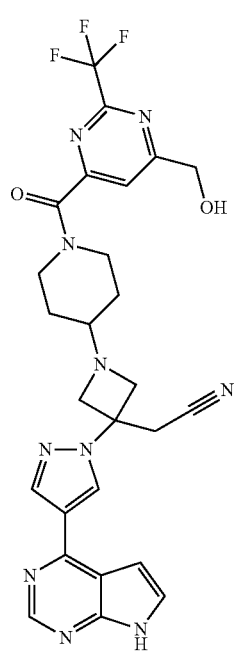 [SMILES: N#CCC1(n2cc(-c3ncnc4[nH]ccc34)cn2)CN(C2CCN(C(=O)c3cc(CO)nc(C(F)(F)F)n3)CC2)C1]

Example 382

{1-(1-{[6-[(isopropylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

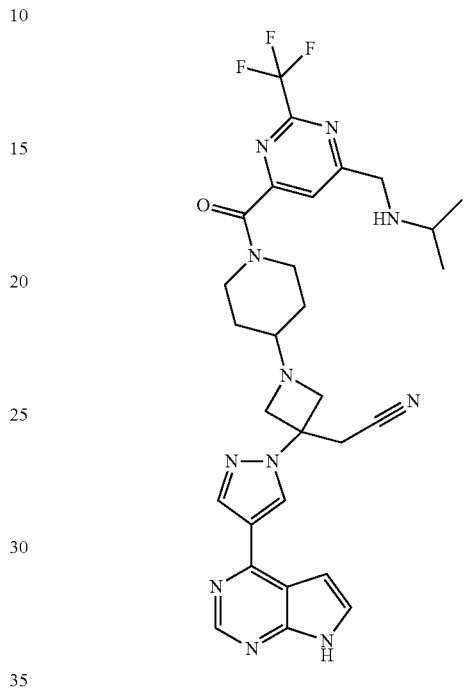

Lithium hydroxide monohydrate (3.6 mg, 0.085 mmol) in water (0.10 mL) was added to a solution of [6-[(4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}piperidin-1-yl)carbonyl]-2-(trifluoromethyl)pyrimidin-4-yl]methyl acetate (21 mg, 0.028 mmol, from Example 376, Step D) in tetrahydrofuran (0.40 mL). The mixture was stirred for 5 minutes and was then treated with 1N HCl to neutralize. Solvent was then removed in vacuo. The residue was stirred in a solution of 1:1 TFA/DCM for one hour, then solvents were removed in vacuo again. The residue was redissolved in MeOH (1 mL) and ethylenediamine (0.2 mL) was added. When deprotection was complete, the product was purified via preparative HPLC-MS (C18 eluting with a gradient of MeCN/H$_2$O containing 0.15% NH$_4$OH). Yield: 0.004 g (25%); LC-MS: 567.3 (M+H)$^+$. $^1$H NMR (400 MHz, DMSO-d$_6$): δ 12.14 (br s, 1H), 8.82 (s, 1H), 8.69 (s, 1H), 8.42 (s, 1H), 7.90 (s, 1H), 7.61 (d, 1H), 7.06 (d, 1H), 5.94 (br s, 1H), 4.71 (s, 2H), 4.12-4.02 (m, 1H), 3.75 (dd, 2H), 3.63-3.46 (m, 5H), 3.31-3.22 (m, 1H), 3.17-3.07 (m, 1h), 2.61-2.53 (m, 1H), 1.84-1.75 (m, 1H), 1.71-1.61 (m, 1H), 1.37-1.18 (m, 2H). $^{19}$F NMR (400 MHz, DMSO-d$_6$): δ −69.46 (s, 3F).

Methanesulfonyl chloride (2.8 μL, 0.036 mmol) in methylene chloride (0.20 mL) was added to a mixture of {1-(1-{[6-(hydroxymethyl)-2-(trifluoromethyl)pyrimidin-4-yl]carbonyl}piperidin-4-yl)-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (21 mg, 0.030 mmol, prepared as in Example 376, Step E) and triethylamine (8.4 μL, 0.060 mmol) in methylene chloride (1.0 mL) at 0° C. After 15 minutes, 2-propanamine (20 μL, 0.3 mmol) was added. The mixture was then heated to 40° C. After 1.5 hours, additional 2-Propanamine (20 μL, 0.3 mmol, Aldrich) was added and the reaction heated for a total of 3 hours at this temperature. The mixture was concentrated in vacuo. The residue was stirred for 1 hour in a 1:1 mixture of TFA/DCM, then concentrated again. The residue was redissolved in MeOH (1.0 mL) and ethylenediamine (0.2 mL) was added. The product was purified via preparative HPLC-MS (C18 eluting with a gradient of MeCN/H$_2$O containing 0.15% NH$_4$OH). Yield: 11.6 mg (63%); LC-MS: 608.4 (M+H)$^+$. $^1$H NMR (400 MHz, DMSO-d$_6$): δ 12.15 (br s, 1H), 8.82 (s, 1H), 8.69 (s, 1H), 8.42 (s, 1H), 7.97 (s, 1H), 7.61 (d, 1H), 7.07 (d, 1H), 41.2-4.02 (m, 1H), 3.94 (s, 2H), 3.75 (dd, 2H), 3.63-3.45 (m, 5H), 3.31-3.22 (m, 1H), 3.16-3.06 (m, 1H), 2.75 (septet, 1H), 2.61-2.53 (m, 1H), 1.84-1.75 (m, 1H), 1.70-1.60 (m, 1H), 1.36-1.19 (m, 2H), 1.01 (d, 6H). $^{19}$F NMR (400 MHz, DMSO-d$_6$): δ −69.46 (s, 3F).

Example 383

{1-(1-{[6-[(ethylamino)methyl]-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

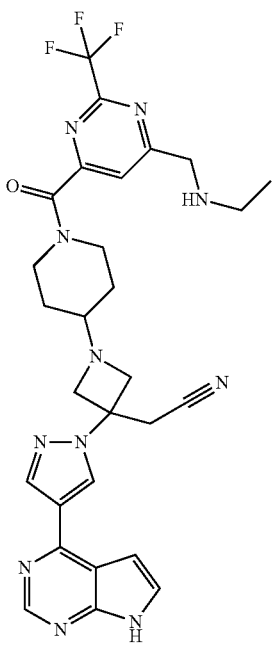 [SMILES: CCNCc1cc(C(=O)N2CCC(N3CC(CC#N)(n4cc(-c5ncnc6[nH]ccc56)cn4)C3)CC2)nc(C(F)(F)F)n1]

Prepared by the method of Example 382, using Ethylamine (0.10 mL, 1.8 mmol, Aldrich) and carrying out the substitution reaction at room temperature for 1 hour. Yield: 8.4 mg (47%); LC-MS: 594.2 (M+H)$^+$. $^1$H NMR (400 MHz, DMSO-d$_6$): δ 12.13 (br s, 1H), 8.82 (s, 1H), 8.69 (s, 1H), 8.42 (s, 1H), 7.95 (s, 1H), 7.61 (d, 1H), 7.06 (d, 1H), 4.13-4.02 (m, 1H), 3.93 (s, 2H), 3.75 (dd, 2H), 3.62-3.46 (m, 5H), 3.31-3.22 (m, 1H), 3.15-3.06 (m, 1H), 2.61-2.53 (m, 3H), 1.84-1.74 (m, 1H), 1.71-1.60 (m, 1H), 1.37-1.18 (m, 2H), 1.04 (t, 3H). $^{19}$F NMR (400 MHz, DMSO-d$_6$): δ −69.45 (s, 3F).

Example 384

{1-(1-{[6-{[(2-methoxyethyl)(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

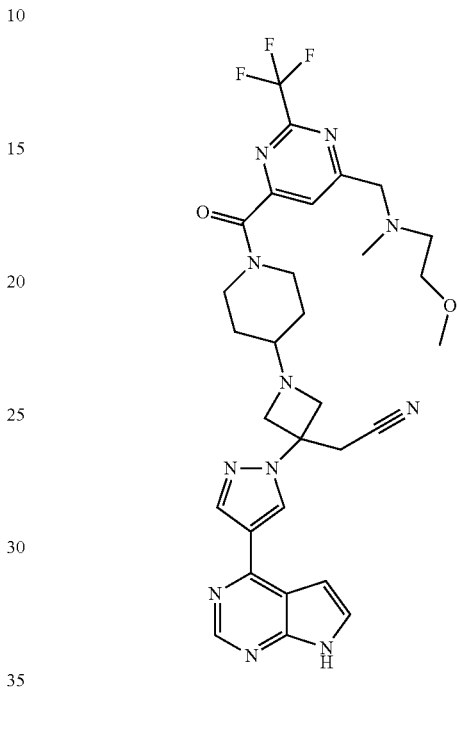

Prepared in the manner of Example 382, using 2-methoxy-N-methylethaneamine (0.077 g, 0.86 mmol, Oakwood) and the substitution carried out in a sealed vial at 60° C. for 7 hours. Yield: 0.007 g (26%); LC-MS: 638.3 (M+H)$^+$. $^1$H NMR (400 MHz, CD$_3$OD): δ 8.69 (s, 1H), 8.67 (s, 1H), 8.40 (s, 1H), 8.01 (s, 1H), 7.51 (d, 1H), 6.98 (d, 1H), 4.32-4.23 (m, 1h), 3.88 (s, 2H), 3.85-3.73 (m, 4H), 3.72-3.64 (m, 1H), 3.54 (t, 2H), 3.50 (s, 2H), 3.38-3.31 (m, 1H), 3.31 (s, 3H), 3.27-3.17 (m, 1H), 2.71 (t, 2H), 2.69-2.61 (m, 1H), 2.37 (s, 3H), 1.97-1.87 (m, 1H), 1.86-1.76 (m, 1H), 1.52-1.38 (m, 2H). $^{19}$F NMR (300 MHz, CD$_3$OD): δ −72.34 (s, 3F).

Example 385

{1-(1-{[6-{[(3-hydroxypropyl)(methyl)amino]methyl}-2-(trifluoromethyl)pyrimidin-4-yl]carbonyl}piperidin-4-yl)-3-[4-(7H-pyrrolo[2,3-d]pyrimidin-4-yl)-1H-pyrazol-1-yl]azetidin-3-yl}acetonitrile

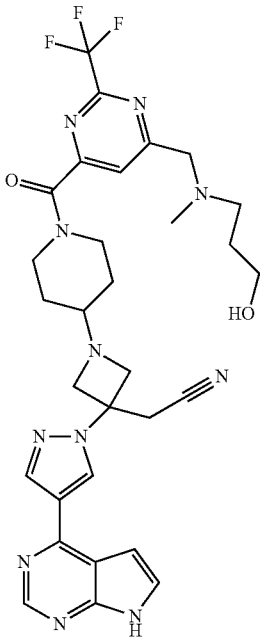 [SMILES: CN(CCCO)Cc1cc(C(=O)N2CCC(N3CC(CC#N)(n4cc(-c5ncnc6[nH]ccc56)cn4)C3)CC2)nc(C(F)(F)F)n1]

Prepared in the manner of Example 382, using 3-(methylamino)propanol (0.038 g, 0.43 mmol, TCI America) and the substitution carried out at 40° C. for 1 hour. Yield: 0.007 g (26%); LC-MS: 638.3 (M+H)⁺. ¹H NMR (400 MHz, CD₃OD): δ 8.69 (s, 1H), 8.67 (s, 1H), 8.40 (s, 1H), 7.94 (s, 1H), 7.51 (d, 1H), 6.99 (d, 1H), 4.33-4.23 (m, 1H), 3.86-3.74 (m, 6H), 3.74-3.66 (m, 1H), 3.63 (t, 2H), 3.50 (s, 2H), 3.38-3.18 (m, 2H), 2.70-2.62 (m, 1H), 2.59 (t, 2H), 2.32 (s, 3H), 1.97-1.88 (m, 1H), 1.86-1.79 (m, 1H), 1.75 (tt, 2H), 1.52-1.39 (m, 2H). ¹⁹F NMR (300 MHz, CD₃OD): δ −71.88 (s, 3F).

Example 386

Propyl 4-{3-(cyanomethyl)-3-[4-(7H-pyrrolo[2,3-d]pyrimidin-4-yl)-1H-pyrazol-1-yl]azetidin-1-yl}piperidine-1-carboxylate

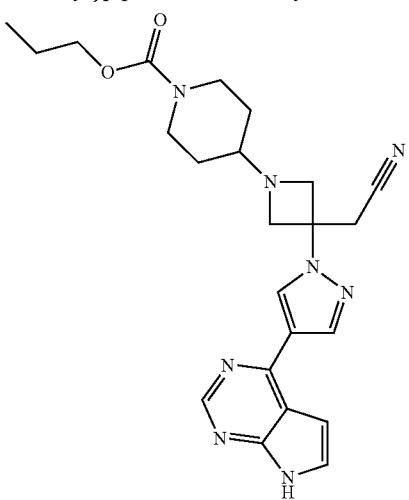

A solution of {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.010 g, 0.020 mmol) and propyl chloroformate (3.0 μL, 0.026 mmol) in methylene chloride (1 mL, 20 mmol) was stirred for 1.5 h. TFA, 1 mL, was added. After 1 hour, the solvent was removed by rotary evaporation to give an oil. The oil was dissolved in 1 mL MeOH and 50 microL ethylenediamine was added. After 1 hour, the reaction was purified by prep-HPLC (pH10) using a Waters XBridge C18, 5 μm particle size, 19×100 mm; mobile phase system: aqueous (0.1% NH₄OH)/acetonitrile; flow rate: 30 mL/min; separation gradient: 40-60% B in 5 min to give 5.3 mg white solid (58%). ¹H NMR (400 MHz, DMSO): δ 12.13 (1H, br); 8.83 (1H, s); 8.7 (1H, s); 8.42 (1H, s); 7.61 (1H, m); 7.05 (1H, m); 3.95 (2H, t); 3.75 (4H, m); 3.55 (4H, m); 3.0 (2H, br); 2.43 (1H, m); 1.65 (2H, m); 1.58 (2H, m); 1.15 (2H, m); 0.95 (3H, t). LCMS (M+1): 449.

Example 387

Cyclobutylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate

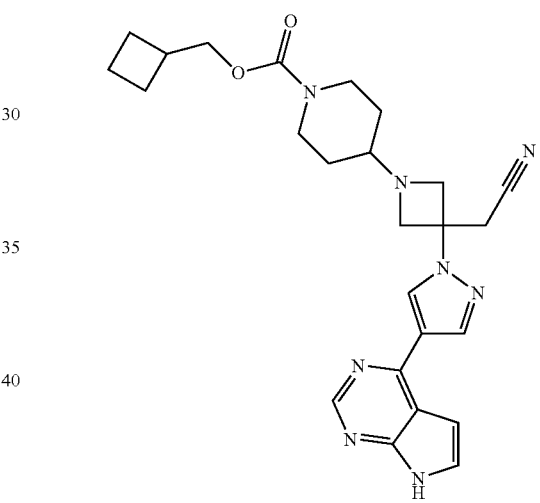

To a solution of cyclobutylmethanol (11 μL, 0.12 mmol) in methylene chloride (1 mL, 20 mmol) was added 2.02 M phosgene in toluene (0.045 mL, 0.091 mmol). After stirred for 2 hours, {1-piperidin-4-yl-3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile (0.020 g, 0.040 mmol) and N,N-diisopropylethylamine (0.040 mL, 0.23 mmol) were added and was stirred overnight. The solvent was removed by rotary evaporation to give an oil. The oil was then dissolved in 1 mL methanol and 100 microL ethylenediamine was added. After 1 hour, the reaction was purified by prep-HPLC (pH10) using a Waters XBridge C18, 5 μm particle size, 19×100 mm; mobile phase system: aqueous (0.1% NH₄OH)/acetonitrile; flow rate: 30 mL/min; separation gradient: 40-60% B in 5 min to give 15 mg white solid (78%). ¹H NMR (400 MHz, DMSO): δ 12.08 (1H, br); 8.75 (1H, s); 8.62 (1H, s); 8.35 (1H, s); 7.55 (1H, m); 7.0 (1H, m); 3.9 (2H, d); 3.65 (4H, m); 3.5 (4H, m); 2.9 (2H, br); 2.38 (1H, m); 1.91 (2H, m); 1.77 (2H, m); 1.61 (5H, m); 1.03 (2H, m). LCMS (M+1): 475.

The following compounds were prepared by methods analogous to those in Examples 386-387.

| Ex. | Structure | Name | MS (M + H) |
|---|---|---|---|
| 388 | 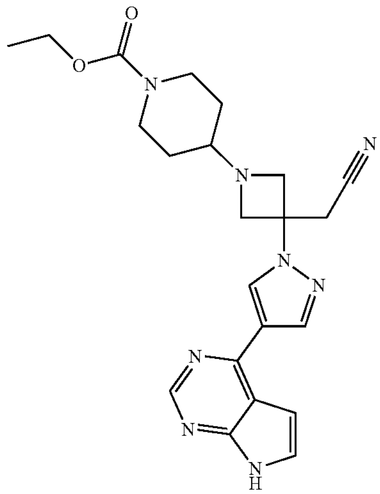 [SMILES: CCOC(=O)N1CCC(N2CC(CC#N)(n3cc(-c4ncnc5[nH]ccc45)cn3)C2)CC1] | ethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 435 |
| 389 | 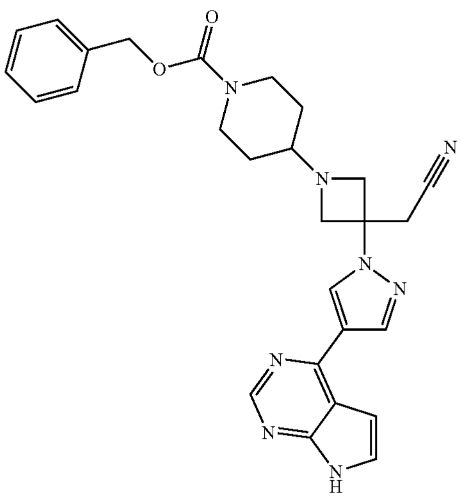 [SMILES: N#CCC1(n2cc(-c3ncnc4[nH]ccc34)cn2)CN(C2CCN(C(=O)OCc3ccccc3)CC2)C1] | benzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 497 |
| 390 | 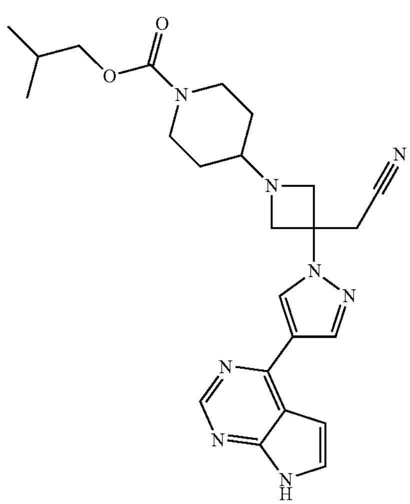 [SMILES: CC(C)COC(=O)N1CCC(N2CC(CC#N)(n3cc(-c4ncnc5[nH]ccc45)cn3)C2)CC1] | isobutyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 463 |

| Ex. | Structure | Name | MS (M + H) |
|---|---|---|---|
| 391 | 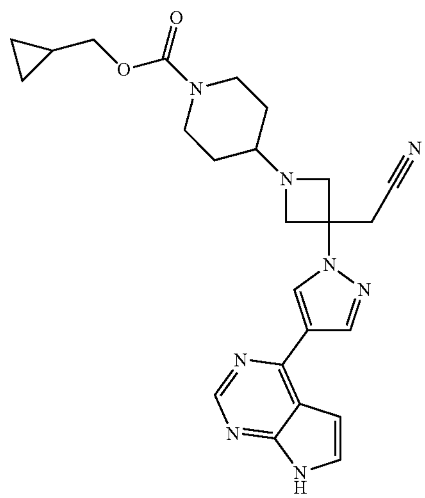 [SMILES: N#CCC1(n2cc(-c3ncnc4[nH]ccc34)cn2)CN(C2CCN(C(=O)OCC3CC3)CC2)C1] | cyclopropylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 461 |
| 392 | 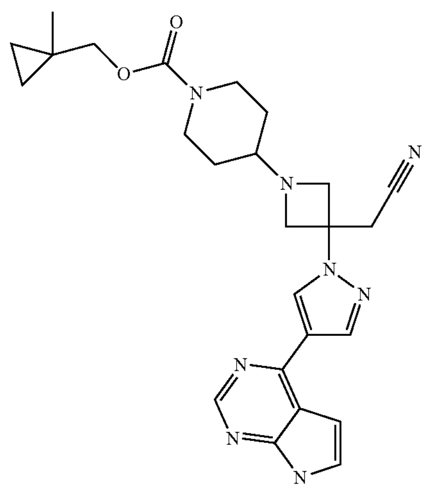 [SMILES: CC1(COC(=O)N2CCC(N3CC(CC#N)(n4cc(-c5ncnc6[nH]ccc56)cn4)C3)CC2)CC1] | (1-methylcyclopropyl)methyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 475 |
| 393 | 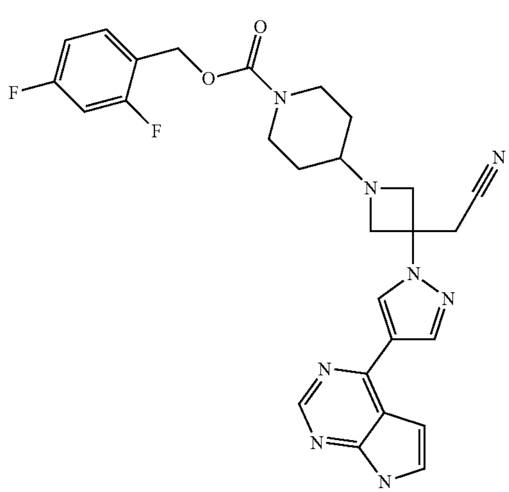 [SMILES: N#CCC1(n2cc(-c3ncnc4[nH]ccc34)cn2)CN(C2CCN(C(=O)OCc3ccc(F)cc3F)CC2)C1] | 2,4-difluorobenzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 533 |

| Ex. | Structure | Name | MS (M + H) |
|---|---|---|---|
| 394 | 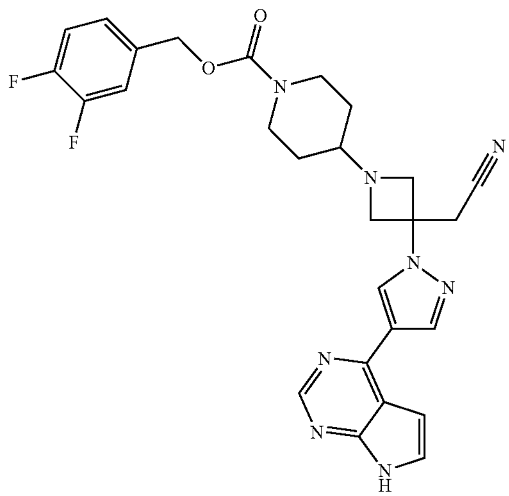 [SMILES: N#CCC1(n2cc(-c3ncnc4[nH]ccc34)cn2)CN(C2CCN(C(=O)OCc3ccc(F)c(F)c3)CC2)C1] | 3,4-difluorobenzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 533 |
| 395 | 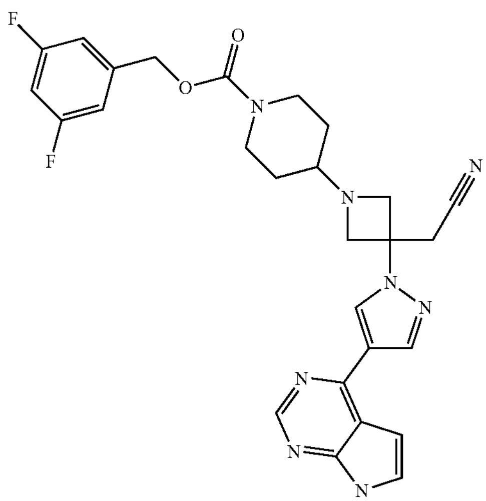 [SMILES: N#CCC1(n2cc(-c3ncnc4[nH]ccc34)cn2)CN(C2CCN(C(=O)OCc3cc(F)cc(F)c3)CC2)C1] | 3,5-difluorobenzyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 533 |
| 396 | 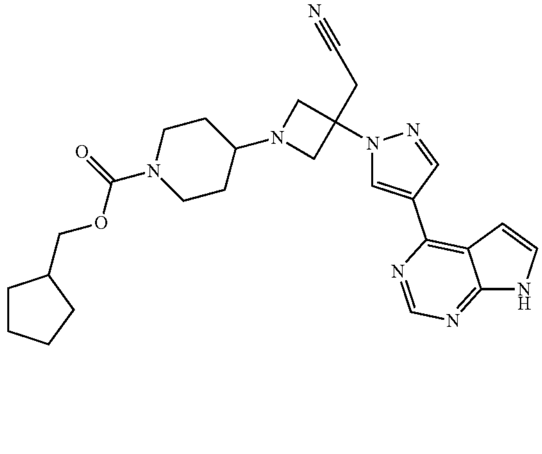 [SMILES: N#CCC1(n2cc(-c3ncnc4[nH]ccc34)cn2)CN(C2CCN(C(=O)OCC3CCCC3)CC2)C1] | cyclopentylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 547 |

| Ex. | Structure | Name | MS (M + H) |
|---|---|---|---|
| 397 | 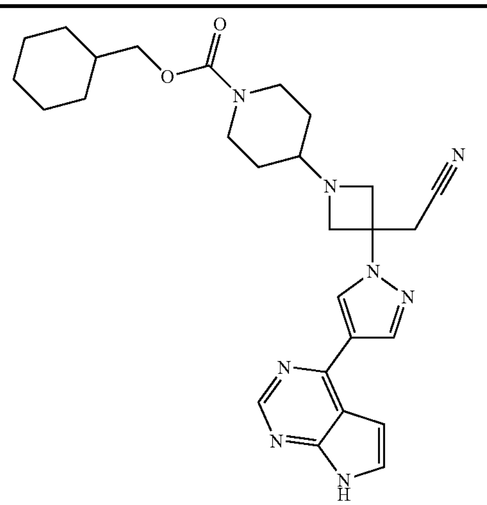 | cyclohexylmethyl 4-{3-(cyanomethyl)-3-[4-(7H-pyrrolo[2,3-d]pyrimidin-4-yl)-1H-pyrazol-1-yl]azetidin-1-yl}piperidine-1-carboxylate | 561 |

Ex. No. $^1$H NMR 388 (DMSO): δ 8.8 (1H, s); 8.68 (1H, s); 8.4 (1H, s); 7.6 (1H, d); 7.02 (1H, d); 4.0 (2H, q); 3.75 (4H, m); 3.55 (4H, m); 2.95 (2H, m); 2.4 (1H, m); 1.62 (2H, m); 1.18 (3H, t); 1.1 (2H, m)

389 (DMSO): δ 12.08 (1H, br); 8.8 (1H, s); 8.68 (1H, s); 8.40 (1H, s); 7.6 (1H, d); 7.35 (5H, m); 7.02 (1H, d); 5.03 (2H, s); 3.75 (4H, m); 3.57 (4H, m); 3.0 (1H, m); 2.42 (2H, m); 1.6 2(2H, m); 1.14 (2H, m)

394 (DMSO): δ 12.08 (1H, br); 8.78 (1H, s); 8.62 (1H, s); 8.37 (1H, s); 7.56 (1H, d); 7.39 (2H, m); 7.16 (1H, m); 7.0 (1H, d); 4.99 (2H, s); 3.7 (4H, m); 3.48 (4H, m); 2.98 (2H, br); 2.38 (1H, m); 1.6 (2H, m); 1.05 (2H, m)

395 (DMSO): δ 12.08 (1H, br); 8.78 (1H, s); 8.62 (1H, s); 8.38 (1H, s); 7.58 (1H, d); 7.13 (1H, m); 7.02 (2H, m); 7.0 (1H, d); 5.0 (2H, s); 3.7 (4H, m); 3.5 (4H, m); 2.98 (2H, br); 2.38 (1H, m); 1.6 (2H, m); 1.1 (2H, m)

396 (DMSO): δ 12.08 (1H, br); 8.77 (1H, s); 8.62 (1H, s); 8.37 (1H, s); 7.55 (1H, m); 7.0 (1H, m); 3.75 (2H, d); 3.65 (4H, m); 3.5 (4H, m); 2.95 (2H, br); 2.38 (1H, m); 2.05 (1H, m); 1.6 (4H, m); 1.46 (4H, m); 1.15 (2H, m); 1.03 (2H, m)

397 (DMSO): δ 12.08 (1H, br); 8.77 (1H, s); 8.62 (1H, s); 8.37 (1H, s); 7.55 (1H, m); 7.0 (1H, m); 3.75 (6H, m); 3.55 (4H, m); 2.95 (2H, br); 2.38 (1H, m); 1.67 (8H, m); 1.15 (5H, m); 0.95 (2H, m)

Example 398

Crystalline salts of {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile A. Glutarate Salt: A flask was charged with {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile free base (37.85 mg, 0.068 mmol, 1 eq) and 2-propanol (0.6 mL). The reaction mixture was stirred for 15 min to give a clear solution followed by adding of glutaric acid (12.1 mg, 0.092 mmol, 1.34 eq, Aldrich, Cat G3407). The reaction mixture was stirred for about 8 min to give a thick slurry, and continuously stirred for 5 h. The solid was collected by filtration, washed with heptane and dried to provide glutarate salt as an off-white crystal (39.9 mg, 85%, 1796-108).

The stoichiometric ratio of free base to glutaric acid was determined by $^1$H NMR as 1:1. The crystallinity of the glutarate salt was confirmed by XRPD. The DSC thermogram exhibited a melting endotherms, with an initial $T_{onset}$ at 206.26° C. and $T_{peak}$ at 207.63° C. The TGA showed a weight loss of 0.037% up to approximately 100° C. SEM image indicated that the glutarate salt has a rod-like crystal shape.

B. Citrate Salt: A reactor was charged with {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile free base (30.97 mg, 0.056 mmol, 1 eq) and ethanol (0.5 mL). To the clear solution was added citric acid (11.92 mg, 0.062 mmol, 1.1 equiv.). After the reaction mixture was stirred for 60 min to give a slurry, the slurry was heated at about 75° C. for 80 min and stirred at room temperature for 4 h. The precipitate was collected by filtration, washed with heptane and dried under vacuum overnight to provide the citrate salt (38.6 mg, 91.9%) as off-white solid.

The stoichiometric ratio of the salt between free base and citric acid was determined by $^1$H NMR as 1:1. The crystallinity of the salt was confirmed by XRPD and further supported by DSC. The TGA showed about 0.57% weight loss up to about 100° C. SEM image indicated that the salt has a plane-like crystal shape.

C. Benzoate Salt: To the solution of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile free base (31.41 mg, 0.0.057 mmol, 1 eq) in 2-propanol (0.5 mL) was added benzoic acid (16.54 mg, 0.135 mmol, 2.39 eq). The colorless solution turns to a slurry after stirring for 20 min. The mixture was stirred at room temperature overnight. The solid was collected by filtration, washed by heptane (1.5 mL) and dried overnight under vacuum to afford the benzoate salt (35 mg, 91.3%) as off-white solid.

The stoichiometric ratio of free base to benzoic acid was determined by $^1$H NMR as 1:1. The crystallinity of the benzoate salt was confirmed by XRPD. The DSC thermogram exhibited melting endotherms. The TGA showed a weight loss of 0.080% up to approximately 100° C. The SEM image showed that the benzoate salt was a plane-like crystal.

Using similar procedures to those described above, the maleate, salicylate, saccharin, camsylate, and nicotinate salts of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile were also found to be good crystalline salts.

Example 399

Pharmaceutical Compositions of {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl] azetidin-3-yl}acetonitrile Adipic Acid Salt Prototype capsules were manufactured using a conventional dry blending process. The initial prototype capsules was performed on a 200 mg weight blend, for both the 10 mg and 50 mg capsules. Silicified microcrystalline cellulose formulation was selected based on manufacturability, dissolution and content uniformity data obtained on development batches. The 1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt ("adipic acid salt") could be formed as shown in Example 358. The composition of the silicified microcrystalline cellulose prototype capsule formulation is listed in Tables A and B below.

TABLE A

Components and Composition of 10 mg Capsule

| Component | Composition in mg/capsule |
|---|---|
| Adipic acid salt | 12.64* |
| Silicified microcrystalline cellulose** | 187.36 |
| Size 2 capsule (white opaque) | — |
| Total | 200.0 |

*Salt conversion factor is 0.7911
**Comprised of 98% Microcrystalline Cellulose NF and 2% Colloidal Silicon Dioxide NF

TABLE B

Components and Composition of 50 mg Capsule

| Component | Composition in mg/capsule |
|---|---|
| Adipic acid salt | 63.20* |
| Silicified microcrystalline cellulose** | 136.80 |
| Size 2 capsule (white opaque) | — |
| Total | 200.0 |

*Salt conversion factor is 0.7911
**Comprised of 98% Microcrystalline Cellulose NF and 2% Colloidal Silicon Dioxide NF Batch formula for 10 mg and 50 mg capsules are shown in Tables C and D. The capsules are made by the steps below:
1. The required amount of adipic acid salt and an approximately equal amount of silicified microcrystalline cellulose (SMCC) are pre-mixed.
2. The mixture from step 1 is passed through a suitable screen (e.g., 40 mesh).
3. The remaining SMCC is screened through the same screen used in step 2.
4. The screened SMCC from step 3 is blended along with the mixture from step 2 in a suitable blender (e.g., a Turbula blender) for approximately 5 minutes.
5. The blend is filled into capsules to the desired fill weight.

TABLE C

Batch Formula for 225 g Blend for 10 mg Capsules

| Component | g/batch |
|---|---|
| Adipic acid salt | 15.80 |
| Silicified microcrystalline cellulos | 209.20 |
| Size 2 capsule (white opaque) | — |
| Total | 225.0 |

TABLE D

Batch Formula for 936 g Blend for 50 mg Capsules

| Component | g/batch |
|---|---|
| Adipic acid salt | 328.66 |
| Silicified microcrystalline cellulose** | 607.34 |
| Size 2 capsule (white opaque) | — |
| Total | 963.0 |

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Table 1 for data related to compounds of the invention.

TABLE 1

$IC_{50}$ data for JAK enzyme assay (measured at 1 mM ATP)

| Example | JAK1 $IC_{50}$ (nM)[1] | JAK2 $IC_{50}$ (nM)[2] | $IC_{50}$ Ratio JAK2/JAK1 |
|---|---|---|---|
| 1 | + | ++++ | 24.5 |
| 2 | + | +++ | 12.3 |
| 3 | + | ++ | 11.0 |

TABLE 1-continued

IC$_{50}$ data for JAK enzyme assay (measured at 1 mM ATP)

| Example | JAK1 IC$_{50}$ (nM)[1] | JAK2 IC$_{50}$ (nM)[2] | IC$_{50}$ Ratio JAK2/JAK1 |
|---|---|---|---|
| 4 | ++ | +++ | 10.2 |
| 5 | + | ++ | 12.0 |
| 6 | + | ++ | 14.3 |
| 7 | + | + | 10.8 |
| 8 | ++ | +++ | 11.0 |
| 9 | + | ++ | 3.2 |
| 10 | ++ | ++ | 4.4 |
| 11 | ++ | ++ | 7.2 |
| 12 | +++ | ++++ | 5.2 |
| 13 | + | ++ | 5.3 |
| 14 | ++ | ++ | 3.2 |
| 15 | ++ | ++ | 5.3 |
| 16 | ++ | ++ | 2.5 |
| 17 | +++ | +++ | 2.6 |
| 18 | ++ | +++ | 8.8 |
| 19 | + | + | 3.8 |
| 20 | + | + | 4.2 |
| 21 | ++ | ++ | 3.2 |
| 22 | ++ | ++ | 3.2 |
| 23 | + | ++ | 6.7 |
| 24 | + | + | 6.6 |
| 25 | + | ++ | 5.8 |
| 26 | + | + | 3.3 |
| 27 | ++ | +++ | 5.1 |
| 28 | + | + | 8.5 |
| 29 | + | + | 7.2 |
| 30 | + | + | 2.8 |
| 31 | + | + | 1.9 |
| 32 | + | ++ | 4.4 |
| 33 | + | + | 0.5 |
| 34 | ++ | ++ | 6.0 |
| 35 | + | ++ | 6.9 |
| 36 | + | + | 2.3 |
| 37 | + | + | 2.1 |
| 38 | + | + | 5.7 |
| 39 | + | + | 3.2 |
| 40 | + | + | 4.8 |
| 41 | + | + | 4.9 |
| 42 | + | + | 6.7 |
| 43 | + | ++ | 5.0 |
| 44 | + | + | 2.9 |
| 45 | + | ++ | 3.1 |
| 46 | + | ++ | 6.3 |
| 47 | + | + | 3.7 |
| 48 | + | ++ | 6.5 |
| 49 | + | + | 6.5 |
| 50 | + | + | 6.9 |
| 51 | + | + | 6.3 |
| 52 | ++ | +++ | 4.4 |
| 53 | + | ++ | 9.4 |
| 54 | ++ | +++ | 9.1 |
| 55 | + | ++ | 7.5 |
| 56 | + | + | 8.8 |
| 57 | ++++ | ++++ | 3.3 |
| 58 | + | ++ | 5.0 |
| 59 | + | + | 4.6 |
| 60 | + | + | 1.8 |
| 61 | ++ | ++ | 4.2 |
| 62 | ++ | +++ | 6.6 |
| 63 | + | ++ | 6.1 |
| 64 | + | + | 2.7 |
| 65 | + | ++ | 4.3 |
| 66 | ++ | +++ | 6.2 |
| 67 | + | + | 4.7 |
| 68 | ++ | ++ | 5.3 |
| 69 | ++ | ++ | 5.3 |
| 70 | + | + | 3.8 |
| 71 | +++ | +++ | 4.4 |
| 72 | + | + | 6.6 |
| 73 | + | + | 4.2 |
| 74 | + | ++ | 3.8 |
| 75 | + | + | 3.4 |
| 76 | + | + | 5.5 |
| 77 | + | + | 5.5 |
| 78 | + | ++ | 5.4 |
| 79 | + | + | 3.9 |
| 80 | + | + | 4.1 |
| 81 | + | + | 4.2 |
| 82 | + | + | 5.3 |
| 83 | + | ++ | 5.8 |
| 84 | + | ++ | 6.5 |
| 85 | ++ | ++++ | 15.9 |
| 86 | + | +++ | 19.4 |
| 87 | + | + | 0.3 |
| 88 | ++ | + | 0.9 |
| 89 | + | + | 2.6 |
| 90 | + | + | 1.5 |
| 91 | + | + | 1.7 |
| 92 | + | + | 2.8 |
| 93 | + | + | 1.5 |
| 94 | ++ | ++ | 1.0 |
| 95 | + | + | 2.7 |
| 96 | + | + | 0.5 |
| 97 | ++ | ++ | 2.2 |
| 98 | ++ | +++ | 3.7 |
| 99 | ++ | ++ | 5.6 |
| 100 | ++ | +++ | 6.6 |
| 101 | ++ | ++++ | 8.3 |
| 102 | ++ | ++ | 4.2 |
| 103 | ++ | ++ | 2.5 |
| 104 | ++ | ++ | 6.3 |
| 105 | ++ | ++++ | 7.2 |
| 106 | ++ | ++ | 4.2 |
| 107 | ++ | +++ | 4.1 |
| 108 | ++ | ++ | 1.4 |
| 109 | +++ | ++ | 1.1 |
| 110 | ++ | ++ | 1.6 |
| 111 | ++ | ++ | 2.6 |
| 112 | ++ | +++ | 8.2 |
| 113 | +++ | +++ | 4.2 |
| 114 | ++ | ++ | 1.5 |
| 115 | + | ++ | 15.7 |
| 116 | + | ++ | 10.6 |
| 117 | + | ++ | 10.0 |
| 118 | + | ++ | 21.5 |
| 119 | + | ++ | 14.0 |
| 120 | + | + | 2.1 |
| 121 | + | + | 3.8 |
| 122 | ++ | ++ | 2.5 |
| 123 | + | + | 3.8 |
| 124 | + | + | 8.4 |
| 125 | + | ++ | 8.1 |
| 126 | + | ++ | 6.3 |
| 127 | ++ | ++ | 4.3 |
| 128 | + | ++ | 3.5 |
| 129 | + | + | 7.9 |
| 130 | + | + | 7.1 |
| 131 | + | ++ | 8.1 |
| 132 | + | + | 5.8 |
| 133 | + | ++ | 7.9 |
| 134 | + | ++ | 6.7 |
| 135 | + | ++ | 7.1 |
| 136 | ++ | ++++ | 5.6 |
| 137 | +++ | ++++ | 6.0 |
| 138 | + | + | 13.9 |
| 139 | + | + | 4.4 |
| 140 | ++ | ++ | 5.4 |
| 141 | + | + | 6.2 |
| 142 | + | + | 7.4 |
| 143 | ++ | ++ | 3.5 |
| 144 | ++ | ++ | 3.9 |
| 145 | ++ | ++ | 3.6 |
| 146 | ++ | ++ | 5.8 |
| 147 | + | + | 6.1 |
| 148 | + | + | 5.7 |
| 149 | + | ++ | 5.0 |
| 150 | + | + | 7.0 |
| 151 | ++ | +++ | 5.8 |
| 152 | ++ | ++ | 4.0 |
| 153 | +++ | ++ | 1.2 |

TABLE 1-continued

IC$_{50}$ data for JAK enzyme assay (measured at 1 mM ATP)

| Example | JAK1 IC$_{50}$ (nM)[1] | JAK2 IC$_{50}$ (nM)[2] | IC$_{50}$ Ratio JAK2/JAK1 |
|---|---|---|---|
| 154 | + | ++ | 22.0 |
| 155 | ++ | +++ | 12.2 |
| 156 | + | ++ | 11.2 |
| 157 | + | +++ | 14.8 |
| 158 | + | ++ | 12.0 |
| 159 | + | ++ | 15.0 |
| 160 | + | ++ | 12.1 |
| 161 | + | ++ | 12.1 |
| 162 | + | ++ | 13.6 |
| 163 | + | ++ | 12.0 |
| 164 | + | ++ | 13.3 |
| 165 | ++ | +++ | 10.4 |
| 166 | + | + | 5.5 |
| 167 | + | + | 2.0 |
| 168 | + | + | 2.6 |
| 169 | + | ++ | 5.5 |
| 170 | + | ++ | 6.9 |
| 171 | + | ++ | 7.5 |
| 172 | ++ | ++ | 4.2 |
| 173 | ++ | ++ | 5.7 |
| 174 | + | + | 7.1 |
| 175 | + | + | 3.6 |
| 176 | + | + | 5.1 |
| 177 | + | + | 8.5 |
| 178 | + | + | 6.5 |
| 179 | ++ | +++ | 3.8 |
| 180 | + | ++ | 4.0 |
| 181 | + | ++ | 4.9 |
| 182 | ++ | ++ | 3.7 |
| 183 | + | + | 3.8 |
| 184 | + | + | 3.9 |
| 185 | + | ++ | 9.5 |
| 186 | + | ++ | 5.5 |
| 187 | + | ++ | 8.8 |
| 188 | ++ | ++ | 2.3 |
| 189 | ++ | ++ | 3.5 |
| 190 | +++ | +++ | 2.1 |
| 191 | +++ | ++ | 1.4 |
| 192 | ++ | ++ | 3.0 |
| 193 | + | + | 0.5 |
| 194 | + | + | 2.2 |
| 195 | +++ | +++ | 3.2 |
| 196 | ++ | +++ | 9.9 |
| 197 | ++ | ++ | 3.2 |
| 198 | + | ++ | 4.4 |
| 199 | + | ++ | 10.0 |
| 200 | + | ++ | 6.7 |
| 201 | ++ | ++ | 3.6 |
| 202 | + | ++ | 6.4 |
| 203 | ++ | +++ | 8.6 |
| 204 | + | ++ | 4.0 |
| 205 | ++ | ++ | 4.4 |
| 206 | + | + | 1.6 |
| 207 | + | + | 2.5 |
| 208 | + | ++ | 4.8 |
| 209 | + | ++ | 19.0 |
| 210 | + | + | 4.3 |
| 211 | ++ | ++ | 5.0 |
| 212 | ++ | +++ | 7.8 |
| 213 | + | ++ | 9.7 |
| 214 | ++ | ++ | 2.5 |
| 215 | + | ++ | 5.7 |
| 216 | ++ | ++ | 4.0 |
| 217 | ++ | ++ | 5.8 |
| 218 | +++ | +++ | 2.6 |
| 219 | ++ | ++ | 2.4 |
| 220 | ++ | +++ | 4.4 |
| 221 | ++ | ++ | 1.3 |
| 222 | ++ | ++ | 2.4 |
| 223 | ++ | ++ | 5.9 |
| 224 | +++ | +++ | 2.4 |
| 225 | + | ++ | 3.8 |
| 226 | ++ | ++ | 1.9 |
| 227 | + | + | 7.9 |
| 228 | + | + | 3.9 |
| 229 | ++ | +++ | 6.4 |
| 230 | ++ | ++++ | 9.3 |
| 231 | ++ | +++ | 5.1 |
| 232 | ++ | + | 0.7 |
| 233 | +++ | +++ | 2.2 |
| 234 | + | ++ | 4.2 |
| 235 | ++ | ++ | 2.5 |
| 236 | + | + | 5.5 |
| 237 | ++ | ++ | 2.3 |
| 238 | + | ++ | 6.8 |
| 239 | ++ | ++ | 2.3 |
| 240 | + | ++ | 8.7 |
| 241 | + | + | 3.8 |
| 242 | + | ++ | 8.3 |
| 243 | +++ | ++++ | 6.4 |
| 244 | ++ | ++ | 1.8 |
| 245 | ++ | ++ | 1.5 |
| 246 | + | ++ | 7.5 |
| 247 | + | + | 5.1 |
| 248 | +++ | ++++ | 5.2 |
| 249 | ++ | ++ | 2.1 |
| 250 | + | ++ | 4.7 |
| 251 | + | + | 4.9 |
| 252 | ++ | ++ | 2.3 |
| 253 | + | + | 5.8 |
| 254 | + | ++ | 3.8 |
| 255 | ++ | ++ | 3.2 |
| 256 | + | ++ | 8.2 |
| 257 | ++ | ++ | 4.4 |
| 258 | + | + | 5.0 |
| 259 | + | + | 4.6 |
| 260 | + | ++ | 7.1 |
| 261 | ++ | ++++ | 20.8 |
| 262 | ++ | +++ | 7.4 |
| 263 | + | +++ | 12.2 |
| 264 | ++ | +++ | 9.5 |
| 265 | ++ | +++ | 6.6 |
| 266 | ++ | +++ | 6.6 |
| 267 | ++ | +++ | 6.6 |
| 268 | ++ | ++ | 3.1 |
| 269 | + | ++ | 5.0 |
| 270 | + | + | 6.1 |
| 271 | + | ++ | 7.8 |
| 272 | ++ | ++ | 6.5 |
| 273 | + | + | 4.4 |
| 274 | + | ++ | 9.0 |
| 275 | ++ | ++ | 3.1 |
| 276 | + | + | 4.0 |
| 277 | + | ++ | 9.8 |
| 278 | + | + | 5.6 |
| 279 | + | + | 4.1 |
| 280 | + | + | 7.5 |
| 281 | + | ++ | 10.0 |
| 282 | ++ | ++ | 3.4 |
| 283 | + | +++ | 35.6 |
| 284 | + | ++ | 5.8 |
| 285 | ++ | ++ | 5.7 |
| 286 | + | ++ | 13.1 |
| 287 | ++ | +++ | 6.7 |
| 288 | + | + | 9.0 |
| 289 | + | ++ | 14.0 |
| 290 | +++ | ++++ | 3.9 |
| 291 | + | +++ | 20.3 |
| 292 | + | ++ | 9.1 |
| 293 | + | ++ | 3.4 |
| 294 | ++ | ++++ | 21.4 |
| 295 | ++ | ++ | 5.1 |
| 296 | + | ++ | 4.6 |
| 297 | + | + | 10.0 |
| 298 | +++ | +++ | 2.8 |
| 299 | +++ | ++++ | 6.6 |
| 300 | ++ | ++++ | 11.7 |
| 301 | +++ | +++ | 3.3 |
| 302 | +++ | ++++ | 6.5 |
| 303 | + | +++ | 19.7 |

TABLE 1-continued

IC$_{50}$ data for JAK enzyme assay (measured at 1 mM ATP)

| Example | JAK1 IC$_{50}$ (nM)[1] | JAK2 IC$_{50}$ (nM)[2] | IC$_{50}$ Ratio JAK2/JAK1 |
|---|---|---|---|
| 304 | + | ++ | 10.3 |
| 305 | + | +++ | 16.0 |
| 306 | ++ | ++ | 3.5 |
| 307 | ++ | +++ | 8.8 |
| 308 | + | +++ | 10.4 |
| 309 | ++ | ++ | 5.3 |
| 310 | + | ++ | 9.0 |
| 311 | ++ | ++++ | 11.1 |
| 312 | ++ | +++ | 5.3 |
| 313 | + | ++ | 14.3 |
| 314 | + | ++ | 11.0 |
| 315 | ++ | +++ | 16.2 |
| 316 | + | ++ | 9.5 |
| 317 | + | ++ | 4.5 |
| 318 | ++ | ++ | 4.7 |
| 319 | + | ++ | 4.0 |
| 320 | + | ++ | 2.8 |
| 321 | + | ++ | 3.0 |
| 322 | + | + | 4.7 |
| 323 | + | + | 5.0 |
| 324 | + | ++ | 5.6 |
| 325 | ++ | +++ | 4.3 |
| 326 | ++ | ++ | 1.7 |
| 327 | ++ | +++ | 4.1 |
| 328 | + | ++ | 12.9 |
| 329 | ++ | +++ | 4.5 |
| 330 | + | ++ | 6.7 |
| 331 | + | ++ | 10.8 |
| 332 | + | +++ | 19.3 |
| 333 | ++ | +++ | 8.8 |
| 334 | +++ | ++++ | 4.3 |
| 335 | + | + | 2.4 |
| 336 | + | + | 2.9 |
| 337 | ++ | ++ | 6.0 |
| 338 | ++ | +++ | 7.4 |
| 339 | ++ | ++ | 4.1 |
| 340 | +++ | ++ | 1.4 |
| 341 | ++ | +++ | 3.2 |
| 342 | + | ++ | 5.7 |
| 343 | ++ | +++ | 5.5 |
| 344 | + | +++ | 18.9 |
| 345 | ++ | +++ | 11.9 |
| 346 | + | ++ | 5.9 |
| 347 | ++ | ++ | 2.7 |
| 348 | + | ++ | 3.2 |
| 349 | +++ | +++ | 3.3 |
| 350 | ++ | ++++ | 15.0 |
| 351 | + | ++ | 3.8 |
| 352 | + | ++ | 18.8 |
| 353 | ++ | ++ | 5.0 |
| 354 | ++ | ++ | 2.1 |
| 355 | + | + | 3.1 |
| 356 | ++ | +++ | 5.8 |
| 357 | + | ++ | 3.8 |
| 358 | + | +++ | 49.2 |
| 359 | + | ++++ | 59.2 |
| 360 | + | ++++ | 56.4 |
| 361 | + | +++ | 20.9 |
| 362 | + | +++ | 22.4 |
| 363 | + | +++ | 32.9 |
| 364 | + | +++ | 37.8 |
| 365 | + | ++ | 15.5 |
| 366 | + | ++ | 68.4 |
| 367 | + | ++ | 33.8 |
| 368 | + | ++ | 54.2 |
| 369 | + | ++++ | 43.8 |
| 370 | + | +++ | 55 |
| 371 | + | +++ | 65.3 |
| 372 | + | ++ | 67.3 |
| 373 | + | ++ | 36.8 |
| 374 | + | ++ | 50 |
| 375 | + | ++ | 12.7 |
| 376 | + | ++ | 69.2 |
| 377 | + | ++ | 35.7 |
| 378 | + | ++ | 32.7 |
| 379 | + | +++ | 36.9 |
| 380 | + | ++ | 15.9 |
| 381 | + | ++ | 20 |
| 382 | + | ++ | 26.7 |
| 383 | + | ++ | 30.5 |
| 384 | + | +++ | 29.6 |
| 385 | + | +++ | 28.9 |
| 386 | + | ++ | 7.7 |
| 387 | + | ++ | 9.7 |
| 388 | ++ | ++ | 7.6 |
| 389 | + | ++ | 6.5 |
| 390 | + | ++ | 8.3 |
| 391 | ++ | +++ | 10.6 |
| 392 | ++ | ++ | 5.6 |
| 393 | + | ++ | 7.1 |
| 394 | ++ | +++ | 11.1 |
| 395 | + | +++ | 24.4 |
| 396 | + | ++ | 7.1 |
| 397 | + | ++ | 21.7 |

[1]For JAK1: 5 nM or less (+); >5 nM to 20 nM (++); >20 nM to 30 nM (+++); and >30 nM (++++)
[2]For JAK2: 10 nM or less (+); >10 nM to 50 nM (++); >50 nM to 100 nM (+++); and >100 nM (++++)

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% CO$_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. *JBC* 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subj ected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiements may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating graft versus host disease in a patient in need thereof, comprising administering to said patient a therapeutically effective amount of a compound, which is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

2. The method of claim 1, wherein said pharmaceutically acceptable salt is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

* * * * *